US006045997A

United States Patent [19]

Futreal et al.

[11] Patent Number: 6,045,997

[45] Date of Patent: Apr. 4, 2000

[54] MATERIALS AND METHODS RELATING TO THE IDENTIFICATION AND SEQUENCING OF THE BRCA2 CANCER SUSCEPTIBILITY GENE AND USES THEREOF

[75] Inventors: Phillip Andrew Futreal, Durham, N.C.; Richard Francis Wooster, Surrey, United Kingdom; Alan Ashworth, South Kensington, United Kingdom; Michael Rudolf Stratton, London, United Kingdom

[73] Assignees: Duke University, Durham, N.C.; Cancer Research Campaign Technology Limited, London, United Kingdom

[21] Appl. No.: 08/755,587

[22] Filed: Nov. 25, 1996

[30] Foreign Application Priority Data

| | | | |
|---|---|---|---|
| Nov. 23, 1995 | [GB] | United Kingdom | 9523959 |
| Dec. 14, 1995 | [GB] | United Kingdom | 9525555 |
| Aug. 28, 1996 | [GB] | United Kingdom | 9617961 |

[51] Int. Cl.[7] .......................... C07H 21/02; C07H 21/04; C12Q 1/68

[52] U.S. Cl. ........................... 435/6; 536/23.5; 536/24.3; 536/24.31; 536/23.1; 435/320.1

[58] Field of Search ................................. 536/23.1, 23.5, 536/24.3, 24.31; 435/6, 320.1

[56] References Cited

U.S. PATENT DOCUMENTS 5,464,758 11/1995 Gossen et al. ........................ 435/69.1

FOREIGN PATENT DOCUMENTS 393 502-A 10/1990 European Pat. Off. .
WO 95/19360 7/1995 WIPO .

OTHER PUBLICATIONS

Schutte et al. PNAS, USA 92:5950–5954, 1995.

R. Wooster et al.; Localization of a Breast Cancer Susceptibility Gene, BRCA2, to Chromosome 13q12–13, *Science* 265 (5181):2088–2090 (1994).

Y. Miki et al.; A Strong Candidate for the Breast and Ovarian Cancer Susceptibility Gene BRCA1, *Science* 266(5182):66–71 (1994).

J. Gudmundsson et al.; Different Tumor Types from BRCA2 Carriers Show Wild–Type Chromosome Deletions on 13q12–q13, *Cancer Res.* 55(21):4830–4832 (1995).

M. Schutte et al.; Identification by representational difference analysis of a homozygous deletion in pancreatic carcinoma that lies within the BRCA2 region, *Proc. Natl. Acad. Sci. USA* 92(13):5950–5054 (1995).

R. Wooster et al.; Identification of the breast cancer susceptibility gene BRCA2, *Nature* 378:789–792 (1995).

K. Foster et al.; Somatic and Germline Mutuations of the BRCA2 Gene in Sporadic Ovarian Cancer, *Cancer Research* 56:3622–3625 (1996).

D. Berman et al.; A Common Mutation in BRCA2 That Predisposes to a Variety of Cancers Is Found in Both Jewish Ashkenazi and Non–Jewish Individuals, *Cancer Research* 56:3409–3414 (1996).

A. Jacob et al.; Isolation of expressed sequences that include a gene for familial breat cancer (BRCA2) and othe rnovel transcripts from a five megabase region on chromosome 13q12, *Oncogene* 13:213–221 (1996).

F. Couch et al.; Generation of an Integrated Transcription Map of the BRCA2 Region on Chromosome 13q12–q13., *Genomics* 36:86–99 (1996).

S. Tavtigian et al.; The Complete BRCA2 Gene and Mutuations in Chromosome 13q–linked Kindreds, *Nature Genetics* 12:333–337 (1996).

S. Fischer et al.; A high–resolution annotated physical map of the human chromosome 13q12–13 region containing the breast cancer susceptibility locus BRCA2, *Proc. Natl. Acad. Sci. USA* 93:690–694 (1996).

J. Hall et al.; Linkage of early–onset familial breast cancer to chromosome 17q21, *Science* 250(4988):1684–1689 (1990).

D. Malkin et al.; Germ line p53 mutations in a familial syndrome of breast cancer, sarcomas and other neoplasms, *Science* 250(4985):1233–1238 (1990).

R. Wooster et al.; A germline mutation in the androgen receptor gene in two brothers with breast cancer and Reifenstein syndrome, *Nat. Genet.* 2(2):132–134 (1992).

M. Frohman et al.; Rapid amplification of full length cDNAs from rare transcripts: Amplification using a single gene–specific oligonucleotide primer, *PNAS USA* 85:8998–9002 (1988).

A. Beaudet et al.; A Suggested Nomenclature for Designating Mutations, *Hum. Mutat.* 2(4):245–248 (1993).

S. Thorlacius et al.; A Single BRCA2 Mutation in Male and Female Breast–Cancer Families from Iceland with Varied Cancer Phenotypes, *Nature Genetics* 13:117–119 (1996).

C. Phelan et al.; Mutation analysis of the BRCA2 Gene in 49 Site–Specific Breast Cancer Families, *Nature Genetics* 13:120–122 (1996).

A. Bowcock et al.; THRA1 and D17S183 Flank an Interval of <4 cM for the Breast–Ovarian Cancer Gene (BRCA1) on Chromosome 17q21, *Am. J. Hum. Genet.* 52:718–722 (1993).

(List continued on next page.)

*Primary Examiner*—Paula K. Hutzell
*Assistant Examiner*—Geetha P. Bansal
*Attorney, Agent, or Firm*—Nixon & Vanderhye P.C.

[57] ABSTRACT

The identification and sequencing of the BRCA2 gene is disclosed as well as the amino acid sequence of the corresponding BRCA2 polypeptides. BRCA2 alleles including those with mutations in the BRCA2 gene which are associated with a predisposition to develop cancer, especially breast and ovarian cancer are also disclosed. The present invention further relates to polypeptides encoded by the above nucleic acid. The present invention further relates to uses of much BRCA2 nucleic acid and BRCA2 polypeptides, in particular in the diagnostic, prognostic or therapeutic treatment of cancer.

6 Claims, 46 Drawing Sheets

OTHER PUBLICATIONS

Easton et al.; Genetic Linkage analysis in Familial Breast and Ovarian Cancer, *Am. J. Hum. Genet.* 52:718–722 (1993).

S. Gayther et al.; Germline Mutations of the Brca1 Gene in Breast and Ovarian–Cancer Families Provide Evidence for a Genotype–Phenotype Correlation, *Nature Genetics* 11:428–433 (1995).

J. Holt et al.; Growth–Retardation and Tumor–Inhibition by BRCA1, *Nature Genetics* 12:298–302 (1996).

S. Gayther et al.; Rapid Detection of Regionally Clustered Germ–Line BRCA1 Mutations by Multiplex Heteroduplex Analysis, *Am. J. Human Gen.* 58:451–456 (1996).

F. Couch et al.; BRCA1 Germline Mutations in Male Breast– Cancer Cases and Breast–Cancer Families, *Nature Genetics* 13:123–125 (1996).

S. Neuhausen et al.; Recurrent BRCA2 617delT Mutations in Ashkenazi Jewish Women Affected by Breast–Cancer, *Nature Genetics* 13:126–128 (1996).

L. Spirio et al.; Alleles of the APC gene: an attenuated form of familial polyposis, *Cell* 75:951–957 (1993).

S. Olschwang et al.; Restriction of ocular fundus lesions to a specific subgroup of APC mutations in adenomatous polyposis coli patients, *Cell* 75:959–968 (1993).

P. Bork et al.; Internal repeats in the BRCA2 protein sequence, *Natue Genetics* 13:22–23 (1996).

S. Cowley et al.; Activation of MAP Kinase Kinase Is Necessary and Sufficient for PC12 differentiation and for Transsformation of NIH 3T3 Cells, *Cell* 77:841–852 (1994).

R. Marais et al.; Ras recruits Raf–1 to the plasma membrane for activation by tyrosine phosphorylation, *EMBO J.* 14:3136–3145 (1995).

G. Hynes et al.; Peptide mass fingerprinting of chaperonin–containing TCP–1 (CCT) and copurifying proteins, *FASEB J.* 10:137–147 (1996).

D. Easton et al.; Genetic Linkage Analysis in Familial Breast and Ovarian Cancer: Results from 214 Families, *Am. J. Hum. Genet.* 52:678–701 (1993).

G. Cyapay et al.; The 1993–94 Généthon human genetic linkage map, *Nature Genetics,* 7:246–339 (1994).

M. Schutte et al.; An Integrated High–Resolution Physical Map of the DPC/BRCA2 Region at Chromosome 13q12, *Cancer Res.* 55:4570–4574 (1995).

C. Cohen et al.; A first–generation of physical map of the human genome, *J. Nature* 366:698–701 (1993).

P. Ioannou et al.; A new bacteriophage P1–derived vector for the propagation of large human DNA fragments, *Nature Genetic* 6:84–89 (1994).

M. Nehls et al.; Exon amplificatio from complete libraries of genomic DNA using a novel phage vector with automatic plasmid excision facility: application to the mouse neurofibromatosis–1 locus, *Oncogene* 9:2169–2175 (1994).

D. Tagle et al.; Magnetic bead capture of expressed sequences encoded within large genomic segments, *Nature* 361:751–753 (1993).

M. Stratton et al.; Familial male breast cancer is not linked to the BRCA1 locus on chromosome 17q, *Nature Genetic* 7:103–107 (1994).

P. Devilee et al.; Somatic genetic changes in human breast cancer, *Biochim. Biophs. Acta* 1198:113–130 (1994).

C. Lundberg et al.; Loss of heterozygosity in human ductal breast tumors indicates a recessive mutation on chromosome 13, *Proc. Natl. Acad. Sci. USA* 84:2372–2376 (1987).

A–M Cleton–Jansen et al.; Loss of heterozygosityin sporadic breast tumors at the BRCA2 locus on chromosome 13q12–q13, *British J. of Cancer* 72:1241–1244 (1995).

International Search Report for PCT/GB 96/02904.

The BRCA2 gene

This sequence was obtained from the cDNA clone known as plaque 14. A 6bp deletion in the sequence was identified in DNA from the breast cancer family IARC2932. This deletion cosegregates with the breast cancer in this family. The deletion would disrupt the splicing of the primary transcript, would introduce a premature stop codon in the messenger RNA and result in the loss of the normal protein. Based on these observations, this cDNA is proposed as part of the BRCA2 gene.

Sequence 1. The BRCA2 cDNA

The sequence is shown 5' to 3'

```
NCNAAAGTTTAAGGGAGTTGTTTAGGAGGAAATTTGATTTAATTCAGAAA
NTGAGCATAGTNTTCCANTATTCACCTACGTTTTAGACCAAAATGTATCA
AAAATACTTCCTTCGTGNTGATAAGAGAAACCCAGAGCACTGTGTAAACT
CCAGAAATGGAAAAAACCTGCAGTAAAGAATTTAAATTATCAAATAACTT
AAATGTTGAAGGTGGTTNTTCAGAAAATAATCACTCTATTAAAGTTTCTC
CATATCTCTCTCAATTTCAACAAGACAAACAACAGTTGGTATTAGGAACC
AAAGTNTCACTTGTTGAGAACATTCATGTTTTGGGAAAAGAACAGGCTTC
ACCTAAAAACGTAAAAATGGAAATTGGTAAAACTGAAACTTTTTCTGATG
TTCCTGTGNAAACAAATATAGAAGTTTGTTCTACTTACTCCAAAGATTCA
GAAAACTACTTTGAAACAGAAGCAGTAGAAATTGCTAAAGCTTTTATGGA
AGATGATGAACTGACAGATTNTAAACTGCCAAGTCATGCCACACATTNTC
TTTTTACATGTCCCGAAAATGAGGAAATGGTTCTGTCAAATTCAAGAATT
GGAAAAAGAAGAGGAGAGCCCCTTATCTTAGTGGGAGAACCCTCAATCAA
AAGAAACTTATTAAATGAATTTGACAGGATAATAGAAAATCAAGAAAAAT
CCTTAAAGGCTTCAAAAAGCACTCCAGATGGCACAATAAAAGATTGAAGA
TTGTTTGTGCATCATGTTTCTTTAGAGCCGATTACCTGTGTACCCTTTCG
CACAACTAAGGAACGTCAAGAGATACAGAATCCAAATTTTACCGCACCTG
GTCAAGAATTTCTGTCTAAATCTCATTTGTATGAACATCTGACTTTGGAA
AAATCTTCAAGCAATTTAGCAGTTTCAGGACATCCATTTTATCAAGTTTC
TGCTACAAGAAATGAAAAAATGAGACACTTGATTACTACAGGCAGACCGA
CCAAAGTCTTTGTTCCACCTTTTAAAACTAAATCACATTTTCACAGAGTT
GAACAGTGTGTTAGGAATATTAACTTGGAGGAAAACAGACAAAAGCAAAA
CATTGATGGACATGGCTCTGATGATAGTAAAAATAAGATTAATGACAATG
AGATTCATCAGTTTAACAAAAACAACTCCAATCAAGCAGCAGCTGTAACT
TTCACAAAGTGTGAAGAAGAACCTTTAGATTTAATTACAAGTCTTCAGAA
TGCCAGAGATATACAGGATATGCGAATTAAGAAGAAACAAAGGCAACGCG
TCTTTCCACAGCCAGGCAGTCTGTATCTTGCAAAAACATCCACTCTGCCT
CGAATCTCTCTGAAAGCAGCAGTAGGAGGCCAAGTTCCCTCTGCGTGTTC
TCATAAACAGCTGTATACGTATGGCGTTTCTAAACATTGCATAAAAATTA
ACAGCAAAAATGCAGAGTCTTTTCAGTTTCACACTGAAGATTATTTTGGT
AAGGAAAGTTTATGGACTGGAAAAGGAATACAGTTGGCTGATGGTGGATG
GCTCATACCCTCCAATGATGGAAAGGCTGGAAAAGAAGAATTTTATAGGG
CTCTGTGTGACGTAAAGGCCACATAGTGGATAAACCATGTGCCACTTGAG
GAATTGAGAAAAAGTCAGTGTGTTTAGAACATAAGGAGAGGGGCAGAGAA
ATGGATCTGGTACAGGAGAATCAATGAGACCGGGTAAGAAACAGAAAAGG
GGCTGCACCAAATGATTGACACGCTCTGCAAACTTCTTTTGTTGGCTCAA
GTTGTGGCTCAAGAGGTGAGAAGGTAAGGCCAGACTTATTTGTTATGATT
TGCCCTTTAAATTGAAGCCTTAAGATTGGAATTCGATATCAAGCTTATCG
ATACCGTCGACCTCGAG
```

Fig.1

Genomic organisation of the BRCA2 gene

The following sequences show the individual exons of the plaque 14 cDNA where they are known. The exons are named f, e, d, bc and a. The cDNA sequence is labelled cDNA and the genomic sequence is labelled genomic. Exon sequence is shown in upper case and intron sequence is shown in lower case. Where the cDNA and genomic sequence are identical they are shown one above the other. Where necessary a - is shown to maintain the alignment of the sequences.

exon29f

```
genomic cgtaaaaatggaaattggtaaaactgaaactttttctgatgttcctgtga

genomic anncaaanatagaagtttgttctacttacncccaagattcagaaaactac

genomic tttgnaacagaancagnagaaattgctaaagcttttatggaagatgatga

genomic actgacagattctaanctcccaantcatgccacacattctctttttacat

cDNA    GTCCCGAAAATGAGGAAATGGTTTAGTCAAATTCAAGAATTGGAAAAAGA
genomic GTCCCGAAAATGAGGAAATGGTTTTGTCNAANTCAAGAATTGGAAAAAGA

cDNA    AGAGGAGAGCCCCTTATCTTA-GTGG
genomic AGAGGAGAGCCCCTTATCTTANCNGGgtaagtnttcatttttacctttcgcc

genomic nttgccaatcactatttttaaagtgtttattcagtagacttggtatgcta

genomic acaattaagagtgttataaactatgtcttttcagccatttttgtgtagtc

genomic agtttgggggagtatggtttgatatacagatacacagattcagtattcgt

genomic atacagatttgatatcttggtatacagattcgatatctctgaatctgtat
```

Fig. 2A exon29e cDNA GAGAACCCTCAATCAAAAGAAACTTATTAAATGAATTTGACAGGATAAT cDNA AGAAAATCAAGAAAAATCCTTAAAGGCTTCAAAAAGCACTCCAGATG
genomic AAATcAaGAAAA-TCCTTAAAGGNTTCAAAAAGCACTCCAGATG genomic gtaaaattagctttttatttatatctgttctccctctataggtatggtat genomic ataatattctgacctcaggtgatccacctgcctctcaaagtgctgggatt genomic acagacatgagccactgtgcctaatcaagggacctctttatactcttaaa genomic aattactgaggacctaaaagagcatttggttatgtggaatatatctattg

Fig. 2B exon29d genomic tgtactgtgagttatttggtgcatagtcattatcaatttgtgaatcaatt genomic tattttcatagttaacatttattgagcatccgttacattcactgaaaatt genomic gtaaagcctataattgtctcaaatttttttgtgtatttacagtaacatgga genomic tattctcttagattttaactaatatgtaatataaaataattgtttcctag cDNA GCACAATAAAAGATCGAAGATTGTTTATGCATCATGTTTCTTTAGAGCCG
genomic GCACAATAAAAGATCGAAGATTGTAGGGCATCAGTT AGCCG cDNA ATTACCTGTGTACCCTTTCG
genomic ATTACCTGTGTACCCTTTCGgtaagacatgtttaaatttttctaaattct genomic aatacagtatgagaaaagtctcgtttttataaatgaacatttctaaaaat genomic aatgacactaacgttaagaagttaacacttcccgttttataaaatttata genomic aaatactttggtagtattttatagtgctgttcatatcattattttatttt genomic ttaattttatgacagctttgtaaagtagacagattttattctaattttat

Fig. 2C

```
exon bc

genomic acacactgagaggtccacacttgacagatttattntattatgngttatgt

genomic gaggtagattgtaagtcaaaggctagccttgaaaaatgtgatattgtttt

genomic ggaatggcaaccatggngaanacaaaacagtnaccagaatngtatcacca

genomic tgtagcaaatgagggtctgcaacaaaggcatattcataaatattnanang

cDNA                                             CACAACTAA
genomic tgtagtagtcaatnaacttataaattttntccccantgcagCACNANTAA

cDNA    GGAACGTCAAGAGATACAGAATCCAAATTTTACCGCACCTGGTCAAGAAT
genomic GGGACGTCAAGAGATACAGAATCCANATTTTACCGCACCTGGTCANGGAT

cDNA    TTCTGTCTAAATCTCATTTGTATGAACATCTGACTTTGGAAAAATCTTCA
genomic TTCTGTNTAAATATCATTTGTATGAACATCTGACTTTGGAAAAATCTTCA

cDNA    AGCAATTTAGCAGTTTCAGGACATCCATTTTATCAAGTTTCTGCTACAAG
genomic AGCAATTTNGCAGTTTCAGGACATCCATTTTATCAAGTTTCTGCTACAAG

cDNA    AAATGAAAAAATGAGACACTTGATTACTACAGGCAGACCAACCAAAGTCT
genomic AAATGAAAAAATGAGACACTTGATTACTACAGGCAGACCAACCAAAGTCT

cDNA    TTGTTCCACCTTTTAAAACTAAATCACATTTTC-ACAGAGTTGAACAGTGT
genomic TTGTTCCACCTTTTAAAACTAAATCACATTTTCCACAGAGTTGAACAGTGT

cDNA    GTTAGGAATATTAACTTGGAGGAAAACAGACAAAAGCAAAACATTGATGG
genomic                       ggangaaacatATTNAAGCAAAACATTGATGG

cDNA    ACATGGCTCTGATGATAGTAAAAATAAGATTAATGACAATGAGATTCATC
genomic ACNTGGCTCTGATGATAGTAAAAATAAGATTAATGACAATGAGATTCATC

cDNA    AGTTTAACAGNAACAACTCCAATCAAGCAGCAGCTGTAACTTTCACAAAG
genomic AGTTTAACAAAAACAACTCCAATCAAGCAGCAGCTGTAACTTTCACAAAG

cDNA    TGTGAAGAAGAACCTTTAG
genomic TGTGAANAAAAACCTTTAGgtattgtatgacaatttgtgtgatgaatttt

genomic tgcctttcagttanatatttccgttgttaaataatgtcctgatggtttnc

genomic cccctttggtggtggtaattttaaagccctttttaatgttttagattttc

genomic taaatccaaagattaggtttaaattattctaatgtttctttcaaanataa
```

Fig. 2D exon a cDNA ATTTAATTACAAGTCTTCAGAATGCCAGAGA
cDNA TATACAGGATATGCGAATTAAGAAGAAACAAAGGCAACGCGTCTTTCCAC
cDNA AGCCAGGCAGTCTGTATCTTGCAAAAACATCCACTCTGCCTCGAATCTCT
cDNA CTGAAAGCAGCAGTAGGAGGCCAAGTTCCCTCTGCGTGTTCTCATAAACA
cDNA GCTGTATACGTATGGCGTTTCTAAACATTGCATAAAAATTAACAGCAAAA
cDNA ATGCAGAGTCTTTTCAGTTTCACACTGAAGATTATTTGGTAAGGAAAGT
cDNA TTATGGACTGGAAAAGGAATACAGTTGGCTGATGGTGGATGGCTCATACC
cDNA CTCCAATGATGGAAAGGCTGGAAAAGAAGAATTTTATAGGGCTCTGTGTG
cDNA ACGTAAAGGCCACATAGTGGATAAACCATGTGCCACTTGAGGAATTGAGA
cDNA AAAAGTCAGTGTGTTTAGAACATAAGGAGAGGGGCAGAGAAATGGATCTG
cDNA GTACAGGAGAATCAATGAGACCGGGTAAGAAACAGAAAAGGGGCTGCACC
cDNA AAATGATTGACACGCTCTGCAAACTTCTTTTGTTGGCTCAAGTTGTGGCT
cDNA CAAGAGGTGAGAAGGTAAGGCCAGACTTATTTGTTATGATTTGCCCTTTA
cDNA AATTGAAGCCTTAAGATTGGAATTCGATATCAAGCTTATCGATACCGTCG
cDNA ACCTCGAG

Fig. 2E

BRCA2 protein sequence

Plaque 14 was translated in all 3 possible frames. The following protein sequence is the most likely of the 3 frames.

KVGSCLGGNLIFRXAXSXIHLRFRPKCIKNTSFVXIRETQSTVTPEMEKT
CSKEFKLSNNLNVEGGXSENNHSIKVSPYLSQFQQDKQQLVLGTKVSLVE
NIHVLGKEQASPKNVKMEIGKTETFSDVPVXTNIEVCSTYSKDSENYFET
EAVEIAKAFMEDDELTDXKLPSHATHXLFTCPENEEMVLSNSRIGKRRGE
PLILVGEPSIKRNLLNEFDRIIENQEKSLKASKSTPDGTIKDRLFVHHVS
LEPITCVPFRTTKERQEIQNPNFTAPGQEFLSKSHLYEHLTLEKSSSNLA
VSGHPFYQVSATRNEKMRHLITTGRPTKVFVPPFKTKSHFHRVEQCVRNI
NLEENRQKQNIDGHGSDDSKNKINDNEIHQFNKNNSNQAAAVTFTKCEEE
PLDLITSLQNARDIQDMRIKKKQRQRVFPQPGSLYLAKTSTLPRISLKAA
VGGQVPSACSHKQLYTYGVSKHCIKINSKNAESFQFHTEDYFGKESLWTG
KGIQLADGGWLIPSNDGKAGKEEFYRALCDVKAT

Fig. 3

BRCA2 cDNA

CCACATTGGAAAGTCAATGCCAAATGTCCTAGAAGATGAAGTATATGAAACAGTTGTAGA

TACCTCTGAAGAAGATAGTTTTTCATTATGTTTTTCTAAATGTAGAACAAAAAATCTACA

AAAAGTAAGAACTAGCAAGACTAGGAAAAAAATTTTCCATGAAGCAAACGCTGATGAATG

TGAAAAATCTAAAAACCAAGTGAAAGAAAAATACTCATTTGTATCTGAAGTGGAACCAAA

TGATACTGATCCATTAGATTCAAATGTAGCAAATCAGAAGCCCTTTGAGAGTGGAAGTGA

CAAAATCTCCAAGGAAGTTGTACCGTCTTTGGCCTGTGAATGGTCTCAACTAACCCTTTC

AGGTCTAAATGGAGCCCAGATGGAGAAAATACCCCTATTGCATATTTCTTCATGTGACCA

AAATATTTCAGAAAAAGACCTATTAGACACAGAGAACAAAAGAAAGAAAGATTTTCTTAC

TTCAGAGAATTCTTTGCCACGTATTTCTAGCCTACCAAAATCAGAGAAGCCATTAAATGA

GGAAACAGTGGTAAATAAGAGAGATGAAGAGCAGCATCTTGAATCTCATACAGACTGCAT

TCTTGCAGTAAAGCAGGCAATATCTGGAACTTCTCCAGTGGCTTCTTCATTTCAGGGTAT

CAAAAAGTCTATATTCAGAATAAGAGAATCACCTAAAGAGACTTTCAATGCAAGTTTTTC

AGGTCATATGACTGATCCAAACTTTAAAAAAGAAACTGAAGCCTCTGAAAGTGGACTGGA

AATACATACTGTTTGCTCACAGAAGGAGGACTCCTTATGTCCAAATTTAATTGATAATGG

AAGCTGGCCAGCCACCACCACACAGAATTCTGTAGCTTTGAAGAATGCAGGTTTAATATC

CACTTTGAAAAAGAAAACAAATAAGTTTATTTATGCTATACATGATGAAACATCTTATAA

AGGAAAAAAAATACCGAAAGACCAAAAATCAGAACTAATTAACTGTTCAGCCCAGTTTGA

AGCAAATGCTTTTGAAGCACCACTTACATTTGCAAATGCTGATTCAGGTTTATTGCATTC

TTCTGTGAAAAGAAGCTGTTCACAGAATGATTCTGAAGAACCAACTTTGTCCTTAACTAG

CTCTTTTGGGACAATTCTGAGGAAATGTTCTAGAAATGAAACATGTTCTAATAATACAGT

AATCTCTCAGGATCTTGATTATAAAGAAGCAAAATGTAATAAGGAAAAACTACAGTTATT

TATTACCCCAGAAGCTGATTCTCTGTCATGCCTGCAGGAAGGACAGTGTGAAAATGATCC

AAAAAGCAAAAAAGTTTCAGATATAAAAGAAGAGGTCTTGGCTGCAGCATGTCACCCAGT

ACAACATTCAAAAGTGGAATACAGTGATACTGACTTTCAATCCCAGAAAAGTCTTTTATA

TGATCATGAAAATGCCAGCACTCTTATTTTAACTCCTACTTCCAAGGATGTTCTGTCAAA

CCTAGTCATGATTTCTAGAGGCAAAGAATCATACAAAATGTCAGACAAGCTCAAAGGTAA

CAATTATGAATCTGATGTTGAATTAACCAAAAATATTCCCATGGAAAAGAATCAAGATGT

ATGTGCTTTAAATGAAAATTATAAAAACGTTGAGCTGTTGCCACCTGAAAAATACATGAG

AGTAGCATCACCTTCAAGAAAGGTACAATTCAACCAAAACACAAATCTAAGAGTAATCCA

AAAAAATCAAGAAGAAACTACTTCAATTTCAAAAATAACTGTCAATCCAGACTCTGAAGA

ACTTTTCTCAGACAATGAGAATAATTTTGTCTTCCAAGTAGCTAATGAAAGGAATAATCT

TGCTTTAGGAAATACTAAGGAACTTCATGAAACAGACTTGACTTGTGTAAACGAACCCAT

Fig. 4A

TTTCAAGAACTCTACCATGGTTTTATATGGAGACACAGGTGATAAACAAGCAACCCAAGT
GTCAATTAAAAAAGATTTGGTTTATGTTCTTGCAGAGGAGAACAAAAATAGTGTAAAGCA
GCATATAAAAATGACTCTAGGTCAAGATTTAAAATCGGACATCTCCTTGAATATAGATAA
AATACCAGAAAAAAATAATGATTACATGAACAAATGGGCAGGACTCTTAGGTCCAATTTC
AAATCACAGTTTTGGAGGTAGCTTCAGAACAGCTTCAAATAAGGAAATCAAGCTCTCTGA
ACATAACATTAAGAAGAGCAAAATGTTCTTCAAAGATATTGAAGAACAATATCCTACTAG
TTTAGCTTGTGTTGAAATTGTAAATACCTTGGCATTAGATAATCAAAAGAAACTGAGCAA
GCCTCAGTCAATTAATACTGTATCTGCACATTTACAGAGTAGTGTAGTTGTTTCTGATTG
TAAAAATAGTCATATAACCCCTCAGATGTTATTTTCCAAGCAGGATTTTAATTCAAACCA
TAATTTAACACCTAGCCAAAAGGAGCAAATTACAGAACTTTCTACTATATTAGAAGATTC
AGGAAGTCAGTTTGAATTTACTCAGTTTAGAAAACCAAGCTACATATTGCAGAAGAGTAC
ATTTGAAGTGCCTGAAAACCAGATGACTATCTTAAAGACCACTTCTGAGGAATGCAGAGA
TGCTGATCTTCATGTCATAATGAATGCCCCATCGATTGGTCAGGTAGACAGCAGCAAGCA
ATTTGAAGGTACAGTTGAAATTAAACGGAAGTTTGCTGGCCTGTTGAAAAATGACTGTAA
CAAAAGTGCTTCTGGTTATTTAACAGATGAAAATGAAGTGGGGTTTAGGGGCTTTTATTC
TGCTCATGGCACAAAACTGAATGTTTCTACTGAAGCTCTGCAAAAAGCTGTGAAACTGTT
TAGTGATATTGAGAATATTAGTGAGGAAACTTCTGCAGAGGTACATCCAATAAGTTTATC
TTCAAGTAAATGTCATGATTCTGTCGTTTCAATGTTTAAGATAGAAAATCATAATGATAA
AACTGTAAGTGAAAAAAATAATAAATGCCAACTGATATTACAAAATAATATTGAAATGAC
TACTGGCACTTTTGTTGAAGAAATTACTGAAAATTACAAGAGAAATACTGAAAATGAAGA
TAACAAATATACTGCTGCCAGTAGAAATTCTCATAACTTAGAATTTGATGGCAGTGATTC
AAGTAAAAATGATACTGTTTGTATTCATAAAGATGAAACGGACTTGCTATTTACTGATCA
GCACAACATATGTCTTAAATTATCTGGCCAGTTTATGAAGGAGGGAAACACTCAGATTAA
AGAAGATTTGTCAGATTTAACTTTTTTGGAAGTTGCGAAAGCTCAAGAAGCATGTCATGG
TAATACTTCAAATAAAGAACAGTTAACTGCTACTAAAACGGAGCAAAATATAAAAGATTT
TGAGACTTCTGATACATTTTTTCAGACTGCAAGTGGGAAAAATATTAGTGTCGCCAAAGA
GTCATTTAATAAAATTGTAAATTTCTTTGATCAGAAACCAGAAGAATTGCATAACTTTTC
CTTAAATTCTGAATTACATTCTGACATAAGAAAGAACAAAATGGACATTCTAAGTTATGA
GGAAACAGACATAGTTAAACACAAAATACTGAAAGAAAGTGTCCCAGTTGGTACTGGAAA
TCAACTAGTGACCTTCCAGGGACAACCCGAACGTGATGAAAAGATCAAAGAACCTACTCT
GTTGGGTTTTCATACAGCTAGCGGGAAAAAAGTTAAAATTGCAAAGGAATCTTTGGACAA
AGTGAAAAACCTTTTTGATGAAAGAGCAAGGTACTAGTGAAATCACCAGTTTTAGCCATC

Fig. 4B

AATGGGCAAAGACCCTAAAGTACAGAGAGGCCTGTAAAGACCTTGAATTAGCATGTGAGA
CCATTGAGATCACAGCTGCCCCAAAGTGTAAAGAAATGCAGAATTCTCTCAATAATGATA
AAAACCTTGTTTCTATTGAGACTGTGGTGCCACCTAAGCTCTTAAGTGATAATTTATGTA
GACAAACTGAAAATCTCAAAACATCAAAAAGTATCTTTTTGAAAGTTAAAGTACATGAAA
ATGTAGAAAAAGAAACAGCAAAAAGTCCTGCAACTTGTTACACAAATCAGTCCCCTTATT
CAGTCATTGAAAATTCAGCCTTAGCTTTTTACACAAGTTGTAGTAGAAAAACTTCTGTGA
GTCAGACTTCATTACTTGAAGCAAAAAAATGGCTTAGAGAAGGAATATTTGATGGTCAAC
CAGAAAGAATAAATACTGCAGATTATGTAGGAAATTATTTGTATGAAAATAATTCAAACA
GTACTATAGCTGAAAATGACAAAAATCATCTCTCCGAAAAACAAGATACTTATTTAAGTA
ACAGTAGCATGTCTAACAGCTATTCCTACCATTCTGATGAGGTATATAATGATTCAGGAT
ATCTCTCAAAAAATAAACTTGATTCTGGTATTGAGCCAGTATTGAAGAATGTTGAAGATC
AAAAAAACACTAGTTTTTCCAAAGTAATATCCAATGTAAAAGATGCAAATGCATACCCAC
AAACTGTAAATGAAGATATTTGCGTTGAGGAACTTGTGACTAGCTCTTCACCCTGCAAAA
ATAAAAATGCAGCCATTAAATTGTCCATATCTAATAGTAATAATTTTGAGGTAGGGCCAC
CTGCATTTAGGATAGCCAGTGGTAAAATCGTTTGTGTTTCACATGAAACAATTAAAAAAG
TGAAAGACATATTTACAGACAGTTTCAGTAAAGTAATTAAGGAAAACAACGAGAATAAAT
CAAAAATTTGCCAAACGAAAATTATGGCAGGTTGTTACGAGGCATTGGATGATTCAGAGG
ATATTCTTCATAACTCTCTAGATAATGATGAATGTAGCACGCATTCACATAAGGTTTTTG
CTGACATTCAGAGTGAAGAAATTTTACAACATAACCAAAATATGTCTGGATTGGAGAAAG
TTTCTAAAATATCACCTTGTGATGTTAGTTTGGAAACTTCAGATATATGTAAATGTAGTA
TAGGGAAGCTTCATAAGTCAGTCTCATCTGCAAATACTTGTGGGATTTTTAGCACAGCAA
GTGGAAAATCTGTCCAGGTATCAGATGCTTCATTACAAAACGCAAGACAAGTGTTTTCTG
AAATAGAAGATAGTACCAAGCAAGTCTTTTCCAAAGTATTGTTTAAAAGTAACGAACATT
CAGACCAGCTCACAAGAGAAGAAAATACTGCTATACGTACTCCAGAACATTTAATATCCC
AAAAAGGCTTTTCATATAATGTGGTAAATTCATCTGCTTTCTCTGGATTTAGTACAGCAA
GTGGAAAGCAAGTTTCCATTTTAGAAAGTTCCTTACACAAAGTTAAGGGAGTGTTAGAGG
AATTTGATTTAATCAGAACTGAGCATAGTCTTCACTATTCACCTACGTCTAGACAAAATG
TATCAAAAATACTTCCTCGTGTTGATAAGAGAAACCCAGAGCACTGTGTAAACTCAGAAA
TGGAAAAAACCTGCAGTAAAGAATTTAAATTATCAAATAACTTAAATGTTGAAGGTGGTT
CTTCAGAAAATAATCACTCTATTAAAGTTTCTCCATATCTCTCTCAATTTCAACAAGACA
AACAACAGTTGGTATTAGGAACCAAAGTCTCACTTGTTGAGAACATTCATGTTTTGGGAA
AAGAACAGGCTTCACCTAAAAACGTAAAAATGGAAATTGGTAAAACTGAAACTTTTTCTG
ATGTTCCTGTGAAAACAAATATAGAAGTTTGTTCTACTTACTCCAAAGATTCAGAAAACT

Fig. 4C

ACTTTGAAACAGAAGCAGTAGAAATTGCTAAAGCTTTTATGGAAGATGATGAACTGACAG

ATTCTAAACTGCCAAGTCATGCCACACATTCTCTTTTTACATGTCCCGAAAATGAGGAAA

TGGTTTTGTCAAATTCAAGAATTGGAAAAAGAAGAGGAGAGCCCCTTATCTTAGTGGGAG

AACCCTCAATCAAAAGAAACTTATTAAATGAATTTGACAGGATAATAGAAAATCAAGAAA

AATCCTTAAAGGCTTCAAAAAGCACTCCAGATGGCACAATAAAAGATCGAAGATTGTTTG

TGCATCATGTTTCTTTAGAGCCGATTACCTGTGTACCCTTTCGCACAACTAAGGAACGTC

AAGAGATACAGAATCCAAATTTTACCGCACCTGGTCAAGAATTTCTGTCTAAATCTCATT

TGTATGAACATCTGACTTTGGAAAAATCTTCAAGCAATTTAGCAGTTTCAGGACATCCAT

TTTATCAAGTTTCTGGTAACAAGAATGGAAAAATGAGAAAATTGATTACTACAGGCAGAC

CAACCAAAGTCTTTGTTCCACCTTTTAAAACTAAATCACATTTTCACAGAGTTGAACAGT

GTGTTAGGAATATTAACTTGGAGGGAAACAGACAAAAGCAAAACATTGATGGACATGGCT

CTGATGATAGTAAAAATAAGATTAATGACAATGAGATTCATCAGTTTAACAAAAACAACT

CCAATCAAGCAGCAGCTGTAACTTTCACAAAGTGTGAAGAAGAACCTTTAGATTTAATTA

CAAGTCTTCAGAATGCCAGAGATATACAGGATATGCGAATTAAGAAGAAACAAAGGCAAC

GCGTCTTTCCACAGCCAGGCAGTCTGTATCTTGCAAAAACATCCACTCTGCCTCGAATCT

CTCTGAAAGCAGCAGTAGGAGGCCAAGTTCCCTCTGCGTGTTCTCATAAACAGCTGTATA

CGTATGGCGTTTCTAAACATTGCATAAAAATTAACAGCAAAAATGCAGAGTCTTTTCAGT

TTCACACTGAAGATTATTTTGGTAAGGAAAGTTTATGGACTGGAAAAGGAATACAGTTGG

CTGATGGTGGATGGCTCATACCCTCCAATGATGGAAAGGCTGGAAAAGAAGAATTTTATA

GGGCTCTGTGTGACGTAAAGGCCACATAGTGGATAAACCATGTGCCACTTGAGGAATTGA

GAAAAAGTCAGTGTGTTTAGAACATAAGGAGAGGGGCAGAGAAATGGATCTGGTACAGGA

GAATCAATGAGACCGGGTAAGAAACAGAAAAGGGGCTGCACCAAATGATTGACACGCTCT

GCAAACTTCTTTTGTTGGCTCAAGTTGTGGCTCAAGAGGTGAGAAGGTAAGGCCAGACTT

ATTTGTTATGATTTGCCCTTTAAATTGAAGCCTTAAGATT

Fig. 4D

HisIleGlyLysSerMetProAsnValLeuGluAspGluValTyrGluThrValValAsp 20

ThrSerGluGluAspSerPheSerLeuCysPheSerLysCysArgThrLysAsnLeuGln 40

LysValArgThrSerLysThrArgLysLysIlePheHisGluAlaAsnAlaAspGluCys 60

GluLysSerLysAsnGlnValLysGluLysTyrSerPheValSerGluValGluProAsn 80

AspThrAspProLeuAspSerAsnValAlaAsnGlnLysProPheGluSerGlySerAsp 100

LysIleSerLysGluValValProSerLeuAlaCysGluTrpSerGlnLeuThrLeuSer 120

GlyLeuAsnGlyAlaGlnMetGluLysIleProLeuLeuHisIleSerSerCysAspGln 140

AsnIleSerGluLysAspLeuLeuAspThrGluAsnLysArgLysLysAspPheLeuThr 160

SerGluAsnSerLeuProArgIleSerSerLeuProLysSerGluLysProLeuAsnGlu 180

GluThrValValAsnLysArgAspGluGluGlnHisLeuGluSerHisThrAspCysIle 200

LeuAlaValLysGlnAlaIleSerGlyThrSerProValAlaSerSerPheGlnGlyIle 220

LysLysSerIlePheArgIleArgGluSerProLysGluThrPheAsnAlaSerPheSer 240

GlyHisMetThrAspProAsnPheLysLysGluThrGluAlaSerGluSerGlyLeuGlu 260

IleHisThrValCysSerGlnLysGluAspSerLeuCysProAsnLeuIleAspAsnGly 280

SerTrpProAlaThrThrThrGlnAsnSerValAlaLeuLysAsnAlaGlyLeuIleSer 300

ThrLeuLysLysLysThrAsnLysPheIleTyrAlaIleHisAspGluThrSerTyrLys 320

GlyLysLysIleProLysAspGlnLysSerGluLeuIleAsnCysSerAlaGlnPheGlu 340

AlaAsnAlaPheGluAlaProLeuThrPheAlaAsnAlaAspSerGlyLeuLeuHisSer 360

SerValLysArgSerCysSerGlnAsnAspSerGluGluProThrLeuSerLeuThrSer 380

SerPheGlyThrIleLeuArgLysCysSerArgAsnGluThrCysSerAsnAsnThrVal 400

IleSerGlnAspLeuAspTyrLysGluAlaLysCysAsnLysGluLysLeuGlnLeuPhe 420

IleThrProGluAlaAspSerLeuSerCysLeuGlnGluGlyGlnCysGluAsnAspPro 440

LysSerLysLysValSerAspIleLysGluGluValLeuAlaAlaAlaCysHisProVal 460

GlnHisSerLysValGluTyrSerAspThrAspPheGlnSerGlnLysSerLeuLeuTyr 480

AspHisGluAsnAlaSerThrLeuIleLeuThrProThrSerLysAspValLeuSerAsn 500

LeuValMetIleSerArgGlyLysGluSerTyrLysMetSerAspLysLeuLysGlyAsn 520

AsnTyrGluSerAspValGluLeuThrLysAsnIleProMetGluLysAsnGlnAspVal 540

Fig. 5A

CysAlaLeuAsnGluAsnTyrLysAsnValGluLeuLeuProProGluLysTyrMetArg 560

ValAlaSerProSerArgLysValGlnPheAsnGlnAsnThrAsnLeuArgValIleGln 580

LysAsnGlnGluGluThrThrSerIleSerLysIleThrValAsnProAspSerGluGlu 600

LeuPheSerAspAsnGluAsnAsnPheValPheGlnValAlaAsnGluArgAsnAsnLeu 620

AlaLeuGlyAsnThrLysGluLeuHisGluThrAspLeuThrCysValAsnGluProIle 640

PheLysAsnSerThrMetValLeuTyrGlyAspThrGlyAspLysGlnAlaThrGlnVal 660

SerIleLysLysAspLeuValTyrValLeuAlaGluGluAsnLysAsnSerValLysGln 680

HisIleLysMetThrLeuGlyGlnAspLeuLysSerAspIleSerLeuAsnIleAspLys 700

IleProGluLysAsnAsnAspTyrMetAsnLysTrpAlaGlyLeuLeuGlyProIleSer 720

AsnHisSerPheGlyGlySerPheArgThrAlaSerAsnLysGluIleLysLeuSerGlu 740

HisAsnIleLysLysSerLysMetPhePheLysAspIleGluGluGlnTyrProThrSer 760

LeuAlaCysValGluIleValAsnThrLeuAlaLeuAspAsnGlnLysLysLeuSerLys 780

ProGlnSerIleAsnThrValSerAlaHisLeuGlnSerSerValValValSerAspCys 800

LysAsnSerHisIleThrProGlnMetLeuPheSerLysGlnAspPheAsnSerAsnHis 820

AsnLeuThrProSerGlnLysGluGlnIleThrGluLeuSerThrIleLeuGluAspSer 840

GlySerGlnPheGluPheThrGlnPheArgLysProSerTyrIleLeuGlnLysSerThr 860

PheGluValProGluAsnGlnMetThrIleLeuLysThrThrSerGluGluCysArgAsp 880

AlaAspLeuHisValIleMetAsnAlaProSerIleGlyGlnValAspSerSerLysGln 900

PheGluGlyThrValGluIleLysArgLysPheAlaGlyLeuLeuLysAsnAspCysAsn 920

LysSerAlaSerGlyTyrLeuThrAspGluAsnGluValGlyPheArgGlyPheTyrSer 940

AlaHisGlyThrLysLeuAsnValSerThrGluAlaLeuGlnLysAlaValLysLeuPhe 960

SerAspIleGluAsnIleSerGluGluThrSerAlaGluValHisProIleSerLeuSer 980

SerSerLysCysHisAspSerValValSerMetPheLysIleGluAsnHisAsnAspLys 1000

ThrValSerGluLysAsnAsnLysCysGlnLeuIleLeuGlnAsnAsnIleGluMetThr 1020

ThrGlyThrPheValGluGluIleThrGluAsnTyrLysArgAsnThrGluAsnGluAsp 1040

AsnLysTyrThrAlaAlaSerArgAsnSerHisAsnLeuGluPheAspGlySerAspSer 1060

SerLysAsnAspThrValCysIleHisLysAspGluThrAspLeuLeuPheThrAspGln 1080

Fig. 5B

HisAsnIleCysLeuLysLeuSerGlyGlnPheMetLysGluGlyAsnThrGlnIleLys 1100

GluAspLeuSerAspLeuThrPheLeuGluValAlaLysAlaGlnGluAlaCysHisGly 1120

AsnThrSerAsnLysGluGlnLeuThrAlaThrLysThrGluGlnAsnIleLysAspPhe 1140

GluThrSerAspThrPhePheGlnThrAlaSerGlyLysAsnIleSerValAlaLysGlu 1160

SerPheAsnLysIleValAsnPhePheAspGlnLysProGluGluLeuHisAsnPheSer 1180

LeuAsnSerGluLeuHisSerAspIleArgLysAsnLysMetAspIleLeuSerTyrGlu 1200

GluThrAspIleValLysHisLysIleLeuLysGluSerValProValGlyThrGlyAsn 1220

GlnLeuValThrPheGlnGlyGlnProGluArgAspGluLysIleLysGluProThrLeu 1240

LeuGlyPheHisThrAlaSerGlyLysLysValLysIleAlaLysGluSerLeuAspLys 1260

ValLysAsnLeuPheAspGluLysGluGlnGlyThrSerGluIleThrSerPheSerHis 1280

GlnTrpAlaLysThrLeuLysTyrArgGluAlaCysLysAspLeuGluLeuAlaCysGlu 1300

ThrIleGluIleThrAlaAlaProLysCysLysGluMetGlnAsnSerLeuAsnAsnAsp 1320

LysAsnLeuValSerIleGluThrValValProProLysLeuLeuSerAspAsnLeuCys 1340

ArgGlnThrGluAsnLeuLysThrSerLysSerIlePheLeuLysValLysValHisGlu 1360

AsnValGluLysGluThrAlaLysSerProAlaThrCysTyrThrAsnGlnSerProTyr 1380

SerValIleGluAsnSerAlaLeuAlaPheTyrThrSerCysSerArgLysThrSerVal 1400

SerGlnThrSerLeuLeuGluAlaLysLysTrpLeuArgGluGlyIlePheAspGlyGln 1420

ProGluArgIleAsnThrAlaAspTyrValGlyAsnTyrLeuTyrGluAsnAsnSerAsn 1440

SerThrIleAlaGluAsnAspLysAsnHisLeuSerGluLysGlnAspThrTyrLeuSer 1460

AsnSerSerMetSerAsnSerTyrSerTyrHisSerAspGluValTyrAsnAspSerGly 1480

TyrLeuSerLysAsnLysLeuAspSerGlyIleGluProValLeuLysAsnValGluAsp 1500

GlnLysAsnThrSerPheSerLysValIleSerAsnValLysAspAlaAsnAlaTyrPro 1520

GlnThrValAsnGluAspIleCysValGluGluLeuValThrSerSerSerProCysLys 1540

AsnLysAsnAlaAlaIleLysLeuSerIleSerAsnSerAsnAsnPheGluValGlyPro 1560

ProAlaPheArgIleAlaSerGlyLysIleValCysValSerHisGluThrIleLysLys 1580

ValLysAspIlePheThrAspSerPheSerLysValIleLysGluAsnAsnGluAsnLys 1600

SerLysIleCysGlnThrLysIleMetAlaGlyCysTyrGluAlaLeuAspAspSerGlu 1620

Fig. 5C

AspIleLeuHisAsnSerLeuAspAsnAspGluCysSerThrHisSerHisLysValPhe 1640
AlaAspIleGlnSerGluGluIleLeuGlnHisAsnGlnAsnMetSerGlyLeuGluLys 1660
ValSerLysIleSerProCysAspValSerLeuGluThrSerAspIleCysLysCysSer 1680
IleGlyLysLeuHisLysSerValSerSerAlaAsnThrCysGlyIlePheSerThrAla 1700
SerGlyLysSerValGlnValSerAspAlaSerLeuGlnAsnAlaArgGlnValPheSer 1720
GluIleGluAspSerThrLysGlnValPheSerLysValLeuPheLysSerAsnGluHis 1740
SerAspGlnLeuThrArgGluGluAsnThrAlaIleArgThrProGluHisLeuIleSer 1760
GlnLysGlyPheSerTyrAsnValValAsnSerSerAlaPheSerGlyPheSerThrAla 1780
SerGlyLysGlnValSerIleLeuGluSerSerLeuHisLysValLysGlyValLeuGlu 1800
GluPheAspLeuIleArgThrGluHisSerLeuHisTyrSerProThrSerArgGlnAsn 1820
ValSerLysIleLeuProArgValAspLysArgAsnProGluHisCysValAsnSerGlu 1840
MetGluLysThrCysSerLysGluPheLysLeuSerAsnAsnLeuAsnValGluGlyGly 1860
SerSerGluAsnAsnHisSerIleLysValSerProTyrLeuSerGlnPheGlnGlnAsp 1880
LysGlnGlnLeuValLeuGlyThrLysValSerLeuValGluAsnIleHisValLeuGly 1900
LysGluGlnAlaSerProLysAsnValLysMetGluIleGlyLysThrGluThrPheSer 1920
AspValProValLysThrAsnIleGluValCysSerThrTyrSerLysAspSerGluAsn 1940
TyrPheGluThrGluAlaValGluIleAlaLysAlaPheMetGluAspAspGluLeuThr 1960
AspSerLysLeuProSerHisAlaThrHisSerLeuPheThrCysProGluAsnGluGlu 1980
MetValLeuSerAsnSerArgIleGlyLysArgArgGlyGluProLeuIleLeuValGly 2000
GluProSerIleLysArgAsnLeuLeuAsnGluPheAspArgIleIleGluAsnGlnGlu 2020
LysSerLeuLysAlaSerLysSerThrProAspGlyThrIleLysAspArgArgLeuPhe 2040
ValHisHisValSerLeuGluProIleThrCysValProPheArgThrThrLysGluArg 2060
GlnGluIleGlnAsnProAsnPheThrAlaProGlyGlnGluPheLeuSerLysSerHis 2080
LeuTyrGluHisLeuThrLeuGluLysSerSerSerAsnLeuAlaValSerGlyHisPro 2100
PheTyrGlnValSerGlyAsnLysAsnGlyLysMetArgLysLeuIleThrThrGlyArg 2120
ProThrLysValPheValProProPheLysThrLysSerHisPheHisArgValGluGln 2140
CysValArgAsnIleAsnLeuGluGlyAsnArgGlnLysGlnAsnIleAspGlyHisGly 2160

Fig. 5D

Figure 5E:
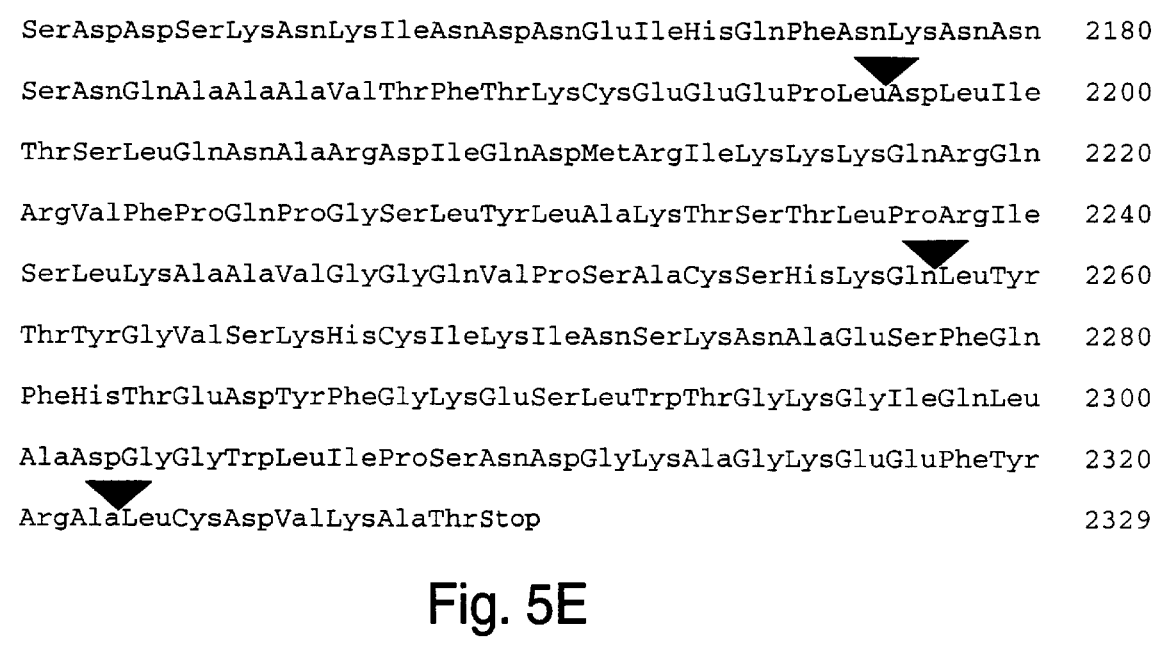

SerAspAspSerLysAsnLysIleAsnAspAsnGluIleHisGlnPheAsnLysAsnAsn 2180

SerAsnGlnAlaAlaAlaValThrPheThrLysCysGluGluGluProLeuAspLeuIle 2200

ThrSerLeuGlnAsnAlaArgAspIleGlnAspMetArgIleLysLysLysGlnArgGln 2220

ArgValPheProGlnProGlySerLeuTyrLeuAlaLysThrSerThrLeuProArgIle 2240

SerLeuLysAlaAlaValGlyGlyGlnValProSerAlaCysSerHisLysGlnLeuTyr 2260

ThrTyrGlyValSerLysHisCysIleLysIleAsnSerLysAsnAlaGluSerPheGln 2280

PheHisThrGluAspTyrPheGlyLysGluSerLeuTrpThrGlyLysGlyIleGlnLeu 2300

AlaAspGlyGlyTrpLeuIleProSerAsnAspGlyLysAlaGlyLysGluGluPheTyr 2320

ArgAlaLeuCysAspValLysAlaThrStop 2329

Fig. 5E gttgcttctgtttactgctcaagcaccttctggaagcagcaaggcccccatgggagcaactctcactgaatccatttgaaggttttgtaggtcttacaac aaaccctattcagccttgtattaggcatgttacagaaccaacgaattcggagatgaagtcaggtcttccagttcagcctgcgaggaagacaggtgatc
ACF cgaatcctaagaatgcaaaagatgggctgggtgtggtggctcatgcctgtaatcccagcgctttgggaggccgaggcaggcagatcacc tgaggt
Oct 1,OBP,NF-A URTF cgggaggttgagaccagactgaccaacaacggagaaaccccgtctctacttaaaaatgcaaagttagccgtgcgtggtggcccatgcctgtattcc
Oct1,OBP,NF-A cagctactcgggaggctgaggcaggagaaccacttgatccctggaggcggaagttgcggtgagcggagattgcgcca ttgcacaccagcccgg
Sp1 MREF gccacaagagcgaaactccgtctcaaaaaaaaaagcaaaagatactaccaagccctgcggagcaaggtacctcacacttcatgagcgagttaaga tgggtttcacaatttttcaagcaaggaaacgggctcggaggtcttgaacacctgctacccaatagcagaacagctactggaactaaaatcctctgattt caaataacagccccgcccactaccactaagtgaagtcatccacaaccacacaccgaccactctaagcttttgtaaga tcggctcgctttggggaaca
Sp1 START OF CpG ISLAND ggtcttgagagaacatcccttttaaggtcagaacaaaggtatttcataggtcccaggtcgtgtcccgagggcgcccacccaaacatgagctggagca
Sp1 aaaagaaagggatgggggacttggagtaggcataggggcggcccctccaagcagggtggcctgggactcttaagggtcagcgagaagagaac
Sp1 Sp1 acacactccaaatcccgctttattcggtcagatactgacggttgggatgcctgacaaggaatttcctttcgccacactgagaaatacccgcagcggcc
NFKB(like) HiNF-A cacccaggcctgacttccgggtggtgcgtgtgctgcgtgtcgcgtcacggcgtcacgtggccagcgcgggctt gtggcgcgagcgtctgaaacta
Sp1 START OF EXON 1 gcggcagagcggagccgctgtggcactctgcgcctctctgcgcctcgggtgtcttttcggcggtgggtcgccgccgggagaagcgtgaggggac agatttgtgaccggcgcggtttttgtcagcttactccggccaaaaaagaactgcgcctctggagcgggttagtggtggtggtagtgggttgggacga

Fig. 6A gcgcgtcttccgcagtcccagtccagcgtggcgggggagcgcctcacgccccgggtcgctgccgcggcttcttgcccttttgtctctgccaaccccc acccatgcctgagagaaaggtccttgcccgaaggcaaattttcgccaagcaaattcgagccccgccccttccctgggtctccatttcccgcctccgg Sp1 cccggcctttgggctccgccttcagctcaagacttaacttccctcccagctgtcccagatgacgccatctgaaatttcttggaaacacgatcactttaac Sp1 / RiPE3B LyF-1 IEF-1, LEF1 ggaatattgctgttttggggaagtgttttacagctgctgggcacgctgtatttgccttacttaagcccctggtaattgctgtattccgaagacatgctgatg ggaattaccaggcggcgttggtctctaaactgagccctctgtcccaactagccacgcgtcactggttagcg tgattgaaactaaatcgtatgaaaatc CP2 END OF CpG ISLAND ctcttctctagtcgcactagccacgtttcgagtgcttaatgtggctagtggcaccggtttggacagcacagctgtaaaatgttcccatcctcacagtaag

CP2 ctgttaccgttccaggagatgggactgaattagaattcaaacaaattttccagcgcttctgagttttacctcagtcacataataaggaatgcatccctgtg taagtgcattttggtcttctgttttgcagacttatttaccaagcattggaggaatatcgtaggtaaaaatgcctattggatccaaagagaggccaacatttt ttgaaatttttaagacacgctgcaacaaagcaggtattgac Putative *BRCA2* promoter region. Potential binding sites for various transcription factors are underlined. CpG are emboldened.

Fig. 6B

The exon/intron structure of the BRCA2 gene.

The exon/intron structure of the BRCA2 was defined by comparing the BRCA2 cDNA sequence with the genomic sequence of chromosome 13q between D13S260 and D13S171. This figure contains all of the exons(UPPER CASE) of the BRCA2 gene flanked by intron sequences (lower case). The amino acid sequence is shown below the open reading frame from exon 2 to 26 the genomic sequence available from:
ftp://sanger.ac.uk/pub/human/sequences/13q
and ftp://genome.wustl.edu/pub/gsc1/brca2
and is present in the Pacs 214k23 and 92m18

| Exon | 1 | 2 | 3 | 4 | 5 | 6 | 7 | 8 | 9 |
|---|---|---|---|---|---|---|---|---|---|
| Size | 188 | 106 | 249 | 109 | 50 | 41 | 115 | 50 | 112 |

| Exon | 10 | 11 | 12 | 13 | 14 | 15 | 16 | 17 | 18 |
|---|---|---|---|---|---|---|---|---|---|
| Size | 1116 | 4932 | 96 | 70 | 428 | 166 | 204 | 171 | 355 |

| Exon | 19 | 20 | 21 | 22 | 23 | 24 | 25 | 26 | 27 |
|---|---|---|---|---|---|---|---|---|---|
| Size | 156 | 145 | 122 | 199 | 164 | 139 | 245 | 147 | 606 |

NB there is 67bp of coding sequence in exon 2

Exon 1

```
................................agggggggnccccccttcccaaaagnaag
ggtggcccttggnaacntcctnaaaggntcaangcnaantaaagaaagaaacacnaacaa
ctcccaaatccccgctttaattcggtcaagaatactaacggttgggaatgccttgaacaa
aggaaatttcctttcgccaacactgagaaaatacccgcaagcgcccnacccnaggcctga
cttccgggtggtgcgtgtgctgcgtgtcgcgtcacggcgtcacgtggccagcgcgggctt
GTGGCGCGAGCTTCTGAAACTAGGCGGCAGAGGCGGAGCCGCTGTGGCACTGCTGCGCCT
CTGCTGCGCCTCGGGTGTCTTTTGCGGCGGTGGGTCGCCGCCGGGAGAAGCGTGAGGGGA
CAGATTTGTGACCGGCGCGGTTTTTGTCAGCTTACTCCGGCCAAAAAAGAACTGCGCCTC
TGGAGCGGgttagtggtggtggtagtgggttgggacgagcgcgtcttccgcagtcccagt
ccagcgtggcgggggagcgcctcacgccccgggtcgctgccgcggcttcttgccctttttg
tctctgccaacccccacccatgcctgagagaaaggtccttgcccgaaggcaaattttcgc
caagcaaattcgagccccgccccttccctgggtctccatttcccgcctccggcccggcct
ttgggctccgccttcagctcaagacttaacttccctcccagctgtcccagatgacgccat
ctgaaatttcttggaaacacgatcactttaacggaatattgctgttttggggaagtgttt
tacagctgctgggcacgctgtatttgccttacttaagcccctggtaattgctgtattccg
aagacatgctgatgggaattaccaggcggcgttggtctctaaactgagccctctgtccca
actagctacgcgtcactggttagcgtga................................
```

Exon 2

```
.gacttaacttccctcccagctgtcccagatgacgccatctgaaatttcttggaaacacg
atcactttaacggaatattgctgttttggggaagtgttttacagctgctgggcacgctgt
atttgccttacttaagcccctggtaattgctgtattccgaagacatgctgatgggaatta
ccaggcggcgttggtctctaaactgagccctctgtcccaactagctacgcgtcactggtt
agcgtgattgaaactaaatcgtatgaaaatcctcttctctagtcgcactagccacgtttc
gagtgcttaatgtggctagtggcaccggtttggacagcacagctgtaaaatgttcccatc
ctcacagtaagctgttaccgttccaggagatgggactgaattagaattcaaacaaatttt
ccagcgcttctgagttttacctcagtcacataataaggaatgcatccctgtgtaagtgca
ttttggtcttctgttttgcagACTTATTTACCAAGCATTGGAGGAATATCGTAGGTAAAA

ATGCCTATTGGATCCAAAGAGAGGCCAACATTTTTTGAAATTTTTAAGACACGCTGCAAC
M  P  I  G  S  K  E  R  P  T  F  F  E  I  F  K  T  R  C  N      20
```

Fig.7A

```
AAAGCAGgtattgacaaattttatataactttataaattacaccgagaaagtgttttcta
K  A  D                                                          23

aaaaatgcttgctaaaaacccagtacgtcacagtgttgcttagaaccataaactgttcct
tatgtgtgtataaatccagttaacaacataatcatcgtttgcaggttaaccacatgataa
atatagaacgtctagtggataaagaggaaactggccccttgactagcagtaggtaacaat
tactaacaaatcagaagcattaatgttactttatggcagaagttgtccaacttttttggtt
tcagtactccttatactcttaaaaatgatctaggacccccggagtgcttttgtttatgta
gcttaccatattagaaatttaaaactaagaatttaaggctgggcgtggtggctcacgcct
gtaatcccagcactttgggaggcccgaggtgggcggatcacttgaggccagaagtttgag
accagcctggccaacatggtgaaaccc.................................

Exon 3
.......................................gactacaggcgtgtgccacc
acgcttggctaatttttgtgtttttagtaaagatggggtttcaacgtgttagcaaggtt
ggtctcgatctgacctcgtgatctgctcgcctcagcctcccaaagtgttgggattacagg
cgtgagccccccgcacctggccgaattttatcgtggaatgtattcttaatgtgaatagttt
ttgattccgaaccatgaataataagaaaataaataaaatttaaatgaaaataaaagctaa
tatatacagcttttaataatatagttaaatgccatcttgtaactttgtgaactcttgtt
acacctttctatagattcgcaagagaatggattaatgatcttgtttaattaatatgcctt
aacaaaagtaatccatagtcaagatcttaagcatttttttccttatgatctttaactgtt
ctgggtcacaaatttgtctgtcactggttaaaactaaggtgggattttttttttaaatag

ATTTAGGACCAATAAGTCTTAATTGGTTTGAAGAACTTTCTTCAGAAGCTCCACCCTATA
  L  G  P  I  S  L  N  W  F  E  E  L  S  S  E  A  P  P  Y  N     43

ATTCTGAACCTGCAGAAGAATCTGAACATAAAAACAACAATTACGAACCAAACCTATTTA
  S  E  P  A  E  E  S  E  H  K  N  N  N  Y  E  P  N  L  F  K     63

AAACTCCACAAAGGAAACCATCTTATAATCAGCTGGCTTCAACTCCAATAATATTCAAAG
  T  P  Q  R  K  P  S  Y  N  Q  L  A  S  T  P  I  I  F  K  E     83

AGCAAGGGCTGACTCTGCCGCTGTACCAATCTCCTGTAAAAGAATTAGATAAATTCAAAT
  Q  G  L  T  L  P  L  Y  Q  S  P  V  K  E  L  D  K  F  K  L    103

TAGACTTAGgtaagtaatgcaatatggtagactggggagaactacaaactaggaatttag
  D  L  G                                                       106

gcaaacctgtgttaaaatcttagctcattcattaattgtgtcatgctgggcaaatcagtc
tctctggcctctttttcctcactcgaaaaatggagacgatgaaaataatgtctcataggt
ttggattaaattaaataatgtaggtacttagtaaatgttctctttcatccctcctttgat
aaatttgccaactgagatttgctgaattacgtctttcttatgccaaaaaaacctaggact
tgttttgatgttaattaaactaaactatatttctgcaagctatcacagaggacagagatt
atttaccgatatactataagtatcatgatttggaaggagtttccctggcgtaggtgccg
catgtttctaagcaattatgtaataagattatatattcagtcattcaaataattattacc
tacttgacataagtaatgaactttccctt...............................

Exon 4
...............tcctttttaggggggtaatcagcaaactgaaaaacctcttcttaca
actccctatacattctcattcccagtatagaggagacttttttgtttttaaacacttccaa
agaatgcaaatttataatccagagtatatacattctcactgaattattgtactgtttcag

GAAGGAATGTTCCCAATAGTAGACATAAAAGTCTTCGCACAGTGAAAACTAAAATGGATC
  R  N  V  P  N  S  R  H  K  S  L  R  T  V  K  T  K  M  D  Q    126

AAGCAGATGATGTTTCCTGTCCACTTCTAAATTCTTGTCTTAGTGAAAGgtatgatgaag
  A  D  D  V  S  C  P  L  L  N  S  C  L  S  E  S                142

ctattatattaaaatatttaaatgaaacattttcctacatatatttgttctataaagatg
aatctgattttttatgctaatattttggctaagagcctggtagaagatcttacatttttaa
ataatcttttaggttgagtcctttaatagaatagtttttacattagaaacatgtaagttg
ttgttcttgtgatgttgaattggctggtttctgtatattctgtgatttttaagtaaca
```

Fig.7B

```
aaaataacagtggtgaaaagcagtaagtcagtccttgaattatcaatttaaaataaattg
tgtacttttcatctttggagagaatatgatttactttacaaatttttttttgttttttt
ttttttgagatggagtctctgtcacccaggctgtagtgcagtggtgcgatctcagctca
ctgcaagctccgcctcccgggttcacgccattctcctgcctcagcctcccaagtagctgg
gactacagg...................................................
```

Exon 5

```
.......................................tgcgatctcagctcactgca
agctccgcctcccgggttcacgccattctcctgcctcagcctcccaagtagctgggacta
caggcgcccgccaccatgcccggctaatttttgtatttttagtagagacggggtttcac
tgtgttagctaggatggtctcgatttcctgacctcgtgatccgcccgcctcagcctccca
gactgctgggattacaggcgtgaaccactgtgcccggcctactttacaaaatttttgagt
ttaaaatacacggtttccagcagctgaaatttgtgagtacatatgtgttggcattttaaa
catcacttgatgattatttaatgcttcatgagagatttacttttaaaatgtaatataaa
atatctaaaagtagtattccaacaatttatatgaatgagaatcttcttttaaaaataaga
taaactagtttttgccagtttttaaaataacctaagggatttgctttgttttattttag

TCCTGTTGTTCTACAATGTACACATGTAACACCACAAAGAGATAAGTCAGgtatgattaa
 P  V  V  L  Q  C  T  H  V  T  P  Q  R  D  K  S  V              159

aaacaatgctttttattcttagaatactagaaatgttaataaaaataaaacttaacaatt
ttccccttttttacccccagtggtatgtgggagtttgtttcatacaccaaagtttgtga
aggtaaatattctacctggtttatttttatgacttagtaattgagaatttgacaatagcg
ttatacctttgccctgagatttacaaatctgtacctagcattctgcctcatacaggcaat
tcagtaaacgttaagtgaaataaagagtgaatgaaaaaataatatccttaatgatcaggg
catttctataaaaaataaactattttctttcctcccagggtcgtcagacaccaaaacata
tttctgaaagtctaggagctgaggtggatcctgatatgtcttggtcaagttctttagcta
caccacccacccttagttctactgtgctcataggtaataatagcaaatgtgtatttacaa
gaaagagcag..................................................
```

Exon 6

```
.......................................gtgttagctaggatggtctc
gatttcctgacctcgtgatccgcccgcctcagcctcccagactgctgggattacaggcgt
gaaccactgtgcccggcctactttacaaaatttttgagtttaaaatacacggtttccagc
agctgaaatttgtgagtacatatgtgttggcatttaaacatcacttgatgattatttaa
tgcttcatgagagatttacttttaaaatgtaatataaaatatctaaaagtagtattcca
acaatttatatgaatgagaatcttcttttaaaaataagataaactagtttttgccagttt
tttaaaataacctaagggatttgctttgttttattttagtcctgttgttctacaatgtac
acatgtaacaccacaaagagataagtcaggtatgattaaaaacaatgctttttattctta
gaatactagaaatgttaataaaaataaaacttaacaattttccccttttttacccccag

TGGTATGTGGGAGTTTGTTTCATACACCAAAGTTTGTGAAGgtaaatattctacctggtt
  V  C  G  S  L  F  H  T  P  K  F  V  K                         172

tatttttatgacttagtaattgagaatttgacaatagcgttatacctttgccctgagatt
tacaaatctgtacctagcattctgcctcatacaggcaattcagtaaacgttaagtgaaat
aaagagtgaatgaaaaaataatatccttaatgatcagggcatttctataaaaaataaact
attttctttcctcccagggtcgtcagacaccaaaacatatttctgaaagtctaggagctg
aggtggatcctgatatgtcttggtcaagttctttagctacaccacccacccttagttcta
ctgtgctcataggtaataatagcaaatgtgtatttacaagaaagagcagatgaggttgat
aattgtcatctctaatacttctgttaaaaggaaatatgaaaagaaaatattagataatgt
ctttgataagtgtgttagtaactgacaataattttattctattaagtgtagattggaata
a...........................................................
```

Exon 7

```
.......................................ccaacaatttatatgaatga
gaatcttcttttaaaaataagataaactagtttttgccagtttttaaaataacctaagg
gatttgctttgttttattttagtcctgttgttctacaatgtacacatgtaacaccacaaa
gagataagtcaggtatgattaaaaacaatgctttttattcttagaatactagaaatgtta
ataaaaataaaacttaacaattttccccttttttacccccagtggtatgtgggagtttg
tttcatacaccaaagtttgtgaaggtaaatattctacctggtttatttttatgacttagt
aattgagaatttgacaatagcgttatacctttgccctgagatttacaaatctgtacctag
```

Fig.7C

```
cattctgcctcatacaggcaattcagtaaacgttaagtgaaataaagagtgaatgaaaaa
ataatatccttaatgatcagggcatttctataaaaaataaactatttctttcctcccag

GGTCGTCAGACACCAAAACATATTTCTGAAAGTCTAGGAGCTGAGGTGGATCCTGATATG
G  R  Q  T  P  K  H  I  S  E  S  L  G  A  E  V  D  P  D  M      192

TCTTGGTCAAGTTCTTTAGCTACACCACCCACCCTTAGTTCTACTGTGCTCATAGgtaat
S  W  S  S  S  L  A  T  P  P  T  L  S  S  T  V  L  I  V        211

aatagcaaatgtgtatttacaagaaagagcagatgaggttgataattgtcatctctaata
cttctgttaaaaggaaatatgaaaagaaaatattagataatgtctttgataagtgtgtta
gtaactgacaataattttattctattaagtgtagattggaataaatacaaatacatttag
tggtagtccagtggtgtcaagcattatgttttagtacgatgtgattaacgtagaatagct
tacaaatattcctttactggcctatataagcgtttaagaggcagtatttggtgtgactga
attctttttacaaatgattgtggtaattggggcattaaagcagc................
```

Exon 8

```
.......................................accagtattacattttgttt
attctagcaaaatagcattctgttttgattcctctttagctgggagtaagttaaccctat
tctgttgcttagatgaaataatatggataaaatcattttgaaaatatgtatttaatatat
agtatgcctttaggctgtagtgttgtctaaatgaatgctaaagtctccaagctttagctt
ttaagtcataacctcacagcatcatctgactttccaactcattgtggacagtattaccat
aaagtaatgatcaccaagccatatcttaccaccttgtgagtagtactaaggaagtaagta
tagtttattcactgtgttgattgacctttctaattactatacttaagtacttgaatcaat
tcattttgtttcaaatgtgtcatgtaatcaaatagtagatgtgctttttgatgtctgaca
aaaaataagtttttgcattctagtgataatatacaatacacataaatttttatcttacag

TCAGAAATGAAGAAGCATCTGAAACTGTATTTCCTCATGATACTACTGCTgtaagtaaat
  R  N  E  E  A  S  E  T  V  F  P  H  D  T  T  A               227

atgacattgattagactgttgaaattgctaacaattttggaatgccttgttaaattattt
atcttacattttttaatttcctaatctgtaatttatctaagcctttgagaaagtctctaaa
cctggtcctatatgtgatttaacttcctgtgaaactctgctgtctctctgttaaagttg
catatatacaatatataccgtagtcccctattcatggggtatacattccaatatcccca
gtgaatgcttgaaaccttagatagtaccgaaccctatatatatatattaaaaatgtgtag
tatttatatatatatatacctataatctttttttctataagcacataccctgtgataaag
tttaattcataaattaggcacagtaagagattaacaagaactaataataaaataggacaa
ttataacaaaataccgtaataaaagttatgtgaatgttgtctctctgtctcaaaatatct
tattgttctg..................................................
```

Exon 9

```
.......................................gcactttatggcttctttt
ggcatatttgaattgccagcatcattatacttgtgctttggggccattgttaagtaaaat
aagggtgacttgaacacaagcactgtggtaccacaatagccgatctgataaccaagacaa
ctactaagtgactaataggtgggtaccatatacagcctggatacgctggacaaagggatg
attcatgtcccaagtgggatggagcaagatggtgcaagtttttttttctccatttccatt
ttcctttcctaagatttccacatcctagtggtgcaagatttcatcacactactcaggatg
acacacaatttaaaacttactaattgcttacttctggaattttccattaaaaatttttgg
acctaggttgattgcagataactgaaatcaccaaaagtgaaaccatggataagggggggac
tactactatatgtgcattgagagtttttatactagtgattttaaactataatttttgcag

AATGTGAAAAGCTATTTTTCCAATCATGATGAAAGTCTGAAGAAAAATGATAGATTTATC
N  V  K  S  Y  F  S  N  H  D  E  S  L  K  K  N  D  R  F  I      247

GCTTCTGTGACAGACAGTGAAAACACAAATCAAAGAGAAGCTGCAAGTCATGgtaagtcc
A  S  V  T  D  S  E  N  T  N  Q  R  E  A  A  S  H  G            265

tctgtttagttgaactacaggtttttttgttgttgttgttttgatttttttttttttgagg
tggagtcttgctctgtcacccgtgatctcagtttaccgcaacctctgcctcccgtgctca
agcgatcctgcctcagcttgccaagtagctgagattacaagcatgcaccaccatgcccaa
ctattgtatttttagtagagatggcatttcaccatgttggccaggctggtctcaaatggt
```

Fig.7D

```
cgtgagccaccatgcccagcctgaactactctttttaattggcaccattgaaggattgct
cctcttttcttaaagagaaaatatattacctttcctttcttgactactgaagtagtattt
tatctcaaagtattgagagtagaaactaacttggtgtgcctgtgatcccagctactcagg
aggctgaggtgggaggatcgcttaagcccaggcggtcaaggttgcagtgagctgtgtgtg
tgccactgcact................................................

Exon 10
................................................tttttgtctg
tgtggtatcatgtacgtatgtatatgcatatgtaaaatcagatttacccttgttataggg
ccacagaattgatttggaacatctgttttgataggtcttagaatatttaattgtatatat
agtaagattaggtgagttttaattgtgtagaactgctaaagaaaggtttttagggattgt
tgtatgaataaaaggctttaggttcattggaatcaggggaatcaggctttactagaagaa
caggagaaggggtgactgaccgaaaaataaaatgccaagtactcagaataaccctttaaa
tactgatatgtaatatttagcacattctacataaactgtttctatgagaaaggttgtgag
aataatataaattatatggcttataaaatattaatgtgcttctgttttatactttaacag

GATTTGGAAAAACATCAGGGAATTCATTTAAAGTAAATAGCTGCAAAGACCACATTGGAA
 F  G  K  T  S  G  N  S  F  K  V  N  S  C  K  D  H  I  G  K     285

AGTCAATGCCAAATGTCCTAGAAGATGAAGTATATGAAACAGTTGTAGATACCTCTGAAG
 S  M  P  N  V  L  E  D  E  V  Y  E  T  V  V  D  T  S  E  E     305

AAGATAGTTTTTCATTATGTTTTTCTAAATGTAGAACAAAAAATCTACAAAAAGTAAGAA
 D  S  F  S  L  C  F  S  K  C  R  T  K  N  L  Q  K  V  R  T     325

CTAGCAAGACTAGGAAAAAAATTTTCCATGAAGCAAACGCTGATGAATGTGAAAAATCTA
 S  K  T  R  K  K  I  F  H  E  A  N  A  D  E  C  E  K  S  K     345

AAAACCAAGTGAAAGAAAAATACTCATTTGTATCTGAAGTGGAACCAAATGATACTGATC
 N  Q  V  K  E  K  Y  S  F  V  S  E  V  E  P  N  D  T  D  P     365

CATTAGATTCAAATGTAGCACATCAGAAGCCCTTTGAGAGTGGAAGTGACAAAATCTCCA
 L  D  S  N  V  A  H  Q  K  P  F  E  S  G  S  D  K  I  S  K     385

AGGAAGTTGTACCGTCTTTGGCCTGTGAATGGTCTCAACTAACCCTTTCAGGTCTAAATG
 E  V  V  P  S  L  A  C  E  W  S  Q  L  T  L  S  G  L  N  G     405

GAGCCCAGATGGAGAAAATACCCCTATTGCATATTTCTTCATGTGACCAAAATATTTCAG
 A  Q  M  E  K  I  P  L  L  H  I  S  S  C  D  Q  N  I  S  E     425

AAAAAGACCTATTAGACACAGAGAACAAAAGAAAGAAAGATTTTCTTACTTCAGAGAATT
 K  D  L  L  D  T  E  N  K  R  K  K  D  F  L  T  S  E  N  S     445

CTTTGCCACGTATTTCTAGCCTACCAAAATCAGAGAAGCCATTAAATGAGGAAACAGTGG
 L  P  R  I  S  S  L  P  K  S  E  K  P  L  N  E  E  T  V  V     465

TAAATAAGAGAGATGAAGAGCAGCATCTTGAATCTCATACAGACTGCATTCTTGCAGTAA
 N  K  R  D  E  E  Q  H  L  E  S  H  T  D  C  I  L  A  V  K     485

AGCAGGCAATATCTGGAACTTCTCCAGTGGCTTCTTCATTTCAGGGTATCAAAAAGTCTA
 Q  A  I  S  G  T  S  P  V  A  S  S  F  Q  G  I  K  K  S  I     505

TATTCAGAATAAGAGAATCACCTAAAGAGACTTTCAATGCAAGTTTTTCAGGTCATATGA
 F  R  I  R  E  S  P  K  E  T  F  N  A  S  F  S  G  H  M  T     525

CTGATCCAAACTTTAAAAAAGAAACTGAAGCCTCTGAAAGTGGACTGGAAATACATACTG
 D  P  N  F  K  K  E  T  E  A  S  E  S  G  L  E  I  H  T  V     545

TTTGCTCACAGAAGGAGGACTCCTTATGTCCAAATTTAATTGATAATGGAAGCTGGCCAG
 C  S  Q  K  E  D  S  L  C  P  N  L  I  D  N  G  S  W  P  A     565
CCACCACCACACAGAATTCTGTAGCTTTGAAGAATGCAGGTTTAATATCCACTTTGAAAA
 T  T  T  Q  N  S  V  A  L  K  N  A  G  L  I  S  T  L  K  K     585

AGAAAACAAATAAGTTTATTTATGCTATACATGATGAAACATCTTATAAAGGAAAAAAAA
```

```
  K  T  N  K  F  I  Y  A  I  H  D  E  T  F  Y  K  G  K  K  I     605

TACCGAAAGACCAAAAATCAGAACTAATTAACTGTTCAGCCCAGTTTGAAGCAAATGCTT
  P  K  D  Q  K  S  E  L  I  N  C  S  A  Q  F  E  A  N  A  F     625

TTGAAGCACCACTTACATTTGCAAATGCTGATTCAGgtacctctgtcttttttttttgt
  E  A  P  L  T  F  A  N  A  D  S  G                             637

aaatagtacatatagttttatagatgacgattccttctgtgtttttttctgctttttaaa
atcttcatatcttatatttaatcttaggcatcatctgtatacatgattgtttaggtcttt
aattaccagtgtttagaatcaggtcactcaaacatggtagataagtttgcatagtttgtg
tatatccatcactcttgagacagttttattttaagttccggggtacatgtgcaggatgtg
caggtttgttacataagtaaacgtatgccatgttggtttgctgcacctgtcaacccttca
cctgagtattaagcccagcatgcattagctatttttcctggtgctctccttccccccaca
caccccccacctcctgacagaccctagtgtgtgttgttcccctccctgtgtccgtgtgttc
tcattgttcagctcccacttatgagtgagaacatgt.......................
```

Exon 11

```
ctgaaaaatagagcatatttaggattctttctgctttaaatttgacattcagttattttc
atgtaatttgtgttttgagcactaccttttaattaatttatttatttttatttttttagag
actgtctcattctgttacctagtctggagtgcactagtgtgatctcagctcaccgtagcc
tcaccctcctgggctcaagcagtccttgcacctcaccctcctgagtaactggcaccacag
gcatacaccaccacacccagctaatttttatttttcatagagtcatggtctcactatgtt
gcccaggctagtctcgaactcctgggctcaagcagtcttcctgcctcagcctcccaaaag
tgctgagattacaggcatgagccactgtgcccaaacactaccttttttaacttagtgaaaa
atatttagtgaatgtgattgatggtactttaatttttgtcactttgtgtttttatgtttag

GTTTATTGCATTCTTCTGTGAAAAGAAGCTGTTCACAGAATGATTCTGAAGAACCAACTT
  L  L  H  S  S  V  K  R  S  C  S  Q  N  D  S  E  E  P  T  L     657

TGTCCTTAACTAGCTCTTTTGGGACAATTCTGAGGAAATGTTCTAGAAATGAAACATGTT
  S  L  T  S  S  F  G  T  I  L  R  K  C  S  R  N  E  T  C  S     677

CTAATAATACAGTAATCTCTCAGGATCTTGATTATAAAGAAGCAAAATGTAATAAGGAAA
  N  N  T  V  I  S  Q  D  L  D  Y  K  E  A  K  C  N  K  E  K     697

AACTACAGTTATTTATTACCCCAGAAGCTGATTCTCTGTCATGCCTGCAGGAAGGACAGT
  L  Q  L  F  I  T  P  E  A  D  S  L  S  C  L  Q  E  G  Q  C     717

GTGRAAATGATCCAAAAAGCAAAAAAGTTTCAGATATAAAAGAAGAGGTCTTGGCTGCAG
  E  N  D  P  K  S  K  K  V  S  D  I  K  E  E  V  L  A  A  A     737

CATGTCACCCAGTACAACATTCAAAAGTGGAATACAGTGATACTGACTTTCAATCCCAGA
  C  H  P  V  Q  H  S  K  V  E  Y  S  D  T  D  F  Q  S  Q  K     757

AAAATCTTTTATATGATCATGAAAATGCCAGCACTCTTATTTTAACTCCTACTTCCAAGG
  S  L  L  Y  D  H  E  N  A  S  T  L  I  L  T  P  T  S  K  D     777

ATGTTCTGTCAAACCTAGTCATGATTTCTAGAGGCAAAGAATCATACAAAATGTCAGACA
  V  L  S  N  L  V  M  I  S  R  G  K  E  S  Y  K  M  S  D  K     797

AGCTCAAAGGTAACAATTATGAATCTGATGTTGAATTAACCAAAAATATTCCCATGGAAA
  L  K  G  N  N  Y  E  S  D  V  E  L  T  K  N  I  P  M  E  K     817

AGAATCAAGATGTATGTGCTTTAAATGAAAATTATAAAAACGTTGAGCTGTTGCCACCTG
  N  Q  D  V  C  A  L  N  E  N  Y  K  N  V  E  L  L  P  P  E     837

AAAAATACATGAGAGTAGCATCACCTTCAAGAAAGGTACAATTCAACCAAAACACAAATC
  K  Y  M  R  V  A  S  P  S  R  K  V  Q  F  N  Q  N  T  N  L     857

TAAGAGTAATCCAAAAAAATCAAGAAGAAACTACTTCAATTTCAAAAATAACTGTCAATC
  R  V  I  Q  K  N  Q  E  E  T  T  S  I  S  K  I  T  V  N  P     877
```

Fig.7F

CAGACTCTGAAGAACTTTTCTCAGACAATGAGAATAATTTTGTCTTCCAAGTAGCTAATG
D S E E L F S D N E N N F V F Q V A N E 897

AAAGGAATAATCTTGCTTTAGGAAATACTAAGGAACTTCATGAAACAGACTTGACTTGTG
R N N L A L G N T K E L H E T D L T C V 917

TAAACGAACCCATTTTCAAGAACTCTACCATGGTTTTATATGGAGACACAGGTGATAAAC
N E P I F K N S T M V L Y G D T G D K Q 937

AAGCAACCCAAGTGTCAATTAAAAAAGATTTGGTTTATGTTCTTGCAGAGGAGAACAAAA
A T Q V S I K K D L V Y V L A E E N K N 957

ATAGTGTAAAGCAGCATATAAAAATGACTCTAGGTCAAGATTTAAAATCGGACATCTCCT
S V K Q H I K M T L G Q D L K S D I S L 977

TGAATATAGATAAAATACCAGAAAAAAATAATGATTACATGAACAAATGGGCAGGACTCT
N I D K I P E K N N D Y M N K W A G L L 997

TAGGTCCAATTTCAAATCACAGTTTTGGAGGTAGCTTCAGAACAGCTTCAAATAAGGAAA
G P I S N H S F G G S F R T A S N K E I 1017

TCAAGCTCTCTGAACATAACATTAAGAAGAGCAAAATGTTCTTCAAAGATATTGAAGAAC
K L S E H N I K K S K M F F K D I E E Q 1037

AATATCCTACTAGTTTAGCTTGTGTTGAAATTGTAAATACCTTGGCATTAGATAATCAAA
Y P T S L A C V E I V N T L A L D N Q K 1057

AGAAACTGAGCAAGCCTCAGTCAATTAATACTGTATCTGCACATTTACAGAGTAGTGTAG
K L S K P Q S I N T V S A H L Q S S V V 1077

TTGTTTCTGATTGTAAAAATAGTCATATAACCCCTCAGATGTTATTTTCCAAGCAGGATT
V S D C K N S H I T P Q M L F S K Q D F 1097

TTAATTCAAACCATAATTTAACACCTAGCCAAAAGGCAGAAATTACAGAACTTTCTACTA
N S N H N L T P S Q K A E I T E L S T I 1117

TATTAGAAGAATCAGGAAGTCAGTTTGAATTTACTCAGTTTAGAAAACCAAGCTACATAT
L E E S G S Q F E F T Q F R K P S Y I L 1137

TGCAGAAGAGTACATTTGAAGTGCCTGAAAACCAGATGACTATCTTAAAGACCACTTCTG
Q K S T F E V P E N Q M T I L K T T S E 1157

AGGAATGCAGAGATGCTGATCTTCATGTCATAATGAATGCCCCATCGATTGGTCAGGTAG
E C R D A D L H V I M N A P S I G Q V D 1177

ACAGCAGCAAGCAATTTGAAGGTACAGTTGAAATTAAACGGAAGTTTGCTGGCCTGTTGA
S S K Q F E G T V E I K R K F A G L L K 1197

AAAATGACTGTAACAAAAGTGCTTCTGGTTATTTAACAGATGAAAATGAAGTGGGGTTTA
N D C N K S A S G Y L T D E N E V G F R 1217

GGGGCTTTTATTCTGCTCATGGCACAAAACTGAATGTTTCTACTGAAGCTCTGCAAAAAG
G F Y S A H G T K L N V S T E A L Q K A 1237

CTGTGAAACTGTTTAGTGATATTGAGAATATTAGTGAGGAAACTTCTGCAGAGGTACATC
V K L F S D I E N I S E E T S A E V H P 1257

CAATAAGTTTATCTTCAAGTAAATGTCATGATTCTGTCGTTTCAATGTTTAAGATAGAAA
I S L S S S K C H D S V V S M F K I E N 1277

ATCATAATGATAAAACTGTAAGTGAAAAAAATAATAAATGCCAACTGATATTACAAAATA
H N D K T V S E K N N K C Q L I L Q N N 1297

ATATTGAAATGACTACTGGCACTTTTGTTGAAGAAATTACTGAAAATTACAAGAGAAATA
I E M T T G T F V E E I T E N Y K R N T 1317

Fig.7G

```
CTGAAAATGAAGATAACAAATATACTGCTGCCAGTAGAAATTCTCATAACTTAGAATTTG
 E  N  E  D  N  K  Y  T  A  A  S  R  N  S  H  N  L  E  F  D   1337

ATGGCAGTGATTCAAGTAAAAATGATACTGTTTGTATTCATAAAGATGAAACGGACTTGC
 G  S  D  S  S  K  N  D  T  V  C  I  H  K  D  E  T  D  L  L   1357

TATTTACTGATCAGCACAACATATGTCTTAAATTATCTGGCCAGTTTATGAAGGAGGGAA
 F  T  D  Q  H  N  I  C  L  K  L  S  G  Q  F  M  K  E  G  N   1377

ACACTCAGATTAAAGAAGATTTGTCAGATTTAACTTTTTTGGAAGTTGCGAAAGCTCAAG
 T  Q  I  K  E  D  L  S  D  L  T  F  L  E  V  A  K  A  Q  E   1397

AAGCATGTCATGGTAATACTTCAAATAAAGAACAGTTAACTGCTACTAAAACGGAGCAAA
 A  C  H  G  N  T  S  N  K  E  Q  L  T  A  T  K  T  E  Q  N   1417

ATATAAAAGATTTTGAGACTTCTGATACATTTTTTCAGACTGCAAGTGGGAAAAATATTA
 I  K  D  F  E  T  S  D  T  F  F  Q  T  A  S  G  K  N  I  S   1437

GTGTCGCCAAAGAGTCATTTAATAAAATTGTAAATTTCTTTGATCAGAAACCAGAAGAAT
 V  A  K  E  L  F  N  K  I  V  N  F  F  D  Q  K  P  E  E  L   1457

TGCATAACTTTTCCTTAAATTCTGAATTACATTCTGACATAAGAAAGAACAAAATGGACA
 H  N  F  S  L  N  S  E  L  H  S  D  I  R  K  N  K  M  D  I   1477

TTCTAAGTTATGAGGAAACAGACATAGTTAAACACAAAATACTGAAAGAAAGTGTCCCAG
 L  S  Y  E  E  T  D  I  V  K  H  K  I  L  K  E  S  V  P  V   1497

TTGGTACTGGAAATCAACTAGTGACCTTCCAGGGACAACCCGAACGTGATGAAAAGATCA
 G  T  G  N  Q  L  V  T  F  Q  G  Q  P  E  R  D  E  K  I  K   1517

AAGAACCTACTCTGTTGGGTTTTCATACAGCTAGCGGGAAAAAAGTTAAAATTGCAAAGG
 E  P  T  L  L  G  F  H  T  A  S  G  K  K  V  K  I  A  K  E   1537

AATCTTTGGACAAAGTGAAAAACCTTTTTGATGAAAAAGAGCAAGGTACTAGTGAAATCA
 S  L  D  K  V  K  N  L  F  D  E  K  E  Q  G  T  S  E  I  T   1557

CCAGTTTTAGCCATCAATGGGCAAAGACCCTAAAGTACAGAGAGGCCTGTAAAGACCTTG
 S  F  S  H  Q  W  A  K  T  L  K  Y  R  E  A  C  K  D  L  E   1577

AATTAGCATGTGAGACCATTGAGATCACAGCTGCCCCAAAGTGTAAAGAAATGCAGAATT
 L  A  C  E  T  I  E  I  T  A  A  P  K  C  K  E  M  Q  N  S   1597

CTCTCAATAATGATAAAAACCTTGTTTCTATTGAGACTGTGGTGCCACCTAAGCTCTTAA
 L  N  N  D  K  N  L  V  S  I  E  T  V  V  P  P  K  L  L  S   1617

GTGATAATTTATGTAGACAAACTGAAAATCTCAAAACATCAAAAAGTATCTTTTTGAAAG
 D  N  L  C  R  Q  T  E  N  L  K  T  S  K  S  I  F  L  K  V   1637

TTAAAGTACATGAAAATGTAGAAAAAGAAACAGCAAAAAGTCCTGCAACTTGTTACACAA
 K  V  H  E  N  V  E  K  E  T  A  K  S  P  A  T  C  Y  T  N   1657

ATCAGTCCCCTTATTCAGTCATTGAAAATTCAGCCTTAGCTTTTTACACAAGTTGTAGTA
 Q  S  P  Y  S  V  I  E  N  S  A  L  A  F  Y  T  S  C  S  R   1677

GAAAAACTTCTGTGAGTCAGACTTCATTACTTGAAGCAAAAAAATGGCTTAGAGAAGGAA
 K  T  S  V  S  Q  T  S  L  L  E  A  K  K  W  L  R  E  G  I   1697

TATTTGATGGTCAACCAGAAAGAATAAATACTGCAGATTATGTAGGAAATTATTTGTATG
 F  D  G  Q  P  E  R  I  N  T  A  D  Y  V  G  N  Y  L  Y  E   1717

AAAATAATTCAAACAGTACTATAGCTGAAAATGACAAAAATCATCTCTCCGAAAAACAAG
 N  N  S  N  S  T  I  A  E  N  D  K  N  H  L  S  E  K  Q  D   1737

ATACTTATTTAAGTAACAGTAGCATGTCTAACAGCTATTCCTACCATTCTGATGAGGTAT
 T  Y  L  S  N  S  S  M  S  N  S  Y  S  Y  H  S  D  E  V  Y   1757
```

Fig.7H

ATAATGATTCCAGGATACTCTCAAAAAATAACTTGGATTCTGGTATTGAGCCAGTATTGA
N D S R I L S K N K L D S G I E P V L K 1777

AGAATGTTGAAGATCAAAAAAACACTAGTTTTTCCAAAGTAATATCCAATGTAAAAGATG
N V E D Q K N T S F S K V I S N V K D A 1797

CAAATGCATACCCACAAACTGTAAATGAAGATATTTGCGTTGAGGAACTTGTGACTAGCT
N A Y P Q T V N E D I C V E E L V T S S 1817

CTTCACCCTGCAAAAATAAAAATGCAGCCATTAAATTGTCCATATCTAATAGTAATAATT
S P C K N K N A A I K L S I S N S N N F 1837

TTGAGGTAGGGCCACCTGCATTTAGGATAGCCAGTGGTAAAATCGTTTGTGTTTCACATG
E V G P P A F R I A S G K I R L C S H E 1857

AAACAATTAAAAAAGTGAAAGACATATTTACAGACAGTTTCAGTAAAGTAATTAAGGAAA
T I K K V K D I D S F S K V I F T K E N 1877

ACAACGAGAATAAATCAAAAATTTGCCAAACGAAAATTATGGCAGGTTGTTACGAGGCAT
N E N K S K I C Q T K I M A G C Y E A L 1897

TGGATGATTCAGAGGATATTCTTCATAACTCTCTAGATAATGATGAATGTAGCACGCATT
D D S E D I L H N S L D N D E C S M H S 1917

CACATAAGGTTTTTGCTGACATTCAGAGTGAAGAAATTTTACAACATAACCAAAATATGT
H K V F A D I Q S E E I L Q H N Q N M S 1937

CTGGATTGGAGAAAGTTTCTAAAATATCACCTTGTGATGTTAGTTTGGAAACTTCAGATA
G L E K V S K I S P C D V S L E T S D I 1957

TATGTAAATGTAGTATAGGGAAGCTTCATAAGTCAGTCTCATCTGCAAATACTTGTGGGA
C K C S I G K L H K S V S S A N T C G I 1977

TTTTTAGCACAGCAAGTGGAAAATCTGTCCAGGTATCAGATGCTTCATTACAAAACGCAA
F S T A S G K S V Q V S D A S L Q N A R 1997

GACAAGTGTTTTCTGAAATAGAAGATAGTACCAAGCAAGTCTTTTCCAAAGTATTGTTTA
Q V F S E I E D S T K Q V F S K V L F K 2017

AAAGTAACGAACATTCAGACCAGCTCACAAGAGAAGAAAATACTGCTATACGTACTCCAG
S N E H S D Q L T R E E N T A I R T P E 2037

AACATTTAATATCCCAAAAAGGCTTTTCATATAATGTGGTAAATTCATCTGCTTTCTCTG
H L I S Q K G F S Y N V V N S S A F S G 2057

GATTTAGTACAGCAAGTGGAAAGCAAGTTTCCATTTTAGAAAGTTCCTTACACAAAGTTA
F S T A S G K Q V S I L E S S L H K V K 2077

AGGGAGTGTTAGAGGAATTTGATTTAATCAGAACTGAGCATAGTCTTCACTATTCACCTA
G V L E E F D L I R T E H S L H Y S P T 2097

CGTCTAGACAAAATGTATCAAAAATACTTCCTCGTGTTGATAAGAGAAACCCAGAGCACT
S R Q N V S K I L P R V D K R N P E H C 2117

GTGTAAACTCAGAAATGGAAAAAACCTGCAGTAAAGAATTTAAATTATCAAATAACTTAA
V N S E M E K T C S K E F K L S N N L N 2137

ATGTTGAAGGTGGTTCTTCAGAAAATAATCACTCTATTAAAGTTTCTCCATATCTCTCTC
V E G G S S E N N H S I K V S P Y L S Q 2157

AATTTCAACAAGACAAACAACAGTTGGTATTAGGAACCAAAGTCTCACTTGTTGAGAACA
F Q Q D K Q Q L V L G T K V S L V E N I 2177

TTCATGTTTTGGGAAAAGAACAGGCTTCACCTAAAAACGTAAAAATGGAAATTGGTAAAA
H V L G K E Q A S P K N V K M E I G K T 2197

Fig. 7I

```
CTGAAACTTTTTCTGATGTTCCTGTGAAAACAAATATAGAAGTTTGTTCTACTTACTCCA
  E  T  F  S  D  V  P  V  K  T  N  I  E  V  C  S  T  Y  S  K    2217

AAGATTCAGAAAACTACTTTGAAACAGAAGCAGTAGAAATTGCTAAAGCTTTTATGGAAG
  D  S  E  N  Y  F  E  T  E  A  V  E  I  A  K  A  F  M  E  D    2237

ATGATGAACTGACAGATTCTAAACTGCCAAGTCATGCCACACATTCTCTTTTTACATGTC
  D  E  L  T  D  S  K  L  P  S  H  A  T  H  S  L  F  T  C  P    2257

CCGAAAATGAGGNAATGGTNTTGTCAAATTCAAGAATTGGAAAAAGAAGAGGAGAGCCCC
  E  N  E  E  M  V  L  S  N  S  R  I  G  K  R  R  G  E  P  L    2277

TTATCTTAGTGGgtaagtgttcatttttacctttcgtgttgccaatcactatttttaaag
  I  L  V  G                                                   2281

tgtttattcagtagacttggtatgctaacaattaagagtgttataaactatgtcttttca
gccattttgtgtagtcagtttgggggagtatggtttgatatacagatacacagattcag
tattcgtatacagatttgatatcttggtatacagattcgatatctctgaatctgtatacc
aagaaatcatgttttaagggtctcaatatattttcaaaaagattattagtataataattg
agaaattactgttaaaaagttttgagtttctctagaaaatttgaaactcttaacaaaacc
tgcataatactaacttaactgttttcatatacatagcaagttcagactctgacttatatg
aactttaaaagttggtttccgggaggccgaggcgggcggatcacgaggtcaggagatcga
gaccatcccggc................................................


Exon 12
gtaatttgataattgtaaaaagcctcttaactctaattcaaggacctacataataaatta
ctccttcagttaatggctgcccccgtgctgaaaaaaaaaaaaaaagagagaaaaagttt
atttgaagaaattttgttaggccttattgccagtaaacctagagttatatttagtgtcag
tttttcaaaaagtagcttatctgtggtatctggtagcatctgtttatcctatttaggatt
tatcctgtttagaccctgttaaatagtggtgttttaaagtggtcaaaacagaacaaaaat
gtaattgacattgaagactgactttactctttcaaacattaggtcactatttgttgtaag
tatttttgtttaacatttaaagagtcaatactttagctttaaaaaaatggtctatagact
tttgagaaataaaactgatattatttgccttaaaaacatatatgaaatatttctttttag

GAGAACCCTCAATCAAAAGAAACTTATTAAATGAATTTGACAGGATAATAGAAAATCAAG
  E  P  S  I  K  R  N  L  L  N  E  F  D  R  I  I  E  N  Q  E    2301

AAAAATCCTTAAAGGCTTCAAAAAGCACTCCAGATGgttaaaattagctttntatttnta
  K  S  L  K  A  S  K  S  T  P  D  G                            2313

tctgttctccctctataggtnatgggtatataatattctgacctcaggtggatccacctg
cctctccaaagtgctgggnattacagacatgagccactgtgcctaatcaaggacctcttt
atactcttaaaaattactgaggacctaaagnggcatttgtttatgtgggantatatctat
tgatatttaccatattnganatgtaaattgattaatggttaaanttagtaantattatgc
gttggtcattgggaggatatgagttcactgagttatgcggatcttccgaaagttgaacag
tttctattatgccagtaattaaaacaatccacctttccattggatgcccattacccgatc
cagaaaagnttaaagtagtagaaagctgtcaagcttacagagcccagatacaagcttccc
caaaaattctgattttcatctaaaagcttgaatttt........................


Exon 13
gagatcgtcctcattctttttttgtggttacatagtagttgatcatctggctgtgtcagtg
tttcctagtttatttaaccaatttccaactagtggacttattgaagatttaattaggttc
cagttacatactgaaaatgaacaatatctaaagcttagcttttaaaccttcataagacta
aattttaaatttggtatttgcatcagaaattagctaacacctttgagttatgatggttaa
catcaactgactaaatttatgctgatttctgttgtatgcttgtactgtgagttatttggt
gcatagtcattatcaatttgtgaatcaatttattttcatagttaacatttattgagcatc
cgttacattcactgaaaattgtaaagcctataattgtctcaaatttttgtgtatttaca
gtaacatggatattctcttagattttaactaatatgtaatataaaataattgtttcctag

GCACAATAAAAGATCGAAGATTGTTTATGCATCATGTTTCTTTAGAGCCGATTACCTGTG
  T  I  K  D  R  R  L  F  M  H  H  V  S  L  E  P  I  T  C  V    2333
```

Fig.7J

```
TACCCTTTCGgtaagacatgtttaaatttttctaaattctaatacagtatgagaaaagtc
  P  F  R                                                        2336

tcgtttttataaatgaacatttctaaaaataatgacactaacgttaagaagttaacactt
cccgttttataaaatttataaaatactttggtagtattttatagtgctgttcatatcatt
attttatttttaatttttatgacagctttgtaaagtagacagattttattctaattttat
ggatgaagtactaaggttgagaggaattaaggaaattgctccgaatcagttaacaaaaag
attgcagatattaaaaatatccttttatctctcctctctaaacctttaaaaaagtactaa
gatagtttttttaatgtataattcccaaggacaatgatgagaagaaacaacaaaagtttg
gaagccaaaaacataaaggatttagtaagcatgagaaagctaaaacctgacactagagca
aacagagatg..................................................

Exon 14
ttcaaaggtaggcaagatttttgggctaaataaaaagggcactttaaaaaaggtataaat
aggtagaagagagaaaagggagcgaggtgggataattgaaagaggggatctcctgtggag
actgaggtattaggcggagtagagagttcaggtgaagatgtgaaggtgagagaagaggat
gggtagacatttccctggtgaaggaggtaaggagtactatgatggaattagaggggacac
actgagagggtccacacttgacagactctcttctattatgtgttatgtgaggtagattgt
aaagtcaaaggctagccttgaaaaatgtgatattgttttggaatggcaaccatggtgaat
acaaaacagttaccagaatagtatcaccatgtagcaaatgaggtctgcaacaaaggcat
attcctaaatatttatatgtgtactagtcaataaacttatatatttctccccattgcag

CACAACTAAGGAACGTCAAGAGATACAGAATCCAAATTTTACCGCACCTGGTCAAGAATT
 T  T  K  E  R  Q  E  I  Q  N  P  N  F  T  A  P  G  Q  E  F      2356

TCTGTCTAAATCTCATTTGTATGAACATCTGACTTTGGAAAAATCTTCAAGCAATTTAGC
 L  S  K  S  H  L  Y  E  H  L  T  L  E  K  S  S  S  N  L  A      2376

AGTTTCAGGACATCCATTTTATCAAGTTTCTGCTACAAGAAATGAAAAAATGAGACACTT
 V  S  G  H  P  F  Y  Q  V  S  A  T  R  N  E  K  M  R  H  L      2396

GATTACTACAGGCAGACCAACCAAAGTCTTTGTTCCACCTTTTAAAACTAAATCACATTT
 I  T  T  G  R  P  T  K  V  F  V  P  P  F  K  T  K  S  H  F      2416

TCACAGAGTTGAACAGTGTGTTAGGAATATTAACTTGGAGGAAAACAGACAAAAGCAAAA
 H  R  V  E  Q  C  V  R  N  I  N  L  E  E  N  R  Q  K  Q  N      2436

CATTGATGGACATGGCTCTGATGATAGTAAAAATAAGATTAATGACAATGAGATTCATCA
 I  D  G  H  G  S  D  D  S  K  N  K  I  N  D  N  E  I  H  Q      2456

GTTTAACAAAAACAACTCCAATCAAGCAGCAGCTGTAACTTTCACAAAGTGTGAAGAAGA
 F  N  K  N  N  S  N  Q  A  A  A  V  T  F  T  K  C  E  E  E      2476

ACCTTTAGgtattgtatgacaatttgtgtgatgaatttttgcctttcagttagatatttc
 P  L  D                                                        2479

cgttgttaaataatgtcctgatggttttccccctttggtggtggtaattttaaagcccctt
tttaatgttttagatttttctaaatccaaagattaggtttaaattattctaatgtttcttt
caaagataacttcttgtggacttgttaaaaaaaattagacacacaatct...........

Exon15
..........................................aacccactgtgcctgg
ccaggggttgtgcttttaaatttcaattttatttttgctaagtatttattctttgatag
ATTTAATTACAAGTCTTCAGAATGCCAGAGATATACAGGATATGCGAATTAAGAAGAAAC
  L  I  T  S  L  Q  N  A  R  D  I  Q  D  M  R  I  K  K  K  Q    2499

AAAGGCAACGCGTCTTTCCACAGCCAGGCAGTCTGTATCTTGCAAAAACATCCACTCTGC
  R  Q  R  V  F  P  Q  P  G  S  L  Y  L  A  K  T  S  T  L  P    2519

CTCGAATCTCTCTGAAAGCAGCAGTAGGAGGCCAAGTTCCCTCTGCgtgtccccataaac
  R  I  S  L  K  A  A  V  G  G  Q  V  P  S  A                    2534

aggtatgtgtttgnctacaatactgatggcttttatgacagagtgtaattttatttcatt
```

Fig. 7K aactagtatcctacaaatggctttgtttaaagaatgaacacattagtgcaggaatggatg
aatgaaatcatccatattttcctaattaagccctgcagtggcagcctctggccccttgct
aggcctgccctcatccctactaaagtgatctgtgccttcccaaattactacttcttttcc
ccccttcaaatctttcttatttgtcattgtaaatgctctcagctaggtgttaaagtagt
cttactgatattcaaatgtgaataactgatagccctgaaccttctatgagctatttatat
tttccaaagaggattctccttaagccaatattatctaggtagaatttaggcaatggaga
ggtgaaaataatattgatgacattaatagctaactttgagcatttt.............

Exon 16
gtctgactccagagtcaaactctgaacaaacaaaaagacactttgggttagatatcctgg
ggtgaaagcaagcactttgaaagtaagccaagcctgtgtacagatctgaccacctgaggt
cacattccctaaaatacttaaacttctccctttgtttcccatctaagtttttgaactta
agagattttgtaaaacatcacatttttttatcctcacagtaccttcctatggcagattta
gcaggaggcgtataaacggggtggaaaaggtacagcagactgtggaatgtatggatcatt
tatattacattaaaattttagtttctagtaaataacttaaatgttttgtagtgaagat
tctagtagttaatgaaaatttttggtaaattcagttttggtttgttataattgtttttat
tgtgtgatacatgtttactttaaattgtttttctttttgtgtgtgtttattttgtgtag GTGTTCTCATAAACAGCTGTATACGTATGGCGTTTCTAAACATTGCATAAAAATTAACAG
C S H K Q L Y T Y G V S K H C I K I N S 2554

CAAAAATGCAGAGTCTTTTCAGTTTCACACTGAAGATTATTTTGGTAAGGAAAGTTTATG
K N A E S F Q F H T E D Y F G K E S L W 2574

GACTGGAAAAGGAATACAGTTGGCTGATGGTGGATGGCTCATACCCTCCAATGATGGAAA
T G K G I Q L A D G G W L I P S N D G K 2594

GGCTGGAAAAGAAGAATTTTATAGgtactctatgcaaaaagattgtgtgttaacttttat
A G K E E F Y R 2602 gtattccctcatccctctttcttctcttaactgtctctcgaactaaaaagttggctagaa
atcaaattttatgcatttaattgttttaagtgcattatggttaagcattctgtagaagt
cttttgaaaagtgctgtttgtcctggggtttaatgaactggattttcttgatttgggaca
tttttcttaggcatttataaatatagcccaatttataaagttaaatttggccgggtacag
tggctcatgcctgtaatcccagcactttgggaggccgaggcgggtagatcacctgaggtc
aggagttcgagaccagcctggccaacgtggcgaaaccccatctctactaaaagtacaaga
actatctgggcgtggtggcaggcacctgtaatcccggctactctggaggctgaggcagga
gaatcgcttgaacctgggaggcag.................................

Exon 17
.......................................ttgttttgttttttatatttt
gagatagggtctcactcttgtccaggctggagtgcagtggcactatcatggctcactgca
gcctcaacctcctgggctcaagcaatcctcccaccacagcctcctaagtagctgggacca
cagatgtgagctaccactcttggctgatttttttttattatttttgtagagatgtggggg
tctcactatgttgcctaggctggtctcaaacttctggcctcaagcaatcctcctgcctca
gcttcccaaaatgctgggagtataggcatgagccaccatgctcagcaatgaagtttttat
cagtatgatactttgatacatgtcaaataattttctgaaattatattgtagatcatatga
actcataaaaacttaatgatcttgaacaatgtagtttttgtacagagaatagttgtagtt
gttgaattcagtatcatcctatgtggtttttatgataatattctacttttatttgttcag GGCTCTGTGTGACACTCCAGGTGTGGATCCAAAGCTTATTTCTAGAATTTGGGTTTATAA
A L C D T P G V D P K L I S R I W V Y N 2622

TCACTATAGATGGATCATATGGAAACTGGCAGCTATGGAATGTGCCTTTCCTAAGGAATT
H Y R W I I W K L A A M E C A F P K E F 2642

TGCTAATAGATGCCTAAGCCCAGAAAGGGTGCTTCTTCAACTAAAATACAGgcaagttta
A N R C L S P E R V L L Q L K Y R 2659 aagcattacattacgtaatcatatacggcagtatgggttaaggtttctgtgtagtctgtg
acttccatgtcaaaatgttgcacaagccagttgtcagtgacagttgccatcccacactgc

Fig.7L

```
tgttctcctgtcatccctagcccccatttaagagagatcacacattcatgcattgcttgc
ttccctctttccccacccccctccttaacctcttgatgtatgagaagaatatgagttacta
atttgatccactatttggggattgctaataaagcattttgcattttatttttttgctttt
taaaaataattgatattttaacaatatgaaacaatatattcctagctacaaaatttttaa
ttctcagtatttcttagataaattcagtttttattctcagttattcagtgacttgtttaa
acagtggaattctagagtcacacttcctaaaatatgcattttttgttttcacttttagata
tgatacggaaa.............................................
```

Exon 18

```
.....................................caactaaaatacaggcaagt
ttaaagcattacattacgtaatcatatacggcagtatgggttaaggtttctgtgtagtct
gtgacttccatgtcaaaatgttgcacaagccagttgtcagtgacagttgccatcccacac
tgctgttctcctgtcatccctagcccccatttaagagagatcacacattcatgcattgct
tgcttccctctttccccacccccctccttaacctcttgatgtatgagaagaatatgagtta
ctaatttgatccactatttggggattgctaataaagcattttgcattttatttttttgct
tttttaaaaataattgatattttaacaatatgaaacaatatattcctagctacaaaatttt
taattctcagtatttcttagataaattcagtttttattctcagttattcagtgacttgtt
taaacagtggaattctagagtcacacttcctaaaatatgcattttttgttttcacttttag

ATATGATACGGAAATTGATAGAAGCAGAAGATCGGCTATAAAAAAGATAATGGAAAGGGA
 Y  D  T  E  I  D  R  S  R  R  S  A  I  K  K  I  M  E  R  D    2679

TGACACAGCTGCAAAAACACTTGTTCTCTGTGTTTCTGACATAATTTCATTGAGCGCAAA
 D  T  A  A  K  T  L  V  L  C  V  S  D  I  I  S  L  S  A  N    2699

TATATCTGAAACTTCTAGCAATAAAACTAGTAGTGCAGATACCCAAAAAGTGGCCATTAT
 I  S  E  T  S  S  N  K  T  S  S  A  D  T  Q  K  V  A  I  I    2719

TGAACTTACAGATGGGTGGTATGCTGTTAAGGCCCAGTTAGATCCTCCCCTCTTAGCTGT
 E  L  T  D  G  W  Y  A  V  K  A  Q  L  D  P  P  L  L  A  V    2739

CTTAAAGAATGGCAGACTGACAGTTGGTCAGAAGATTATTCTTCATGGAGCAGAACTGGT
 L  K  N  G  R  L  T  V  G  Q  K  I  I  L  H  G  A  E  L  V    2759

GGGCTCTCCTGATGCCTGTACACCTCTTGAAGCCCCAGAATCTCTTATGTTAAAGgtaaa
 G  S  P  D  A  C  T  P  L  E  A  P  E  S  L  M  L  K          2777

ttaatttgcactcttggtaaaaatcagtcattgattcagttaaattctagaagttttaca
tttaaattttaaatgcttactaaggatgctcaatttcttagatgtactgataattttagt
ataaaaagcatattcttcagacagttaaagtttttgtgcagtttttgggaggtccagaga
tctttcttgagcttaaataatgcatttccaattaaaaagcaaaataaatttgcaccattt
gattttggtatctgtagcttgctgccctcttgttctcatagctttgctttgatcagatcc
ctattccactctggattagagaattacattttagtacttttcaaatatgtaatagataca
ctttttatctctatgtagattttaaactacataacaggactctttgtcatattgaatggt
ctgcagtattgctatctgaaattaccgataatattgtacattcagattcacttaagaggt
aaccttgcagagaat.........................................
```

Exon 19

```
.....................................cttaacaccatgccaggta
ccttagtaagtgttcgatgaatatttgcttttttgtattagccataatcattctcaggctg
ctttgtcatttacttgttccacaaattcttagcttccaaaattttggtgatacctcattt
cctattctctctagttgcctttgtccatgtagatttttttgaggaagcttgggtaaataag
tgtattttaaactattatgtttaaatcgaagttccttttatctgttttctaatagaaaca
tttaaatagcattaagaacttgtagcagtataaacaatatgtttgagaagtactatattg
tgaaaatattttcacttttatacagtttttttacttatttactgtcttactaatcttccta
agacttttttaaagtgaatattttttaaggcagttctagaagaatgaaaactcttatgatat
ctgtaatagaattgaatacatatttaactactaaatcaatatatttattaatttgtccag

ATTTCTGCTAACAGTACTCGGCCTGCTCGCTGGTATACCAAACTTGGATTCTTTCCTGAC
I  S  A  N  S  T  R  P  A  R  W  Y  T  K  L  G  F  F  P  D     2797

CCTAGACCTTTTCCTCTGCCCTTATCATCGCTTTTCAGTGATGGAGGAAATGTTGGTTGT
P  R  P  F  P  L  P  L  S  S  L  F  S  D  G  G  N  V  G  C     2817
```

Fig.7M

GTTGATGTAATTATTCAAAGAGCATACCCTATACAGgtatgatgtattcttgaaacttac
V D V I I Q R A Y P I Q 2829 catatatttctttcttttgatacaattaatttgtttgtttgtttgagatggagtttcggt
ctcttgcccaggctggagtgcaatggcgtgatcttggttcactgcagcctcccacctccc
gggttcaagtgattctcctgcctcagcctctcaagtagctgagccaccacacctggctaa
ttttgtatttttggtagagaaggggtttcatcatgttggtcaggctgatctcgaactcct
gacctcaggtgatccactaatctcagcctcccaaagttctgggattacagatgtgagcca
ctgtgcctggcctgatacaattaacttgaatgttatatatgtgactttttttggtgtgtgt
aacacattattacagtggatggagaagacatcatctggattatacatatttcgcaatgaa
agagaggaagaaaaggaagcagcaaaatatgtggaggcccaacaaaagagactaga....

Exon 20
.......................................ctgaccctagaccttttcct
ctgccccttatcatcgcttttcagtgatggaggaaatgttggttgtgttgatgtaattatt
caaagagcataccctatacaggtatgatgtattcttgaaacttaccatatatttctttct
tttgatacaattaatttgtttgtttgtttgagatggagtttcggtctcttgcccaggctg
gagtgcaatggcgtgatcttggttcactgcagcctcccacctcccgggttcaagtgattc
tcctgcctcagcctctcaagtagctgagccaccacacctggctaattttgtatttttggt
agagaaggggtttcatcatgttggtcaggctgatctcgaactcctgacctcaggtgatcc
actaatctcagcctcccaaagttctgggattacagatgtgagccactgtgcctggcctga
tacaattaacttgaatgttatatatgtgactttttttggtgtgtgtaacacattattacag TGGATGGAGAAGACATCATCTGGATTATACATATTTCGCAATGAAAGAGAGGAAGAAAAG
R M E K T S S G L Y I F R N E R E E E K 2849

GAAGCAGCAAAATATGTGGAGGCCCAACAAAAGAGACTAGAAGCCTTATTCACTAAAATT
E A A K Y V E A Q Q K R L E A L F T K I 2869

CAGGAGGAATTTGAAGAACATGAAGgtaaaattagttatatggtacacattgttatttct
Q E E F E E H E E 2878 aatatgagaacaaagtcttagagactttgaatttaacatttttaatgagtaaattgtttt
tattttgagtagtaaattgactttatttttagtatctagggtattctttttttggtgtta
gacaaagaatagcaacaagggacagaaatatcaggtctaagccatttgtaatatttttcc
tgaattcttacctatatgatgtggcttttgcatttttgtcatggtagttattagctttca
tgtgttattatgcctggaactaggacctattgtggtgtcaatttttaatattaaaaatcat
ggtgttttgatgtttatatgacataaatttatttttcgtatctccctttttgttgttgc
tgaagattttatgtttttctgcatttcctcatgatttatatagatgtaacatgttctata
ggacatgtaatttacatgtcctatagaactataagttacatgtcc..............

Exon 21
.....................atncattatacgaagttatggatcacaccactgcactc
ccagattgggtgacagagtgagaccctgtctcaaaaaaaaaaaaaagaaaaaacttttag
cagttatatagtttcttatctttaaatctcccttctttgggtgttttatgcttggttctt
tagttttagttgcttttgaatttacagtttagtgaattaataatcctttgttttcttag AAAACACAACAAAACCATATTTACCATCACGTGCACTAACAAGACAGCAAGTTCGTGCTT
N T T K P Y L P S R A L T R Q Q V R A L 2898
TGCAAGATGGTGCAGAGCTTTATGAAGCAGTGAAGAATGCAGCAGACCCAGCTTACCTTG
Q D G A E L Y E A V K N A A D P A Y L E 2918

AGgtgagagagtaagaggacatataatgaggcttgatgattattcaaggtgagaagctgt
tttanactctctggccatcacaggaaggaatatgttgaaatgctgcatttctccaaaagg
gatntgttcatttctgggattttccagtgatgttgcccagac.................

Exon 22
......................................gtatctactatttcaaagtt
aatggaattatactcctggggctaagaatgagggttctagggccaacctctactacctat
gtggcttgtgcaaattagttgtcccctttgtgcctcagttttacctacaacacagaaaca
atgatattacctaccccatggactgttgtgaagattaaatgaattagtacatttactaca

Fig. 7N

```
catagatctatttctcaaaataatgagcattcagatattagccatctgtaatgtagttgg
tgatgattatgattattagagtacatttataattggaggatcatttttgccgtagggaaa
tagaattattaatagtttgaggcacctgagaatattatgtgagaaactgattacattaac
cacacccttaagatgagctctaattttgttgtatttgtcctgtttaaagccatctagtta
caatagatggaactttttgttctgattgctttttattccaatatcttaaatggtcacag

GGTTATTTCAGTGAAGAGCAGTTAAGAGCCTTGAATAATCACAGGCAAATGTTGAATGAT
G  Y  F  S  E  E  Q  L  R  A  L  N  N  H  R  Q  M  L  N  D     2938

AAGAAACAAGCTCAGATCCAGTTGGAAATTAGGAAGGCCATGGAATCTGCTGAACAAAAG
K  K  Q  A  Q  I  Q  L  E  I  R  K  A  M  E  S  A  E  Q  K     2958

GAACAAGGTTTATCAAGGGATGTCACAACCGTGTGGAAGTTGCGTATTGTAAGCTATTCA
E  Q  G  L  S  R  D  V  T  T  V  W  K  L  R  I  V  S  Y  S     2978

AAAAAAGAAAAAGATTCAGgtaagtatgtaaatgctttgtttttatcagttttattaact
K  K  E  K  D  S  V                                            2985

taaaaaatgaccttactaacaaaatgattataaatccagataaagtataaagttagttta
tatcagagaagcaaaatccactactaatgcccacaaagagataatataaaagaggatctg
tatttattttgaaacaaacatttaaatgataatcacttcttccattgcatctttctcatc
tttctccaaacagttatactgagtatttggcgtccatcatcagatttatattctctgtta
acagaaggaaagagatacagaatttatcatcttgcaacttcaaaatctaaaagtaaatct
gaaagagctaacatacagttagcagcgacaaaaaaaactcagtatcaacaactaccggta
caaacctttcattgtaatttttcagttttgataagtgcttgttagtttatggaatctcca
tatgttgaatttttgttttgttttctgtaggtttcagat.....................
```

Exon 23

```
.......................................ctagttacaatagatggaac
tttttgttctgattgctttttattccaatatcttaaatggtcacagggttatttcagtg
aagagcagttaagagccttgaataatcacaggcaaatgttgaatgataagaaacaagctc
agatccagttggaaattaggaaggccatggaatctgctgaacaaaaggaacaaggtttat
caagggatgtcacaaccgtgtggaagttgcgtattgtaagctattcaaaaaaagaaaaag
attcaggtaagtatgtaaatgctttgtttttatcagttttattaacttaaaaaatgacct
tactaacaaaatgattataaatccagataaagtataaagttagtttatatcagagaagca
aaatccactactaatgcccacaaagagataatataaaagaggatctgtatttattttgaa
acaaacatttaaatgataatcacttcttccattgcatctttctcatctttctccaaacag

TTATACTGAGTATTTGGCGTCCATCATCAGATTTATATTCTCTGTTAACAGAAGGAAAGA
  I  L  S  I  W  R  P  S  S  D  L  Y  S  L  L  T  E  G  K  R   3005

GATACAGAATTTATCATCTTGCAACTTCAAAATCTAAAAGTAAATCTGAAAGAGCTAACA
  Y  R  I  Y  H  L  A  T  S  K  S  K  S  K  S  E  R  A  N  I   3025

TACAGTTAGCAGCGACAAAAAAAACTCAGTATCAACAACTACCGgtacaaacctttcatt
  Q  L  A  A  T  K  K  T  Q  Y  Q  Q  L  P                     3039

gtaatttttcagttttgataagtgcttgttagtttatggaatctccatatgttgaatttt
tgttttgttttctgtaggtttcagatgaaattttatttcagatttaccagccacgggagc
cccttcacttcagcaaatttttagatccagactttcagccatcttgttctgaggtggacc
taataggatttgtcgtttctgttgtgaaaaaaacaggtaatgcacaatatagttaatttt
ttttattgattcttttaaaaaacattgtcttttaaaatctcttatgattagttggagcta
ccagttggcaaatttgctagctaactagtgatctgaaagtaagcctctttgaacctctga
tttttcatgaaaagcaattctctcaattctatattatttcaagggtaacaagttacatcc
tagtctgtgtacttaattttatagaaattgtccttaattttattttctgcaatttatgtt
ttct........................................................
```

Exon 24

```
.......................................aagattcaggtaagtatgta
aatgctttgtttttatcagttttattaacttaaaaaatgaccttactaacaaaatgatta
taaatccagataaagtataaagttagtttatatcagagaagcaaaatccactactaatgc
ccacaaagagataatataaaagaggatctgtatttattttgaaacaaacatttaaatgat
aatcacttcttccattgcatctttctcatctttctccaaacagttatactgagtatttgg
```

Fig.7O cgtccatcatcagatttatattctctgttaacagaaggaaagagatacagaatttatcat
cttgcaacttcaaaatctaaaagtaaatctgaaagagctaacatacagttagcagcgaca
aaaaaaactcagtatcaacaactaccggtacaaacctttcattgtaatttttcagttttg
ataagtgcttgttagtttatggaatctccatatgttgaattttgttttgttttctgtag GTTTCAGATGAAATTTTATTTCAGATTTACCAGCCACGGGAGCCCCTTCACTTCAGCAAA
V S D E I L F Q I Y Q P R E P L H F S K 3059

TTTTTAGATCCAGACTTTCAGCCATCTTGTTCTGAGGTGGACCTAATAGGATTTGTCGTT
F L D P D F Q P S C S E V D L I G F V V 3079

TCTGTTGTGAAAAAAACAGgtaatgcacaatatagttaattttttttattgattctttta
S V V K K T G 3086 aaaaacattgtcttttaaaatctcttatgattagttggagctaccagttggcaaatttgc
tagctaactagtgatctgaaagtaagcctctttgaacctctgatttttcatgaaaagcaa
ttctctcaattctatattatttcaagggtaacaagttacatcctagtctgtgtacttaat
tttatagaaattgtccttaatttttatttctgcaatttatgtttcttactatttctggt
gtatgtgtttatcccattgtgatgttatattggtgtcctcaatttatttccttagccata
cactctacttttcattgtacagggctatttattatctcagagtcaagcttttttttttt
ttttttttccccgagatggagtctcactctgttgcccaggctggagtncagtggcgnaat
ntcagcccacngcaagttctgcctcccaggttnanacca....................

Exon 25
.....................................tgtatatgagctaataaaag
ttgcttccaatattttataattataatgttttcagtgagtaaccttgttcataggtgttt
tcatgaactttatgttcatgtgtattttactattattagaggtctatcttcagagaggag
tacaagaaatgggattactgggtgcaaaggtaaatggatatgtgtctttgctaggtattg
ccaaatttatctccagaaatcttgcacaaatctgtactcctgttagcaatgtgtgcgtat
acctgcttaccacatgacctcagtaaaagaatgtgttgtcatattggtattgaaatttta
gcactgtaagcaacaggtcattttggaaaacctgagctttcgccaaattcagctatttttg
atttgcttttattattagcatataccaaaataaataggcatattagagtttcctttcttg
catcttaaaattcatctaacacatctataataacattcttttcttttttttccattctag GACTTGCCCCTTTCGTCTATTTGTCAGACGAATGTTACAATTTACTGGCAATAAAGTTTT
L A P F V Y L S D E C Y N L L A I K F W 3106

GGATAGACCTTAATGAGGACATTATTAAGCCTCATATGTTAATTGCTGCAAGCAACCTCC
I D L N E D I I K P H M L I A A S N L Q 3126

AGTGGCGACCAGAATCCAAATCAGGCCTTCTTACTTTATTTGCTGGAGATTTTTCTGTGT
W R P E S K S G L L T L F A G D F S V F 3146

TTTCTGCTAGTCCAAAAGAGGGCCACTTTCAAGAGACATTCAACAAAATGAAAAATACTG
S A S P K E G H F Q E T F N K M K N T V 3166

TTGAGgtaaggttacttttcagcatcaccacacattttggtatttttctattttgacagt
E 3167 ccagtatcaaggaaatagcttttatacaaattggatagttgaggtagtatgtgaggtaaa
gtttaatcatatattaattgcccatgaacctcaggagatgggggaatggggaaatgacag
cagctagaaagagaagaatgacttgaagggaaatgagttaggagaaattgtgagaaggat
gttcagaaatgcagactttgtaagcaaactggaaattggttacaagaataatatgagtta
tctgtggtttgcagcagtcagcagtgtgattagttaataatatagagactacaggtttac
atttaaactccatatctagtgttttatacagattatatttctttgacttgatttaatccc
agataagagacactgatattattttccctagatcatgt....................

Exon 26
.....................................tatttgaccagttgtgattt
ctcaagcaacagtttcatgtagtttaacctataaatcatttcaattaattcttggaacag
acgtgaggtaggtgaggcaattctttcttttctctaaccaaagaagtacctttatagatg
tgagatgattcccagctattaagtagtaaatagagctaggacttgagccccaatcttcca
gcttcaatccagatcatatgacagcttgctgattaaactagatgacagagaagatctctt

Fig.7P tccttcagatacacatacttttctctgttcccctctccctatcagctagattcccctaa
atcactgatactggttttgtaattttgcatcggcatgtttgacaattggtatcacattta
gggtttttcattctttttggtcccaaacttttcatttctgcttttaaaggaaatacttt
tggaaacataaatatgtgggtttgcaatttataaagcagcttttccacttattttcttag AATATTGACATACTTTGCAATGAAGCAGAAAACAAGCTTATGCATATACTGCATGCAAAT
N I D I L C N E A E N K L M H I L H A N 3187

GATCCCAAGTGGTCCACCCCAACTAAAGACTGTACTTCAGGGCCGTACACTGCTCAAATC
D P K W S T P T K D C T S G P Y T A Q I 3207

ATTCCTGGTACAGGAAACAAGCTTCTGgtaagttaatgtaaactcaaggaatattataag
I P G T G N K L L 3216 aagtatatatggaggccatcgtatattctgttgtatacctagtaaacatggtaaaatgta
attaaacttaattagaaaatgtggttgttatgtggctcctgtaagtatagttatttagaa
attttatttattgaagcaagatatgaaactctgggtgcacactttccaaacaggtgcttt
catttacatgtgattgaaaagtgtttttttgccatttatttcactgttccatacaattagg
gttgtttctaagctgtttgtaagctgtttctaagctatttaagtggttaaatcacagtag
atgcaaatcaagctaaagtctttaacattggctaatggctgattcttaaatagctaatac
ttgctaagggtatctatattaactcatttaatcctcataacaaccctatgagataaaacc
taagtcctcacttaacattgtcaataggtttttggaaactgatttta............

Exon 27 taatctgtt
aataataaaaaacaaaagattaaagcataagtgacgtcccctacctcctttttatcttt
tactgtgattattcttcatcttccttcctttcatgtcatttatatgttcttatgtaaa
attactttcatctagaataggaataatgtgaactgaaatcacctaacctattaggagtta
ggggagggagactgtgtgtaatatttgcgtgcttaaatattttcaatgaaaagttacttt
gatttagtttttatgttactacataattatgataggctacgttttcatttttttatcag ATGTCTTCTCCTAATTGTGAGATATATTATCAAAGTCCTTTATCACTTTGTATGGCCAAA
M S S P N C E I Y Y Q S P L S L C M A K 3236

AGGAAGTCTGTTTCCACACCTGTCTCAGCCCAGATGACTTCAAAGTCTTGTAAAGGGGAG
R K S V S T P V S A Q M T S K S C K G E 3256

AAAGAGATTGATGACCAAAAGAACTGCAAAAAGAGAAGAGCCTTGGATTTCTTGAGTAGA
K E I D D Q K N C K K R R A L D F L S R 3276

CTGCCTTTACCTCCACCTGTTAGTCCCATTTGTACATTTGTTTCTCCGGCTGCACAGAAG
L P L P P P V S P I C T F V S P A A Q K 3296

GCATTTCAGCCACCAAGGAGTTGTGGCACCAAATACGAAACACCCATAAAGAAAAAAGAA
A F Q P P R S C G T K Y E T P I K K K E 3316

CTGAATTCTCCTCAGATGACTCCATTTAAAAAATTCAATGAAATTTCTCTTTTGGAAAGT
L N S P Q M T P F K K F N E I S L L E S 3336
AATTCAATAGCTGACGAAGAACTTGCATTGATAAATACCCAAGCTCTTTTGTCTGGTTCA
N S I A D E E L A L I N T Q A L L S G S 3356

ACAGGAGAAAAACAATTTATATCTGTCAGTGAATCCACTAGGACTGCTCCCACCAGTTCA
T G E K Q F I S V S E S T R T A P T S S 3376

GAAGATTATCTCAGACTGAAACGACGTTGTACTACATCTCTGATCAAAGAACAGGAGAGT
E D Y L R L K R R C T T S L I K E Q E S 3396

TCCCAGGCCAGTACGGAAGAATGTGAGAAAAATAAGCAGGACACAATTACAACTAAAAAA
S Q A S T E E C E K N K Q D T I T T K K 3416

TATATCTAAGCATTTGCAAAGGCGACAATAAATTATTGACGCTTAACCTTTCCAGTTTAT
Y I STOP 3418

AAGACTGGAATATAATTTCAAACCACACATTAGTACTTATGTTGCACAATGAGCAAAGAA

Fig.7Q

ATTAGTTTCAAATTTACCTCAGCGTTTGTGTATCGGGCAAAAATCGTTTTGCCCGATTCC

GTATTGGTATACTTTTGCTTCAGTTGCATATCTTAAAACTAAATGTAATTTATTAACTAA

TCAAGAAAAACATCTTTGGCTGAGCTCGGTGGCTCATGCCTGTAATCCCAACACTTTGAG

AAGCTGAGGTGGGAGGAGTGCTTGAGGCCAGGAGTTCAAGACCAGCCTGGGCAACATAGG

GAGACCCCCATCTTTACAAAGAAAAAAAAAAGGGGAAAAGAAAATCTTTTAAATCTTTGG

ATTTGATCACTACAAGTATTATTTACAAGTGAAATAAACATACCATTTTCTTTTAGATT

GTGTCATTAAATGGAATGAGGTCTCTTAGTACAGTTATTTTGATGCAGATAATTCCTTTT

AGTTTAGCTACTATTTTAGGGGATTTTTTTAGAGGTAACTCACTATGAAATAGTTCTCC

TTAATGCAAATATGTTGGTTCTGCTATAGTTCCATCCTGTTCAAAAGTCAGGATGAATAT

GAAGAGTGGTGTTTCCTTTTGAGCAATTCTTCATCCTTAAGTCAGCATGATTATAAGAAA

AATAGAACCCTCAGTGTAACTCTAATTCCTTTTTACTATTCCAGTGTGATCTCTGAAATT

AAATTACTTCAACTAAAAATTCAAATACTTTAAATCAGAAGATTTCATAGTTAATTTATT

TTTTTTTTcaacaaaatggtcatccaaactcaaacttgagaaaatatcttgctttcaaat tggcactgattctgcctgctttattttagcgctatcacaggacccagagcctatgccct
tttaaacttaccacaaaagcagaagattaattcaatttaagatgatactctcatttgtta
cgtcctttttttttttttttggagatggagtcttgctttgtcgcccatgctggagtgcag
tggcatgatcctggctcactgcagcctccacttcccgggttcaagtaattctcccacctc
aagcctccctagtagctgggattacagggacgcaccaccatgcccagctaatttttgcat
ttttagtagagactgggttttaccatgttggccaagctggtctcaaactcctgatgtcag
gtgatccatctgcctcagcctcccaaagtgctgggattataggcgtgagccactgtgccc
ggccaatatttgttactttcttaggtttaatagagaaaagggataaaacatttctaactg
ggagttaatagcatggagaaggtcttaaatcagatgttttaatgccttaaatgtctgtat
aatatcatgttttcaaatctaattataaatacgtttaaagccaagaataaatcttttaaa
aaattgacttgtttccttccataactctgagccatgatttttctgttctgtaaaaagcat
taacaaaattgtctattttgctactccctgtaacttaagtattctgcaagtcttattaat
gagacttgttttgtttctaaaacagtttggttttcacatcctaattttgcagtgatccac
tctagaacaaggaaataaaacttgggtttcaaacaggagaacagaaaaaattacaagaat
ttaaccttttctttttttgaatccttggtacaactgctattgtctgttctcatgtagaaca
cccattatgttgatagatatgtaatgcgcacactttttttataaattataaataacatcca
agctacatgaaacaaaatatgaagcttgagtatatgtgcatattatcccctcaaaagtga
caatttaatgactacaaagtcaacatactgcatcataagggataatggtaaaaatttgtg
ttatttattcagcaatcatttaatgagaccctattgcccataaagagcatttgccagttc
tatgaatgatgcaaacagcgaacacaatacaagtcaatattgggtgttcaaagagttaca
caaatcagaagccatgggagttgaaaaacagatcacttctacaggggataaagttgatgg
catttaatcaatttttatggtttacaaaccaaatatttcaggggtcagctagggaaagaa
gagacattaaataggccaggaaactattctttagagctctagaaaagttatgtaacccag
agccacttctccatagtggtcactcacttaacccaagtgagcca................

Fig.7R

BRCA2 SSCP PRIMERS

These primers have been designed to amplify the *BRCA2* gene by the PCR for the identification of sequence changes in genomic DNA that may predispose to the development of breast cancer. The primers are located in the intron sequences flanking each of the 26 exons that contain the open reading frame of the gene. The amplified products include the splice site consensus sequences. Two or more sets of primers have been designed for the larger exons of the gene.

The primers are labelled by: their exon number, the subsection of the exon and as forward or reverse. The PCR products range from 160 to 360bp. The column labelled CON indicates the conditions that we have used. The primers have been tested using a limited set of conditions which were all based on touchdown (TD) PCR where the figures indicate the first and final annealing temperature respectively.

When mutations have been identified, the PCR products have been sequenced using the same primers and fluorescent cycle sequencing.

| EXON | PRIMER F | PRIMER R | SIZE(bp) | CON |
|---|---|---|---|---|
| 1 | | | | |
| | | | | |
| 2 | CTCAGTCACATAATAAGGAAT | ACACTGTGACGTACTGGGTTTT | 256 | TD60-50 |
| | | | | |
| 3 | TCTGGGTCACAAATTTGTCTGTCA | TTCCTAGTTTGTAGTTCTCCCCAGTC | 356 | TD60-50 |
| | | | | |
| 4 | AGAATGCAAATTTATAATCCAGAGTA | AATCAGATTCATCTTTATAGAACAAA | 249 | TD60-50 |
| | | | | |
| 5 | AACAATTTATATGAATGAGAATC | AATTGTTAAGTTTTATTTTTATTA | 220 | TD55-45 |
| | | | | |
| 6 | CCACAAAGAGATAAGTCAGGTA | TGTAAATCTCAGGGCAAAGGTA | 234 | TD55-45 |
| | | | | |
| 7 | TAAGTGAAATAAAGAGTGAA | AACAGAAGTATTAGAGATGAC | 275 | TD55-45 |
| | | | | |
| 8 | AATAGTAGATGTGCTTTTTGA | ACATATAGGACCAGGTTTAGAGAC | 285 | TD60-50 |
| | | | | |
| 9 | GTTCAACTAAACAGAGGACT | CTAGTGATTTTAAACTATAATTTTTG | 164 | TD68-60 |
| | | | | |
| 10A | TATAAAATATTAATGTGCTTCTGTT | AAAGGGCTTCTGATTTGCTAC | 374 | TD55-45 |
| 10B | ATCTGAAGTGGAACCAAATGATAC | ACGTGGCAAAGAATTCTCTGAAGTAA | 270 | TD60-50 |
| 10C | TTTCAGAAAAAGACCTATTAGACA | CTTTTTGATACCCTGAAATGAAGAAG | 260 | TD60-50 |
| 10D | TAAAGCAGGCAATATCTGGAACTTCT | GTGGATATTAAACCTGCATTCTTCAA | 280 | TD60-50 |
| 10E | TATGTCCAAATTTAATTGATAAT | AAACACAGAAGGAATCGTCATC | 320 | TD55-45 |

Fig. 8A

| | | | | |
|---|---|---|---|---|
| 11A | GATGGTACTTTAATTTTGTCACTTTG | TTCCTTATTACATTTTGCTTCTTTAT | 220 | TD55-45 |
| 11B | CTAGCTCTTTTGGGACAATTCTGAGG | TTTCATGATCATATAAAAGANT | 300 | TD55-45 |
| 11C | CAAAAGTGGAATACAGTGATAC | ATAATTTTCATTTAAAGCACATACAT | 250 | TD60-50 |
| 11D | TCTAGAGGCAAAGAATCATA | TCATTGTCTGAGAAAAGTTC | 305 | TD55-45 |
| 11E | TTCAAAAATAACTGTCAATCC | GTTGCTTGTTTATCACCTGT | 230 | TD60-50 |
| 11F | AACCCATTTTCAAGAACTCTACCA | CTGAAGCTACCTCCAAAACTGTG | 274 | TD60-50 |
| 11G | ACAAATGGGCAGGACTCTTAGG | CCTGCTTGGAAAATAACATCTG | 300 | TD60-50 |
| 11H | AGTTGTTTCTGATTGTAAAAATAGTC | GCTGCTGTCTACCTGACCAA | 310 | TD60-50 |
| 11I | GATGCTGATCTTCATGTCATAA | TACCTCTGCAGAAGTTTCCTCACTA | 300 | TD60-50 |
| 11J | GGGTTTAGGGGCTTTTATTC | TATCAGTTGGCATTTATTATTTTT | 237 | TD60-50 |
| 11K | CTTCAAGTAAATGTCATGATTCTGTC | CTGGCAGCAGTATATTTGTTATCT | 202 | TD60-50 |
| 11L | ATTACTGAAAATTACAAGAGAAATA | AAAAAGTTAAATCTGACTCAAATCT | 244 | TD60-50 |
| 11M | TTTATGAAGGAGGGAAACACTCA | TTCAGAATTTAAGGAAAAGTTATGC | 282 | TD60-50 |
| 11N | AAAAATATTAGTGTCGCCAAAGAG | TGTATGAAAACCCAACAGAGTAGG | 278 | TD60-50 |
| 11O | GTTAAACACAAAATACTGAAAG | CATTGATGGCTAAAACTGGTG | 233 | TD60-50 |
| 11P | TCATACAGCTAGCGGGAAAAA | TGGCACCACAGTCTCAATAG | 265 | TD60-50 |
| 11Q | CTGCCCCAAAGTGTAAAGAAAT | AATGACTGAATAAGGGGACTGAT | 230 | TD60-50 |
| 11R | GTCCTGCAACTTGTTACAC | GATTTTTGTCATTTTCAGC | 230 | TD60-50 |
| 11S | AACCAGAAAGAATAAATACT | TCCTCAACGCAAATATCTTCAT | 334 | TD55-45 |
| 11T | TTTCCAAAGTAATATCCAATGTA | ATTTTTGATTTATTCTCGTTGTT | 291 | TD55-45 |
| 11U | AAGACATATTTACAGACAGT | TGAAGCTTCCCTATACTACAT | 300 | TD60-50 |
| 11V | CACCTTGTGATGTTAGTTTG | TTGGGATATTAAATGTTCTGGAGTA | 350 | TD60-50 |
| 11W | AAAGTAACGAACATTCAGACCA | CTGGGTTTCTCTTATCAACNCGA | 310 | TD60-50 |
| 11X | AGTCTTCACTATTCACCTACG | GTGAGACTTTGGTTCCTAAT | 280 | TD60-50 |
| 11Y | TTCAACAAGACAAACAACAGT | TGTCAGTTCATCATCTTCCATAAA | 270 | TD60-50 |
| 11Z | TTACTCCAAAGATTCAGAAAACTAC | AGCATACCAAGTCTACTGAATAAAC | 290 | TD60-50 |
| | | | | |
| 12 | AGGTCACTATTTGTTGTAAG | AGTGGCTCATGTCTGTAAT | 358 | TD60-50 |
| | | | | |
| 13 | TAAAGCCTATAATTGTCTCA | CTTCTTAACGTTAGTGTCATT | 271 | TD55-45 |
| | | | | |
| 14A | ATGTAGCAAATGAGGGTCTG | GTCTGCCTGTAGTAATCAAGTGT | 289 | TD60-50 |
| 14B | CTTCAAGCAATTTAGCAGTTTCAG | TGCTGCTTGATTGGAGTTGTT | 292 | TD55-45 |
| 14C | TATTAACTTGGAGGAAAACAGACA | CAAAGGGGGAAAACCATCAG | 250 | TD60-50 |
| | | | | |
| 15 | GGCCAGGGGTTGTGCTTTTT | AGGATACTAGTTAATGAAATA | 314 | TD60-50 |
| | | | | |

Fig.8B

| | | | | |
|---|---|---|---|---|
| 16 | TTTGGTAAATTCAGTTTTGGTTT | AACACACAATCTTTTTGCATAGA | 330 | TD60-50 |
| | | | | |
| 17 | CAGAGAATAGTTGTAGTTGTTGAA | AGAAACCTTAACCCATACTGC | 306 | TD60-50 |
| | | | | |
| 18A | ATTCAGTTTTTATTCTCAGTTATTC | ACCACCCATCTGTAAGTTCA | 296 | TD60-50 |
| 18B | ATCTGAAACTTCTAGCAATAA | TTTAACTGAATCAATGACTG | 281 | TD60-50 |
| | | | | |
| 19 | AAGTGAATATTTTTAAGGCAGTT | TATATGGTAAGTTTCAAGAAT | 296 | TD60-50 |
| | | | | |
| 20 | CACTGTGCCTGGCCTGATAC | ATGTTAAATTCAAAGTCTCTA | 296 | TD60-50 |
| | | | | |
| 21 | GGGTGTTTTATGCTTGGTTCT | CATTTCAACATATTCCTTCCTG | 304 | TD60-50 |
| | | | | |
| 22 | TTTTGTTCTGATTGCTTTTTATTC | AATCATTTTGTTAGTAAGGTCAT | 314 | TD60-50 |
| | | | | |
| 23 | ACTTCTTCCATTGCATCTTTCTCA | AAAACAAAACAAAAATTCAACATA | 290 | TD60-50 |
| | | | | |
| 24 | CAGTTTTGATAAGTGCTTGTT | AGCTCCAACTAATCATAAGA | 290 | TD60-50 |
| | | | | |
| 25A | TAAAATTCATCTAACACATCTAT | ACCTCAACAGTATTTTTCATT | 302 | TD55-45 |
| 25B | AATCCCAAATCAGGCCTTCTTACTT | ATTTCCCCATTCCCCCATCT | 283 | TD60-50 |
| | | | | |
| 26 | AAGGAAATACTTTTGGAAACATAA | TTTACTAGGTATACAACAGAA | 299 | TD55-45 |
| | | | | |
| 27A | TAGGAGTTAGGGGAGGGAGACTGTGT | TTTCTCCCCTTTACAAGACTTTGAAG | 252 | TD60-50 |
| 27B | TTGTATGGCCAAAAGGAAGTCTG | TTTTTAAATGGAGTCATCTGAGGAGA | 285 | TD60-50 |
| 27C | AAGGCATTTCAGCCACCAAGGAGT | CAACGTCGTTTCAGTCTGAGATAATC | 272 | TD60-50 |
| 27D | AGGAGAAAAACAATTTATATCTGTCA | GTGGTTTGAAATTATATTCCAGTCTT | 264 | TD60-50 |

Fig.8C

Alignment Workspace of ALIGN.MEG, using Clustal method with PAM250 residue weight table.

```
              ---GS--KNCS-NDP-------------------------NNTIISQDLDYKEAKCNKEKLQLFITPEADSLSCLQEGQCENDPKSPKVSDIKEEVLAAACHP-VQHS
                      10        20        30        40        50        60        70        80        90       100       110
HUMAN.PRO     ---GTILRKCSRNET-----------------------CSNNIVISQDLDYKEAKCNKEKLQLFITPEADSLSCLQEGQCXNDPKSKKVSDIKEEVLAAACHP-VQHS   82
MONKEY.PRO    ---------CS--------------------------SNNTIISQDLDYKEAKCNKEKLQLFITPEADSLSFLQEGQYENDPKSRKVSDIKEEVLAAAHHP-VQHS   71
DOG.PRO       ---SSIKKNCLQNDSEKPALSLTSSFGTILRKVSSNGASSPNNKIISQDPDYKEAKINKKKLESFITTETDCLSSLQEKHWEDDAKKQRVSDIKEKVLPTVSHPPVPHS   107
PIG.PRO       ---GP-------------------------------------------------------------------------------------------------------   3
HAMSTER.PR    -------KNCSHIQP----------------------------------------------------WETDCLSCLPERQCEYDPKGPKVSDGKEEVLVSACHPAGQHT   51
MOUSE.PRO     IPDSSDKKRCLPNDPEEP--SLTNSFGTATSKEISY-----IHALISQDLNDKEAIVIEEKPQPYTAREADFLLCLPERTCENDQKSPKVSNGKEKVLVSACLPS----   99

              -VEYSDISFQSQKSPLYDHENTSTLILTPSSKDVLSNLVMISRGKESYKMSEKLKCENYESDFELTKNIPMEKNQDICALSENSKNVELLPPEKYITVASPSVKVQFNQ
                    120       130       140       150       160       170       180       190       200       210       220
HUMAN.PRO     -VEYSDTDFQSQKNLLYDHENASTLILTPTSKDVLSNLVMISRGKESYKMSDKLKGNNYESDVELTKNIPMEKNQDVCALNENYKNVELLPPEKYMRVASPSRKVQFNQ   191
MONKEY.PRO    -AEYSDTDFQSQKSPLYDHENASTLILTPTSKDVLSNLLMISRGKKSYKMSDELKGNNYESDFELTKNIPMEKNQDVCALSENSKHVELLPPEKYIRGASPSRKVQFNQ   180
DOG.PRO       -VEGSDIHFQSPKSFSFDCDNTS--LLTPSSRDSPSSLVVMSRGKESYKISEKLKCKNHETGFELTKNIPMEKNQDIHVLNADSKNAKLLSTEKHITVASSSVKVQFNQ   214
PIG.PRO       ------------------------------------------------------------------------------------------------------------   3
HAMSTER.PR    AAQPSSISFELQEDPVNGHNSTSP-KETPSLKVLLSKPVVLSRGKVSCKMPEKLQCESYKDNTELSKSIPLGGNK-IHILSENSKPPELLPPGKYVTEASPTVKSQFNQ   159
MOUSE.PRO     AVQLSSISFESQENPLGDHNGTSTLKLTPSSKLPLSKADMVSREKM-CKMPEKLQCESCKVNIELSKNI-LEVNE-ICILSENSKTPGLLPPGENIIEVASSMKSQFNQ   205

              TNLRVIQKDQEEITLISKITVNPDSEELFPDNENNFVFQVINERNNPALGNTKELHETDLTCVNGPILKNSTMVVDGDIGDKQAAQVSIKKDLDSSAIVHDLAEENRNS
                    230       240       250       260       270       280       290       300       310       320       330
HUMAN.PRO     TNLRVIQKNQEETTSISKITVNPDSEELFSDNENNFVFQVANERNNLALGNTKELHETDLTCVNEPIFKNSTMVLYGDTGDKQATQVSIKKDL-----VYVLAEENKNS   296
MONKEY.PRO    TNLRVIQKDQEETTLIPKITVHPDSEELFSDNENNFVFQVANERNNFALGNTKELHETDLTCVNEPIFKNSTMVLYADIGDKQATQVSIKKDLDSSNIVYDLAEENKNS   290
DOG.PRO       ANLTTIQKDQKETTLISKITVNPNSEELFPDDENNFVLKITNESNTPVLGNTKELHDSNLCCVRDSVPKNSTMVVCTDLDDKQTAKVSIMKDCYSSSID-DLTERNRST   323
PIG.PRO       ------------------------------------------------------------------------------------------------------------   3
HAMSTER.PR    TNLAVKKNDQEETPFISEVTVNVSSGELFPDNENNFAFQVTHENNKTALGSTVELQEEDLRHAKGPNLNNSPTAVDGDIGDEQAAHALIMEDSDSSALVHECAKKSRNT   269
MOUSE.PRO     AKIVIQK-DQKGSPFISEVAVNMNSEELFPDSGNNFAFQVTNKCNKPDLGSSVELQEEDLSHTQGPSLKNSPMAVDEDVDDAHAAQVLITKDSDSLAVVHDYTEKSRNN   314

              KQHLKMTLDQDLKSDISLNI--KSDGNSDYMDKWAGLLDPISNHSFGGSFRTASNKEIKLSEHNIKKSKMFFKDIEEQYPTSLACVEIVNTLALANQKKLSK----DPQ
                    340       350       360       370       380       390       400       410       420       430       440
HUMAN.PRO     KQHIKMTLGQDLKSDISLNIDKIPEKNNDYMNKWAGLLGPISNHSFGGSFRTASNKEIKLSEHNIKKSKMFFKDIEEQYPTSLACVEIVNTLALDNQKKLSK-----PQ   401
MONKEY.PRO    KQHLKMTLGQDLQPDI-LNIDKIPDKIDDCMDKWAGPLDPISNHSFGGSFRTASNKEIKVSEHNIKKSKMFFKDIEEQYPTSLACVEIVNTLALDNQKKLSK-----PQ   394
DOG.PRO       KQQLKMTLDQDSKSDITSDIVRKSNGNSDYMDNWARLSDPISNHSFENGFKTASNKEIKLSENNIRKSKMLFKDIEEHYPTNLACLEIVNTSSLESQKKPSKSHALDPQ   433
PIG.PRO       ------------------------------------------------------------------------------------------------------------   3
HAMSTER.PR    EQHLKGTTDKDF--NSSLDV--KSDGNNDYTDKWPGFLDPVFKHKFGGSFRTASNKEIKLSEHNVKKSKMFFKDIEEEYPTSLTCIDIVNASPLANQEILSGPYTFDLQ   375
MOUSE.PRO     EQHQKGTEDKDFKSNSSLNM--KSDGNSDCSDKWSEFLDPVLNHNFGGSFRTASNKEIKLSEHNVKKSKMFFKDIEEQYPTRLACIDIVNTLPLANQKKISEPHIFDLK   422
```

Fig.9A

```
             INTVSAHLQSSVVVSDCEDSHTAPQMLSSKQDFNSNHNLTPSQKAEITELSTILEESGSQFEFTQFRKPSHIAQKNTFEVPENQMTILNTTSEEWKDADLHLIVNAPSI
             450       460       470       480       490       500       510       520       530       540       550
HUMAN.PRO    INTVSAHLQSSVVVSDCKNSHITPQMLFSKQDFNSNHNLTPSQKAEITELSTILEESGSQFEFTQFRKPSYILQKSTFEVPENQMTILKTTSEECRDADLHVIMNAPSI 511
MONKEY.PRO   INTVSAHLQSSVVVSDCKNSHITPQMSFSKQDFNSNHNLTPSQKAEITELSTILEESGSQFEFTQFRKPSYILQKNTFEVPENQVTILNTTTEENRDAGL-VIMNAPSI 503
DOG.PRO      INIISGFVQNSTYVSDSESGHTAPPTLSLKQDFDSNRNLTPSQKAEITELSTILEESGSQFEFTQFRKPSHIIQKNPFEMPENQLTILNSTSKEWKDDDLHLTTNAPSI 543
PIG.PRO      -------------------------------------------------------------------------------------------------------- 3
HAMSTER.PR   VTTMSAHPQSQASVS-CEDTHTSLQVLPSKQDFHSNHNLTPSQKAEITELSTILEESGSQFEFTQFKKPSHVAQNNIPEVPGKQTVAINTTSEGWKRIGLHLTVDPASV 484
MOUSE.PRO    VTTVSTQSHNQSSVS-HEDTDTAPQMLSSKQDFHSNN-LTTSQKAEITELSTILEESGSQFEFTQFRKPSHIAQNT-SEVPGNQMVVLSTASKEWKDTDLHLPVDP-SV 528

             QVDSSKQFEGSAGIKQKFACLLKSSCNKSASGYLTDENEVEFRGFYSALGTKLNVSSEALQKAVKLFSDIENISEETSAEVDPISLSSSKYHDSVASMFKIENQN-DKS
             560       570       580       590       600       610       620       630       640       650       660
HUMAN.PRO    QVDSSKQFEGTVEIKRKFAGLLKNDCNKSASGYLTDENEVGFRGFYSAHGTKLNVSTEALQKAVKLFSDIENISEETSAEVHPISLSSSKCHDSVVSMFKIENHN-DKT 620
MONKEY.PRO   QVNSSKQFEGTVGIKQKFAGLLKSDCNKSASGYLTDENEVEFRGFYSAHGVKLNVSTEALQKAVKLFSDIENISEKTSAEVDPISLSSSKFHDSVVSMFKIENHN-DKT 612
DOG.PRO      QVDSKKS-EGIIGGKQKFACLSRTSCNRSASGYSTDKNEVEFRGFYSARGTKLNVGSEALQKAKKLFSDLENINEETSVEVDR-SFSSSKYNDSV-SMIQIEDCN-DKN 649
PIG.PRO      -----------------GCFSSSKCN--------------------------------------------DSDVSI----FKVENYS-----------S-DKS 29
HAMSTER.PR   QTDDSKKFEGSAGFRQSFPCLLKSSCNKNTSSFLANVNEMEFRGFRSALGTKLSVSSEALQKAVKLFSDIESGSEETSTKVDPRALSSGARHDSGASVFKIRKQNSGKS 594
MOUSE.PRO    QTDHSKQFEGSAGVKQSFPHLLEDTCNKNTSCFLPNINEMEFGGFCSALGTKLSVSNEALRKAMKLFSDIEN-SEEPSAKVGPRGFSSSAHHDSVASVFKIKKQNTEKS 637

             SEKNNKCQLILQNNIEMTTGIFVEENTENYKRNTENEDNKYTGASRNS-NLE-SDGSDSSKNDTVYIHKDETDLPFIDQH-NICLKLSGQFMKEGNTQIKEGLSDLTCL
             670       680       690       700       710       720       730       740       750       760       770
HUMAN.PRO    SEKNNKCQLILQNNIEMTTGTFVEEITENYKRNTENEDNKYTAASRNSHNLE-FDGSDSSKNDTVCIHKDETDLLFTDQH-NICLKLSGQFMKEGNTQIKEDLSDLTFL 728
MONKEY.PRO   SEKN-KCQLMLQNNIEMTTGTFVEEITENYKINTENEDNKYTAASRNSRNLE-FVGSDSSKNDTVCIHKDEKDLPFTDQR-NICLKLSGQLMKEGNTQIKEGLSDLTFL 719
DOG.PRO      NEPNNKCRLILQNNIEMTTDIFVEEYTESYRRNTENEGNQCTDAGRNTCNSE-SDGSDSSKNDTVYIHEEENGLPCIDQH-NIDLKLFSQFMKEGNTQIKEGLSDLTCL 757
PIG.PRO      SEKYNKCQLILKNNIERTADIFVEENTDGYKRNTENKDNKCTGLASNL-GGS-WMDSASSKTDTVYMHEDETGLPFID-H-NIHLKLPNHFMKKGNTQIKEGLSDLTCL 135
HAMSTER.PR   DEKTSKCQVTLQNNTEVTTGIFVDRNPENYARNTKCEDNNSTGFQRSPYKLKNSEDSESSTSGTVSVHQDDGDLPCAADHCSKYPESCSQYVREENTQIKECVSDLTCL 704
MOUSE.PRO    DEKSSKCQVTLQNNIEMTTCIFVGRNPEKYIKNTKHEDSYTSS-QRN--NLENSDGSMSSTSGPVYIHKGDSDLP--ADQGSKCPESCTQYAREENTQIKENISDLTCL 742

             VMKAEETCHGNTSNKEQLTATKTEQNIKDFDTFDISFQTASGKNIRVSKESLNKAVNFFDQK-TTEELNNFSDSLNSELLSGINKNKMDISSHE--ETDIVKNKILKES
             780       790       800       810       820       830       840       850       860       870       880
HUMAN.PRO    VAKAQEACHGNTSNKEQLTATKTEQNIKDFETSDTFFQTASGKNISVAKESFNKIVNFFDQK--PEELHNFS--LNSELHSDIRKNKMDILSYE--ETDIVKHKILKES 832
MONKEY.PRO   VVKAQETCHGNTSNKEQLTATKTEQNIKDFETFDISFQTASGKNISVTKESFNKIVNFFDPK--PEELHNFS--LNSKLHSDIRKNKMDILSHE--ETDTVKNKILKES 823
DOG.PRO      VMKAEETSHVTMSNKQQLTA-NTGQNIKDFDTFYLSFQTASRKNIRVSRESLNKARSLLNQKWTEEELNNFSDSLNSELLPGIDIKKTDISNHEVIENTERKDKITKES 866
PIG.PRO      VMRAEETFHINTSNKQSTVN-KRSQKIKDFDVFDLSFQSASGKNIRVSKESLNKAVNFFDEKCTEEELNNFSDSSNSEILPGININKINISSHK--ETDSDKNKLLKES 242
HAMSTER.PR   VMKAEETCYIQPSDKEQLPSGKMEQNRKDFN---ISFQTASGKNVRVSEESLSKSMNILNQ--VTDESIISSDSLNSKFHCGTNNNKMGISHHK---ETTSTKKVFEER 806
MOUSE.PRO    IMKAEETC-MKSSDKKQLPSDKMEQNIKEFN---ISFQTASGKNTRVSKESLNKSVNIFNR--ETDELTVISDSLNSKILHGINKDKMHTSCHK---KAISIKKVFEDH 843
```

Fig.9B

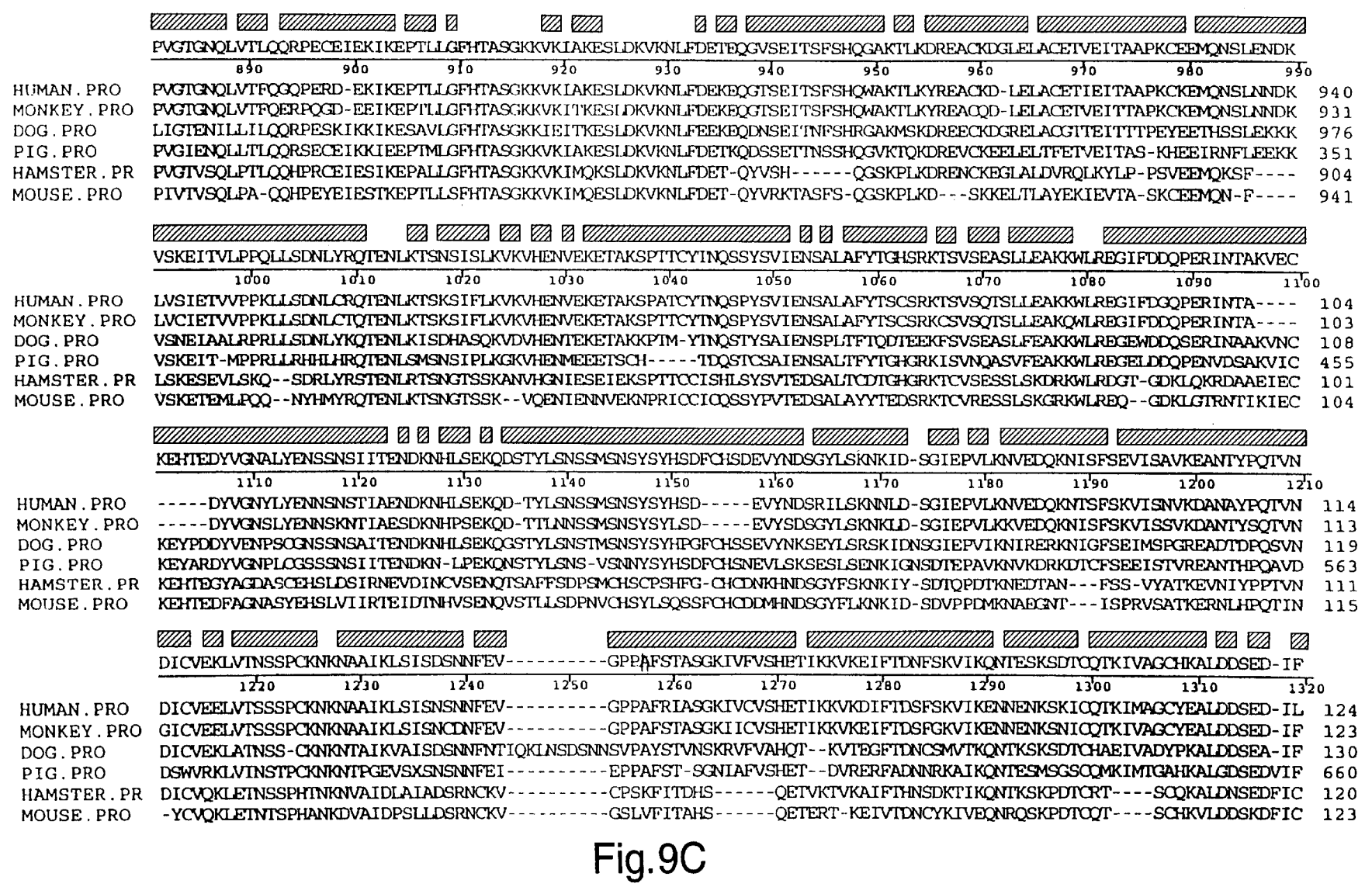

```
              PVGTGNQLVTLQQRPECEIEKIKEPTLLGFHTASGKKVKIAKESLDKVKNLFDETEQGVSEITSFSHQGAKTLKDREACKDGLELACETVEITAAPKCEEMQNSLENDK
                 890       900       910       920       930       940       950       960       970       980       990
HUMAN.PRO     PVGTGNQLVTFQGQPERD-EKIKEPTLLGFHTASGKKVKIAKESLDKVKNLFDEKEQGTSEITSFSHQWAKTLKYREACKD-LELACETIEITAAPKCKEMQNSLNNDK  940
MONKEY.PRO    PVGTGNQLVTFQERPQGD-EEIKEPTLLGFHTASGKKVKITKESLDKVKNLFDEKEQGTSEITSFSHQWAKTLKYREACQD-LELACETVEITTAPKCKEMQNSLNNDK  931
DOG.PRO       LIGTENILLILQQRPESKIKKIKESAVLGFHTASGKKIEITKESLDKVKNLFEEKEQDNSEITNFSHRGAKMSKDREECKDGRELACGITEITTTPEYEETHSSLEKKK  976
PIG.PRO       PVGIENQLLTLQQRSECEIKKIEEPTMLGFHTASGKKVKIAKESLDKVKNLFDETKQDSSETTNSSHQGVKTQKDREVCKEELELTFETVEITAS-KHEEIRNFLEEKK  351
HAMSTER.PR    PVGTVSQLPTLQQHPRCEIESIKEPALLGFHTASGKKVKIMQKSLDKVKNLFDET-QYVSH------QGSKPLKDRENCKEGLALDVRQLKYLP-PSVEEMQKSF----  904
MOUSE.PRO     PIVTVSQLPA-QQHPEYEIESTKEPTLLSFHTASGKKVKIMQESLDKVKNLFDET-QYVRKTASFS-QGSKPLKD---SKKELTLAYEKIEVTA-SKCEEMQN-F----  941

              VSKEITVLPPQLLSDNLYRQTENLKTSNSISLKVKVHENVEKETAKSPTTCYINQSSYSVIENSALAFYTGHSRKTSVSEASLLEAKKWLREGIFDDQPERINTAKVEC
                  1000      1010      1020      1030      1040      1050      1060      1070      1080      1090      1100
HUMAN.PRO     LVSIETVVPPKLLSDNLCRQTENLKTSKSIFLKVKVHENVEKETAKSPATCYTNQSPYSVIENSALAFYTSCSRKTSVSQTSLLEAKKWLREGIFDGQPERINTA----  104
MONKEY.PRO    LVCIETVVPPKLLSDNLCTQTENLKTSKSIFLKVKVHENVEKETAKSPTTCYTNQSPYSVIENSALAFYTSCSRKCSVSQTSLLEAKQWLREGIFDDQPERINTA----  103
DOG.PRO       VSNEIAALRPRLLSDNLYKQTENLKISDHASQKVDVHENTEKETAKKPTM-YTNQSTYSAIENSPLTFTQDTEEKFSVSEASLFEAKKWLREGEWDDQSERINAAKVNC  108
PIG.PRO       VSKEIT-MPPRLLRHHLHRQTENLSMSNSIPLKGKVHENMEEETSCH-----TDQSTCSAIENSALTFYTGHGRKISVNQASVFEAKKWLREGELDDQPENVDSAKVIC  455
HAMSTER.PR    LSKESEVLSKQ--SDRLYRSTENLRTSNGTSSKANVHGNIESEIEKSPTTCCISHLSYSVTEDSALTCDTGHGRKTCVSESSLSKDRKWLRDGT-GDKLQKRDAAEIEC  101
MOUSE.PRO     VSKETEMLPQQ--NYHMYRQTENLKTSNGTSSK--VQENIENNVEKNPRICCICQSSYPVTEDSALAYYTEDSRKTCVRESSLSKGRKWLREQ--GDKLGTRNTIKIEC  104

              KEHTEDYVGNALYENSSNSIITENDKNHLSEKQDSTYLSNSSMSNSYSYHSDFCHSDEVYNDSGYLSKNKID-SGIEPVLKNVEDQKNISFSEVISAVKEANTYPQTVN
                  1110      1120      1130      1140      1150      1160      1170      1180      1190      1200      1210
HUMAN.PRO     -----DYVGNYLYENNSNSTIAENDKNHLSEKQD-TYLSNSSMSNSYSYHSD-----EVYNDSRILSKNNLD-SGIEPVLKNVEDQKNTSFSKVISNVKDANAYPQTVN  114
MONKEY.PRO    -----DYVGNSLYENNSKNTIAESDKNHPSEKQD-TTLNNSSMSNSYSYLSD-----EVYSDSGYLSKNKLD-SGIEPVLKKVEDQKNISFSKVISSVKDANTYSQTVN  113
DOG.PRO       KEYPDDYVENPSCGNSSNSAITENDKNHLSEKQGSTYLSNSTMSNSYSYHPGFCHSSEVYNKSEYLSRSKIDNSGIEPVIKNIRERKNIGFSEIMSPGREADTDPQSVN  119
PIG.PRO       KEYARDYVGNPLCGSSSNSIITENDKN-LPEKQNSTYLSNS-VSNNYSYHSDFCHSNEVLSKSESLSENKIGNSDTEPAVKNVKDRKDTCFSEEISTVREANTHPQAVD  563
HAMSTER.PR    KEHTEGYAGDASCEHSLDSIRNEVDINCVSENQTSAFFSDPSMCHSCPSHFG-CHCDNKHNDSGYFSKNKIY-SDTQPDTKNEDTAN---FSS-VYATKEVNIYPPTVN  111
MOUSE.PRO     KEHTEDFAGNASYEHSLVIIRTEIDTNHVSENQVSTLLSDPNVCHSYLSQSSFCHCDDMHNDSGYFLKNKID-SDVPPDMKNAEGNT---ISPRVSATKERNLHPQTIN  115

              DICVEKLVTNSSPCKNKNAAIKLSISDSNNFEV----------GPPAFSTASGKIVFVSHETIKKVKEIFTDNFSKVIKQNTESKSDTCQTKIVAGCHKALDDSED-IF
                  1220      1230      1240      1250      1260      1270      1280      1290      1300      1310      1320
HUMAN.PRO     DICVEELVTSSSPCKNKNAAIKLSISNSNNFEV----------GPPAFRIASGKIVCVSHETIKKVKDIFTDSFSKVIKENNENKSKICQTKIMAGCYEALDDSED-IL  124
MONKEY.PRO    GICVEELVTSSSPCKNKNAAIKLSISNCDNFEV----------GPPAFSTASGKIICVSHETIKKVKEIFTDSFGKVIKENNENKSNICQTKIVAGCYEALDDSED-IF  123
DOG.PRO       DICVEKLATNSS-CKNKNTAIKVAISDSNNFNTIQKINSDSNNSVPAYSTVNSKRVFVAHQT--KVTEGFTDNCSMVTKQNTKSKSDTCHAEIVADYPKALDDSEA-IF  130
PIG.PRO       DSWVRKLVINSTPCKNKNTPGEVSXSNSNNFEI----------EPPAFST-SGNIAFVSHET--DVRERFADNNRKAIKQNTESMSGSCQMKIMTGAHKALGDSEDVIF  660
HAMSTER.PR    DICVQKLETNSSPHTNKNVAIDLAIADSRNCKV----------CPSKFITDHS------QETVKTVKAIFTHNSDKTIKQNTKSKPDTCRT----SCQKALDNSEDFIC  120
MOUSE.PRO     -YCVQKLETNTSPHANKDVAIDPSLLDSRNCKV----------GSLVFITAHS------QETERT-KEIVTDNCYKIVEQNRQSKPDTCQT----SCHKVLDDSKDFIC  123
```

Fig.9C

```
             NSLDSDECSTNSHKVFADIQSEQILQHNQSMSGLEKVSEIPPCDVSLETSDICKCSIGKLPKSVSSSNTCGIFSTASGKSVQVSDASLQKARQVFSEIEDSAKQLFSKV
                  1330      1340      1350      1360      1370      1380      1390      1400      1410      1420      1430
HUMAN.PRO    NSLDNDECSTHSHKVFADIQSEEILQHNQNMSGLEKVSKISPCDVSLETSDICKCSIGKLHKSVSSANTCGIFSTASGKSVQVSDASLQNARQVFSEIEDSTKQVFSKV 135
MONKEY.PRO   NSLDSDECSMHSHKVFADIQSDEILQHNQNMSGLEQVSKMSPCDVSLETSDICKCSIGKLPKSIPSTNTCGIFSTASGKSVQVSDASLQKARQVFSEIEDNTKQVFSKV 134
DOG.PRO      NSLGAIE-CSPSHKVFADIQSEQTSQLNQSMSGLEKVSETPPCQINSKTSDRCELPRGKLPKSVSYTNACGIFSTASGKSVQVSDAAIQKAREVFSKLEDSAKQLFPEV 141
PIG.PRO      NSPDSEEHITRSQEVFPEIQSEQILQHDPSVSGLEKVSEMPPCHINLKTFDIHKFDMKRHPMSVSSMNDCGVFSTASGKSVQVSDTALQKARQVFSKTEDVAKPFFSR- 769
HAMSTER.PR   AL--RDD-YMNSHKILFITHDEQILQHNLSVSGLEK-AQIPP--VHLETWDKCK-STRELAQAACSSHMPGIFSTASGKAVQVSDASLEKARQVFSEMDGGAKQLLSTL 130
MOUSE.PRO    SS--SGDVCINSRKDSFCPHNEQILQHNQSMSGLKK-AATPP--VGLETWDTSK-SIREPPQAAHPSRTYGIFSTASGKAIQVSDASLEKARQVFSEMDGDAKQLSSMV 134

             LKSNE-HSDQLTREENTVVHTPENLLSSQK-FS-NVVNSSAFSGFSTASGKQVSVSESALHKVKGMLEEFDLIRTEHSLQHSPTSRQDVSKILPQSCVDKRTPEHSVNS
                  1440      1450      1460      1470      1480      1490      1500      1510      1520      1530      1540
HUMAN.PRO    FKSNE-HSDQLTREENTAIRTPEHLIS-QKGFSYNVVNSSAFSGFSTASGKQVSILESSLHKVKGVLEEFDLIRTEHSLHYSPTSRQNVSKILP--RVDKRNPEHCVNS 145
MONKEY.PRO   FKSNE-HSDQLTREENTTVHTPKHLISSQKDFSYNVVNSSAFSGFSTASGKQVSISESSLHKVKGMLEEFDIIRTEHSLHYSPTSRQNVSKILP--CVDKRTPEHCVNS 145
DOG.PRO      LKDNEEHSEKFTNEENTVIYTSQNLLSS------------AFSGFRTASGKQVPVSESALCKVKGMLEEFNLIRTESCLQHSSTSRQDVSKMPPPSCIGKRTPEHSRNS 150
PIG.PRO      VKSDEEHSDKYTREENAMMHPPPNFLSS------------AFSGFSTASGKQVPVSESALCKVKGMFEEFDLMGTECRLQHSPTSRQDVSKILPLSEIDERTPEHSVSS 867
HAMSTER.PR   LESHE-QSDHSGRRENSVTHNPEDVLSLPKTFA-SNANSSVFSGFSTAGGKRVTVSESALHKVKGMLEEFDLIGTEHTLQCPPTS-EGVSKILPQYCVEKRTPEYPINS 141
MOUSE.PRO    LEGNE-KPHHSVKRENSVVHSTQGVLSLPKPLP-GNVNSSVFSGFSTAGGKLVTVSESALHKVKGMLEEFDLIRTEHTLQHSPIP-EDVSKILPQPCAEIRTPEYPVNS 144

             LEKTYSDEFSLPNNYNVESGSSENNHSIKVSPQLSQFKQDKQ-QLVLGTKVSLVENIHVLGKEQTSPENVKMEIGKTETFSDVPVKTN------YSK------------
                  1550      1560      1570      1580      1590      1600      1610      1620      1630      1640      1650
HUMAN.PRO    MEKTCSKEFKLSNNLNVEGGSSENNHSIKVSPYLSQFQQDKQ-QLVLGTKVSLVENIHVLGKEQASPKNVKMEIGKTETFSDVPVKTNIEVCSTYSKDSENYFETEAVE 156
MONKEY.PRO   MEKACSKEFNLSNNFNVEGGSSENNHSIKVSPSLSQFKQDKQ-QLVLGTKVSLVENIHVLGKEQTSPENVKMEIGKTEAFSDVPVKTNIEVCSTYSK------------ 154
DOG.PRO                                                                                                                 150
PIG.PRO      TEKAYNEQFKLPDSCNTESSSSENNHSVKVSPDLSRFKQDKQ--LVSGAKVSLVENIHPSGK-RTQTENLK                                         935
HAMSTER.PR   LQKTYDDKFSLPNNYK-ESASLGNTHSLEASPQLSQF--KQDTRLVLGTKVS------LLEKEQTFPQNIKTESGVMET                                148
MOUSE.PRO    LQKTYNDKSSLPSNYK-ESGSSGNTQSIEVSLQLSQMERNQDTQLVLGTKVSH-SKANLLGKEQTLPQNIKVKTDEMKTFSDVPVKTNVGEY--YSKESENYFETEAVE 155

             ----------------------------------------------
                  1660      1670      1680      1690
HUMAN.PRO    AKAFMEDDELTDSXLPXHATHSLFTC                                                                                      159
MONKEY.PRO   -------------D--S                                                                                               154
DOG.PRO                                                                                                                      150
PIG.PRO                                                                                                                      935
HAMSTER.PR                                                                                                                   148
MOUSE.PRO    AKAFMEDDELTDSE-QTHAKCSLFTCPQNETLFNSRTRKRRRMTVDAV                                                                160
```

Fig.9D

BRCA2 PTT primers

| Exon | Primers | PTT primer sequence | Size |
|---|---|---|---|
| 10 | JAD20F CAAAGACCACATTGGAAAGTC<br>x<br>JAD20R GCAAATGTAAGTGGTGCTTC | PTTH2 GAAACAGTTGTAGATACCTCTGAAGA | 1kb<br>approx. 37kd |
| 11 | JAD53F GATGGTACTTTAATTTTGTCAC<br>x<br>JAD13R AAATGACTCTTTGGCGACAC | PTTD2 GATTCTGAAGAACCAACTTTGTCC | 2.4kb<br>approx. 89kd |
| 11 | JAD12F AGATTTTGAGACTTCTGATAC<br>x<br>JAD1R AGCATACCAAGTCTACTGAATAAAC | PTTA GACATTCTAAGTTATGAGGA | 2.4kb<br>approx. 89kd |
| 27 | JAD43F ACATAATTATGATAGGCTACG<br>x<br>JAD45R AAGCGTCAATAATTTATTGTC | PTTJ TCTTCTCCTAATTGTGAGATA | 0.6kb<br>approx. 22kd |

Fig.10

MATERIALS AND METHODS RELATING TO THE IDENTIFICATION AND SEQUENCING OF THE BRCA2 CANCER SUSCEPTIBILITY GENE AND USES THEREOF

FIELD OF THE INVENTION

The present invention relates to the identification and sequencing of the BRCA2 cancer susceptibility gene, and to materials and methods deriving from these findings. In particular, the present invention relates to nucleic acid molecules encoding BRCA2 polypeptides, and alleles of the BRCA2 gene, including those with mutations which are associated with a predisposition to develop cancer, especially breast and ovarian cancer, and to polypeptides encoded by this nucleic acid. The present invention further relates to uses of such BRCA2 nucleic acid and BRCA2 polypeptides, in particular in the diagnostic, prognostic or therapeutic treatment of cancer.

BACKGROUND OF THE INVENTION

Over a lifetime approximately 1 in 12 women develops cancer of the breast. While a large majority of these cancers are thought to be sporadic, a proportion of breast cancer cases, often quoted at approximately 5%, is attributable to a predisposition to the disease which is transmitted as a highly penetrant autosomal dominant trait. This usually manifests as familial clustering of early onset breast cancer cases which is often associated with cancers of other organs, notably the ovary.

Abnormalities of several genes are known to confer susceptibility to breast cancer. The BRCA1 gene is located on chromosome 17q21 (1). BRCA1 encodes a 1863 aa protein which contains a RING finger domain and has little other homology to previously characterized proteins (3). Germline mutations of BRCA1 usually result in truncation or absence of the protein and hence presumed inactivation of one or more of its critical functions. BRCA1 accounts for approximately a third of families with cite specific breast cancer. A small proportion of familial breast cancers are attributable to germline mutations in the p53 gene and rare clusters of male breast cancers (4) are due to mutations in the androgen receptor. Work relating to the BRCA1 gene, methods used to isolate it and applications of the BRCA1 nucleic acid and polypeptides are disclosed in EP-A-0705902.

Using families with multiple cases of early onset breast cancer showing evidence against linkage to $BRCA_1$, the present inventors recently demonstrated the existence of a second major breast cancer susceptibility locus, BRCA2, on chromosome 13q12-q13 (5). Preliminary studies indicate that mutations in BRCA2 confer a similar risk of breast cancer to BRCA1. However, the risk of ovarian cancer appears to be lower and the risk of male breast cancer substantially higher. Together BRCA1 and BRCA2 account for three quarters of families with multiple early onset breast cancer cases, and almost all families with both breast and ovarian cancer.

SUMMARY OF THE INVENTION

Broadly, the work described in this application is based on the identification of the BRCA2 gene, and the disclosure of its sequence and the amino acid sequence of the corresponding BRCA2 polypeptides. BRCA2 alleles, including those with mutations in the normal sequence, are also disclosed.

The inventors initially found a portion of exon 16 of the BRCA2 gene and used this to sequence approximately 10% of the coding sequence. The BRCA2 cDNA sequence corresponding to this portion of the BRCA2 gene is shown in FIG. 1 (SEQ ID NO: 1), the genomic sequence of the introns and exons initially sequenced by the inventors is shown in FIG. 2 (SEQ ID NOS: 2, 5, 6, 8, 9, 11 & 12), with the translated protein sequence being shown in FIG. 3 (SEQ ID NO: 14).

Just after the identification of 10% of the coding sequence of the BRCA2 gene by the present inventors, a 900,000 bp sequence was released on the Internet on Nov. 23, 1995 and can be accessed at ftp://ftp.sanger.ac.uk/pub/human/sequences/13q and on ftp://genome/wust1.edu/pub/gsc1/brca2.

Further work by the present inventors using this sequence and other known methods isolated around 75% of the BRCA2 coding sequence. This is shown in the cDNA sequence of FIG. 4 (SEQ ID NO: 15), with the corresponding translated amino acid sequence shown in FIG. 5 (SEQ ID NO: 16). The inventors also at this time identified 6 mutations in the BRCA2 gene, most notably a mutation at 6174delT from analysis of pedigrees from Ashkenazi Jewish families from Montreal.

The full BRCA2 sequence, showing the intron and exon structure is set out in FIG. 7 (SEQ ID NO: 17–43), with the promoter region of the BRCA2 locus shown in FIG. 7. Primers suitable for amplifying the BRCA2 sequence are shown in FIG. 8 (SEQ ID NOS: 45–168) and are also published on Dec. 3, 1996 in Nature Genetics, 12:333–337, 1996.

Following the initial sequencing of the BRCA2 gene described above, and using the information contained in FIGS. 1 to 3 (SEQ ID NOS: 1–14), the skilled person could readily assemble the full length sequence of the BRCA2 gene included in the Internet sequence using the techniques described in detail below.

In a first aspect, the present invention provides a nucleic acid molecule comprising a part of the BRCA2 gene as set out in FIGS. 1 or 2 (SEQ ID NOS: 1–13), or alleles thereof.

This nucleic acid can be used to obtain the full length sequence of the BRCA2 gene. Accordingly, in a further aspect, the present invention provides a nucleic acid molecule comprising the full length coding sequence or complete BRCA2 gene as obtainable by:

(a) using the nucleic acid sequences shown in FIGS. 1 (SEQ ID NO: 1) or 2 (SEQ ID NOS: 2–13) to construct probes for screening cDNA or genomic libraries, sequencing the positive clones obtained and repeating this process to assemble the full length BRCA2 sequence from the sequences thus obtained;

(b) using the sequences shown in FIGS. 1 (SEQ ID NO: 1) or 2 (SEQ ID NO: 2–13) to obtain oligonucleotides for priming BRCA2 nucleic acid fragments, these oligonucleotides being used in conjunction with oligonucleotides designed to prime from a cloning vector, to amplify by PCR nucleic acid fragments in a library that contains fragments of the BRCA2 sequence, sequencing the amplified fragments to obtain the BRCA2 sequence between known parts of the sequence and the cloning vector, and repeating this process to assemble the full length BRCA2 sequence from the sequences thus obtained; and/or, (c) using rapid amplification of cDNA ends (RACE), by synthesizing cDNAs from a number of different tissue RNAs, the cDNAs, being ligated to an oligonucleotide linker, and amplifying by PCR the BRCA2 cDNAs using one primer that primes from the BRCA2 cDNA sequence of FIG. 1 (SEQ ID NO: 1) and a second primer that primes from the oligonucleoside linker, sequencing the amplified nucleic acid and repeating this process to assemble the full length BRCA2 sequence from the sequences thus obtained.

In a further aspect, the present invention provides a nucleic acid molecule comprising a part of the BRCA2 gene as set out in FIG. 4 (SEQ ID NO: 15), or alleles thereof. The nucleic acid of FIG. 4 (SEQ ID NO: 15) can be used in the same way as the nucleic acid set out in FIGS. 1 and 2 (SEQ ID NO: 1–13) to obtain the coding sequence of the full length BRCA2 gene.

The sequences set out in FIGS. 1, 2 and 4 (SEQ ID NOS: 1; 2–13; & 15, respectively) are believed to be a rare alternative splice of BRCA2 including nucleic acid at the 3' end of exon 16 coding for an additional 8 amino acids (ALCDVKAT). The sequence in FIG. 7 (SEQ ID NO: 44) shows what is thought to be the normal amino acid sequence of the BRCA2 polypeptide at this position. However, the presence of the alternative splice has no effect on the methodology outlined above for isolating the full length BRCA2 gene using the 10% and 75% sequences initially isolated by the present inventors.

In a further aspect, the present invention provides a nucleic acid molecule which has a nuclectide sequence encoding a BRCA2 polypeptide including the amino acid sequence set out in any one of FIGS. 3, 5 or 7.

In a further aspect, the present invention provides a nucleic acid molecule which has a nucleotide sequence encoding a polypeptide which is an allele (including mutant alleles) or variant of a BRCA2 polypeptide including the amino acid sequence set out in any one of FIG. 3, 5 or 7 (SEQ ID NOS: 14, 16, & 44, respectively). Where the nucleic acid sequence is a mutant allele sequence, preferably it includes one or more of the exemplary mutations set out in table 1. Preferred mutations from table 1 include the 6174delT and 6503delTT mutations.

In a further aspect, the present invention provides a nucleic acid molecule which has a nucleotide sequence encoding a fragment or active portion of a BRCA2 polypeptide including the amino acid sequence set out in any one of FIG. 3, 5, or 7 (SEQ ID NOS: 14, 16, & 44, respectively).

In a further aspect, the present invention provides nucleic acid encoding all or a part the BRCA2 promoter region, the nucleic acid sequence of which is set out in FIG. 6 (SEQ ID NO: 170).

In further aspects, the present invention includes replicable vectors comprising the above nucleic acid operably linked to control sequences to direct its expression, host cells transformed with these vectors, and methods of producing BRCA2 polypeptide comprising culturing the host cells and recovering the polypeptide produced.

In a further aspect, the present invention provides the above nucleic acid molecules for use in methods of medical treatment, especially in the diagnosis and therapy of cancer. Also included herein is the use of the above nucleic acid molecules in the preparation of a medicament for treating cancer. This is discussed further below.

In a further aspect, the present invention provides the use of one of the above nucleic acid sequences in the design of primers for use in the polymerase chain reaction.

In a further aspect, the present invention provides substances comprising polypeptides encoded by the above nucleic acid, or an active portions, derivatives or functional mimetics thereof.

In a further aspect, the present invention provides a method of diagnosing a susceptibility or predisposition to cancer in a patient by analysing a sample from the patient for the BRCA2 gene or the polypeptide encoded by it. By way of example, this could be carried out by:

(a) comparing the sequence of nucleic acid in the sample with the BRCA2 nucleic acid sequence to determine whether the sample from the patient contains mutations; or, (b) determining the presence in a sample from a patient of the polypeptide encoded by the BRCA2 gene as set out in the partial sequences of FIGS. 3 and 5 (SEQ ID NOS: 14 & 16 respectively) or the full length sequence set out in FIG. 7 (SEQ ID NO: 44) and, if present, determining whether the polypeptide is full length, and/or is mutated, and/or is expressed at the normal level; or, (c) using DNA fingerprinting to compare the restriction pattern produced when a restriction enzyme cuts a sample of nucleic acid from the patient with the restriction pattern obtained from normal BRCA2 gene comprising the sequence met out in FIGS. 1 (SEQ ID NO: 1), 2 (SEQ ID NOS: 2–13), 4 (SEQ ID NO: 15) or 7 (SEQ ID NOS: 17–43) or from known mutations thereof; or, (d) using a specific binding member capable of binding to a BRCA2 nucleic acid sequence (either a normal sequence or a known mutated sequence), the specific binding member comprising nucleic acid hybridisable with the BRCA2 sequence, or substances comprising an antibody domain with specificity for a native or mutated BRCA2 nucleic acid sequence or the polypeptide encoded by it, and detecting the binding of the specific binding member to its binding partner by means of a label; or, (e) using PCR involving one or more primers based on normal or mutated BRCA2 gene sequence to screen for normal or mutant BRCA2 gene in a sample from a patient.

While diagnostic methods (a)–(e) are provided as examples, other assay formats are well known in the art and will be apparent to the skilled person.

The detection of mutations in the BRCA2 gene indicates a susceptibility to cancer, especially female breast cancer, male breast cancer and ovarian cancer. Risks of other cancers; including prostate cancer, pancreatic cancer, ocular melanoma, colorectal cancer and leukaemia are also likely to be elevated in carriers of BRCA2 mutations.

BRIEF DESCRIPTION OF THE DRAWINGS

The above and further aspects of the present invention will now be further described by way of example with reference to the accompanying drawings, by way of example and not limitation. Still further aspects of the invention will be apparent to those or ordinary skill in the art.

FIG. 1 (SEQ ID NO: 1) shows the partial sequence of the BRCA2 gene obtained from a cDNA clone 14.

FIG. 2(*a*)–(*e*) (SEQ ID NOS: 2, 5, 6, 8, 9, 11, & 12) shows the sequences of the exon and introns of clone 14 where they are known.

FIG. 3 shows the translated amino acid sequence (SEQ ID NO: 14) of nucleic acid sequence shown in FIG. 1 (SEQ ID NO: 1). Of the 3 possible reading frames, the one used to translate the amino acid sequence shown in this figure is the most likely candidate as the nucleic acid obtained when the reading frame is in the other positions contains stop codons in the sequence.

FIG. 4 shows the second part of the cDNA sequence (SEQ ID NO: 15) of the BRCA2 gene isolated by the inventors, including the cDNA sequence set out in FIG. 1 (SEQ ID NO: 1).

FIG. 5(*a*)–(*d*) shows the translated amino acid sequence (SEQ ID NO: 16) of nucleic acid sequence shown in FIG. 4 (SEQ ID NO: 15), with the bold arrows over the sequence indicating the boundaries between the parts of the protein encoded by different exons in the gene.

FIG. 6 shows the sequences of the BRCA2 promoter region (SEQ ID NO: 170) with the binding sites for potential transcription factors underlined and CpG shown in bold. The promoter sequence may be of use in screening for substances which modulate the expression of the BRCA2 gene for use a therapeutics.

FIG. 7 shows the sequence of the BRCA2 gene (SEQ ID NO: 17–43), including the exon/intron structure defined by comparing the BRCA2 cDNA sequence with the genomic sequence of chromosome 13q between D13S260 and D13S171. Exons are shown in upper case with the flanking intron sequence shown in lower case. The amino acid sequence (SEQ ID NO: 44) is shown below the open reading frame from exon 2 to 26.

FIG. 8 shows primers (SEQ ID NOS: 45–168) for single stranded conformation polymorphism (SSCP) testing which have been designed to amplify the BRCA2 gene by the PCR for the identification of sequence changes in genomic DNA that may predispose to the development of breast cancer. The primers are located in the intron sequences flanking each of the 26 exons that contain the open reading frame of the gene. The amplified products include the splice site consensus sequences. Two or more sets of primers have been designed for the larger exons of the gene. The primers are labelled by: their exon number, the subsection of the exon and as forward or reverse. The PCR products range from 160 to 360 bp. The column labelled CON indicates the conditions that we have used.

The primers have been tested using a limited set of conditions which were all based on touchdown (TD) PCR where the figures indicate the first and final annealing temperature respectively. When mutations have been identified, the PCR products have been sequenced using the same primers and fluorescent cycle sequencing.

FIG. 9 shows the alignment of amino acid motifs in exon 11 of BRCA2 from different species (SEQ ID NOS: 183–189).

FIG. 10 shows exemplary primers for use in PTT assays (SEQ ID NOS: 171–182).

Figure 11:
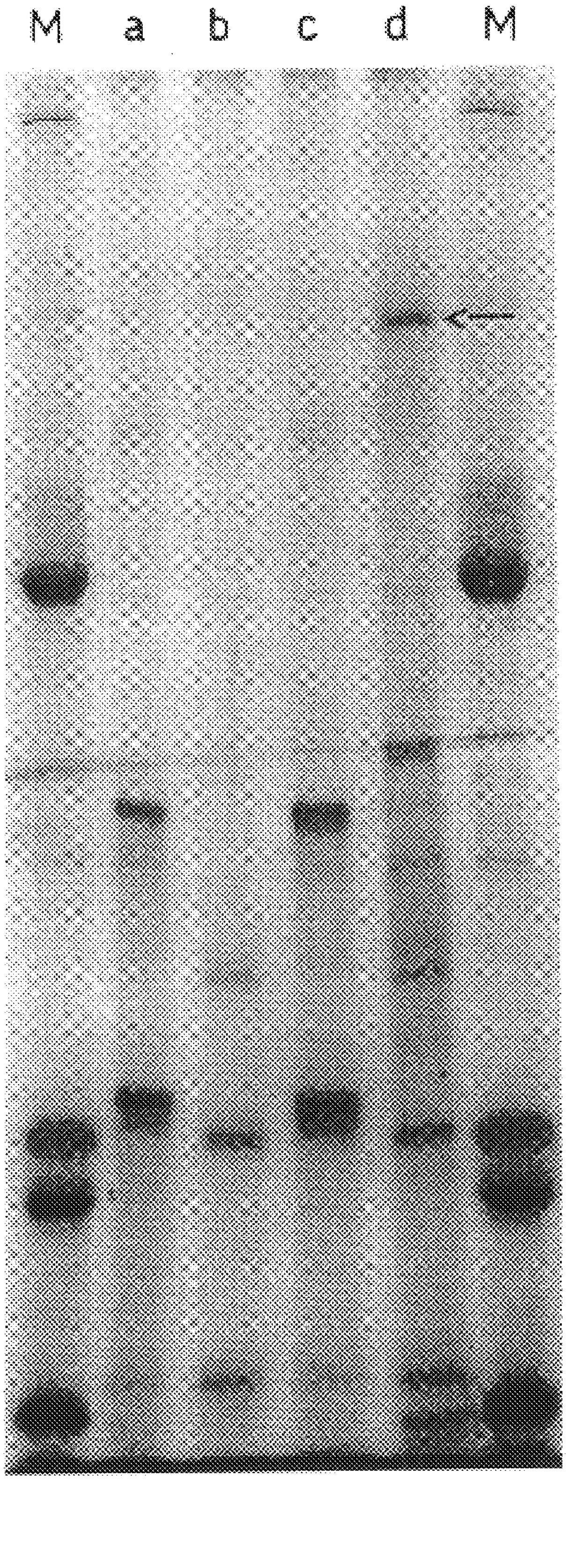

FIG. 11 shows immunoprecipitation of FLAG-tagged BRCA2 protein from COS cells transfected with expression plasmid p13120. Total cell lysates from transfected, (lanes a and b) and untransfected (lanes c and d) COS cells subjected to immunoprecipitation with anti-FLAG antibody (lanes b and d) or with a control antibody against a Golgi protein (lanes a and c). Anti-FLAG antibody immunoprecipitates a protein of approximately 400 kDa (arrow) from transfected, but not from untransfected COS cell lysate (compare lanes d and b). The control antibody does not immunoprecipitate this protein (see lane c). The strong, high molecular weight protein in the marker lanes is 220 kDa.

Figure 12:
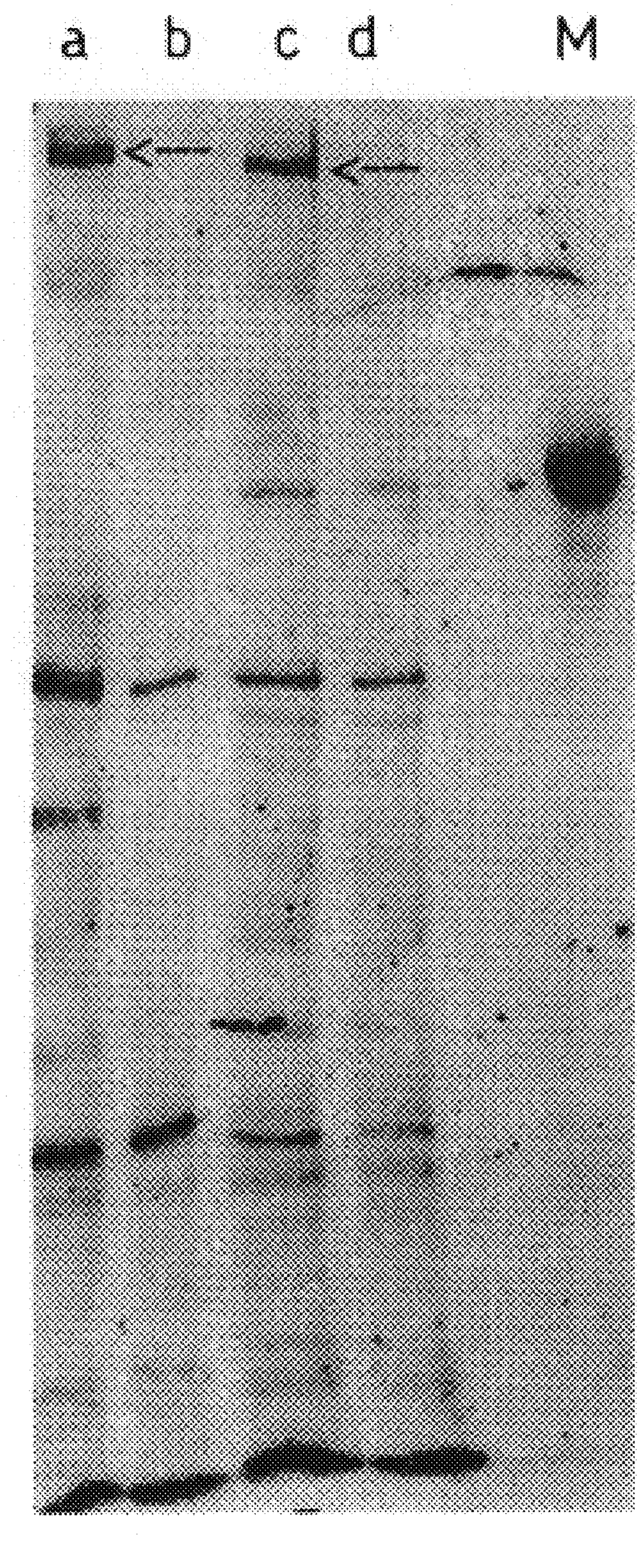

FIG. 12 shows a Western blot of FLAG-tagged BRCA2 protein. Total cell lysates of COS cells (lanes a and b) and 293T cells (lanes c and d) transfected with expression plasmid p13120 (lanes a and c) or no DNA (lanes b and d). Anti-FLAG antibody detects a protein of approximately 400 kDa (arrow) in the transfected, but not in the untransfected cell lysates. The protein in the marker lane has a molecular weight of 220 kDa.

Figure 13A:
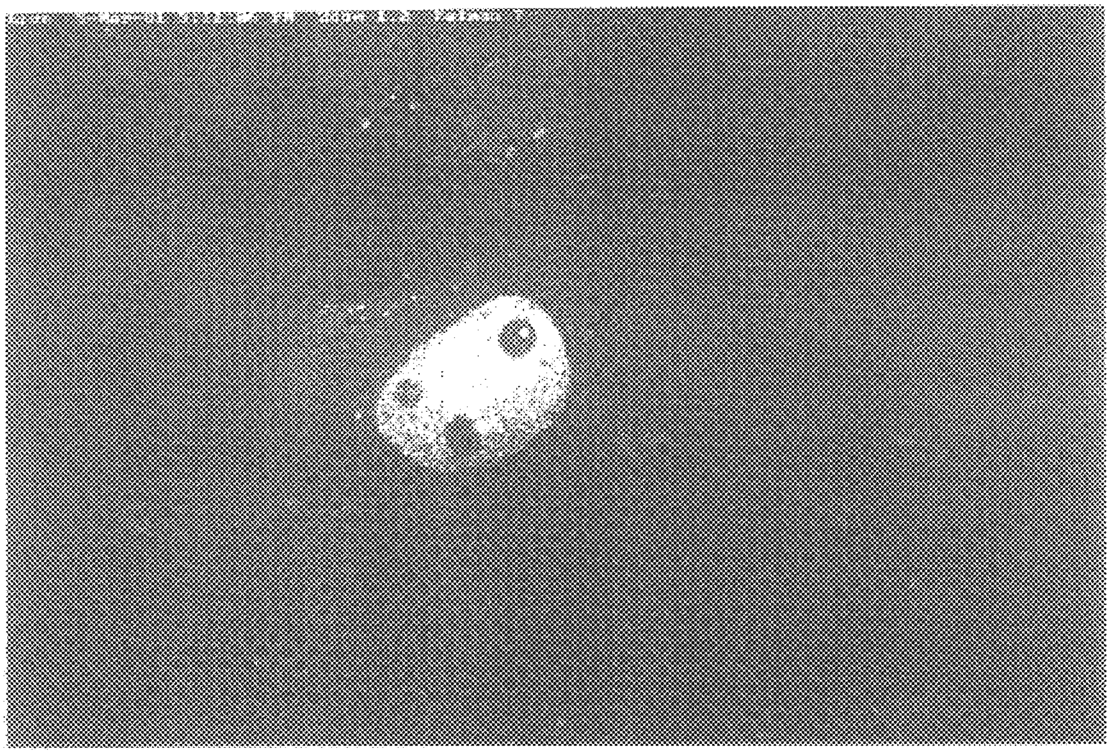
Figure 13B:
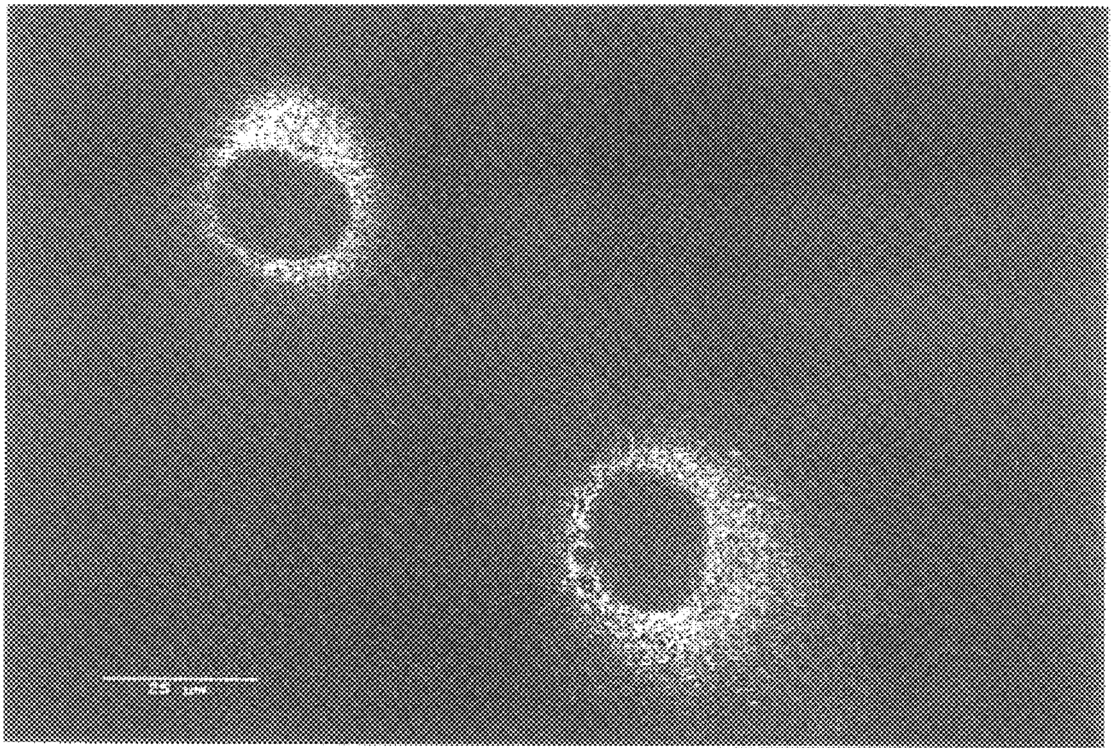

FIG. 13 shows the detection of FLAG-tagged BRCA2 protein by immunofluorescence. COS cells transfected with expression plasmid, p13120 and fixed, 48 hours later, with 4% formaldehyde, then permeablised with 0.4% Triton-X100. Anti-FLAG antibody reveals variation in the cellular localisation of FLAG-tagged BRCA2 protein. Whilst BRCA2 protein is equally distributed between the nucleus and the cytoplasm in 14% of cells, it is predominantly nuclear (A) in 42% and cytoplasmic (B) in 44% of cells (n=50). Expression in the cytoplasm appears granular, which may indicate an association with the endoplasmic reticulum. Staining is not seen in untransfected cells.

DETAILED DESCRIPTION

Preparation BRCA2 nucleic acid, and vectors and host cells incorporating the nucleic acid "BRCA2 region" refers to the portion of human chromosome 13q12-13 identified in Wooster et al (s), containing the BRCA2 locus.

The "BRCA2 locus" includes the BRCA2 gene, both the coding sequence (exons) and intervening sequences (introns), and its regulatory elements for controlling transcription and/or translation. The BRCA2 locus covers allelic variations within the locus.

The term "BRCA2 gene" or "BRCA2 nucleic acid" includes normal alleles of the BRCA2 gene, both silent alleles having no effect on the amino acid sequence of the BRCA2 polypeptide and alleles leading to amino acid sequence variants of BRCA2 polypeptide that do not substantially affect its function. These terms also includes alleles having one or more mutations that are linked to a predisposition to develop cancer, especially male and female breast cancer or ovarian cancer. A mutation may be a change in the BRCA2 nucleic acid sequence which produces a deleterious change in the amino acid sequence of the BRCA2 polypeptide, resulting in partial or complete loss of BRCA2 function, or may be a change in the nucleic acid sequence which results in the loss of effective BRCA2 expression or the production of aberrant forms of the BRCA2 polypeptide. Examples of such mutations are shown in table 1. Alleles including such mutations are also known in the art as susceptibility alleles.

The BRCA2 nucleic acid may be that shown in FIGS. 1 (SEQ ID NO: 1), 2 (SEQ ID NOS: 2–13), 4 (SEQ ID NO: 15) or 7 (SEQ ID NOS: 17–43), or it may be an allele as described above, or a variant or derivative, differing from that shown by a change which is one or more of addition, insertion, deletion and substitution of one or more nucleotides of the sequence shown. Changes to a nucleotide sequence may result in an amino acid change at the protein level, or not, as determined by the genetic code.

Thus, nucleic acid according to the present invention may include a sequence different from the sequence shown in FIGS. 1 (SEQ ID NO: 1), 2 (SEQ ID NOS: 2–13), 4 (SEQ ID NO: 15) or 7 (SEQ ID NOS: 17–43) yet encode a polypeptide with the same amino acid sequence. The amino acid sequence shown in FIG. 7 consists of 3418 residues (SEQ ID NO: 44).

On the other hand, the encoded polypeptide may comprise an amino acid sequence which differs by one or more amino acid residues from the amino acid sequence shown in FIGS. 3, 5 or 7 (SEQ ID NOS: 14, 16, & 44, respectively). Nucleic acid encoding a polypeptide which is an amino acid sequence variant, derivative or allele of the sequence shown in FIGS. 3, 5 or 7 (SEQ ID NOS: 14, 16, & 44) is further provided by the present invention. Such polypeptides are discussed below. Nucleic acid encoding such a polypeptide may show greater than about 60% homology with the coding sequence shown in FIGS. 1 (SEQ ID NO: 1), 2 (SEQ ID NOS: 2–13), 4 (SEQ ID NO: 15) or 7 (SEQ ID NOS: 17–43) greater than about 70% homology, greater than about 80% homology, greater than about 90% homology or greater than about 95% homology.

Particular mutant alleles of the present invention are set out in table 1, using the nomenclature first proposed in (8). These mutations are generally associated with the production of truncated forms of the BRCA2 gene product. These have been shown by the experimental work described herein to be associated with susceptibility to male and female breast cancer and/or ovarian cancer. Implications for screening, e.g. for diagnostic or prognostic purposes, are discussed below.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA. Where nucleic acid according to the invention includes RNA, reference to the sequence shown should be construed as reference to the RNA equivalent, with U substituted for T.

Nucleic acid sequences encoding all or part of the BRCA2 gene and/or its regulatory elements can be readily prepared by the skilled person using the information and references contained herein and techniques known in the art (for example, see Sambrook, Fritsch and Maniatis, Molecular Cloning, A Laboratory Manual, Cold Spring harbor Laboratory Press, 1989, and Ausubel et al, Short Protocols in Molecular Biology, John Wiley and Sons, 1992). These techniques include (i) the use of the polymerase chain reaction (PCR) to amplify samples of such nucleic acid, e.g. from genomic sources, (ii) chemical synthesis, or (iii) preparing cDNA sequences. Modifications to the BRCA2 sequences can be made, e.g. using site directed mutagenesis, to provide expression of modified BRCA2 polypeptide or to take account of codon preference in the host cells used to express the nucleic acid.

In order to obtain expression of the BRCA2 nucleic acid sequences, the sequences can be incorporated in a vector having control sequences operably linked to the BRCA2 nucleic acid to control its expression. The vectors may include other sequences such as promoters or enhancers to drive the expression of the inserted nucleic acid, nucleic acid sequences so that the BRCA2 polypeptide is produced as a fusion and/or nucleic acid encoding secretion signals so that the polypeptide produced in the host cell is secreted from the cell. BRCA2 polypeptide can then be obtained by transforming the vectors into host cells in which the vector is functional, culturing the host cells so that the BRCA2 polypeptide in produced and recovering the BRCA2 polypeptide from the host cells or the surrounding medium. Prokaryotic and eukaryotic cells are used for this purpose in the art, including strains of *E. coli,* yeast, and eukaryotic cells such as COS or CHO cells. The choice of host cell can be used to control the properties of the BRCA2 polypeptide expressed in those cells, e.g. controlling where the polypeptide is deposited in the host cells or affecting properties such as its glycosylation.

PCR techniques for the amplification of nucleic acid are described in U.S. Pat. No. 4,683,195. In general, such techniques require that sequence information from the ends of the target sequence is known to allow suitable forward and reverse oligonucleotide primers to be designed to be identical or similar to the polynucleotide sequence that is the target for the amplification. PCR comprises steps of denaturation of template nucleic acid (if double-stranded), annealing of primer to target, and polymerisation. The nucleic acid probed or used as template in the amplification reaction may be genomic DNA, cDNA or RNA. PCR can be used to amplify specific sequences from genomic DNA, specific RNA sequences and cDNA transcribed from mRNA, bacteriophage or plasmid sequences. The BRCA2 nucleic acid sequences provided herein readily allow the skilled parson to design PCR primers, see for example FIG. 8 (SEQ ID NOS: 45–168). References for the general use of PCR techniques include Mullis et al, Cold Spring Harbor Symp. Quant. Biol., 51:263, (1987), Ehrlich (ed), PCR technology, Stockton Press, NY, 1989, Ehrlich et al, Science, 252:1643–1650, (1991), PCR protocols; A Guide to Methods and Applications, Eds. Innis et al, Academic Press, New York, (1990).

Also included within the scope of the invention are antisense oligonucleotide sequences based on the BRCA2 nucleic acid sequences described herein. Antisense oligonucleotides may be designed to hybridise to the complementary sequence of nucleic acid, pre-mRNA or mature mRNA, interfering with the production of polypeptide encoded by a given DNA sequence (e.g. either native BRCA2 polypeptide or a mutant form thereof), go that its expression is reduce or prevented altogether. In addition to the BRCA2 coding sequence, antisense techniques can be used to target the control sequences of the BRCA2 gene, e.g. in the 5' flanking sequence of the BRCA2 coding sequence, whereby the antisense oligonucleotides can interfere with BRCA2 control sequences. The construction of antisense sequences and their use is described in Peyman and Ulman, Chemical Reviews, 90:543–584, (1930), Crooke, Ann. Rev. Pharmacol. Toxicol., 32:329–376, (1992), and Zamecnik and Stephenson, P.N.A.S, 75:280–284, (1974).

The nucleic acid sequences provided in FIGS. 1 (SEQ ID NO: 1), 2 (SEQ ID NOS: 2–13), 4 (SEQ ID NO: 15) and 7 (SEQ ID NOS: 17–43) are useful for identifying nucleic acid of interest (and which may be according to the present invention) in a test sample. The present invention provides a method of obtaining nucleic acid of interest, the method including hybridisation of a probe having the sequence shown in FIGS. 1 (SEQ ID NO: 1), 2 (SEQ ID NOS: 2–13), 4 (SEQ ID NO: 15) or 7 (SEQ ID NOS: 17–43) or a complementary sequence, to target nucleic acid.

Hybridisation is generally followed by identification of successful hybridization and isolation of nucleic acid which has hybridised to the probe, which may involve one or more steps of PCR.

Nucleic acid according to the present invention is obtainable using one or more oligonucleotide probes or primers designed to hybridize with one or more fragments of the nucleic acid sequence shown in FIGS. 1 (SEQ ID NO: 1), 2 (SEQ ID NOS: 2–13), 4 (SEQ ID NO: 15) or 7 (SEQ ID NOS: 17–43), particularly fragments of relatively rare sequence, based on codon usage or statistical analysis. A primer designed to hybridize with a fragment of the nucleic acid sequence shown in the above figures may be used in conjunction with one or more oligonucleotides designed to hybridize to a sequence in a cloning vector within which target nucleic acid has been cloned, or in so-called "RACE" (rapid amplification of cDNA ends) in which cDNA's in a library are ligated to an oligonucleotide linker and PCR is performed using a primer which hybridizes with the sequence shown in FIGS. 1 (SEQ ID NO: 1), 2 (SEQ ID NOS: 2–13), 4 (SEQ ID NO: 15) or 7 (SEQ ID NOS: 17–43) and a primer which hybridises to the oligonucleotide linker.

Such oligonucleotide probes or primers, as well as the full-length sequence (and alleles, variants and derivatives) are also useful in screening a test sample containing nucleic acid for the presence of alleles and variants, especially those that confer susceptibility or predisposition to cancers, the probes hybridizing with a target sequence from a sample obtained from the individual being tested. The conditions of the hybridisation can be controlled to minimise non-specific binding, and preferably stringent to moderately stringent hybridisation conditions are preferred. The skilled person is readily able to design such probes, label them and devise suitable conditions for the hybridization reactions, assisted by textbooks such as Sambrook et al (1989) and Ausubel et al (1992).

As well as determining the presence of polymorphisms or mutations in the BRCA2 sequence, the probes may also be used to determine whether mRNA encoding BRCA2 is present in a cell or tissue.

Nucleic acid isolated and/or purified from one or more cells (e.g. human) or a nucleic acid library derived from nucleic acid isolated and/or purified from cells (e.g. a cDNA library derived from mRNA isolated from the cells), may be probed under conditions for selective hybridization and/or subjected to a specific nucleic acid amplification reaction such as the polymerase chain reaction (PCR).

In the context of cloning, it may be necessary for one or more gene fragments to be ligated to generate a full-length coding sequence. Also, where a full-length encoding nucleic acid molecule has not been obtained, a smaller molecule representing part of the full molecule, may be used to obtain full-length clones. Inserts may be prepared from partial cDNA clones and used to screen cDNA libraries. The full-length clones isolated may be subcloned into expression vectors and activity assayed by transfection into suitable host cells, e.g. with a reporter plasmid.

A method may include hybridisation of one or more (e.g. two) probes or primers to target nucleic acid. Where the nucleic acid is double-stranded DNA, hybridisation will generally be preceded by denaturation to produce single-stranded DNA. The hybridization may be as part of a PCR procedure, or as part of a probing procedure not involving PCR. An example procedure would be a combination of PCR and low stringency hybridisation. A screening procedure, chosen from the many available to those skilled in the art, is used to identify successful hybridization events and isolated hybridised nucleic acid.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RNAase cleavage and allele specific oligonucleotide probing.

Probing may employ the standard southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and minding determined. DNA for probing may be prepared from RNA preparations from cells.

Preliminary experiments may be performed by hybridizing under low stringency conditions various probes to Southern blots of DNA digested with restriction enzymes. Suitable conditions would be achieved when a large number of hybridizing fragments were obtained while the background hybridisation was low. Using these conditions nucleic acid libraries, e.g. cDNA libraries representative of expressed sequences, may be searched.

Those skilled in the art are well able to employ suitable conditions of the desired stringency for selective hybridization, taking into account factors such as oligonucleotide length and base composition, temperature and so on.

On the basis of amino acid sequence information, oligonucleotide probes or primers may be designed, taking into account the degeneracy of the genetic code, and, where appropriate, codon usage of the organism from the candidate nucleic acid is derived. An oligonucleotide for use in nucleic acid amplification may have about 10 or fewer codons (e.g. 6, 7 or 8), i.e. be about 30 or fewer nucleotides in length (e.g. 18, 21 or 24). Generally specific primers are upwards of 14 nucleotides in length, but not more than 18–20. Those skilled in the art are well versed in the design of primers for use processes such as PCR.

A further aspect of the present invention provides an oligonucleotide or polynucleotide fragment of the nucleotide sequence shown in FIG. 1 (SEQ ID NO: 1), 2 (SEQ ID NOS: 2–13), 4 (SEQ ID NO: 15) or 7 (SEQ ID NOS: 17–43), or a complementary sequence, in particular for use in a method of obtaining and/or screening nucleic acid. The sequences referred to above may be modified by addition, substitution, insertion or deletion of one or more nucleotides, but preferably without abolition of ability to hybridise selectively with nucleic acid with the sequence shown in FIGS. 1 (SEQ ID NO: 1), 2 (SEQ ID NOS: 2–13), 4 (SEQ ID NO: 15) or 7 (SEQ ID NOS: 17–43), that is wherein the degree of homology of the oligonucleotide or polynucleotide with one of the sequences given is sufficiently high.

In some preferred embodiments, oligonucleotides according to the present invention that are fragments of any of the sequences shown in FIGS. 1 (SEQ ID NO: 1), 2 (SEQ ID NOS: 2–13), 4 (SEQ ID NO: 15) or 7 (SEQ ID NOS: 17–43), or any allele associated with cancer susceptibility, are at least about 10 nucleotides in length, more preferably at least about 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with determining the presence in a test sample of a sequence indicative of cancer susceptibility.

Methods involving use of nucleic acid in diagnostic and/or prognostic contexts, for instance in determining susceptibility to cancer, and other methods concerned with determining the presence of sequences indicative of cancer susceptibility are discussed below.

Nucleic acid according to the present invention may be used in methods of gene therapy, for instance in treatment of individuals with the aim of preventing or curing (wholly or partially) cancer. This too is discussed below.

Nucleic acid according to the present invention, such as a full-length coding sequence or oligonucleotide probe or primer, may be provided as part of a kit, e.g. in a suitable container such as a vial in which the contents are protected from the external environment. The kit may include instructions for use of the nucleic acid, e.g. in PCR and/or a method for determining the presence of nucleic acid of interest in a test sample. A kit wherein the nucleic acid is intended for use in PCR may include one or more other reagents required for the reaction, such as polymerase, nucleotides, buffer solution ate. The nucleic acid may be labelled. A kit for use in determining the presence or absence of nucleic acid of interest may include one or more articles and/or reagents for performance of the method, such as means for providing the test sample itself, e.g. a swab for removing cells from the buccal cavity or a syringe for removing a blood sample (such components generally being sterile). In a further aspect, the present invention provides an apparatus for screening BRCA2 nucleic acid, the apparatus comprising storage means including the BRCA2 nucleic acid sequence as set out in any one of FIGS. 1 (SEQ ID NO: 1), 2 (SEQ ID NOS: 2–13), 4 (SEQ ID NO: 15) or 7 (SEQ ID NOS: 17–43), the stored sequence being used to compare the sequence of the test nucleic acid to determine the presence of mutations.

A convenient way of producing a polypeptide according to the present invention is to express nucleic acid encoding it, by use of the nucleic acid in an expression system. The use of expression system has reached an advanced degree of sophistication today.

Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow expression of the polypeptide. Polypeptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli.*

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage, or phagemid, as appropriate. For further details see, for example, Molecular cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into calls and gene expression, and analysis of proteins, are described in detail in Current Protocols in Molecular Biology, Ausubel et al. eds., John Wiley & Sons, 1992.

Thus, a further aspect of the present invention provides a host cell containing nucleic acid as disclosed herein. The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal Leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipient, vehicles or carriers (e.g. see below).

Introduction of nucleic acid may take place in vivo by way of gene therapy, as discussed below.

A host cell containing nucleic acid according to the present invention, e.g. as a result of introduction of the nucleic acid into the cell or into an ancestor of the cell and/or genetic alteration of the sequence endogenous to the cell or ancestor (which introduction or alteration may take place in vivo or ex vivo), may be comprised (e.g. in the soma) within an organism which is an animal, particularly a mammal, which may be human or non-human, such as rabbit, guinea pig, rat, mouse or other rodent, cat, dog, pig, sheep, goat, cattle or horse, or which is a bird, such as a chicken. Genetically modified or transgenic animals or birds comprising such a cell are also provided as further aspects of the present invention.

This may have a therapeutic aim. (Gene therapy is discussed below.) The presence of a mutant, allele or variant sequence within cells of an organism, particularly when in place of a homologous endogenous sequence, may allow the organism to be used as a model in testing and/or studying the role of the BRCA2 gene or substances which modulate activity of the encoded polypeptide in vitro or the promoter sequence shown in FIG. 6 (SEQ ID NO: 170) are otherwise indicated to be of therapeutic potential.

Instead of or as well as being used for the production of a polypeptide encoded by a transgene, host cells may be used as a nucleic acid factory to replicate the nucleic acid of interest in order to generate large amounts of it. Multiple copies of nucleic acid of interest may be made within a cell when coupled to an amplifiable gene such as DHFR. Host calls transformed with nucleic acid of interest, or which are descended from host cells into which nucleic acid was introduced, may be cultured under suitable conditions, e.g. in a fermenter, taken from the culture and subjected to processing to purify the nucleic acid. Following purification, the nucleic acid or one or more fragments thereof may be used as desired, for instance in a diagnostic or prognostic assay as discussed elsewhere herein.

Production of BRCA2 Polypeptides

The skilled person can use the techniques described herein and others well known in the art to produce large amounts of the BRCA2 polypeptide, or fragments or active portion thereof, for use as pharmaceuticals, in the developments of drugs and for further study into its properties and role in vivo. Experimental work confirming the production of BRCA2 polypeptide is set out in example 3 below.

Thus, a further aspect of the present invention provides a polypeptide which has the amino acid sequence shown in FIGS. 3, 5 or 7 (SEQ ID NOS: 14, 16, & 44, respectively), which may be in isolated and/or purified form, free or substantially free of material with which it is naturally associated, such as other polypeptides or such as human polypeptides other than BRCA2 polypeptide or (for example if produced by expression in a prokaryotic cell) lacking in native glycosylation, e.g. unglycosylated.

Polypeptides which are amino acid sequence variant, alleles or derivatives are also provided by the present invention. A polypeptide which is a variant, allele, or derivative may have an amino acid sequence which differs from that given in FIGS. 3, 5 or 7 (SEQ ID NOS: 14, 16, & 44 respectively) by one or more of addition, substitution, deletion and insertion of one or more amino acids. Preferred such polypeptides have BRCA2 function, that is to say have one or more of the following properties: immunological cross-reactivity with an antibody reactive the polypeptide for which the sequence is given in FIGS. 3, 5 or 7 (SEQ ID NOS: 14, 16, & 44, respectively); sharing an epitope with the polypeptide for which the amino acid sequence is shown in FIGS. 3, 5 or 7 (SEQ ID NOS: 14, 16, &44, respectively) (as determined for example by immunological cross-reactivity between the two polypeptides.

A polypeptide which is an amino acid sequence variant, or allele. derivative of the amino acid sequence shown in FIGS. 3, 5, or 7 (SEQ ID NOS: 14, 16, & 44, respectively) may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. The sequence may share greater than about 60% similarity, greater than about 70% similarity, greater than about 80% similarity or greater than about 90% similarity with the amino acid sequence shown in any one of FIGS. 3, 5 or 7 (SEQ ID NOS: 14, 16, & 44, respectively). Particular amino acid sequence variants may differ from those shown in FIGS. 3, 5 or 7 (SEQ ID NOS: 14, 16, & 44, respectively) by insertion, addition, substitution or deletion of 1 amino acid, 2, 3, 4, 5–10, 10–20 20–30, 30–50 , 50–100, 100–150, or more than 150 amino acids.

By way of example, mutation variants representative of preferred embodiments of the present invention are shown in table 1. Screening for the presence of one or more of these in a test sample has a diagnostic and/or prognostic use, for instance in determining cancer susceptibility, as discussed below.

The present invention also includes active portions, fragments, derivatives and functional mimetics of the BRCA2 polypeptides of the invention.

An "active portion" of BRCA2 polypeptide means a peptide which is less than said full length BRCA2 polypeptide, but which retains its essential biological activity.

A "fragment" of the BRCA2 polypeptide means a stretch of amino acid residues of at least about five to seven contiguous amino acids, often at least about seven to nine contiguous amino acids, typically at least about nine to 13 contiguous amino acids and, moat preferably, at least about 20 to 30 or more contiguous amino acids. Fragments of the BRCA2 polypeptide sequence antigenic determinants or epitopes useful for raising antibodies to a portion of the BRCA2 amino acid sequence.

A "derivative" of the BRCA2 polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, without fundamentally altering the essential activity of the wild type BRCA2 polypeptide.

"Fuctional mimetic" means a substance which may not contain an active portion of the BRCA2 amino acid sequence, and probably is not a peptide at all, but which retains the essential biological activity of natural BRCA2 polypeptide. The design and screening of candidate mimetics is described in detail below.

A polypeptide according to the present invention may be isolated and/or purified (e.g. using an antibody) for instance after production by expression from encoding nucleic acid (for which see below). Polypeptides according to the present invention may also be generated wholly or partly by chemical synthesis. The isolated and/or purified polypeptide may be used in formulation of a composition, which may include at least one additional component, for example a pharmaceutical composition including a pharmaceutically acceptable excipient, vehicle or carrier. A composition including a polypeptide according to the invention may be used in prophylactic and/or therapeutic treatment as discussed below.

A polypeptide, peptide fragment, allele, or variant according to the present invention may be used as an immunogen or otherwise in obtaining specific antibodies. Antibodies are useful in purification and other manipulation of polypeptides and peptides, diagnostic screening and therapeutic contexts. This is discussed further below.

A polypeptide according to the present invention may be used in screening for molecules which affect or modulate its activity or function. Such molecules may be useful in a therapeutic (possibly including prophylactic) context.

Production of BRCA2 Antibodies

A further important use of the BRCA2 polypeptides is in raising antibodies that have the property of specifically binding to the BRCA2 polypeptides, or fragments or active portions thereof.

The production of monoclonal antibodies is well established in the art. Monoclonal antibodies can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-239400. A hybridoma producing a monoclonal antibody may be subject to genetic mutation or other changes, which may or may not alter the binding specificity of antibodies produced.

The provision of the novel BRCA2 polypeptides enables for the first time the production of antibodies able to bind it specifically. Accordingly, a further aspect of the present invention provides an antibody able to bind specifically to the polypeptide whose sequence is given in FIGS. 3, 5 or 7 (SEQ ID NOS: 14, 16, & 44, respectively). Such an antibody may be specific in the sense of being able to distinguish between the polypeptide it is able to bind and other human polypeptides for which it has no or substantially no binding affinity (e.g. a binding affinity of about 1000× worse). specific antibodies bind an epitope on the molecule which is either not present or is not accessible on other molecules. Antibodies according to the present invention may be specific for the wild-type polypeptide. Antibodies according to the invention may be specific for a particular variant, allele or derivative polypeptide as between that molecule and the wild-type BRCA2 polypeptide, so as to be useful in diagnostic and prognostic methods as discussed below. Antibodies are also useful in purifying the polypeptide or polypeptides to which they bind, e.g. following production by recombinant expression from encoding nucleic acid.

Preferred antibodies according to the invention are isolated, in the sense of being free from contaminants such as antibodies able to bind other polypeptides and/or free of serum components. Monoclonal antibodies are preferred for some purposes, though polyclonal antibodies are within the scope of the present invention.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al, nature, 357:80–82, 1992). Isolation of antibodies and/or antibody-producing calls from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Humanised antibodies in which CDRs from a non-human source are grafted onto human framework regions, typically with the alteration of some of the framework amino acid residues, to provide antibodies which are less immunogenic than the parent non-human antibodies, are also included within the present invention.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a call capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyze reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge.

Antibodies according to the present invention may be used in screening for the presence of a polypeptide, for example in a test sample containing cells or cell lysate as discussed, and may be used in purifying and/or isolating a polypeptide according to the present invention, for instance following production of the polypeptide by expression from encoding nucleic acid therefor. Antibodies may modulate the activity of the polypeptide to which they bind and so, if that polypeptide has a deleterious effect in an individual, may be useful in a therapeutic context (which may include prophylaxis).

An antibody may be provided in a kit, which may include instructions for use of the antibody, e.g. in determining the presence of a particular substance in a test sample. One or more other reagents may be included, such as labelling molecules, buffer solutions, elutants and so on. Reagents may be provided within containers which protect them from the external environment, such as a sealed vial.

Diagnostic Methods

A number of methods are known in the art for analysing biological samples from individuals to determine whether the individual carries a BRCA2 allele predisposing them to cancer, especially breast cancer (female or male) or ovarian cancer. The purpose of such analysis may be used for diagnosis or prognosis, and serve to detect the presence of an existing cancer, to help identify the type of cancer, to assist a physician in determining the severity or likely course of the cancer and/or to optimize treatment of it. Alternatively, the methods can be used to detect BRCA2 alleles that are statistically associated with a susceptibility to cancer in the future, e.g. early onset breast cancer, identifying individuals who would benefit from regular screening to provide early diagnosis of cancer. Examples of methods of screening for BRCA2 mutations are set out in example 5 below.

Broadly, the methods divide into those screening for the presence of BRCA2 nucleic acid sequences or alleles or variants thereof, and those that rely on detecting the presence or absence of the BRCA2 polypeptide. The methods make use of biological samples from individuals that are suspected of contain the nucleic acid sequences or polypeptide. Examples of biological samples include blood, plasma, serum, tissue samples, tumour samples, saliva and urine.

Exemplary approaches for detecting BRCA2 nucleic acid or polypeptides include:

(a) comparing the sequence of nucleic acid in the sample with the BRCA2 nucleic acid sequence to determine whether the sample from the patient contains mutations; or, (b) determining the presence in a sample from a patient of the polypeptide encoded by the BRCA2 gene and, if present, determining whether the polypeptide is full length, and/or is mutated, and/or is expressed at the normal level; or, (c) using DNA fingerprinting to compare the restriction pattern produced when a restriction enzyme cuts a sample of nucleic acid from the patient with the restriction pattern obtained from normal BRCA2 gene or from known mutations thereof; or, (d) using a specific binding member capable of binding to a BRCA2 nucleic acid sequence (either a normal sequence or a known mutated sequence), the specific binding member comprising nucleic acid hybridisable with the BRCA2 sequence, or substances comprising an antibody domain with specificity for a native or mutated BRCA2 nucleic acid sequence or the polypeptide encoded by it, the specific binding member being labelled so that binding of the specific binding member to its binding partner is detectable; or, (e) using PCR involving one or more primers based on normal or mutated BRCA2 gene sequence to screen for normal or mutant BRCA2 gene in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, molecules and receptors and complementary nucleotide sequences. The skilled person will be able to think of many other examples and they do not need to be listed here. Further, the term "specific binding pair" is also applicable where either or both of the specific binding member and the binding partner comprise a part of a larger molecule. In embodiments in which the specific binding pair are nucleic acid sequences, they will be of a length to hybridize to each other under the conditions of the assay, preferably greater than 10 nucleotides long, more preferably greater than 15 or 20 nucleotides long.

In most embodiments for screening for BRCA2 susceptibility alleles, the BRCA2 nucleic acid in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

The identification of the BRCA2 gene and its association with cancer paves the way for aspects of the present invention to provide the use of materials and methods, such as are disclosed and discussed above, for establishing the presence or absence in a test sample of an variant form of the gene, in particular an allele or variant specifically associated with cancer, especially breast and ovarian cancer. This may be for diagnosing a predisposition of an individual to cancer. It may be for diagnosing cancer of a patient with the disease as being associated with the gene.

This allows for planning of appropriate therapeutic and/or prophylactic treatment, permitting streamlining of treatment by targeting those most likely to benefit.

A variant form of the gene may contain one or more insertions, deletions, substitutions and/or additions of one or more nucleotides compared with the wild-type sequence (such as shown in table 1) which may or may not disrupt the gene function. Differences at the nucleic acid level are not necessarily reflected by a difference in the amino acid sequence of the encoded polypeptide. However, a mutation or other difference in a gene may result in a frame-shift or stop codon, which could seriously affect the nature of the polypeptide produced (if any), or a point mutation or gross mutational change to the encoded polypeptide, including insertion, deletion, substitution and/or addition of one or more amino acids or regions in the polypeptide. A mutation in a promoter sequence or other regulatory region may prevent or reduce expression from the gene or affect the processing or stability of the mRNA transcript.

There are various methods for determining the presence or absence in a test sample of a particular nucleic acid sequence, such as the sequence shown in FIGS. 1 (SEQ ID NO: 1), 2(SEQ ID NOS: 2–13), 4 (SEQ ID NO: 15) or 7 (SEQ ID NOS: 17–43) or a variant or allele thereof.

Tests may be carried out on preparations containing genomic DNA, cDNA and/or mRNA. Testing cDNA or mRNA has the advantage of the complexity of the nucleic acid being reduced by the absence of intron sequences, but the possible disadvantage of extra time and effort being required in making the preparations. RNA is more difficult to manipulate then DNA because of the wide-spread occurrence of RN'ases.

Nucleic acid in a test sample may be sequenced and the sequence compared with the sequence shown in FIGS. 1 (SEQ ID NO: 1), 2 (SEQ ID NOS: 2–13), 4 (SEQ ID NO: 15) or 7 (SEQ ID NOS: 17–43), to determine whether or not a difference is present. If so, the difference can be compared with known susceptibility alleles (e.g. as summarised in table 1) to determine whether the test nucleic acid contains one or more of the variations indicated, or the difference can be investigated for association with cancer.

Since it will not generally be time- or labour-efficient to sequence all nucleic acid in a test sample or even the whole BRCA2 gene, a specific amplification reaction such as PCR using one or more pairs of primers may be employed to amplify the region of interest in the nucleic acid, for instance the BRCA2 gene or a particular region in which mutations associated with cancer susceptibility occur. Exemplary primers for this purpose are shown in FIG. 8 (SEQ ID NOS: 45–168). The amplified nucleic acid may then be sequenced as above, and/or tested in any other way to determine the presence or absence of a particular feature. Nucleic acid for testing may be prepared from nucleic acid removed from cells or in a library using a variety of other techniques such as restriction enzyme digest and electrophoresis.

Nucleic acid may be screened using a variant- or allele-specific probe. Such a probe corresponds in sequence to a region of the BRCA2 gene, or its complement, containing a sequence alteration known to be associated with cancer susceptibility. Under suitably stringent conditions, specific hybridization of such a probe to test nucleic acid is indicative of the presence of the sequence alteration in the test nucleic acid. For efficient screening purposes, more than one probe may be used on the same test sample.

Allele- or variant-specific oligonucleotides may similarly be used in PCR to specifically amplify particular sequences if present in a test sample. Assessment of whether a PCR band contains a gene variant may be carried out in a number of ways familiar to those skilled in the art. The PCR product may for instance be treated in a way that enables one to display the mutation or polymorphism on a denaturing polyacrylamide DNA sequencing gel, with specific bands that are linked to the gene variants being selected.

An alternative or supplement to looking for the presence of variant sequences in a test sample is to look for the presence of the normal sequence, e.g. using a suitably specific oligonucleotide probe or primer.

Use of oligonucleotide probes and primers has been discussed in more detail above.

Approaches which rely on hybridisation between a probe and test nucleic acid and subsequent detection of a mismatch may be employed. Under appropriate conditions (temperature, pH etc.), an oligonucleotide probe will hybridise with a sequence which is not entirely complementary. The degree of base-pairing between the two molecules will be sufficient for them to anneal despite a mis-match. Various approaches are well known in the art for detecting the presence of a mis-match between two annealing nucleic acid molecules.

For instance, RN'ase A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid. Other approaches rely on the use of enzymes such as resolvases or endonucleases.

Thus, an oligonucleotide probe that has the sequence of a region of the normal BRCA2 gene (either sense or anti-sense strand) in which mutations associated with cancer susceptibility are known to occur (e.g. see table 1) may be annealed to test nucleic acid and the presence or absence of a mis-match determined. Detection of the presence of a mis-match may indicate the presence in the test nucleic acid of a mutation associated with cancer susceptibility. On the other hand, an oligonucleotide probe that has the sequence of a region of the BRCA2 gene including a mutation associated with cancer susceptibility may be annealed to test nucleic acid and the presence or absence of a mis-match determined. The absence of a mismatch may indicate that the nucleic acid in the test sample has the normal sequence. In either case, a battery of probes to different regions of the gene may be employed.

The presence of differences in sequence of nucleic acid molecules may be detected by means of restriction enzyme digestion, such as in a method of DNA fingerprinting where the restriction pattern produced when one or more restriction enzymes are used to cut a sample of nucleic acid is compared with the pattern obtained when a sample containing the normal gene or a variant or allele is digested with the same enzyme or enzymes.

The presence of absence of a lesion in a promoter or other regulatory sequence may also be assessed by determining the level of mRNA production by transcription or the level of polypeptide production by translation from the mRNA.

A test sample of nucleic acid may be provided for example by extracting nucleic acid from cells, e.g. in saliva or preferably blood, or for pre-natal testing from the amnion, placenta or foetus itself.

There are various methods for determining the presence or absence in a test sample of a particular polypeptide, such as the polypeptide with the amino acid sequence shown in FIG. 3, 5 or 7 (SEQ ID NOS: 14, 16, & 44, respectively) or an amino acid sequence variant or allele thereof.

A sample may be tested for the presence of a bending partner for a specific binding member such as an antibody (or mixture of antibodies), specific for one or more particular variants of the polypeptide shown in FIGS. 3, 5 or 7 (SEQ ID NOS: 14, 16, & 44, respectively).

A sample may be tested for the presence of a binding partner for a specific binding member such as an antibody (or mixture of antibodies). specific for the polypeptide shown in FIGS. 3, 5 or 7 (SEQ ID NOS: 14, 16, & 44, respectively).

In such cases, the sample may be tested by being contacted with a specific binding member such as an antibody under appropriate conditions for specific binding, before binding is determined, for instance using a reporter system as discussed. Where a panel of antibodies is used, different reporting labels may be employed for each antibody so that binding of each can be determined.

A specific binding member such as an antibody may be used to isolate and/or purify its binding partner polypeptide from a test sample, to allow for sequence and/or biochemical analysis of the polypeptide to determine whether it has the sequence and/or properties of the polypeptide whose sequence is shown in FIGS. 3, 5 or 7 (SEQ ID NOS: 14, 16, & 44, respectively), or if it is a mutant or variant form. Amino acid sequence is routine in the art using automated sequencing machines.

There is also an increasing tendency in the diagnostic field towards miniaturisation of such assays, e.g. making use of binding agents (such as antibodies or nucleic acid sequences) immobilised in small, discrete locations (microspots) and/or as arrays on solid supports or on diagnostic chips. These approaches can be particularly valuable as they can provide great sensitivity (particularly through the use of fluorescently labelled reagents), require only very small amounts of biological sample from individuals being tested and allow a variety of separate assays can be carried out simultaneously. This latter advantage can be useful as it provides an assay for different mutations in the BRCA2 gene or another cancer susceptibility gene (such as BRCA1, see EP-A-705902) to be carried out using a single sample. Examples of techniques enabling this miniaturised technology are provided in WO84/01031, WO88/1058, WO89/01157, WO93/8472, WO95/18376/ WO95/18377, WO95/24649 and EP-A-0373203. Thus, in a further aspect, the present invention provides a kit comprising a support or diagnostic chip having immobilised thereon one or more binding agents capable of specifically binding BRCA2 nucleic acid or polypeptides, optionally in combination with other reagents (such as labelled developing reagents) needed to carrying out an assay.

Therapeutics

Pharmaceuticals and Peptide Therapies

The BRCA2 polypeptides, antibodies, peptides and nucleic acid of the invention can be formulated in pharmaceutical compositions. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection, lactated Ringer's injection. Preservatives, stabilisers, buffers, antioxidants and/or other additives may he included, as required.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficiant to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

Alternatively, targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

Instead of administering these agents directly, they could be produced in the target cells by expression from an encoding gene introduced into the cells, eg in a viral vector (a variant of the VDEPT technique—see below). The vector could be targeted to the specific cells to be treated, or it could contain regulatory elements which are switched on more or less selectively by the target cells.

Alternatively, the agent could be administered in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, eg an enzyme, in a vector by expression from encoding DNA in a viral vector (see for example, EP-A-415731 and WO90/07936).

A composition may be administered alone or in combination with other treatments, either simultaneously or sequentially dependent upon the condition to be treated.

Methods of Gene Therapy

As a further alternative, the nucleic acid encoded the authentic biologically active BRCA2 polypeptide could be used in a method of gene therapy, to treat a patient who is unable to synthesize the active polypeptide or unable to synthesize it at the normal level, thereby providing the effect provided by wild-type BRCA2 and suppressing the occurrence of cancer and/or reduce the size or extent of existing cancer in the target cells.

Vectors such as viral vectors have been used in the prior art to introduce genes into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted tumour cells, providing long lasting effect, or alternatively the treatment may have to be repeated periodically.

A variety of vectors, both viral vectors and plasmid vectors, are known in the art, see U.S. Pat. No. 5,252,479 and WO93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer.

As mentioned above, the aim of gene therapy using nucleic acid encoding the BRCA2 polypeptide, or an active portion thereof, is to increase the amount of the expression product of the nucleic acid in cells in which the level of the wild-type BRCA2 polypeptide in absent or present only at reduced levels. Such treatment may be therapeutic in the treatment of cells which are already cancerous or prophylactic in the treatment of individuals known through screening to have a BRCA2 susceptibility allele and hence a predisposition to cancer.

Gene transfer techniques which selectively target the BRCA2 nucleic acid to breast and/or ovarian tissues are preferred. Examples of this included receptor-mediated gene transfer, in which the nucleic acid is linked to a protein ligand via polylysine, with the ligand being specific for a receptor present on the surface of the target cells.

Antisense technology based on the BRCA2 nucleic acid sequences is discussed above.

Methods of Screening for Drugs

A polypeptide according to the present invention may be used in screening for molecules which affect or modulate its activity or function. Such molecules may be useful in a therapeutic (possibly including prophylactic) context.

It is well known that pharmaceutical research leading to the identification of a new drug may involve the screening of very large numbers of candidate substances, both before and even after a lead compound has been found. This is one factor which makes pharmaceutical research very expensive and time-consuming. Means for assisting in the screening process can have considerable commercial importance and utility. Such means for screening for substances potentially useful in treating or preventing cancer is provided by polypeptides according to the present invention. Substances identified as modulators of the polypeptide represent an advance in the fight against cancer since they provide basis for design and investigation of therapeutics for in vivo use.

A method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Combinatorial library technology provides an efficient way of testing a potentially vast number of different substances for ability to modulate activity of a polypeptide. Such libraries and their use are known in the art. The use of peptide libraries is preferred.

Prior to or as well as being screened for modulation of activity, test substances may be screened for ability to interact with the polypeptide, e.g. in a yeast two-hybrid system (which requires that both the polypeptide and the teat substance can be expressed in yeast from encoding nucleic acid). This may be used as a coarse screen prior to testing a substance for actual ability to modulate activity of the polypeptide. Alternatively, the screen could be used to screen test substances for binding to a BRCA2 specific binding partner, to find mimetics of the BRCA2 polypeptide, e.g. for testing as cancer therapeutics.

Following identification of a substance which modulates or affects polypeptide activity, the substance may be investigated further. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition to a patient, e.g. for treatment (which may include preventative treatment) of cancer, use of such a substance in manufacture of a composition for administration, e.g. for treatment of cancer, and a method of making a pharmaceutical composition comprising admixing such a substance with a pharmaceutically acceptable excipient, vehicle or carrier, and optionally other ingredients.

A substance identified using as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, eg by substituting each residue in turn. Alanine scans of peptide are commonly used to refine such peptide motifs. These parts or residues constituting the active region of the compound are known as its "pharmacophore".

Once the pharmacophore has been found, its structure is modelled to according its physical properties, eg stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesize, is likely to be pharmacologically acceptable, and does rot degrade in vivo, while retaining the biological activity of the lead compound. Alternatively, where the mimetic is peptide based, further stability can be achieved by cyclising the peptide, increasing its rigidity. The mimetic or mimetics found by this approach can then be screened to see whether they have the target property, or to what extent they exhibit it. Further optimisation or modification can then be carried out to arrive at one or more final mimetics for in vivo or clinical testing.

Screening for Substances Affecting BRCA2 Expression

The present invention also provides the use of all or part of the nucleic acid sequence of the BRCA2 promoter region shown in FIG. 6 (SEQ ID NO: 170) in methods of screening for substances which modulate the activity of the promoter and increase or decrease the level of BRCA2 expression.

"Promoter activity" is used to refer to ability to initiate transcription. The level of promoter activity is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction Such as the polymerase chain reaction. Use of a reporter gene facilitates determination of promoter activity by reference to protein production.

Further provided by the present invention is a nucleic acid construct comprising a BRCA2 promoter region set out in FIG. 6 (SEQ ID NO: 170) or a fragment, mutant, allele, derivative or variant thereof able to promoter transcription, operably linked to a heterologous gene, e.g. a coding sequence. A "heterologous" or "exogenous" gene is generally not a modified form of BRCA2 Generally, the gene may be transcribed into mRNA which may be translated into a peptide or polypeptide product which may be detected and preferably quantitated following expression. A gene whose encoded product may be assayed following expression is termed a "reporter gene", i.e. a gene which "reports" on promoter activity.

The reporter gene preferably encodes an enzyme which catalyses a reaction which produces a detectable signal, preferably a visually detectable signal, such as a coloured product. Many examples are known, including β-galactosidase and luciferase. β-galactosidase activity may be assayed by production of blue colour on substrate, the assay being by eye or by use of a spectrophotometer to measure absorbance. Fluorescence, for example that produced as a result of luciferase activity, may be quantitated using a spectrophotometer. Radioactive assays may be used, for instance using choloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labelled directly or indirectly using any standard technique.

Those skilled in the art are well aware of a multitude of possible reporter genes and assay techniques which may be used to determine gene activity. Any suitable reporter/assay may be used and it should be appreciated that no particular choice is essential to or a limitation of the present invention.

Nucleic acid constructs comprising a promoter (as disclosed herein) and a heterologous gene (reporter) may be employed in screening for a substance able to modulate activity of the promoter. For therapeutic purposes, e.g. for treatment of cancer a substance able to up-regulate expression of the promoter directing the expression of normal may be sought. Alternatively, substances to down-regulate the promoter may help to prevent or inhibit the production of mutated BRCA2 polypeptide, if this is an agent implicated in the development of cancer. A method of screening for ability of a substance to modulate activity of a promoter may comprise contacting an expression system, such as a host cell, containing & nucleic acid construct as herein disclosed with a test or candidate substance and determining expression of the heterologous gene.

The level of expression in the presence of the test substance may be compared with the level of expression in the absence of the test substance. A difference in expression in the presence of the test substance indicates ability of the substance to modulate gene expression. An increase in expression of the heterologous gene compared with expression of another gene not linked to a promoter as disclosed herein indicates specificity of the substance for modulation of the promoter.

A promoter construct may be introduced into a cell line using any technique previously described to produce a stable call line containing the reporter construct integrated into the genome. The cells may be grown and incubated with test compounds for varying times. The cells may be grown in 96 well plates to facilitate the analysis of large numbers of compounds. The cells may then be washed and the reporter gene expression analysed. For some reporters, such as luciferase the cells will be lysed then analysed.

Following identification of a substance which modulates or affects promoter activity, the substance may be investigated further. Furthermore, it may be manufactured and/or used in preparation, i.e. manufacture or formulation, of a composition such as a medicament, pharmaceutical composition or drug. These may be administered to individuals.

Construction of Animal Models for BRCA2 Deficiency

The construction of animal models for BRCA2 deficiency can be carried out using standard techniques for introducing mutations into, for example, a mouse germ-line. In one example of this approach, a vector carrying an insertional mutation within exon 11 of the mouse BRCA2 gene is transfected into embryonic stem cells. Clones in which the mutant version of the gene has replaced with wild type are identified by Southern blot hybridization. The clones are then amplified and cells are injected into mouse blastocyst stage embryos. Mice in which the injected cells have contributed to the development of the mouse are identified by Southern blotting. These chimeric mice are then bred to produce mice which carry one copy of the mutation in the germ line. These heterozygous mutant animals are then bred to produce mice carrying mutations in the BRCA2 gene homozygously. The mice having a heterozygous mutation in BRCA2 may be a suitable model for human individuals having one copy of the gene mutated in the germ line who are at high risk of developing breast cancer.

EXAMPLE 1

Identification of the BRCA2 Gene

Following the definition of the interval D13S289-D13S267 in which the BRCA2 gene is believed to be located (Wooster et al (1994)), the following set of procedures were used identify the gene itself. A yeast artificial chromosome (YAC) contig was constructed of YACs believed to be in the region from the CEPH database. Chimerism of YACs was examined using fluorescent in situ hybridisation. Overlaps between YACs were established by amplification of sequence tagged sites (STS), hybridisation of STS PCR products and alu-PCR fingerprinting.

Using probes localized to and derived from the YAC contig, a P1 artificial chromosome (PAC) library was screened and positive PACs isolated. PACs were rehybridised to the PAC library to fill in gaps between clones. A PAC contig over a 1 megabase region was then assembled.

Overlaps between PACs were identified by:

(a) amplification of STS;

(b) hybridization of end probes produced by linear PCR;

(c) HindIII/Sau3A fingerprinting.

Additional polymorphic markers from the region were identified by screening M13 libraries constructed from PACs, with oligonucleotides containing repetitive sequences that are commonly polymorphic (GTn, GAn, CAGn, GATAn, GAATn). Using new markers, the region in which BRCA2 is likely to be located was narrowed further.

Transcripts from the region were identified by use of PAC DNAs in:

(a) exon trapping experiments using a lambda GET vector;

(b) hybrid selection between PAC genomic DNA and cDNA libraries.

Exons and cDNA fragments identified by these methods were sequenced.

Using primers synthesised from these sequences as probes, 15 kb genomic subclones of the PACs that carry all or part of the cDNAs and exons were identified. These were sequenced from the cDNA sequence out into adjacent flanking genomic sequences.

Using oligonucleotide primers synthesised on the basis of these flanking genomic sequences, genomic DNA fragments containing the potential transcript were amplified and screened for mutations through the following DNA samples; DNAs from 46 families that show evidence of linkage to BRCA2 and/or show evidence against linkage to ERCA1 and/or do not have BRCA1 mutations and/or do have evidence of male breast cancer. Also screened were cancer cell lines that are homozygous for all polymorphic markers through the BRCA2 region; DNAs from 12 primary human tumour DNAs that show evidence of loss of heterozygosity in the BRCA2 region.

Sequence variants were detected by running $^{32}P$ labelled amplification products through:

(a) non denaturing polyacrylamide gels, at room temperature and at 4° C.;

(b) denaturing polyacrylamide gels.

Fragments that showed altered mobility were reamplified using the PCR and directly sequenced. Sequences were run on an ABI 377 DNA sequencer.

In the course of this work, several sequence variants were detected, most of which are believed to be non disease associated polymorphisms. However, an abnormality detected in one fragment was predicted to destroy a splice site and create a termination codon in a family that shows strong linkage to BRCA2. The variant segregates with the disease chromosome. This is precisely the type of abnormality that would be expected within a cancer susceptibility gene and made this fragment a strong candidate for part of the BRCA2 gene.

This fragment was then used (a) as a probe in screening of cDNA libraries, (b) starting sequence for PCR amplification experiments from cDNAs and cDNA libraries. Positive clones and amplification fragments were sequenced. These results are shown in the FIGS. 1 and 2.

From the initial isolation of this part of exon 16 of the BRCA2 gene, a variety of conventional techniques were then used to isolate the remaining portions of the BRCA2 sequence. The 900,000 bp sequence released on the Internet (the Sanger sequence) assisted in this procedure. FIG. 4 shows around 75% of the cDNA sequence isolated by the inventors (SEQ ID NO: 15), while the complete BRCA2 gene sequence, including the exon/intron structure, is shown in FIG. 7 (SEQ ID NOS: 17–43). The promoter region of the gene is set out in FIG. 6 (SEQ ID NO: 170). These sequences could be downloaded from the ftp web sites to a local computer. The sequences can then be analysed using programs such as BLAST, FASTA, GRAIL or GeneFinder to identify putative coding regions. Oligos can then be designed to these predicted coding regions and these would be used in RT-PCR to confirm or refute the coding regions. The coding regions would also be compared with the experimental results obtained from the procedures set out herein.

Thus, given knowledge of a part of the BRCA2 sequence and its orientation within the Sanger sequence the skilled person could readily isolate the rest of the sequence using a conventional exon prediction program to localize potential exons/open reading frames in the same orientation as the known portion of the BRCA2 sequence, and then do exon connection in which potential exons are used to design primers that sit in putative coding sequence. The primers could be designed in such a way as to have a primer based on known BRCA2 sequence and an unknown primer, such that when these are used to prime from cDNA, a product contiguous with known sequence would be produced if the unknown primer is a part of the BRCA2 gene. This process could be continued in an iterative manner, readily allowing the skilled person to walk through the Sanger sequence to obtain the full BRCA2 sequence, obtaining the intron/exon boundaries as part of the procedure. In the case of BRCA2, a large portion of the coding sequence (about 5 kb) is in exon 11, part of which is included in the 10% of the sequence disclosed in FIGS. 1 and 2.

By way of reference, the techniques described above and others useful in the isolation of genes by positional cloning are reviewed in Monaco, Curr. Opinion Gen. Devel., 4:360–365, 1994 and summarised in EP-A-0705902.

By way of further assistance, a protocol for the isolation of the full length sequence and the polypeptide encoded by the BRCA2 gene from the sequence shown in FIGS. 1, 2 and 4 is set out below, and could be used iteratively to isolate successive portions of the BRCA2 gene.

Screening cDNA libraries by hybridisation.

Presently identified cDNA fragments can be $^{32}P$ labelled and hybridized to various widely available plated or gridded cDNA libraries. Positive clones can then be isolated, and subject to replating and rehybridisation if necessary until a pure clone has been isolated. DNA can then be made from pure clones and will be sequenced by conventional Sanger dideoxy sequencing on a ABI 377 DNA sequencer.

Screening cDNA libraries by PCR amplification.

Oligonucleotides based on sequences within the BRCA2 sequences disclosed herein can be used in conjunction with oligonucleotides designed to prime from the cloning vector in PCR amplifications of aliquots of widely available cDNA libraries. This will allow amplification of fragments of the BRCA2 cDNA positioned between the currently known fragment and the cloning insertion site. Products of the PCR amplification can then be sequenced using Sanger dideoxy sequencing on an ABI 377 sequencer.

Rapid amplification of cDNA ends (RACE).

Primary cDNAs synthesised from a number of different tissue RNAs can be ligated to an oligonucleotide linker. After purification, PCR amplifications can be performed using an oligonucleotide that primes from the current BRCA2 cDNA sequence and a second oligonucleotide that primes from the linker. Amplification products will be directly sequenced using Sanger dideoxy sequencing. RACE is described in (6).

The new sequences can then be integrated into the full sequence of the gene by detection of overlaps with previously known components of the sequence.

The screening of cDNA or genomic libraries with selected probes can be conducted using standard procedures, for instance as described in Ausubel et al and Sambrook et al (supra).

These techniques allow the full coding sequence to be isolated based on the information disclosed in FIGS. 1, 2 and 4. The full length sequence is defined as the sequence between a translation initiation codon (ATG) and a translation termination codon (TAA, TAG, TGA) between which there is an open reading frame. This in turn can be used to define the intron-exon structure of the gene. Primers can then be designed to flank each exon so that the whole coding sequence of the gene can be amplified from genomic DNA, see for example the primers disclosed in FIG. 8 or in Nature Genetics, 12:333–337, 1996.

Further fragments of coding sequence were then amplified from genomic DNA in the previously described mutation testing set in order to detect additional disease associated mutations in the BRCA2 gene.

EXAMPLE 2

Mutations in the BRCA2 Gene Identification of Six Mutations in the BRCA2 Gene In a first study, the inventors found a series of mutations in the BRCA2 sequence by comparing the native sequence with sequences obtained from families with a history of multiple cases of early onset breast cancer. The locations of these mutations in the amino acid sequence are shown by boxing the residues in the native sequence which are affected (see FIG. 5). The mutations to the BRCA2 gene are summarised in table 3, which shows the families in the left hand column against mutations in the BRCA2 gene in the right hand column (SEQ ID NOS: 190–193). The remaining columns in table 3 from left to right are as follows:

| | |
|---|---|
| Number of FBCs | Number of female breast cancers in the family. |
| Number of FBCs < 50 | Number of female breast cancers occurring in individuals under 50 years of age. |
| Number of OvCs | Number of ovarian cancers in the family. |
| Number of MBcs | Number of male breast cancers. |

The columns referring to LOD scores at BRCA1 and BRCA2 show the chance that the incidence of the cancers in a family is linked to the BRCA3 or BRCA2 genes, with a more positive value indicating a greater chance of linkage. Thus, for example, a LOD score of +3 indicates a strong linkage between the incidence of cancer and the given gene in that family.

To identify BRCA2, genomic DNA fragments of less than 300 bp containing putative coding sequences were screened for mutations. At least one affected member of 46 breast cancer families was examined. Each family included in this set either shows evidence of linkage to BRCA2, and/or shows evidence of breast cancer. The majority, but probably not all, of these families would be expected to be due to BRCA2 mutations.

Disease associated mutations in most known cancer susceptibility genes usually result in truncation of the encoded protein and inactivation of critical functions. In the course of the mutational screen of candidate coding sequences from the BRCA2 region, the first detected sequence variant that was predicted to disrupt translation of an encoded protein was observed in IARC 2932. This family is clearly linked to BRCA2 with a multipoint LOD score of 3.01 using D13S260 and D13S267. A six base pair deletion removes the last five bases of the exon examined (exon S66), deletes the conserved G of the 5' splice site of the intron, and directly converts the codon TTT for phenylalanine to the termination codon TAA. By sequencing this mutation has been detected in lymphocyte DNA from two other early onset breast cancer cases in this family. The individuals examined share only the disease-associated haplotype. The mutation is absent in more than 500 chromosomes from normal individuals or in the remaining families and cancers. This finding therefore identified the candidate gene which was proved by the work described herein to be the BRCA2 gene.

To characterise the BRCA2 gene further, exon S66 was used to isolate a series of cDNA clones which represented segments of the BRCA2 candidate. From alignment of the cDNA and genomic sequence data, the candidate BRCA2 gene was found to lie in three sequence contigs which also contained other previously isolated transcribed sequences. The exon and open reading frame prediction program Genemark was used to define putative additional 5' exons of the gene. Contiguity of the transcription unit was confirmed by RT-PCR on cDNA and sequence analysis. The availability of extensive sequence information at the cDNA and genomic level allowed mutational analysis of further coding regions of the putative BRCA2 gene in samples from breast cancer families.

A TG deletion (6819delTG) and a TT (6503delTT) deletion were detected in families CRC B196 and CRC B211 respectively (tables 1 and 2). In both families the mutation has been detected by sequencing other individuals with early onset breast cancer who share only the haplotype of 13q microsatellite markers that segregates with the disease.

Therefore, the mutations are on the disease associated chromosomes. A CT deletion was detected in family IARC 3594. This mutation has arisen within a short repetitive sequence (CTCTCT), a feature that is characteristic of deletion/insertion mutations in many genes and which is presumed to be due to slippage during DNA synthesis. Finally, a T deletion (6174delT) and an AAAC deletion have been found in Montreal 681 and 440 respectively. Both these families include a male breast cancer case and previous analyses have indicated that the large majority of such families will have BRCA2 mutations. All these mutations are predicted to generate frame shifts leading to premature termination codons. None of the mutations have been found in chromosomes from over 500 healthy women and are therefore unlikely to be polymorphisms. The identification of several different germline mutations that truncate the encoded protein in breast cancer families that are highly likely to be due to BRCA2 strongly suggests that we have identified the BRCA2 gene. In particular, the 6174delT mutation from Ashkenazi Jewish family data is reproduced in other families examined and so may be useful in screening individuals for a susceptibility to cancer, especially male or female breast cancer or ovarian cancer.

Northern analysis has demonstrated that BRCA2 is encoded by a transcript of 10–12 kb which is present in normal breast epithelial cells, placenta, and the breast cancer cell line MCF7. This suggests that our present contig of cDNAs covering approximately 9kb (including 1.6 kb of 3' untranslated sequence) may not include the whole BRCA2 coding sequence. The known sequence of 2329 amino acids encoded by the BRCA2 gene does not show strong homology to sequences in the publicly available DNA or protein databases. The homology and motifs of BRCA2 found in an analysis of the corresponding genes in other species is described in example 6. however, some weak matches were detected including, intriguingly, a very weak similarity to the BRCA1 protein over a restricted region (amino acids 1394–1474 in BRCA1 and 1783–1863 in the portion of BRCA2 shown in FIG. 5).

Identification of Further Mutations in the BRCA2 Gene

Patient material

Families were identified which contained a minimum of either three cases of breast cancer and for which DNA samples were available from a least one affected individual. Complete or partial analysis of the BRCA1 gene identified those families with disease associated germline mutations. The remaining families were analysed throughout the complete BRCA2 coding sequence for germline mutations, which are shown in table 1 against the incidences of breast cancer (including early onset breast cancer) and ovarian cancer. Borderline ovarian cancer was not included. Confirmation of diagnosis was available from pathology reports or death certificates.

Mutation analysis of BRCA2 in ovarian cancer families

Seventy seven families with two or more first degree relatives with epithelial ovarian cancer were analysed for BRCA2 mutations. Mutation screening was performed using a combination of the protein truncation test (PTT) and non-radioactive single-strand conformation analysis/heteroduplex analysis (SSCA/HA). PTT was performed from genomic DNA for exon 11 in all cases and for the entire coding region in those individuals in which RNA derived from lymphoblastoid cell lines was available to perform reverse-transcriptase PCR. Primers were designed to PCR amplify exon 11 or the complete coding sequence in overlapping fragments ranging in size from 10 to 1.3 kb.

PTT was performed using the TNT rabbit reticulocyte lysate system (Promega) incorporating $^{35}S$ methionine (Amersham) for protein detection. Protein products were electrophoresed on 12–15% SDS polyacrylamide gels at 30–60 mA for 12–16 hours. SDS-PAGE gels were fixed in 30% methanol/10% glacial acetic acid, dried and exposed to Kodak X-Omat film for 16–72 hours. The approximate location of the sequence alteration resulting in truncated protein variants was localised and the region sequenced to confirm the precise nucleotide alteration. SSCA/HA was performed on genomic DNA for coding exons 2–10 and 12–27. The 5' and 3' splice boundaries for exon 11 were also analysed. SSCA and HA variant conformers were sequenced as previously described (3) in order to characterize the precise nucleotide change. The ability to detect mutations identified by PTT using SSCA/HA was detectable using SSCA/HA on fragments ranging in size from 300–600 bp. All primer sequences designed for PTT and SSCA/HA are available on request (e-mail sg200@cam.ac.uk).

Mutation analysis of BRCA2 in breast cancer families

Statistical methods

We tested for an association between mutation location and disease phenotype using a permutation argument similar to that used by Gayther et al (12) . Test statistics were based on standard chi-squared statistics for the difference in the rate of ovarian cancers, as a proportion of all ovarian and breast cancers, confirmed by position. In the main analysis, the statistic X was calculated assuming an alternative hypothesis in which different rates applied for mutations in three different regions, i.e. before codon n1–n2 and after n2 (i.e. a 2 degree of freedom chi-squared) The three putative missense mutations were ignored in this analysis as their significance is unclear. The statistic X was maximised over all possible values of the cutpoints n1 and n2 giving the statistic Xm. The significance of this maximised chi-squared was then computed empirically by calculating the value of Xm in 50,000 datasets in which the 26 mutations were randomly permuted among the families. We also computed a statistic to test for a trend in the ratio of ovarian:breast cancer risk along the gene, based on a chi-squared test for trend, as in (12) which was not significant.

In an attempt to confirm the association using other data from previously published reports, we computed the chi-squared statistic (two degrees of freedom) using data from five studies (9,10,15–17), with the cutpoints n1 and n2 fixed at the best values for the UK dataset. The significance of this result was then based on permuting the mutations among families as before.

Discussion

BRCA2 probably accounts for the majority of high risk families not accounted for by ERCA1. The identification of BRCA2 should, therefore allow more comprehensive evaluation of families at high risk of developing breast cancer. However, the role of environmental, lifestyle or genetic factors in modifying the risks of cancer in gene carriers is unknown and further studies will be required before routine diagnosis of carrier status can be considered.

Although, many of the mutations described in these examples are not is common to the BRCA2 genes of different families, these mutations may nevertheless prove to be a useful in methods of diagnosing or detecting a predisposition to cancer, especially breast cancer. In addition, on further routine analysis of a larger sample of families, it may emerge that a given mutation is common to a significant portion of cancer cases and so might form the basis of a simple diagnostic test. Even if this is not the case, knowing the location of the mutations may help to reduce the amount of sequencing work that would be needed in carrying out a test on a patient, e.g. by sequencing all or part of their BRCA2 gene, thereby to determine a predisposition or susceptibility to cancer. Further applications and uses of the mutations are set out in the general section above.

Germline mutations of BRCA2 are predicted to cause approximately 35% of families with multiple case, early onset female breast cancer, and they are also associated with an increased risk of male breast cancer, ovarian cancer, prostrate cancer and pancreatic cancer (5,9,10) Germline mutations of a second cancer susceptibility gene BRCA1 (3), are associated with a strong predisposition to ovarian cancer as well as female breast cancer (11). Recent studies have suggested that the phenotype in BRCA1 families with respect to the ratio of breast to ovarian cancer varies with the location of the ERCA1 mutation (12,13). To determine whether germline mutations in BRCA2 are associated with a similar variation in phenotypic risk, we have analysed the distribution of mutations of families with multiple cases of breast and/or ovarian cancer ascertained in the United Kingdom and Eire. The majority of these mutations lead to premature truncation of BRCA2 as a result of frameshift deletions, insertions, nonsense mutations or splice Site alterations. Analysis of the mutation distribution along the length of the gene indicates a significant genotype-phenotype correlation. Truncating mutations in families with the highest risk of ovarian cancer relative to breast cancer are clustered in a region of approximately 3.3 kb in exon 11 (p=0.0005). Published data on mutations in 45 other BRCA2 linked families provide support for this correlation.

Families were ascertained on the basis of either three or more cases of breast cancer or two or more first degree relatives with epithelial ovarian cancer diagnosed at any age. Mutations of the BRCA1 gene were then identified and genomic DNA of a single affected individual from each of the remaining families was used to Screen for mutations throughout the coding sequence of BRCA2 using a combination of single-strand conformation polymorphism (SSCP) and protein truncation (PTT) assays. The BRCA 2 coding sequence consists of 10,248 nucleotides encoded by 26 exons (15). The majority of exons are relatively small although exons 10 and 11 represent approximately 60% of the entire coding region. The mutations found are set out in tables 1 and 2. The mutation spectrum consisted of 22 frameshift deletions or insertions, 3 nonsense mutations and one splice site alteration. These mutations are all predicted to result in premature truncation of the predicted BRCA2 peptide. Three novel putative missense mutations were also detected. Mutations were distributed throughout the gene and only one additional mutation, 6503delTT, was found to be recurrent.

BRCA2 mutation data from families ascertained outside the UK derived from previous reports and unpublished data from our own laboratories provide support for this clustering. BRCA2 mutations have been identified in 45 such families (9,10,15–17). The 17 families with mutations in the OCCR are reported to contain 11 ovarian and 45 breast cancer cases compared to 22 ovarian and 282 breast cancer cases in the remaining families (odds ratio 22.9; permutation test for differences p=0.007). Consistent with this, there are three large BRCA2 families where reasonably systematic evidence on cancer risks are available, namely UTAH 107 (15), CRC 186 and the Icelandic family (10). Mutations in all three families are located near the 5' or 3' end of the gene and appear to be associated with a high lifetime risk of breast cancer, with mutations in the OCCR being associated with a higher ovarian cancer risk than average, or a lower breast cancer risk, or both. In this regard, future data on the 6174delT mutation will be particularly important. This mutation, which lies in the OCCR, is common in Ashkenazi Jews and direct population based estimates of its prevalence in breast and ovarian cancer patients should be possible.

The observed genotype-phenotype correlation is somewhat surprising given that, unlike in BRCA1, a region in the centre of the gene appears to be associated with a distinct risk. There are precedents in cancer susceptibility genes, for example the adenomatous polyposis coli gene, where regions of mutation clustering within the gene are associated with predisposition to a specific phenotype (18,19). We do not yet know why truncating mutations in a central portion of the BRCA2 gene should result in increased risk to ovarian cancer. No regions of functional homology between BRCA2 and other genes have been identified. A series of eight internal amino acid repeats have recently been observed in exon 11 but these have little homology to other known genes (20). It is perhaps interesting that all eight repeats are contained within the OCCR. That the mutations cluster in a single exon suggests an explanation based on alternative splicing. Complete or partial splicing of exon 11 may produce alternatively spliced forms with the ability to "rescue" mutations in breast but not ovarian epithelium. Our results suggest that they may be interesting differences in the structure or function of BRCA2 between breast or ovarian epithelium.

EXAMPLE 3

Expression of BRCA2 Polypeptide

Construction of Full-Length cDNA Clones for Human BRCA2

The approximately 10.5 kb cDNA coding for human BRCA2 was assembled from fragments of cDNA amplified by PCR and from cloned genomic DNA. All residue numbers are from Genbank accession number U43746.

The 5' end of the cDNA (residues 204–2357) was amplified by PCR from cDNA made from RNA from MCF7 cells using the primers:

CATTGGAGGAATATCGTAGG (bases 204–223) (SEQ ID NO: 194) and

GACAGAGAATCAGCTTCTGG (bases 2338–2357) (SEQ ID NO: 195).

This 2.1 kb fragment was cloned into pBluescript and the sequence determined.

This plasmid (p12302) was then digested with Asp718 which cuts in the plasmid polylinker and partially with BamHI which cuts as bases 238 and 792. The double-stranded oligonucleotide:

GTACCGCCGCCATGGAACAGAAGATTTC-CGAAGAAGATCTGCCTATTG (SEQ ID NO: 196)

GCGGCGGTACCTTGTCTTCTAAAGGCT-TCTTCTAGACGGATAACCTAG (SEQ ID NO: 197)

was then ligated into the plasmid and recombinant carrying the oligo ligated to the plasmid digested at base 238 were selected.

This plasmid was digested with NdeI which cuts at bp 1795 and SmaI which cuts in the polylinker of the plasmid. This was ligated in a three-way ligation to a PCR product (1795–2280) which had been digested with NdeI and BstY1 and residues 2280–6571 as a BstY1-BsiHKAI fragment. The latter fragment consists of exon 11 of the BRCA2 gene and was isolated from a plasmid carrying genomic DNA. This generated plasmid p12672.

The 3' end of the BRCA2 cDNA was generated by RT-PCR with primers:

AAAAGTAACGAACATTCAGACCA (bases 6277–6299) (SEQ ID NO: 198) and

ATTGTCGCCTTTGCAAATGC (bases 10,486–10,505 (SEQ ID NO: 199)) on cDNA from MCF7 cells.

This fragment was subcloned into pBluescript to generate plasmid p12661. Subsequently this fragment was amplified with a primer (GTACTCCAGAACATTTAATATCC bases 6325–6344 (SEQ ID NO: 200)) and the T3 primer from bluescript.

This fragment digested with Bsp1201 was then ligated into SnaBI-NotI cut p12672 to generate the full-length clone p12806.

This plasmid was subsequently modified to include a FLAG epitope as follows. p12806 was digested with Asp718 and SalI and then ligated to pBlueBac2B digested with the same enzymes. This generated plasmid p13013. This was digested with SacI and BglII and ligated to a linker coding for a consensus Kozak sequence and a Flag epitope as detailed below:

CGGGTACCAGATCTGCCGCCACCATG-GATTACAAGGACGACGATGACAAG (SEQ ID NO: 201)

TCGAGCCCATGGTCTAGACGGCGGTGG-TACCTAATGTTCCTGCTGCTACTGTTCCTAG (SEQ ID NO: 202)

This full-length BRCA2 cDNA was ligated into expression vectors. In particular a modified version of the vector pMTSM was used this vector carries an adenovirus major late promoter and SV40 origin of replication.

Expression of BRCA2 Mammalian Cells

The full-length BRCA2 expression vector was transfected into COS cells using standard techniques. The expression of the protein was monitored by Western blotting immunoprecipitation and immunofluorescence. This demonstrated that the BRCA2 protein could be detected as an approximately 400 kD protein similar in size to that predicted by the sequence of the cDNA. Under these conditions, in this cell-type, the protein had a complex subcellular localisation being located in either a membrane-like compartment (most probably the endoplasmic reticulum) or in the nucleus or in both (see FIGS. 11 to 13).

Interaction of BRCA2 With Other Proteins

This can be assessed using a yeast two-hybrid system to clone proteins which interact with BRCA2. Am this procedure is potentially complicated by the size of the BRCA2 ORF, the ORF may be divided up into 5–10 fragments and screened separately. These fragments will be used as 'bait' both episomally and as integrants into the yeast genome and used to screen peptide libraries such as those derived from HeLa cells, human fetal brain and a new library derived from normal human breast. Clones confirmed as interacting in the two hybrid system will assayed for interaction both in vivo and in vitro. Bacterially expressed GEX-fusion proteins will be tested for direct interaction in vitro. Epitope-tagged versions of BRCA2 and the potential interacting proteins will be co-microinjected into cell lines and their sub-cellular location determined by immunofluorescence to establish co-localization. Co-transfection and cross-immunoprecipitation could be used to establish that the two proteins interact in vivo. In addition to identifying novel BRCA2 interacting proteins, the above approaches may be used to ascertain whether BRCA2 can dimerise or interact directly with BRCA1.

The nature of BRCA2 interacting proteins can also be directly determined by biochemical fractionation followed by mass spectroscopy. Immunoprecipitation of $^{35}S$-labelled extracts followed by SDS-gel electrophoresis can be used produce molecular weight estimates of these proteins. These would be further analysed by analytical 2D gel electrophoresis followed by MALDI-TOF mass-spectroscopy and peptide mass-mapping (23). This technique allows the certain identification of proteins whose sequences are present in the databases and assignment of likely family members (>80% identity).

Biological Function of BRCA2

An experiment can be performed to test whether BRCA2 expression can block the growth of breast and ovarian cancer cell lines specifically. Ideally such experiments make use of breast tumour cells that do not express BRCA2, which can readily be identified by screening existing breast cancer cell lines for absence of BRCA2 expression. Alternatively, cell lines could be established from patients shown to lack wild type BRCA2. It is also possible that over-expression of BRCA2 in cancer cells that still express will also suppress growth.

BRCA2 cDNA can suitably be expressed under the control retroviral LTR (pBABE) or elongation factor 1α promoters (the pEFBos series—(22)). Plasmide can be co-transfected with drug resistance markers and the number of colonies that grow our compared to vector controls. surviving colonies can be expanded and tested for tumourgenecity by injection into nude mice. In instances where the inhibitory action of the proteins cannot be detected in the relatively long term colony growth assay as the transfected plasmids do not stably express, microinjection of BRCA2 expression constructs can be used whereby the injected cells are detected by immunocytochemistry of the exogenous protein or by co-injection of a marker plasmid (21). In addition, time-lapse video recording, as described above, could be used to determine whether any growth inhibition effect is cell autonomous, i.e. whether the effect is paracrine or autocrine. These systems will also be useful for detecting any apoptotic effect.

EXAMPLE 5

Methods for Detecting BRCA2 Mutations

Migration shift assays to detect BRCA2 mutations.

DNA amplification in the PCR.

25 ng of genomic DNA from each individual to be screened for mutations is amplified in 35 cycles of the PCR using the pertinent oligonucleotide primers (see primer list). Prior to incorporation into the PCR, both oligonucleotide primers are end radiolabelled with gamma $^{32}P$ using T4 polynucleotide kinase. Following amplification in the PCR, formamide loading dye is added to each sample and the sample denatured at 94° C. for 3 minutes. Following denaturation the sample is placed immediately on ice.

DNA fragment sizing.

2 μl of each sample is loaded immediately onto a well formed by a 40 slot sharks' tooth comb in conventional 0.4 mm thick denaturing 6% polyacrylamide gel. The sample is electrophoresed through the gel for 2–5 hours at 90 Watts at room temperature.

SSCP heteroduplex analysis

SSCP is a PCR based assay for screening DNA fragments for sequence variants/mutations. It involves amplifying radiolabelled 100–300 bp fragments of the BRCA2 gene, diluting these products and denaturing at 95° C. The fragments are quick-cooled on ice so that the DNA remains in single stranded form. These single stranded fragments of BRCA2 are run through acrylamide based gels. Differences in the sequence composition will cause the single stranded molecules to adopt difference conformations in this gel matrix making their mobility different from wild type fragments, thus allowing detecting of mutations in the fragments being analysed relative to a control fragment upon exposure of the gel to X-ray film.

These fragments with altered mobility/conformations are directly excised from the gel and directly sequenced for the mutation. Following denaturation the sample is cooled on ice for 10 minutes to allow the heteroduplex to form. Each sample is electrophoresed through two different types of gel.

A typical set of conditions for SSCP analysis are as follows. 3 μl are electrophoresed overnight at 4 Watts at room temperature through a 6% non denaturing polyacrylamide gel containing 10% glycerol.

3 μl are electrophoresed for four hours at 30 Watts in a 4° C. cold room through a 4.5% non denaturing polyacrylamide acrylamide gel without glycerol.

Following electrophoresis, gels are dried onto Whatman 3MM paper, and placed in an autoradiography cassette at room temperature for a period ranging from two hours to several days.

Following development of the autoradiograph band shifts in individual samples are detected by eye.

Sequencing of PCR product.

Where a band shift is seen in SSCP heteroduplex or DNA fragment sizing gels, the fragment concerned is reamplified from the relevant stock genomic DNA and directly sequenced. To sequence PCR product, the product is precipitated with isopropanol, resuspended and sequenced using TaqFS+ Dye terminator sequencing kit. Extension products are electrophoresed on an ABI 377 DNA sequencer and data analysed using Sequence Navigator software.

BRCA2 PTT Assay

PTT is another PCR based screening assay. Fragments of BRCA2 are amplified with primers that contain the consensus Kozak initiation sequences and a T7 RNA polymerase promoter. These extra sequences are incorporated into the 5' primer such that they are in frame with the native coding sequence of the fragment being analysed. These PCR products are introduced into a coupled transcription/translation system. This reaction is allows the production of BRCA2 RNA from the fragment and translation of this RNA into a BRCA2 protein fragment. PCR products from controls make a protein product of a wild type size relative to the size of the fragment being analysed. If the PCR product analysed has a frame-shift or nonsense mutation, the assay will yield a truncated protein product relative to controls. The size of the truncated product is related to the position of the mutation, and the relative region of the BRCA2 gene from this patient is sequenced to identify the truncating mutation.

The following protocol was adapted for a BRCA2 PTT assay. The PTT primers are shown in FIG. 10.

Each PTT primer is preceded by the T7/Kozak sequence

GGATCCTAATACGACTCACTATAGGGAGACCACCATG (SEQ ID NO: 203)

1. Thirty five cycle primary PCR reaction in 20 ul.
2. Product confirmation by electrophoresis on 2% agarose gel.
3. Three ul aliquot amplification with nested PTT prime for 15 cycles.
4. Product confirmation by electrophoresis on 2% agarose gel.
5. In vitro transcription/translation using Promega (CA) TNT kit, incorporating 35S radiolabelled methionine.
6. Laemmli buffer reaction stop and denaturation.
7. Gel electrophoresis of product on 15% acrylamide gel at 16 mA.
8. Fix, amplify and dry gel.
9. Autoradiographic exposure for 2 hours.

These approaches can be combined to provide an accurate and effective screen, in terms of results achieved, the economical cost and the time taken to provide the results. By way of example, a combined protocol used by the inventors involves the following:

1) DNA samples from familial reference cases (probands) are first screened via PTT. Exons 10, 11, and the terminal exon 27 are analysed using this technique. Exons 10 and 27 are done in 1 fragment, whilst the larger exon 11 is done in 2 fragments. If protein truncations are seen, the corresponding genomic region is sequenced from the patient to identify the exact mutation. This approach is able to screen approximately 60% of the coding region in rapid fashion.

2) samples negative for the PTT screening are then analysed using SSCP. The entire coding region, including those regions already examined via PTT, is screened for mutations using SSCP. The coding sequence is amplified from genomic DNA using primer sets as described in this application. In addition, radiolabelled PCR products generated for SSCP analysis are also run on denaturing acrylamide sequencing gels which allows for detection of small size changes relative to control fragments, indicative of insertions or deletions. Any mutant fragments seen are excised directly from the gels and direct sequenced along with the matching genomic DNA fragment to determine the exact mutation Examples of screening carried out using these methods are set out in the table below.

BRCA2 screening in breast cancer family probands:

| Family | Mutation | No. Female Br Ca | Exon | Method of Detection |
|---|---|---|---|---|
| M107 | 2810insA | 8 | 11 | SSCP/PTT, mutation detected on both assays |
| M742 | 259insT | 6 | 2 | SSCP |
| M688 | 594delCT | 2 (2 Ov) | 11 | PTT |
| M347 | 1003delAG | 3 | 9 | SSCP |
| D-MBC2 | 1485delT | 5 (1 Mbr) | 10 | PTT |
| M269 | 8764delAG | 19 | 20 | SSCP |
| M612 | 8764delAG | 4 | 20 | SSCP |
| M133 | 2034insA | 11 | 10 | SSCP, too close to end of exon to be reliably up by PTT |

EXAMPLE 6

Results of Sequence Alignment

Materials and Methods

Total genomic DNA was obtained for green monkey (*Ceropithecus aethiopg*), hamster (*Critetulus griseus*), pig (*Sus scrofa*), dog (*Canis familiaris*), cow, chimpanzee, chicken, snake, zebra fish, *X.laevis, S.pombe* and *S. cerevisiae*. PCR primers were designed from a consensus sequence for the human BRC motif. These included primers that were an exact match to the human DNA sequence and degenerate primers based on the BRCA2 protein sequence. The sequences were as follows.

Motif forward set 1: pure primer -AAAGCTGTGAAACTGTT (SEQ ID NO: 204) and a degenerate set which was an equal mixture of -AA(AG) GCIIIIAA(AG)CTITT (SEQ ID NO: 205) and -AA (AG)GCIIII(AG)TT(AG)TT (SEQ ID NO: 206) where I is inosine.

Motif forward set 2: pure primer as for set 1 and a degenerate set made with -AA(AG)GCIGTIAA(AG)CTITT (SEQ ID NOS: 207 & 208, respectively) and -AA(AG) GCIGTIAA(AG)TT(AG)TT.

Motif reverse set: pure primer -TTCCCACTTGCAGTCTGAAA (SEQ ID NO: 209) and a mixed set of -TICC(GA)CTIGCIGT(CT)TG (GA)AA (SEQ ID NOS: 210 & 211, respectively) and -TTICCIGAIGCIGT(CT)TG(GA)AA.

Further sets of primers were designed to a region of BRCA2 that is conserved between human and mouse. These were a pure primer of AGCAAGCAATTTCAGG (SEQ ID NO: 212) and a degenerate set of -TCIAA(AG)CA(AG)TT (TC)GA(AG)GG (SEQ ID NOS: 213 & 214) and -AG(TC) AA(AG)CA(AG)TT(TC)GA(AG)GG. The PCR was performed using each forward primer in conjunction with a relevant reverse primer. The reaction conditions were as described in (4) except for the cycling conditions of the PCR. These were 94° C. 1 mix X° C. for 1 min. 72 C. for 1 min, where X was 85 C. for the first two cycles and then decreased by 2° C. every two cycles until it reached either 55, 49, 45, 39 or 35° C., at which point X remained constant. A further 30 cycles were performed at the final annealing temperature. PCR products were resolved on agarose gels and discrete bands were excised and sequenced using a Taq dideoxy termination protocol (Perkin-Elmer). Sequence products were separated on an ABI377 automated DNA sequencer.

All of the sequencing reactions were performed at least twice and on both strands of the template. Species-specific PCR primers were designed to exon 11 of the BRCA2 gene using the above DNA sequence. These were used in conjunction with a set of 52 pairs of PCR primers designed to the human BRCA2 gene to amplify and sequence further segments of exon 11 from the monkey, dog, pig and hamster. A human BRCA2 probe (exon 11) was used to identify a λ clone containing a portion of the mouse BRCA2 gene. This was used to obtain a mouse-specific BRCA2 sequence that was in turn used to design mouse-specific PCR primers. These were used to identify positive clones in a mouse BAC library. Fragments of positive BACs were cloned, at random, and those shown to contain fragments of exon 11 of the BRCA2 gene were sequenced.

Sequencing the BRC motifs

Two approaches were used to obtain the sequence of BRCA2 exon 11 (including the BRC motifs) in five mammalian species, using the sequence of human BRCA2 was taken from earlier work, see also FIG. 7. The sequence of exon 11 of the mouse BRCA2 gene was obtained from a BAC clone isolated by low stringency hybridisation with fragments of the human BRCA2 gene. Fragments of BAC were cloned at random and those shown to contain fragments of the BRCA2 gene were sequenced. PCR primers were then designed to the BRC motifs and to regions that were conserved between human and mouse. These were used to amplify fragments of the BRCA2 gene in DNAs from 12 species (as described in Materials and methods). A sequence showing similarity to human BRCA2 was obtained from green monkey, hamster, pig, dog, cow and chimpanzee. The sequences obtained from chicken, snake, zebra fish, *Xenopus laevis, Schizosaccharomyces prombe* and *Saccharomyces cerevisiae* showed no similarity to any BRCA2 sequence. Species-specific PCR primers were designed for green monkey, hamster, pig and dog. These were used in combination with all of the PCR primer pairs used to amplify human BRCA2 exon 11 to amplify further segments of the exon. The process was repeated until all of the sequences between and including BRC motifs one and eight had been obtained for the green monkey, hamster and dog. Using this approach, it was only possible to obtain the sequence for repeats 3–8 for the pig. In total, 46 BRC repeats were sequenced in six different mammals (including human).

The BRC motif is conserved in mammalian species

The percentage identity of the translation of exon 11 of the BRCA2 gene (approximately half of the whole coding sequence) between the six mammals is shown in Table 1. Overall, the degree of conservation is low, with 58% identity between the 1602 residues of the human and mouse, 54% identity between mouse or hamster and dog and 49% between pig and mouse (over 928 amino acids). Even between closely related species such as human and monkey, and mouse and hamster, amino acid identity is only 93 and 72% respectively. However, an alignment of the sequences from the six mammals studied demonstrates that exon 11 translations can be aligned along their whole lengths and that the degree of conservation is variable (FIG. 9). There are a number of short regions of high identity. Some of these regions coincide with BRC motifs, for example BRC1, 2, 3, 4, 7 and 8 (FIG. 9). There are other highly conserved segments, for example amino acids 469–493 (using the numbering of the human sequence in FIG. 9) that show no similarity to the BRC motifs or anything else reported in the databases. None of the latter are repeated within BRCA2.

An alignment of all 46 motifs sequenced demonstrates the high degree of interspecies and intraspecies conservation between BRC1, 3, 4, 7 and 8. From this alignment, we have identified a region of 26 amino acids that is conserved in all of the BRC motifs (FIG. 2) which has allowed us to generate a BRC consensus sequence. It is possible to align some residues outside this common region; however, such alignments are not robust, being very sensitive to the parameters used. There are motifs that contain all of the consensus sequence, for example BRC4, while others, for example BRC6, show a considerable divergence from the consensus. In total, 30/46 of the BRC motifs (65%) have 11 or more of the 13 consensus residues while 87% have eight or more of the consensus sequence.

The following table shows the percentage identities between the translation of exon 11 of the BRCA2 gene from human, monkey, pig, dog, hamster and mouse.

| | Human | Monkey | Pig | Dog | Hamster | Mouse |
|---|---|---|---|---|---|---|
| Human | 100 | 93 | 62 | 70 | 57 | 58 |
| Monkey | | 100 | 61 | 68 | 58 | 58 |
| Pig | | | 100 | 64 | 50 | 49 |
| Dog | | | | 100 | 54 | 54 |
| Hamster | | | | | 100 | 72 |
| Mouse | | | | | | 100 |

Discussion

The low sequence identities for exon 11 (shown in the table above) suggest that BRCA2 is evolving at a faster rate than most other cancer susceptibility/tumour suppressor genes. For example, there is 98% identity between human and mouse NF1 with 95 and 91% between human and mouse WT1 and Rb1 respectively. A notable exception, however, is BRCA1 which only shows 58% amino acid identity between mouse and human. Therefore, although BRCA1 and BRCA2 do not show substantial sequence similarity, they are similar by virtue of a high rate of evolution, unusual gene structure (both have a large exon 11, see (3) and (7) and lack of somatic mutations in sporadic cancers. Whether one or more of these features relates to a function congruence remains to be elucidated.

Although the identity for the translation of exon 11 of the BRCA2 gene is low, most of the BRC motifs are highly conserved between the species analysed. This suggests that there has been pressure to maintain the BRC repeats in BRCA2 and, therefore, that they are important in its function. However, from our alignment, BRC6 is much less conserved than BRC1, 2, 3, 4, 7 and 8 (31 and 85% identity between human and mouse BRC6 and BRC7 respectively). Moreover, it has been altered by insertions or deletions such that the length of the motif differs between species. BRC3 and BRC5 also shows less conservation than BRC1, 2, 3, 4, 7 and 8 (62 and 58% identity respectively between human and mouse BRC3 and BRC5). however, both exhibit a higher level of conservation than the exon 11 translation overall. The data suggests that multiplication of the motif took place prior to the mammalian radiation. For instance, several amino acid residues within motif units (especially in BRC2) are different from the equivalent residues in other units, but are highly conserved in mammalian species. Moreover, the sequences flanking the motifs are not conserved between repeats, but in some cases are conserved across species (for example BRC1 and 4, FIG. 9).

The PCR products that we derived from non-mammalian DNA did not exhibit any similarity to mammalian BRCA2. This suggests that either BRCA2 is restricted to mammals or that the non-mammalian orthologues of BRCA2 have diverged to such an extent that they cannot be identified by the techniques that we used. However, there is evidence of a weak similarity between the BRC sequence and a *Caenorhabditis elegans* gene (CET07E3_2), suggesting that the BRC motif is not restricted to mammals.

There are few clues to the function of the BRC sequences. Truncating germline mutations in the BRCA2 gene that predispose to the development of breast cancer are located throughout the coding region of the gene. In many cases, the mutations leave all the BPC repeats intact, giving little information on the relationship between the motifs and their role in the normal function of BRCA2. The spacing between individual motifs varies from –60 to 300 amino acids, but is reasonably well conserved between mammals. Furthermore, there are multiple elements of secondary structure within each motif which may indicate that they form globular domains. However, it is unclear how these may function. Therefore, direct investigation will be necessary to elucidate the biochemical functions of the BRC motifs.

Conserved regions such as the BRC motifs identified in exon 11 provide valuable indications of domains of the BRCA2 polypeptide that are likely to be important in determining its activity. Thus, these motifs are good candidates for screening studies described above, to find mimetics for BRCA2 polypeptide.

Motifs from exon 11 that are conserved between some or all of the species examined and depicted in FIG. 9 and are summarised in table 4 (SEQ ID NOS: 215–222):

TABLE 4

| Start Amino Acid | End Amino Acid | Motif |
|---|---|---|
| 379 | 404 | SFRTASNKEIKLSEHNIKKSKMFFKD |
| 594 | 619 | GFYSALGTKLNVSSEALQKAVKLFSD |
| 806 | 831 | SFQTASGKNIRVSKESLNKAVNFFDQ |
| 909 | 934 | GFHTASGKKVKIAKESLDKVKNLFDE |
| 1057 | 1082 | AFYTGHSRKTSVSEASLLEAKKWLRE |
| 1257 | 1271 | AFSTASGKIVFVSHE |
| 1392 | 1417 | IFSTASGKSVQVSDASLQKARQVFSE |
| 1474 | 1499 | GFSTASGKQVSVSESALHKVKGMLEE |

TABLE 1

Germline mutations of the BRCA2 gene in breast and ovarian cancer families

| | Number of cases of cancer | | | Description of mutation | | | | Mutation |
|---|---|---|---|---|---|---|---|---|
| Family | Breast | Breast ≦60 yrs | Ovarian | Exon | Codon | Nucleotide | Alteration | Type# |
| B061 | 2 | 2 | 0 | 2 | 9 | 253 | 253delC | FS |
| B091 | 4 | 4 | 0 | 7 | 194 | 809 G > T | Trp194ter | N |
| B135 | 5 | 3 | 0 | 10 | 397 | 1418 | 1418ins4 | FS |
| B105 | 2 | 2 | 0 | 10 | 434 | 1529 | 1529del4 | FS |
| B022 | 4 | 3 | 0 | 10 | 598 | 2022 | 2022del5 | FS |
| B169 | 3 | 3 | 0 | 11 | 643 | 2157 | 2157delG | FS |
| B124 | 3 | 3 | 0 | 11 | 936 | 3034 | 3034del4 | FS |
| B211 | 4 | 4 | 4 | 11 | 2092 | 6503 | 6503delTT | FS |
| B150 | 6 | 5 | 0 | 11 | 2092 | 6503 | 6503delTT | FS |
| B160 | 4 | 2 | 0 | 11 | 2134 | 6630 | 6630del5 | FS |
| B245 | 7 | 3 | 0 | 11 | 2154 | 6690 | 6690delTC | FS |
| B196 | 18 | 14 | 0 | 11 | 2197 | 6919 | 6819delTG | FS |
| B097 | 4 | 3 | 0 | 11 | 2277 | 7057 | 7057del5 | FS |
| B007[d] | 11 | 5 | 0 | 17 | 2637 | 8138 | 8138del5 | FS |
| B028[d] | 3 | 3 | 0 | 17 | 2654 | 6162 | 8162delG | FS |
| B186 | 18 | 18 | 1 | 22 | 2984 | 9179 C > G | Ser2984ter | N |
| B247 | 3 | 3 | 0 | 23 | 2994 | 9208 | 9208ins4 | FS |
| B001 | 4 | 3 | 0 | 25 | 3167 | 9729 G > A | 9729 G > A | SS |
| M681[d] | 3 | 3 | 0 | 11 | 1982 | 6174 | 6174delT | FS |
| M440[d] | 2 | 2 | 0 | 11 | 936 | 3034 | 3034del4 | FS |

| | Number of cases of cancer | | | Description | | | Mutation |
|---|---|---|---|---|---|---|---|
| Family | Breast | Breast ≦50 yrs | Ovarian | Exon | Nucleotide | Alteration | Type# |
| M107 | 8 | 6 | 0 | 11 | 2810 | 2910insA | FS |
| M133 | 11 | 4 | 1 | 10 | 2034 | 2034insA | FS |
| M174 | 9 | 8 | 0 | 11 | 3034 | 3034del4 | FS |
| M269[d] | 21 | 11 | 0 | 20 | 8764 | 8764delAG | FS |
| M280 | 4 | 0 | 0 | 11 | 6085 | G6085Tns | N |
| M284 | 3 | 2 | 1 | 11 | 4304 | 4304delC | FS |
| M347[d] | 4 | 0 | 0 | 9 | 1003 | 1003delAG | FS |
| M372 | 6 | 0 | 0 | 25 | 9661 | 9661delGT | PS |
| M609 | 12[d] | 0 | 0 | 10 | 2024 | 2024del5 | FS |
| M612 | 4 | 3 | 0 | 20 | 8764 | 8764delAG | FS |
| M688 | 2 | 0 | 2 | 11 | 5946 | 5946delCT | FS |

TABLE 1-continued

Germline mutations of the BRCA2 gene in breast and ovarian cancer families

| | | | | | | | |
|---|---|---|---|---|---|---|---|
| M733 | 2 | 0 | 0 | 11 | 6437 | 6437del4 | FS |
| M742 | 6 | 4 | 0 | 2 | 259 | 259insT | FS |
| W9052 | 4 | 3 | 0 | 10 | 2034 | 2034delA | FS |
| W9116 | 4 | 3 | 0 | 10 | 1917 | G1917Ans | N |
| DMBC2 | 6[d] | 2 | 0 | 10 | 1485 | 1485delT | FS |
| W9012 | 1[d] | 0 | 0 | 11 | 5839 | 5839del4 | FS |

[d]These families also contain one or two male breast cancer cases.
#Mutation types characterised as frameshift deletions or insertion (FS), nonsense mutations (N), missense mutations (M) or splice site alterations (SS).

TABLE 2

| Family | Mutation description | Mutation type | sub sequence | d/i sequence | Location exon | Location fragment | Location base | Location codon |
|---|---|---|---|---|---|---|---|---|
| CRC B001 | Splice | 8 | G -> A | | 25 | B | 9729 | 0 |
| CRC B007 | Frameshift | d5 | | CCTTT | 17 | | 8138 | 2637 |
| CRC B022 | Frameshift | d5 | | ATCTT | 10 | E | 2022 | 598 |
| CRC B028 | Frameshift | d1 | | G | 17 | | 8162 | 2645 |
| CRC B061 | Frameshift | d1 | | C | 2 | | 253 | 9 |
| CRC B097 | Frameshift | d5 | | CTTAT | 11 | Z | 7057 | 2277 |
| CRC B105 | Frameshift | d4 | | AAAG | 10 | B | 1525 | 434 |
| CRC B124 | Frameshift | d4 | | AAAC | 11 | F | 3034 | 936 |
| CRC B135 | Frameshift | i4 | | TTAG | 10 | B | 1418 | 397 |
| CRC B150 | Frameshift | d2 | | TT | 11 | W | 6503 | 2092 |
| CRC B160 | Frameshift | d5 | | TAACT | 11 | X | 6630 | 2134 |
| CRC B169 | Frameshift | d1 | | G | 11 | A | 2157 | 643 |
| CRC B196 | Frameshift | d2 | | TG | 11 | Y | 6819 | 2197 |
| CRC B211 | Frameshift | d2 | | TT | 11 | W | 6503 | 2092 |
| CRC B245 | Frameshift | d2 | | TC | 11 | X | 6690 | 2154 |
| CRC B247 | Frameshift | i4 | | AGAT | 23 | | 5208 | 2994 |
| IARC3594 | Frameshift | d2 | | CT | 11 | | 5946 | 1906 |
| IARC2932 | Frameshift | d6 | | TTTCGg | 13 | | 7231 | 2334 |

TABLE 3

| | Number of FBCs | Number of FBCs < 50 | Number of OvCs | Number of MBCs | LOD score at BRCA1 | LOD score at BRCA2 | BRCA2 mutation |
|---|---|---|---|---|---|---|---|
| IARC 2932 | 15 | 10 | 0 | 0 | −2.38 | 3.01 | CCC.TTT.CGgtaa |
| IARC 3594 | 6 | 5 | 0 | 0 | nd | nd | CAT.AAC.TCT.CTA |
| CRC B211 | 5 | 3 | 4 | 0 | −0.48 | 0.49 | AGT.CTT.CAC |
| CRC B196 | 17 | 12 | 0 | 0 | −2.21 | 0.92 | AAA.ACT.GAA.ACT |
| Montreal 681 | 3 | 2 | 0 | 1 | nd | nd | GCA.AGT.GGA |
| Montreal 440 | 2 | 2 | 0 | 2 | nd | nc | GAT.AAA.CAA.GCA |

References:

The references cited below and in the above description are all incorporated by reference in their entirety.

1. Hall et al. Linkage of early-onset familial breast cancer to chromosome 17q21. Science, 250(4988):1684–1689, 1990.

2. Malkin et al. Germ line p53 mutations in a familial syndrome of breast cancer, sarcomas, and other neoplasms. Science, 250(4985):1233–1238, 1990.

3. Miki et al. A strong candidate for the breast and ovarian cancer susceptibility gene BRCA1. Science, 266(5182):66–71, 1994.

4. Wooster et al. A germline mutation in the androgen receptor gene in two brothers with breast cancer and Reifenstein syndrome. Nat. Genet., 2(2):132–134, 1992.

5. Wooster et al. Localization of a breast cancer susceptibility gene, BRCA2, to chromosome 13q12-13. Science, 2655(181):2088–2090, 1994.

6. Frohman et al. Rapid amplification of full length cDNAs from rare transcripts: Amplification using a single gene-specific oligonucleotide primer. PNAS USA, 85:8998–9002, 1988.

7. Wooster et al. Identification of the Breast-Cancer Susceptibility Gene BRCA2. Nature, 378:789–792, 1995.

8. Beaudet and Tsui. A Suggested Nomenclature for Designating Mutations. Hum. Mutat., 2(4):245–8, (1993).

9. Thorlacius et al. A Single BRCA2 Mutation In Male and Female Breast-Cancer Families From Iceland With Varied Cancer Phenotypes. Nature Genetics, 13:117–119, 1996.

10. Phelan et al. Mutation Analysis of the BRCA2 Gene In 49 Site-Specific Breast-Cancer Families. Nature Genetics, 13:120–122, 1996.

11. Easton et al. Genetic Linkage Analysis in Familial Breast and Ovarian Cancer. Am. J. Hum. Genet., 52:718–722, 1993.

12. Gayther et al. Germline Mutations of the Brca1 Gene In Breast and Ovarian-Cancer Families Provide Evidence For a Genotype-Phenotype Correlation. Nature Genetics, 11:428–433, 1995.

13. Yolt et al. Growth-Retardation and Tumor-Inhibition by BRCA1. Nature Genetics, 12:298–302, 1996.

14. Gayther et al. Rapid Detection Of Regionally Clustered Germ-Line BRCA1 Mutations By Multiplex Heteroduplex Analysis. Am. J. Human Gen., 58:451–456, 1996.

15. Tavtigian et al. The Complete BRCA2 Gene and Mutations In Chromosome 13q-Linked Kindreds. Nature Genetics, 12:333–337, 1996.

16. Couch et al. BRCA2 Germline Mutations In Male Breast-Cancer Cases and Breast-Cancer Families. Nature Genetics, 13:123–125, 1996.

17. Neuhausen et al. Recurrent BRCA2 6174delT Mutations In Ashkenazi Jewish Women Affected By Breast-Cancer. Nature Genetics, 13:126–128, 1996.

18. Spirio et al. Alleles of the APC gene: an attenuated form of familial polyposis. Cell, 75:951–957, 1993.

19. Olschwang et al. Restriction of ocular fundus lesions to a specific subgroup of APC mutations in adenomatous polyposis coli patients. Cell, 75:959–968, 1993.

20. Bork et al. Internal Repeats In the BRCA2 Protein-Sequence. Nature Genetics, 13:22–23, 1996.

21. Cowley, S., Paterson, H. F., Kemp, P. and Marshall, C. J., Cell, 77:841–852, 1994.

22. Marais, R., Light, Y., Paterson, H. F. and Marshall, C. J., EMBO J., 14:3136–3145, 1995.

23. Hynes, G. et al, FASEB J. 10:137–147, 1996.

We claim:

1. A nucleic acid molecule consisting of the sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or SEQ ID NO:15, or portion of said sequence of at least 20 consecutive bases.

2. A nucleic acid molecule consisting of a sequence of bases encoding the amino acid sequence set forth in SEQ ID NO:14 or SEQ ID NO:16, or portion of said amino acid sequence of at least 7 consecutive amino acids.

3. A construct comprising a vector and said nucleic acid molecule according to claim 1 or 2.

4. The nucleic acid molecule according to claim 1 or 2 wherein said nucleic acid molecule is bound to a solid support.

5. The nucleic acid molecule according to claim 1 or 2 wherein said nucleic acid molecule bears a detectable label.

6. A nucleic acid consisting of a sequence of bases fully complementary to the nucleic acid molecule according to claim 1 or 2.

* * * * *

SEQUENCE LISTING (1) GENERAL INFORMATION:

(iii) NUMBER OF SEQUENCES: 222

(2) INFORMATION FOR SEQ ID NO:1:

(i) SEQUENCE CHARACTERISTICS:
(A) LENGTH: 1917 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:1:

```
NCNAAAGTTT AAGGGAGTTG TTTAGGAGGA AATTTGATTT AATTCAGAAA NTGAGCATAG     60
TNTTCCANTA TTCACCTACG TTTTAGACCA AAATGTATCA AAAATACTTC CTTCGTGNTG    120
ATAAGAGAAA CCCAGAGCAC TGTGTAAACT CCAGAAATGG AAAAAACCTG CAGTAAAGAA    180
TTTAAATTAT CAAATAACTT AAATGTTGAA GGTGGTTNTT CAGAAAATAA TCACTCTATT    240
AAAGTTTCTC CATATCTCTC TCAATTTCAA CAAGACAAAC AACAGTTGGT ATTAGGAACC    300
AAAGTNTCAC TTGTTGAGAA CATTCATGTT TTGGGAAAAG AACAGGCTTC ACCTAAAAAC    360
GTAAAAATGG AAATTGGTAA AACTGAAACT TTTTCTGATG TTCCTGTGNA AACAAATATA    420
GAAGTTTGTT CTACTTACTC CAAAGATTCA GAAAACTACT TTGAAACAGA AGCAGTAGAA    480
ATTGCTAAAG CTTTTATGGA AGATGATGAA CTGACAGATT NTAAACTGCC AAGTCATGCC    540
ACACATTNTC TTTTTACATG TCCCGAAAAT GAGGAAATGG TTCTGTCAAA TTCAAGAATT    600
GGAAAAAGAA GAGGAGAGCC CCTTATCTTA GTGGGAGAAC CCTCAATCAA AAGAAACTTA    660
TTAAATGAAT TTGACAGGAT AATAGAAAAT CAAGAAAAAT CCTTAAAGGC TTCAAAAAGC    720
ACTCCAGATG GCACAATAAA AGATTGAAGA TTGTTTGTGC ATCATGTTTC TTTAGAGCCG    780
ATTACCTGTG TACCCTTTCG CACAACTAAG GAACGTCAAG AGATACAGAA TCCAAATTTT    840
ACCGCACCTG GTCAAGAATT TCTGTCTAAA TCTCATTTGT ATGAACATCT GACTTTGGAA    900
AAATCTTCAA GCAATTTAGC AGTTTCAGGA CATCCATTTT ATCAAGTTTC TGCTACAAGA    960
AATGAAAAAA TGAGACACTT GATTACTACA GGCAGACCGA CCAAAGTCTT TGTTCCACCT   1020
TTTAAAACTA AATCACATTT TCACAGAGTT GAACAGTGTG TTAGGAATAT TAACTTGGAG   1080
GAAAACAGAC AAAAGCAAAA CATTGATGGA CATGGCTCTG ATGATAGTAA AAATAAGATT   1140
AATGACAATG AGATTCATCA GTTTAACAAA AACAACTCCA ATCAAGCAGC AGCTGTAACT   1200
```

-continued

```
TTCACAAAGT GTGAAGAAGA ACCTTTAGAT TTAATTACAA GTCTTCAGAA TGCCAGAGAT   1260

ATACAGGATA TGCGAATTAA GAAGAAACAA AGGCAACGCG TCTTTCCACA GCCAGGCAGT   1320

CTGTATCTTG CAAAAACATC CACTCTGCCT CGAATCTCTC TGAAAGCAGC AGTAGGAGGC   1380

CAAGTTCCCT CTGCGTGTTC TCATAAACAG CTGTATACGT ATGGCGTTTC TAAACATTGC   1440

ATAAAAATTA ACAGCAAAAA TGCAGAGTCT TTTCAGTTTC ACACTGAAGA TTATTTTGGT   1500

AAGGAAAGTT TATGGACTGG AAAAGGAATA CAGTTGGCTG ATGGTGGATG GCTCATACCC   1560

TCCAATGATG GAAAGGCTGG AAAAGAAGAA TTTTATAGGG CTCTGTGTGA CGTAAAGGCC   1620

ACATAGTGGA TAAACCATGT GCCACTTGAG GAATTGAGAA AAAGTCAGTG TGTTTAGAAC   1680

ATAAGGAGAG GGGCAGAGAA ATGGATCTGG TACAGGAGAA TCAATGAGAC CGGGTAAGAA   1740

ACAGAAAAGG GGCTGCACCA AATGATTGAC ACGCTCTGCA AACTTCTTTT GTTGGCTCAA   1800

GTTGTGGCTC AAGAGGTGAG AAGGTAAGGC CAGACTTATT TGTTATGATT TGCCCTTTAA   1860

ATTGAAGCCT TAAGATTGGA ATTCGATATC AAGCTTATCG ATACCGTCGA CCTCGAG      1917
```

(2) INFORMATION FOR SEQ ID NO:2:

(i) SEQUENCE CHARACTERISTICS:
(A) LENGTH: 502 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:2:

```
CGTAAAAATG GAAATTGGTA AAACTGAAAC TTTTTCTGAT GTTCCTGTGA ANNCAAANAT     60

AGAAGTTTGT TCTACTTACN CCCAAGATTC AGAAAACTAC TTTGNAACAG AANCAGNAGA    120

AATTGCTAAA GCTTTTATGG AAGATGATGA ACTGACAGAT TCTAANCTCC CAANTCATGC    180

CACACATTCT CTTTTTACAT GTCCCGAAAA TGAGGAAATG GTTTTGTCNA ANTCAAGAAT    240

TGGAAAAAGA AGAGGAGAGC CCCTTATCTT ANCNGGGTAA GTNTTCATTT TTACCTTTCG    300

CCNTTGCCAA TCACTATTTT TAAAGTGTTT ATTCAGTAGA CTTGGTATGC TAACAATTAA    360

GAGTGTTATA AACTATGTCT TTTCAGCCAT TTTTGTGTAG TCAGTTTGGG GGAGTATGGT    420

TTGATATACA GATACACAGA TTCAGTATTC GTATACAGAT TTGATATCTT GGTATACAGA    480

TTCGATATCT CTGAATCTGT AT                                             502
```

(2) INFORMATION FOR SEQ ID NO:3:

(i) SEQUENCE CHARACTERISTICS:
(A) LENGTH: 75 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:3:

```
GTCCCGAAAA TGAGGAAATG GTTTAGTCAA ATTCAAGAAT TGGAAAAAGA AGAGGAGAGC     60

CCCTTATCTT AGTGG                                                      75
```

(2) INFORMATION FOR SEQ ID NO:4:

(i) SEQUENCE CHARACTERISTICS:
(A) LENGTH: 96 base pairs
(B) TYPE: nucleic acid
(C) STRANDEDNESS: single -continued (D) TOPOLOGY: linear (ii) MOLECULE TYPE: cDNA (xi) SEQUENCE DESCRIPTION: SEQ ID NO:4:

GAGAACCCTC AATCAAAAGA AACTTATTAA ATGAATTTGA CAGGATAATA GAAAATCAAG 60

AAAAATCCTT AAAGGCTTCA AAAAGCACTC CAGATG 96

(2) INFORMATION FOR SEQ ID NO:5:

(i) SEQUENCE CHARACTERISTICS:
(A) LENGTH: 243 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:5:

AAATCAAGAA AATCCTTAAA GGNTTCAAAA AGCACTCCAG ATGGTAAAAT TAGCTTTTTA 60

TTTATATCTG TTCTCCCTCT ATAGGTATGG TATATAATAT TCTGACCTCA GGTGATCCAC 120

CTGCCTCTCA AAGTGCTGGG ATTACAGACA TGAGCCACTG TGCCTAATCA AGGGACCTCT 180

TTATACTCTT AAAAATTACT GAGGACCTAA AAGAGCATTT GGTTATGTGG AATATATCTA 240

TTG 243

(2) INFORMATION FOR SEQ ID NO:6:

(i) SEQUENCE CHARACTERISTICS:
(A) LENGTH: 236 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:6:

TGTACTGTGA GTTATTTGGT GCATAGTCAT TATCAATTTG TGAATCAATT TATTTTCATA 60

GTTAACATTT ATTGAGCATC CGTTACATTC ACTGAAAATT GTAAAGCCTA TAATTGTCTC 120

AAATTTTTTG TGTATTTACA GTAACATGGA TATTCTCTTA GATTTTAACT AATATGTAAT 180

ATAAAATAAT TGTTTCCTAG GCACAATAAA AGATCGAAGA TTGTAGGGCA TCAGTT 236

(2) INFORMATION FOR SEQ ID NO:7:

(i) SEQUENCE CHARACTERISTICS:
(A) LENGTH: 70 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

GCACAATAAA AGATCGAAGA TTGTTTATGC ATCATGTTTC TTTAGAGCCG ATTACCTGTG 60

TACCCTTTCG 70

(2) INFORMATION FOR SEQ ID NO:8:

(i) SEQUENCE CHARACTERISTICS:
(A) LENGTH: 255 base pairs
(B) TYPE: nucleic acid
(C) STRANDEDNESS: double
(D) TOPOLOGY: linear -continued (ii) MOLECULE TYPE: DNA (genomic)

(xi) SEQUENCE DESCRIPTION: SEQ ID NO:8:

AGCCGATTAC CTGTGTACCC TTTCGGTAAG ACATGTTTAA ATTTTTCTAA ATTCTAATAC 60

AGTATGAGAA AAGTCTCGTT TTTATAAATG AACATTTCTA AAAATAATGA CACTAACGTT 120

AAGAAGTTAA CACTTCCCGT TTTATAAAAT TTATAAAATA CTTTGGTAGT ATTTTATAGT 180

GCTGTTCATA TCATTATTTT ATTTTTTAAT TTTATGACAG CTTTGTAAAG TAGACAGATT 240

TTATTCTAAT TTTAT 255

(2) INFORMATION FOR SEQ ID NO:9:

(i) SEQUENCE CHARACTERISTICS:
(A) LENGTH: 501 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:9:

ACACACTGAG AGGTCCACAC TTGACAGATT TATTNTATTA TGNGTTATGT GAGGTAGATT 60

GTAAGTCAAA GGCTAGCCTT GAAAAATGTG ATATTGTTTT GGAATGGCAA CCATGGNGAA 120

NACAAAACAG TNACCAGAAT NGTATCACCA TGTAGCAAAT GAGGGTCTGC AACAAAGGCA 180

TATTCATAAA TATTNANANG TGTAGTAGTC AATNAACTTA TAAATTTTNT CCCCANTGCA 240

GCACNANTAA GGGACGTCAA GAGATACAGA ATCCANATTT TACCGCACCT GGTCANGGAT 300

TTCTGTNTAA ATATCATTTG TATGAACATC TGACTTTGGA AAAATCTTCA AGCAATTTNG 360

CAGTTTCAGG ACATCCATTT TATCAAGTTT CTGCTACAAG AAATGAAAAA ATGAGACACT 420

TGATTACTAC AGGCAGACCA ACCAAAGTCT TTGTTCCACC TTTTAAAACT AAATCACATT 480

TTCCACAGAG TTGAACAGTG T 501

(2) INFORMATION FOR SEQ ID NO:10:

(i) SEQUENCE CHARACTERISTICS:
(A) LENGTH: 428 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:10:

CACAACTAAG GAACGTCAAG AGATACAGAA TCCAAATTTT ACCGCACCTG GTCAAGAATT 60

TCTGTCTAAA TCTCATTTGT ATGAACATCT GACTTTGGAA AAATCTTCAA GCAATTTAGC 120

AGTTTCAGGA CATCCATTTT ATCAAGTTTC TGCTACAAGA AATGAAAAAA TGAGACACTT 180

GATTACTACA GGCAGACCAA CCAAAGTCTT TGTTCCACCT TTTAAAACTA AATCACATTT 240

TCACAGAGTT GAACAGTGTG TTAGGAATAT TAACTTGGAG GAAAACAGAC AAAAGCAAAA 300

CATTGATGGA CATGGCTCTG ATGATAGTAA AAATAAGATT AATGACAATG AGATTCATCA 360

GTTTAACAGN AACAACTCCA ATCAAGCAGC AGCTGTAACT TTCACAAAGT GTGAAGAAGA 420

ACCTTTAG 428

(2) INFORMATION FOR SEQ ID NO:11:

(i) SEQUENCE CHARACTERISTICS:

-continued (A) LENGTH: 232 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:11:

```
GGANGAAACA TATTNAAGCA AAACATTGAT GGACNTGGCT CTGATGATAG TAAAAATAAG     60

ATTAATGACA ATGAGATTCA TCAGTTTAAC AAAAACAACT CCAATCAAGC AGCAGCTGTA    120

ACTTTCACAA AGTGTGAANA AAAACCTTTA GGTATTGTAT GACAATTTGT GTGATGAATT    180

TTTGCCTTTC AGTTANATAT TTCCGTTGTT AAATAATGTC CTGATGGTTT NC            232
```

(2) INFORMATION FOR SEQ ID NO:12:

(i) SEQUENCE CHARACTERISTICS:
(A) LENGTH: 100 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:12:

```
CCCCTTTGGT GGTGGTAATT TTAAAGCCCT TTTTAATGTT TTAGATTTTC TAAATCCAAA     60

GATTAGGTTT AAATTATTCT AATGTTTCTT TCAAANATAA                          100
```

(2) INFORMATION FOR SEQ ID NO:13:

(i) SEQUENCE CHARACTERISTICS:
(A) LENGTH: 689 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:13:

```
ATTTAATTAC AAGTCTTCAG AATGCCAGAG ATATACAGGA TATGCGAATT AAGAAGAAAC     60

AAAGGCAACG CGTCTTTCCA CAGCCAGGCA GTCTGTATCT TGCAAAAACA TCCACTCTGC    120

CTCGAATCTC TCTGAAAGCA GCAGTAGGAG GCCAAGTTCC CTCTGCGTGT TCTCATAAAC    180

AGCTGTATAC GTATGGCGTT TCTAAACATT GCATAAAAAT TAACAGCAAA AATGCAGAGT    240

CTTTTCAGTT TCACACTGAA GATTATTTTG GTAAGGAAAG TTTATGGACT GGAAAAGGAA    300

TACAGTTGGC TGATGGTGGA TGGCTCATAC CCTCCAATGA TGGAAAGGCT GGAAAAGAAG    360

AATTTTATAG GGCTCTGTGT GACGTAAAGG CCACATAGTG GATAAACCAT GTGCCACTTG    420

AGGAATTGAG AAAAAGTCAG TGTGTTTAGA ACATAAGGAG AGGGGCAGAG AAATGGATCT    480

GGTACAGGAG AATCAATGAG ACCGGGTAAG AAACAGAAAA GGGGCTGCAC CAAATGATTG    540

ACACGCTCTG CAAACTTCTT TTGTTGGCTC AAGTTGTGGC TCAAGAGGTG AGAAGGTAAG    600

GCCAGACTTA TTTGTTATGA TTTGCCCTTT AAATTGAAGC CTTAAGATTG GAATTCGATA    660

TCAAGCTTAT CGATACCGTC GACCTCGAG                                      689
```

(2) INFORMATION FOR SEQ ID NO:14:

(i) SEQUENCE CHARACTERISTICS:
(A) LENGTH: 534 amino acids
(B) TYPE: amino acid
(D) TOPOLOGY: linear -continued (ii) MOLECULE TYPE: protein (xi) SEQUENCE DESCRIPTION: SEQ ID NO:14:

```
Lys Val Gly Ser Cys Leu Gly Gly Asn Leu Ile Phe Arg Xaa Ala Xaa
1               5                   10                  15

Ser Xaa Ile His Leu Arg Phe Arg Pro Lys Cys Ile Lys Asn Thr Ser
            20                  25                  30

Phe Val Xaa Ile Arg Glu Thr Gln Ser Thr Val Thr Pro Glu Met Glu
        35                  40                  45

Lys Thr Cys Ser Lys Glu Phe Lys Leu Ser Asn Asn Leu Asn Val Glu
    50                  55                  60

Gly Gly Xaa Ser Glu Asn Asn His Ser Ile Lys Val Ser Pro Tyr Leu
65                  70                  75                  80

Ser Gln Phe Gln Gln Asp Lys Gln Gln Leu Val Leu Gly Thr Lys Val
                85                  90                  95

Ser Leu Val Glu Asn Ile His Val Leu Gly Lys Glu Gln Ala Ser Pro
            100                 105                 110

Lys Asn Val Lys Met Glu Ile Gly Lys Thr Glu Thr Phe Ser Asp Val
        115                 120                 125

Pro Val Xaa Thr Asn Ile Glu Val Cys Ser Thr Tyr Ser Lys Asp Ser
    130                 135                 140

Glu Asn Tyr Phe Glu Thr Glu Ala Val Glu Ile Ala Lys Ala Phe Met
145                 150                 155                 160

Glu Asp Asp Glu Leu Thr Asp Xaa Lys Leu Pro Ser His Ala Thr His
                165                 170                 175

Xaa Leu Phe Thr Cys Pro Glu Asn Glu Glu Met Val Leu Ser Asn Ser
            180                 185                 190

Arg Ile Gly Lys Arg Arg Gly Glu Pro Leu Ile Leu Val Gly Glu Pro
        195                 200                 205

Ser Ile Lys Arg Asn Leu Leu Asn Glu Phe Asp Arg Ile Ile Glu Asn
    210                 215                 220

Gln Glu Lys Ser Leu Lys Ala Ser Lys Ser Thr Pro Asp Gly Thr Ile
225                 230                 235                 240

Lys Asp Arg Leu Phe Val His His Val Ser Leu Glu Pro Ile Thr Cys
                245                 250                 255

Val Pro Phe Arg Thr Thr Lys Glu Arg Gln Glu Ile Gln Asn Pro Asn
            260                 265                 270

Phe Thr Ala Pro Gly Gln Glu Phe Leu Ser Lys Ser His Leu Tyr Glu
        275                 280                 285

His Leu Thr Leu Glu Lys Ser Ser Ser Asn Leu Ala Val Ser Gly His
    290                 295                 300

Pro Phe Tyr Gln Val Ser Ala Thr Arg Asn Glu Lys Met Arg His Leu
305                 310                 315                 320

Ile Thr Thr Gly Arg Pro Thr Lys Val Phe Val Pro Pro Phe Lys Thr
                325                 330                 335

Lys Ser His Phe His Arg Val Glu Gln Cys Val Arg Asn Ile Asn Leu
            340                 345                 350

Glu Glu Asn Arg Gln Lys Gln Asn Ile Asp Gly His Gly Ser Asp Asp
        355                 360                 365

Ser Lys Asn Lys Ile Asn Asp Asn Glu Ile His Gln Phe Asn Lys Asn
    370                 375                 380

Asn Ser Asn Gln Ala Ala Ala Val Thr Phe Thr Lys Cys Glu Glu Glu
385                 390                 395                 400
```

-continued

```
Pro Leu Asp Leu Ile Thr Ser Leu Gln Asn Ala Arg Asp Ile Gln Asp
                405                 410                 415

Met Arg Ile Lys Lys Lys Gln Arg Gln Arg Val Phe Pro Gln Pro Gly
            420                 425                 430

Ser Leu Tyr Leu Ala Lys Thr Ser Thr Leu Pro Arg Ile Ser Leu Lys
        435                 440                 445

Ala Ala Val Gly Gly Gln Val Pro Ser Ala Cys Ser His Lys Gln Leu
    450                 455                 460

Tyr Thr Tyr Gly Val Ser Lys His Cys Ile Lys Ile Asn Ser Lys Asn
465                 470                 475                 480

Ala Glu Ser Phe Gln Phe His Thr Glu Asp Tyr Phe Gly Lys Glu Ser
                485                 490                 495

Leu Trp Thr Gly Lys Gly Ile Gln Leu Ala Asp Gly Gly Trp Leu Ile
            500                 505                 510

Pro Ser Asn Asp Gly Lys Ala Gly Lys Glu Glu Phe Tyr Arg Ala Leu
        515                 520                 525

Cys Asp Val Lys Ala Thr
    530
```

(2) INFORMATION FOR SEQ ID NO:15:

(i) SEQUENCE CHARACTERISTICS:
(A) LENGTH: 7240 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:15:

```
CCACATTGGA AAGTCAATGC CAAATGTCCT AGAAGATGAA GTATATGAAA CAGTTGTAGA     60

TACCTCTGAA GAAGATAGTT TTTCATTATG TTTTTCTAAA TGTAGAACAA AAAATCTACA    120

AAAAGTAAGA ACTAGCAAGA CTAGGAAAAA AATTTTCCAT GAAGCAAACG CTGATGAATG    180

TGAAAAATCT AAAAACCAAG TGAAAGAAAA ATACTCATTT GTATCTGAAG TGGAACCAAA    240

TGATACTGAT CCATTAGATT CAAATGTAGC AAATCAGAAG CCCTTTGAGA GTGGAAGTGA    300

CAAAATCTCC AAGGAAGTTG TACCGTCTTT GGCCTGTGAA TGGTCTCAAC TAACCCTTTC    360

AGGTCTAAAT GGAGCCCAGA TGGAGAAAAT ACCCCTATTG CATATTTCTT CATGTGACCA    420

AAATATTTCA GAAAAAGACC TATTAGACAC AGAGAACAAA AGAAAGAAAG ATTTTCTTAC    480

TTCAGAGAAT TCTTTGCCAC GTATTTCTAG CCTACCAAAA TCAGAGAAGC CATTAAATGA    540

GGAAACAGTG GTAAATAAGA GAGATGAAGA GCAGCATCTT GAATCTCATA CAGACTGCAT    600

TCTTGCAGTA AAGCAGGCAA TATCTGGAAC TTCTCCAGTG GCTTCTTCAT TTCAGGGTAT    660

CAAAAAGTCT ATATTCAGAA TAAGAGAATC ACCTAAAGAG ACTTTCAATG CAAGTTTTTC    720

AGGTCATATG ACTGATCCAA ACTTTAAAAA AGAAACTGAA GCCTCTGAAA GTGGACTGGA    780

AATACATACT GTTTGCTCAC AGAAGGAGGA CTCCTTATGT CCAAATTTAA TTGATAATGG    840

AAGCTGGCCA GCCACCACCA CACAGAATTC TGTAGCTTTG AAGAATGCAG GTTTAATATC    900

CACTTTGAAA AAGAAAACAA ATAAGTTTAT TTATGCTATA CATGATGAAA CATCTTATAA    960

AGGAAAAAAA ATACCGAAAG ACCAAAAATC AGAACTAATT AACTGTTCAG CCCAGTTTGA   1020

AGCAAATGCT TTTGAAGCAC CACTTACATT TGCAAATGCT GATTCAGGTT TATTGCATTC   1080

TTCTGTGAAA AGAAGCTGTT CACAGAATGA TTCTGAAGAA CCAACTTTGT CCTTAACTAG   1140

CTCTTTTGGG ACAATTCTGA GGAAATGTTC TAGAAATGAA ACATGTTCTA ATAATACAGT   1200
```

-continued

```
AATCTCTCAG GATCTTGATT ATAAAGAAGC AAAATGTAAT AAGGAAAAAC TACAGTTATT   1260
TATTACCCCA GAAGCTGATT CTCTGTCATG CCTGCAGGAA GGACAGTGTG AAAATGATCC   1320
AAAAAGCAAA AAAGTTTCAG ATATAAAAGA AGAGGTCTTG GCTGCAGCAT GTCACCCAGT   1380
ACAACATTCA AAAGTGGAAT ACAGTGATAC TGACTTTCAA TCCCAGAAAA GTCTTTTATA   1440
TGATCATGAA AATGCCAGCA CTCTTATTTT AACTCCTACT TCCAAGGATG TTCTGTCAAA   1500
CCTAGTCATG ATTTCTAGAG GCAAAGAATC ATACAAAATG TCAGACAAGC TCAAAGGTAA   1560
CAATTATGAA TCTGATGTTG AATTAACCAA AAATATTCCC ATGGAAAAGA ATCAAGATGT   1620
ATGTGCTTTA AATGAAAATT ATAAAAACGT TGAGCTGTTG CCACCTGAAA AATACATGAG   1680
AGTAGCATCA CCTTCAAGAA AGGTACAATT CAACCAAAAC ACAAATCTAA GAGTAATCCA   1740
AAAAAATCAA GAAGAAACTA CTTCAATTTC AAAAATAACT GTCAATCCAG ACTCTGAAGA   1800
ACTTTTCTCA GACAATGAGA ATAATTTTGT CTTCCAAGTA GCTAATGAAA GGAATAATCT   1860
TGCTTTAGGA AATACTAAGG AACTTCATGA AACAGACTTG ACTTGTGTAA ACGAACCCAT   1920
TTTCAAGAAC TCTACCATGG TTTTATATGG AGACACAGGT GATAAACAAG CAACCCAAGT   1980
GTCAATTAAA AAAGATTTGG TTTATGTTCT TGCAGAGGAG AACAAAAATA GTGTAAAGCA   2040
GCATATAAAA ATGACTCTAG GTCAAGATTT AAAATCGGAC ATCTCCTTGA ATATAGATAA   2100
AATACCAGAA AAAAATAATG ATTACATGAA CAAATGGGCA GGACTCTTAG GTCCAATTTC   2160
AAATCACAGT TTTGGAGGTA GCTTCAGAAC AGCTTCAAAT AAGGAAATCA AGCTCTCTGA   2220
ACATAACATT AAGAAGAGCA AAATGTTCTT CAAAGATATT GAAGAACAAT ATCCTACTAG   2280
TTTAGCTTGT GTTGAAATTG TAAATACCTT GGCATTAGAT AATCAAAAGA AACTGAGCAA   2340
GCCTCAGTCA ATTAATACTG TATCTGCACA TTTACAGAGT AGTGTAGTTG TTTCTGATTG   2400
TAAAAATAGT CATATAACCC CTCAGATGTT ATTTTCCAAG CAGGATTTTA ATTCAAACCA   2460
TAATTTAACA CCTAGCCAAA AGGAGCAAAT TACAGAACTT TCTACTATAT TAGAAGATTC   2520
AGGAAGTCAG TTTGAATTTA CTCAGTTTAG AAAACCAAGC TACATATTGC AGAAGAGTAC   2580
ATTTGAAGTG CCTGAAAACC AGATGACTAT CTTAAAGACC ACTTCTGAGG AATGCAGAGA   2640
TGCTGATCTT CATGTCATAA TGAATGCCCC ATCGATTGGT CAGGTAGACA GCAGCAAGCA   2700
ATTTGAAGGT ACAGTTGAAA TTAAACGGAA GTTTGCTGGC CTGTTGAAAA ATGACTGTAA   2760
CAAAAGTGCT TCTGGTTATT TAACAGATGA AAATGAAGTG GGGTTTAGGG GCTTTTATTC   2820
TGCTCATGGC ACAAAACTGA ATGTTTCTAC TGAAGCTCTG CAAAAAGCTG TGAAACTGTT   2880
TAGTGATATT GAGAATATTA GTGAGGAAAC TTCTGCAGAG GTACATCCAA TAAGTTTATC   2940
TTCAAGTAAA TGTCATGATT CTGTCGTTTC AATGTTTAAG ATAGAAAATC ATAATGATAA   3000
AACTGTAAGT GAAAAAAATA ATAAATGCCA ACTGATATTA CAAAATAATA TTGAAATGAC   3060
TACTGGCACT TTTGTTGAAG AAATTACTGA AAATTACAAG AGAAATACTG AAAATGAAGA   3120
TAACAAATAT ACTGCTGCCA GTAGAAATTC TCATAACTTA GAATTTGATG GCAGTGATTC   3180
AAGTAAAAAT GATACTGTTT GTATTCATAA AGATGAAACG GACTTGCTAT TTACTGATCA   3240
GCACAACATA TGTCTTAAAT TATCTGGCCA GTTTATGAAG GAGGGAAACA CTCAGATTAA   3300
AGAAGATTTG TCAGATTTAA CTTTTTTGGA AGTTGCGAAA GCTCAAGAAG CATGTCATGG   3360
TAATACTTCA AATAAAGAAC AGTTAACTGC TACTAAAACG GAGCAAAATA TAAAAGATTT   3420
TGAGACTTCT GATACATTTT TTCAGACTGC AAGTGGGAAA AATATTAGTG TCGCCAAAGA   3480
GTCATTTAAT AAAATTGTAA ATTTCTTTGA TCAGAAACCA GAAGAATTGC ATAACTTTTC   3540
```

-continued

| | | | | | | |
|---|---|---|---|---|---|---|
| CTTAAATTCT | GAATTACATT | CTGACATAAG | AAAGAACAAA | ATGGACATTC | TAAGTTATGA | 3600 |
| GGAAACAGAC | ATAGTTAAAC | ACAAAATACT | GAAAGAAAGT | GTCCCAGTTG | GTACTGGAAA | 3660 |
| TCAACTAGTG | ACCTTCCAGG | GACAACCCGA | ACGTGATGAA | AAGATCAAAG | AACCTACTCT | 3720 |
| GTTGGGTTTT | CATACAGCTA | GCGGGAAAAA | AGTTAAAATT | GCAAAGGAAT | CTTTGGACAA | 3780 |
| AGTGAAAAAC | CTTTTTGATG | AAAGAGCAAG | GTACTAGTGA | AATCACCAGT | TTTAGCCATC | 3840 |
| AATGGGCAAA | GACCCTAAAG | TACAGAGAGG | CCTGTAAAGA | CCTTGAATTA | GCATGTGAGA | 3900 |
| CCATTGAGAT | CACAGCTGCC | CCAAAGTGTA | AAGAAATGCA | GAATTCTCTC | AATAATGATA | 3960 |
| AAAACCTTGT | TTCTATTGAG | ACTGTGGTGC | CACCTAAGCT | CTTAAGTGAT | AATTTATGTA | 4020 |
| GACAAACTGA | AAATCTCAAA | ACATCAAAAA | GTATCTTTTT | GAAAGTTAAA | GTACATGAAA | 4080 |
| ATGTAGAAAA | AGAAACAGCA | AAAAGTCCTG | CAACTTGTTA | CACAAATCAG | TCCCCTTATT | 4140 |
| CAGTCATTGA | AAATTCAGCC | TTAGCTTTTT | ACACAAGTTG | TAGTAGAAAA | ACTTCTGTGA | 4200 |
| GTCAGACTTC | ATTACTTGAA | GCAAAAAAAT | GGCTTAGAGA | AGGAATATTT | GATGGTCAAC | 4260 |
| CAGAAAGAAT | AAATACTGCA | GATTATGTAG | GAAATTATTT | GTATGAAAAT | AATTCAAACA | 4320 |
| GTACTATAGC | TGAAAATGAC | AAAAATCATC | TCTCCGAAAA | ACAAGATACT | TATTTAAGTA | 4380 |
| ACAGTAGCAT | GTCTAACAGC | TATTCCTACC | ATTCTGATGA | GGTATATAAT | GATTCAGGAT | 4440 |
| ATCTCTCAAA | AAATAAACTT | GATTCTGGTA | TTGAGCCAGT | ATTGAAGAAT | GTTGAAGATC | 4500 |
| AAAAAAACAC | TAGTTTTTCC | AAAGTAATAT | CCAATGTAAA | AGATGCAAAT | GCATACCCAC | 4560 |
| AAACTGTAAA | TGAAGATATT | TGCGTTGAGG | AACTTGTGAC | TAGCTCTTCA | CCCTGCAAAA | 4620 |
| ATAAAAATGC | AGCCATTAAA | TTGTCCATAT | CTAATAGTAA | TAATTTTGAG | GTAGGGCCAC | 4680 |
| CTGCATTTAG | GATAGCCAGT | GGTAAAATCG | TTTGTGTTTC | ACATGAAACA | ATTAAAAAAG | 4740 |
| TGAAAGACAT | ATTTACAGAC | AGTTTCAGTA | AAGTAATTAA | GGAAAACAAC | GAGAATAAAT | 4800 |
| CAAAAATTTG | CCAAACGAAA | ATTATGGCAG | GTTGTTACGA | GGCATTGGAT | GATTCAGAGG | 4860 |
| ATATTCTTCA | TAACTCTCTA | GATAATGATG | AATGTAGCAC | GCATTCACAT | AAGGTTTTTG | 4920 |
| CTGACATTCA | GAGTGAAGAA | ATTTTACAAC | ATAACCAAAA | TATGTCTGGA | TTGGAGAAAG | 4980 |
| TTTCTAAAAT | ATCACCTTGT | GATGTTAGTT | TGGAAACTTC | AGATATATGT | AAATGTAGTA | 5040 |
| TAGGGAAGCT | TCATAAGTCA | GTCTCATCTG | CAAATACTTG | TGGGATTTTT | AGCACAGCAA | 5100 |
| GTGGAAAATC | TGTCCAGGTA | TCAGATGCTT | CATTACAAAA | CGCAAGACAA | GTGTTTTCTG | 5160 |
| AAATAGAAGA | TAGTACCAAG | CAAGTCTTTT | CCAAAGTATT | GTTTAAAAGT | AACGAACATT | 5220 |
| CAGACCAGCT | CACAAGAGAA | GAAAATACTG | CTATACGTAC | TCCAGAACAT | TTAATATCCC | 5280 |
| AAAAAGGCTT | TTCATATAAT | GTGGTAAATT | CATCTGCTTT | CTCTGGATTT | AGTACAGCAA | 5340 |
| GTGGAAAGCA | AGTTTCCATT | TTAGAAAGTT | CCTTACACAA | AGTTAAGGGA | GTGTTAGAGG | 5400 |
| AATTTGATTT | AATCAGAACT | GAGCATAGTC | TTCACTATTC | ACCTACGTCT | AGACAAAATG | 5460 |
| TATCAAAAAT | ACTTCCTCGT | GTTGATAAGA | GAAACCCAGA | GCACTGTGTA | AACTCAGAAA | 5520 |
| TGGAAAAAAC | CTGCAGTAAA | GAATTTAAAT | TATCAAATAA | CTTAAATGTT | GAAGGTGGTT | 5580 |
| CTTCAGAAAA | TAATCACTCT | ATTAAAGTTT | CTCCATATCT | CTCTCAATTT | CAACAAGACA | 5640 |
| AACAACAGTT | GGTATTAGGA | ACCAAAGTCT | CACTTGTTGA | GAACATTCAT | GTTTTGGGAA | 5700 |
| AAGAACAGGC | TTCACCTAAA | AACGTAAAAA | TGGAAATTGG | TAAAACTGAA | ACTTTTTCTG | 5760 |
| ATGTTCCTGT | GAAAACAAAT | ATAGAAGTTT | GTTCTACTTA | CTCCAAAGAT | TCAGAAAACT | 5820 |
| ACTTTGAAAC | AGAAGCAGTA | GAAATTGCTA | AAGCTTTTAT | GGAAGATGAT | GAACTGACAG | 5880 |
| ATTCTAAACT | GCCAAGTCAT | GCCACACATT | CTCTTTTTAC | ATGTCCCGAA | AATGAGGAAA | 5940 |

-continued

```
TGGTTTTGTC AAATTCAAGA ATTGGAAAAA GAAGAGGAGA GCCCCTTATC TTAGTGGGAG   6000
AACCCTCAAT CAAAAGAAAC TTATTAAATG AATTTGACAG GATAATAGAA AATCAAGAAA   6060
AATCCTTAAA GGCTTCAAAA AGCACTCCAG ATGGCACAAT AAAAGATCGA AGATTGTTTG   6120
TGCATCATGT TTCTTTAGAG CCGATTACCT GTGTACCCTT TCGCACAACT AAGGAACGTC   6180
AAGAGATACA GAATCCAAAT TTTACCGCAC CTGGTCAAGA ATTTCTGTCT AAATCTCATT   6240
TGTATGAACA TCTGACTTTG GAAAAATCTT CAAGCAATTT AGCAGTTTCA GGACATCCAT   6300
TTTATCAAGT TTCTGGTAAC AAGAATGGAA AAATGAGAAA ATTGATTACT ACAGGCAGAC   6360
CAACCAAAGT CTTTGTTCCA CCTTTTAAAA CTAAATCACA TTTTCACAGA GTTGAACAGT   6420
GTGTTAGGAA TATTAACTTG GAGGGAAACA GACAAAAGCA AAACATTGAT GGACATGGCT   6480
CTGATGATAG TAAAAATAAG ATTAATGACA ATGAGATTCA TCAGTTTAAC AAAAACAACT   6540
CCAATCAAGC AGCAGCTGTA ACTTTCACAA AGTGTGAAGA AGAACCTTTA GATTTAATTA   6600
CAAGTCTTCA GAATGCCAGA GATATACAGG ATATGCGAAT TAAGAAGAAA CAAAGGCAAC   6660
GCGTCTTTCC ACAGCCAGGC AGTCTGTATC TTGCAAAAAC ATCCACTCTG CCTCGAATCT   6720
CTCTGAAAGC AGCAGTAGGA GGCCAAGTTC CCTCTGCGTG TTCTCATAAA CAGCTGTATA   6780
CGTATGGCGT TTCTAAACAT TGCATAAAAA TTAACAGCAA AAATGCAGAG TCTTTTCAGT   6840
TTCACACTGA AGATTATTTT GGTAAGGAAA GTTTATGGAC TGGAAAAGGA ATACAGTTGG   6900
CTGATGGTGG ATGGCTCATA CCCTCCAATG ATGGAAAGGC TGGAAAAGAA GAATTTTATA   6960
GGGCTCTGTG TGACGTAAAG GCCACATAGT GGATAAACCA TGTGCCACTT GAGGAATTGA   7020
GAAAAAGTCA GTGTGTTTAG AACATAAGGA GAGGGGCAGA GAAATGGATC TGGTACAGGA   7080
GAATCAATGA GACCGGGTAA GAAACAGAAA AGGGGCTGCA CCAAATGATT GACACGCTCT   7140
GCAAACTTCT TTTGTTGGCT CAAGTTGTGG CTCAAGAGGT GAGAAGGTAA GGCCAGACTT   7200
ATTTGTTATG ATTTGCCCTT TAAATTGAAG CCTTAAGATT                         7240
```

(2) INFORMATION FOR SEQ ID NO:16:

(i) SEQUENCE CHARACTERISTICS:
(A) LENGTH: 2329 amino acids
(B) TYPE: amino acid
(D) TOPOLOGY: linear (ii) MOLECULE TYPE: protein (xi) SEQUENCE DESCRIPTION: SEQ ID NO:16:

```
His Ile Gly Lys Ser Met Pro Asn Val Leu Glu Asp Glu Val Tyr Glu
1               5                   10                  15

Thr Val Val Asp Thr Ser Glu Glu Asp Ser Phe Ser Leu Cys Phe Ser
            20                  25                  30

Lys Cys Arg Thr Lys Asn Leu Gln Lys Val Arg Thr Ser Lys Thr Arg
        35                  40                  45

Lys Lys Ile Phe His Glu Ala Asn Ala Asp Glu Cys Glu Lys Ser Lys
    50                  55                  60

Asn Gln Val Lys Glu Lys Tyr Ser Phe Val Ser Glu Val Glu Pro Asn
65                  70                  75                  80

Asp Thr Asp Pro Leu Asp Ser Asn Val Ala Asn Gln Lys Pro Phe Glu
                85                  90                  95

Ser Gly Ser Asp Lys Ile Ser Lys Glu Val Val Pro Ser Leu Ala Cys
            100                 105                 110

Glu Trp Ser Gln Leu Thr Leu Ser Gly Leu Asn Gly Ala Gln Met Glu
```

-continued

```
        115                 120                 125

Lys Ile Pro Leu Leu His Ile Ser Ser Cys Asp Gln Asn Ile Ser Glu
    130                 135                 140

Lys Asp Leu Leu Asp Thr Glu Asn Lys Arg Lys Lys Asp Phe Leu Thr
145                 150                 155                 160

Ser Glu Asn Ser Leu Pro Arg Ile Ser Ser Leu Pro Lys Ser Glu Lys
                165                 170                 175

Pro Leu Asn Glu Glu Thr Val Val Asn Lys Arg Asp Glu Glu Gln His
            180                 185                 190

Leu Glu Ser His Thr Asp Cys Ile Leu Ala Val Lys Gln Ala Ile Ser
        195                 200                 205

Gly Thr Ser Pro Val Ala Ser Ser Phe Gln Gly Ile Lys Lys Ser Ile
    210                 215                 220

Phe Arg Ile Arg Glu Ser Pro Lys Glu Thr Phe Asn Ala Ser Phe Ser
225                 230                 235                 240

Gly His Met Thr Asp Pro Asn Phe Lys Lys Glu Thr Glu Ala Ser Glu
                245                 250                 255

Ser Gly Leu Glu Ile His Thr Val Cys Ser Gln Lys Glu Asp Ser Leu
            260                 265                 270

Cys Pro Asn Leu Ile Asp Asn Gly Ser Trp Pro Ala Thr Thr Thr Gln
        275                 280                 285

Asn Ser Val Ala Leu Lys Asn Ala Gly Leu Ile Ser Thr Leu Lys Lys
    290                 295                 300

Lys Thr Asn Lys Phe Ile Tyr Ala Ile His Asp Glu Thr Ser Tyr Lys
305                 310                 315                 320

Gly Lys Lys Ile Pro Lys Asp Gln Lys Ser Glu Leu Ile Asn Cys Ser
                325                 330                 335

Ala Gln Phe Glu Ala Asn Ala Phe Glu Ala Pro Leu Thr Phe Ala Asn
            340                 345                 350

Ala Asp Ser Gly Leu Leu His Ser Ser Val Lys Arg Ser Cys Ser Gln
        355                 360                 365

Asn Asp Ser Glu Glu Pro Thr Leu Ser Leu Thr Ser Ser Phe Gly Thr
    370                 375                 380

Ile Leu Arg Lys Cys Ser Arg Asn Glu Thr Cys Ser Asn Asn Thr Val
385                 390                 395                 400

Ile Ser Gln Asp Leu Asp Tyr Lys Glu Ala Lys Cys Asn Lys Glu Lys
                405                 410                 415

Leu Gln Leu Phe Ile Thr Pro Glu Ala Asp Ser Leu Ser Cys Leu Gln
            420                 425                 430

Glu Gly Gln Cys Glu Asn Asp Pro Lys Ser Lys Lys Val Ser Asp Ile
        435                 440                 445

Lys Glu Glu Val Leu Ala Ala Ala Cys His Pro Val Gln His Ser Lys
    450                 455                 460

Val Glu Tyr Ser Asp Thr Asp Phe Gln Ser Gln Lys Ser Leu Leu Tyr
465                 470                 475                 480

Asp His Glu Asn Ala Ser Thr Leu Ile Leu Thr Pro Thr Ser Lys Asp
                485                 490                 495

Val Leu Ser Asn Leu Val Met Ile Ser Arg Gly Lys Glu Ser Tyr Lys
            500                 505                 510

Met Ser Asp Lys Leu Lys Gly Asn Asn Tyr Glu Ser Asp Val Glu Leu
        515                 520                 525

Thr Lys Asn Ile Pro Met Glu Lys Asn Gln Asp Val Cys Ala Leu Asn
    530                 535                 540
```

-continued

```
Glu Asn Tyr Lys Asn Val Glu Leu Leu Pro Pro Glu Lys Tyr Met Arg
545                 550                 555                 560

Val Ala Ser Pro Ser Arg Lys Val Gln Phe Asn Gln Asn Thr Asn Leu
                565                 570                 575

Arg Val Ile Gln Lys Asn Gln Glu Glu Thr Thr Ser Ile Ser Lys Ile
            580                 585                 590

Thr Val Asn Pro Asp Ser Glu Glu Leu Phe Ser Asp Asn Glu Asn Asn
        595                 600                 605

Phe Val Phe Gln Val Ala Asn Glu Arg Asn Asn Leu Ala Leu Gly Asn
    610                 615                 620

Thr Lys Glu Leu His Glu Thr Asp Leu Thr Cys Val Asn Glu Pro Ile
625                 630                 635                 640

Phe Lys Asn Ser Thr Met Val Leu Tyr Gly Asp Thr Gly Asp Lys Gln
                645                 650                 655

Ala Thr Gln Val Ser Ile Lys Lys Asp Leu Val Tyr Val Leu Ala Glu
            660                 665                 670

Glu Asn Lys Asn Ser Val Lys Gln His Ile Lys Met Thr Leu Gly Gln
        675                 680                 685

Asp Leu Lys Ser Asp Ile Ser Leu Asn Ile Asp Lys Ile Pro Glu Lys
    690                 695                 700

Asn Asn Asp Tyr Met Asn Lys Trp Ala Gly Leu Leu Gly Pro Ile Ser
705                 710                 715                 720

Asn His Ser Phe Gly Gly Ser Phe Arg Thr Ala Ser Asn Lys Glu Ile
                725                 730                 735

Lys Leu Ser Glu His Asn Ile Lys Lys Ser Lys Met Phe Phe Lys Asp
            740                 745                 750

Ile Glu Glu Gln Tyr Pro Thr Ser Leu Ala Cys Val Glu Ile Val Asn
        755                 760                 765

Thr Leu Ala Leu Asp Asn Gln Lys Lys Leu Ser Lys Pro Gln Ser Ile
    770                 775                 780

Asn Thr Val Ser Ala His Leu Gln Ser Ser Val Val Val Ser Asp Cys
785                 790                 795                 800

Lys Asn Ser His Ile Thr Pro Gln Met Leu Phe Ser Lys Gln Asp Phe
                805                 810                 815

Asn Ser Asn His Asn Leu Thr Pro Ser Gln Lys Glu Gln Ile Thr Glu
            820                 825                 830

Leu Ser Thr Ile Leu Glu Asp Ser Gly Ser Gln Phe Glu Phe Thr Gln
        835                 840                 845

Phe Arg Lys Pro Ser Tyr Ile Leu Gln Lys Ser Thr Phe Glu Val Pro
    850                 855                 860

Glu Asn Gln Met Thr Ile Leu Lys Thr Thr Ser Glu Glu Cys Arg Asp
865                 870                 875                 880

Ala Asp Leu His Val Ile Met Asn Ala Pro Ser Ile Gly Gln Val Asp
                885                 890                 895

Ser Ser Lys Gln Phe Glu Gly Thr Val Glu Ile Lys Arg Lys Phe Ala
            900                 905                 910

Gly Leu Leu Lys Asn Asp Cys Asn Lys Ser Ala Ser Gly Tyr Leu Thr
        915                 920                 925

Asp Glu Asn Glu Val Gly Phe Arg Gly Phe Tyr Ser Ala His Gly Thr
    930                 935                 940

Lys Leu Asn Val Ser Thr Glu Ala Leu Gln Lys Ala Val Lys Leu Phe
945                 950                 955                 960
```

-continued

Ser Asp Ile Glu Asn Ile Ser Glu Glu Thr Ser Ala Glu Val His Pro
965 970 975

Ile Ser Leu Ser Ser Ser Lys Cys His Asp Ser Val Val Ser Met Phe
980 985 990

Lys Ile Glu Asn His Asn Asp Lys Thr Val Ser Glu Lys Asn Asn Lys
995 1000 1005

Cys Gln Leu Ile Leu Gln Asn Asn Ile Glu Met Thr Thr Gly Thr Phe
1010 1015 1020

Val Glu Glu Ile Thr Glu Asn Tyr Lys Arg Asn Thr Glu Asn Glu Asp
1025 1030 1035 1040

Asn Lys Tyr Thr Ala Ala Ser Arg Asn Ser His Asn Leu Glu Phe Asp
1045 1050 1055

Gly Ser Asp Ser Ser Lys Asn Asp Thr Val Cys Ile His Lys Asp Glu
1060 1065 1070

Thr Asp Leu Leu Phe Thr Asp Gln His Asn Ile Cys Leu Lys Leu Ser
1075 1080 1085

Gly Gln Phe Met Lys Glu Gly Asn Thr Gln Ile Lys Glu Asp Leu Ser
1090 1095 1100

Asp Leu Thr Phe Leu Glu Val Ala Lys Ala Gln Glu Ala Cys His Gly
1105 1110 1115 1120

Asn Thr Ser Asn Lys Glu Gln Leu Thr Ala Thr Lys Thr Glu Gln Asn
1125 1130 1135

Ile Lys Asp Phe Glu Thr Ser Asp Thr Phe Phe Gln Thr Ala Ser Gly
1140 1145 1150

Lys Asn Ile Ser Val Ala Lys Glu Ser Phe Asn Lys Ile Val Asn Phe
1155 1160 1165

Phe Asp Gln Lys Pro Glu Glu Leu His Asn Phe Ser Leu Asn Ser Glu
1170 1175 1180

Leu His Ser Asp Ile Arg Lys Asn Lys Met Asp Ile Leu Ser Tyr Glu
1185 1190 1195 1200

Glu Thr Asp Ile Val Lys His Lys Ile Leu Lys Glu Ser Val Pro Val
1205 1210 1215

Gly Thr Gly Asn Gln Leu Val Thr Phe Gln Gly Gln Pro Glu Arg Asp
1220 1225 1230

Glu Lys Ile Lys Glu Pro Thr Leu Leu Gly Phe His Thr Ala Ser Gly
1235 1240 1245

Lys Lys Val Lys Ile Ala Lys Glu Ser Leu Asp Lys Val Lys Asn Leu
1250 1255 1260

Phe Asp Glu Lys Glu Gln Gly Thr Ser Glu Ile Thr Ser Phe Ser His
1265 1270 1275 1280

Gln Trp Ala Lys Thr Leu Lys Tyr Arg Glu Ala Cys Lys Asp Leu Glu
1285 1290 1295

Leu Ala Cys Glu Thr Ile Glu Ile Thr Ala Ala Pro Lys Cys Lys Glu
1300 1305 1310

Met Gln Asn Ser Leu Asn Asn Asp Lys Asn Leu Val Ser Ile Glu Thr
1315 1320 1325

Val Val Pro Pro Lys Leu Leu Ser Asp Asn Leu Cys Arg Gln Thr Glu
1330 1335 1340

Asn Leu Lys Thr Ser Lys Ser Ile Phe Leu Lys Val Lys Val His Glu
1345 1350 1355 1360

Asn Val Glu Lys Glu Thr Ala Lys Ser Pro Ala Thr Cys Tyr Thr Asn
1365 1370 1375

Gln Ser Pro Tyr Ser Val Ile Glu Asn Ser Ala Leu Ala Phe Tyr Thr

-continued

```
            1380                1385                1390

Ser Cys Ser Arg Lys Thr Ser Val Ser Gln Thr Ser Leu Leu Glu Ala
        1395                1400                1405

Lys Lys Trp Leu Arg Glu Gly Ile Phe Asp Gly Gln Pro Glu Arg Ile
    1410                1415                1420

Asn Thr Ala Asp Tyr Val Gly Asn Tyr Leu Tyr Glu Asn Asn Ser Asn
1425                1430                1435                1440

Ser Thr Ile Ala Glu Asn Asp Lys Asn His Leu Ser Glu Lys Gln Asp
                1445                1450                1455

Thr Tyr Leu Ser Asn Ser Ser Met Ser Asn Ser Tyr Ser Tyr His Ser
            1460                1465                1470

Asp Glu Val Tyr Asn Asp Ser Gly Tyr Leu Ser Lys Asn Lys Leu Asp
        1475                1480                1485

Ser Gly Ile Glu Pro Val Leu Lys Asn Val Glu Asp Gln Lys Asn Thr
    1490                1495                1500

Ser Phe Ser Lys Val Ile Ser Asn Val Lys Asp Ala Asn Ala Tyr Pro
1505                1510                1515                1520

Gln Thr Val Asn Glu Asp Ile Cys Val Glu Glu Leu Val Thr Ser Ser
                1525                1530                1535

Ser Pro Cys Lys Asn Lys Asn Ala Ala Ile Lys Leu Ser Ile Ser Asn
            1540                1545                1550

Ser Asn Asn Phe Glu Val Gly Pro Pro Ala Phe Arg Ile Ala Ser Gly
        1555                1560                1565

Lys Ile Val Cys Val Ser His Glu Thr Ile Lys Lys Val Lys Asp Ile
    1570                1575                1580

Phe Thr Asp Ser Phe Ser Lys Val Ile Lys Glu Asn Asn Glu Asn Lys
1585                1590                1595                1600

Ser Lys Ile Cys Gln Thr Lys Ile Met Ala Gly Cys Tyr Glu Ala Leu
                1605                1610                1615

Asp Asp Ser Glu Asp Ile Leu His Asn Ser Leu Asp Asn Asp Glu Cys
            1620                1625                1630

Ser Thr His Ser His Lys Val Phe Ala Asp Ile Gln Ser Glu Glu Ile
        1635                1640                1645

Leu Gln His Asn Gln Asn Met Ser Gly Leu Glu Lys Val Ser Lys Ile
    1650                1655                1660

Ser Pro Cys Asp Val Ser Leu Glu Thr Ser Asp Ile Cys Lys Cys Ser
1665                1670                1675                1680

Ile Gly Lys Leu His Lys Ser Val Ser Ser Ala Asn Thr Cys Gly Ile
                1685                1690                1695

Phe Ser Thr Ala Ser Gly Lys Ser Val Gln Val Ser Asp Ala Ser Leu
            1700                1705                1710

Gln Asn Ala Arg Gln Val Phe Ser Glu Ile Glu Asp Ser Thr Lys Gln
        1715                1720                1725

Val Phe Ser Lys Val Leu Phe Lys Ser Asn Glu His Ser Asp Gln Leu
    1730                1735                1740

Thr Arg Glu Glu Asn Thr Ala Ile Arg Thr Pro Glu His Leu Ile Ser
1745                1750                1755                1760

Gln Lys Gly Phe Ser Tyr Asn Val Val Asn Ser Ser Ala Phe Ser Gly
                1765                1770                1775

Phe Ser Thr Ala Ser Gly Lys Gln Val Ser Ile Leu Glu Ser Ser Leu
            1780                1785                1790

His Lys Val Lys Gly Val Leu Glu Glu Phe Asp Leu Ile Arg Thr Glu
        1795                1800                1805
```

-continued

```
His Ser Leu His Tyr Ser Pro Thr Ser Arg Gln Asn Val Ser Lys Ile
    1810                1815                1820

Leu Pro Arg Val Asp Lys Arg Asn Pro Glu His Cys Val Asn Ser Glu
1825                1830                1835                1840

Met Glu Lys Thr Cys Ser Lys Glu Phe Lys Leu Ser Asn Asn Leu Asn
                1845                1850                1855

Val Glu Gly Gly Ser Ser Glu Asn Asn His Ser Ile Lys Val Ser Pro
            1860                1865                1870

Tyr Leu Ser Gln Phe Gln Gln Asp Lys Gln Gln Leu Val Leu Gly Thr
        1875                1880                1885

Lys Val Ser Leu Val Glu Asn Ile His Val Leu Gly Lys Glu Gln Ala
    1890                1895                1900

Ser Pro Lys Asn Val Lys Met Glu Ile Gly Lys Thr Glu Thr Phe Ser
1905                1910                1915                1920

Asp Val Pro Val Lys Thr Asn Ile Glu Val Cys Ser Thr Tyr Ser Lys
                1925                1930                1935

Asp Ser Glu Asn Tyr Phe Glu Thr Glu Ala Val Glu Ile Ala Lys Ala
            1940                1945                1950

Phe Met Glu Asp Asp Glu Leu Thr Asp Ser Lys Leu Pro Ser His Ala
        1955                1960                1965

Thr His Ser Leu Phe Thr Cys Pro Glu Asn Glu Glu Met Val Leu Ser
    1970                1975                1980

Asn Ser Arg Ile Gly Lys Arg Arg Gly Glu Pro Leu Ile Leu Val Gly
1985                1990                1995                2000

Glu Pro Ser Ile Lys Arg Asn Leu Leu Asn Glu Phe Asp Arg Ile Ile
                2005                2010                2015

Glu Asn Gln Glu Lys Ser Leu Lys Ala Ser Lys Ser Thr Pro Asp Gly
            2020                2025                2030

Thr Ile Lys Asp Arg Arg Leu Phe Val His His Val Ser Leu Glu Pro
        2035                2040                2045

Ile Thr Cys Val Pro Phe Arg Thr Thr Lys Glu Arg Gln Glu Ile Gln
    2050                2055                2060

Asn Pro Asn Phe Thr Ala Pro Gly Gln Glu Phe Leu Ser Lys Ser His
2065                2070                2075                2080

Leu Tyr Glu His Leu Thr Leu Glu Lys Ser Ser Ser Asn Leu Ala Val
                2085                2090                2095

Ser Gly His Pro Phe Tyr Gln Val Ser Gly Asn Lys Asn Gly Lys Met
            2100                2105                2110

Arg Lys Leu Ile Thr Thr Gly Arg Pro Thr Lys Val Phe Val Pro Pro
        2115                2120                2125

Phe Lys Thr Lys Ser His Phe His Arg Val Glu Gln Cys Val Arg Asn
    2130                2135                2140

Ile Asn Leu Glu Gly Asn Arg Gln Lys Gln Asn Ile Asp Gly His Gly
2145                2150                2155                2160

Ser Asp Asp Ser Lys Asn Lys Ile Asn Asp Asn Glu Ile His Gln Phe
                2165                2170                2175

Asn Lys Asn Asn Ser Asn Gln Ala Ala Ala Val Thr Phe Thr Lys Cys
            2180                2185                2190

Glu Glu Glu Pro Leu Asp Leu Ile Thr Ser Leu Gln Asn Ala Arg Asp
        2195                2200                2205

Ile Gln Asp Met Arg Ile Lys Lys Lys Gln Arg Gln Arg Val Phe Pro
    2210                2215                2220
```

-continued

Gln Pro Gly Ser Leu Tyr Leu Ala Lys Thr Ser Thr Leu Pro Arg Ile
2225 2230 2235 2240

Ser Leu Lys Ala Ala Val Gly Gly Gln Val Pro Ser Ala Cys Ser His
2245 2250 2255

Lys Gln Leu Tyr Thr Tyr Gly Val Ser Lys His Cys Ile Lys Ile Asn
2260 2265 2270

Ser Lys Asn Ala Glu Ser Phe Gln Phe His Thr Glu Asp Tyr Phe Gly
2275 2280 2285

Lys Glu Ser Leu Trp Thr Gly Lys Gly Ile Gln Leu Ala Asp Gly Gly
2290 2295 2300

Trp Leu Ile Pro Ser Asn Asp Gly Lys Ala Gly Lys Glu Glu Phe Tyr
2305 2310 2315 2320

Arg Ala Leu Cys Asp Val Lys Ala Thr
2325

(2) INFORMATION FOR SEQ ID NO:17:

(i) SEQUENCE CHARACTERISTICS:
(A) LENGTH: 956 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:17:

AGGGGGGNCC CCCCTTCCCA AAAGNAAGGG TGGCCCTTGG NAACNTCCTN AAAGGNTCAA 60

NGCNAANTAA AGAAAGAAAC ACNAACAACT CCCAAATCCC CGCTTTAATT CGGTCAAGAA 120

TACTAACGGT TGGGAATGCC TTGAACAAAG GAAATTTCCT TTCGCCAACA CTGAGAAAAT 180

ACCCGCAAGC GCCCNACCCN AGGCCTGACT TCCGGGTGGT GCGTGTGCTG CGTGTCGCGT 240

CACGGCGTCA CGTGGCCAGC GCGGGCTTGT GGCGCGAGCT TCTGAAACTA GGCGGCAGAG 300

GCGGAGCCGC TGTGGCACTG CTGCGCCTCT GCTGCGCCTC GGGTGTCTTT TGCGGCGGTG 360

GGTCGCCGCC GGGAGAAGCG TGAGGGGACA GATTTGTGAC CGGCGCGGTT TTTGTCAGCT 420

TACTCCGGCC AAAAAAGAAC TGCGCCTCTG GAGCGGGTTA GTGGTGGTGG TAGTGGGTTG 480

GGACGAGCGC GTCTTCCGCA GTCCCAGTCC AGCGTGGCGG GGGAGCGCCT CACGCCCCGG 540

GTCGCTGCCG CGGCTTCTTG CCCTTTTGTC TCTGCCAACC CCCACCCATG CCTGAGAGAA 600

AGGTCCTTGC CCGAAGGCAA ATTTTCGCCA AGCAAATTCG AGCCCCGCCC CTTCCCTGGG 660

TCTCCATTTC CCGCCTCCGG CCCGGCCTTT GGGCTCCGCC TTCAGCTCAA GACTTAACTT 720

CCCTCCCAGC TGTCCCAGAT GACGCCATCT GAAATTTCTT GGAAACACGA TCACTTTAAC 780

GGAATATTGC TGTTTTGGGG AAGTGTTTTA CAGCTGCTGG GCACGCTGTA TTTGCCTTAC 840

TTAAGCCCCT GGTAATTGCT GTATTCCGAA GACATGCTGA TGGGAATTAC CAGGCGGCGT 900

TGGTCTCTAA ACTGAGCCCT CTGTCCCAAC TAGCTACGCG TCACTGGTTA GCGTGA 956

(2) INFORMATION FOR SEQ ID NO:18:

(i) SEQUENCE CHARACTERISTICS:
(A) LENGTH: 1106 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS

-continued (B) LOCATION: 540..606

(ix) FEATURE:
(A) NAME/KEY: exon
(B) LOCATION: 501..606

(xi) SEQUENCE DESCRIPTION: SEQ ID NO:18:

```
GACTTAACTT CCCTCCCAGC TGTCCCAGAT GACGCCATCT GAAATTTCTT GGAAACACGA     60

TCACTTTAAC GGAATATTGC TGTTTTGGGG AAGTGTTTTA CAGCTGCTGG GCACGCTGTA    120

TTTGCCTTAC TTAAGCCCCT GGTAATTGCT GTATTCCGAA GACATGCTGA TGGGAATTAC    180

CAGGCGGCGT TGGTCTCTAA ACTGAGCCCT CTGTCCCAAC TAGCTACGCG TCACTGGTTA    240

GCGTGATTGA AACTAAATCG TATGAAAATC CTCTTCTCTA GTCGCACTAG CCACGTTTCG    300

AGTGCTTAAT GTGGCTAGTG GCACCGGTTT GGACAGCACA GCTGTAAAAT GTTCCCATCC    360

TCACAGTAAG CTGTTACCGT TCCAGGAGAT GGGACTGAAT TAGAATTCAA ACAAATTTTC    420

CAGCGCTTCT GAGTTTTACC TCAGTCACAT AATAAGGAAT GCATCCCTGT GTAAGTGCAT    480

TTTGGTCTTC TGTTTTGCAG ACTTATTTAC CAAGCATTGG AGGAATATCG TAGGTAAAA     539

ATG CCT ATT GGA TCC AAA GAG AGG CCA ACA TTT TTT GAA ATT TTT AAG      587
Met Pro Ile Gly Ser Lys Glu Arg Pro Thr Phe Phe Glu Ile Phe Lys
  1               5                  10                  15

ACA CGC TGC AAC AAA GCA G GTATTGACAA ATTTTATATA ACTTTATAAA           636
Thr Arg Cys Asn Lys Ala
            20

TTACACCGAG AAAGTGTTTT CTAAAAAATG CTTGCTAAAA ACCCAGTACG TCACAGTGTT    696

GCTTAGAACC ATAAACTGTT CCTTATGTGT GTATAAATCC AGTTAACAAC ATAATCATCG    756

TTTGCAGGTT AACCACATGA TAAATATAGA ACGTCTAGTG GATAAAGAGG AAACTGGCCC    816

CTTGACTAGC AGTAGGTAAC AATTACTAAC AAATCAGAAG CATTAATGTT ACTTTATGGC    876

AGAAGTTGTC CAACTTTTTG GTTTCAGTAC TCCTTATACT CTTAAAAATG ATCTAGGACC    936

CCCGGAGTGC TTTTGTTTAT GTAGCTTACC ATATTAGAAA TTTAAAACTA AGAATTTAAG    996

GCTGGGCGTG GTGGCTCACG CCTGTAATCC CAGCACTTTG GGAGGCCCGA GGTGGGCGGA   1056

TCACTTGAGG CCAGAAGTTT GAGACCAGCC TGGCCAACAT GGTGAAACCC              1106
```

(2) INFORMATION FOR SEQ ID NO:19:

(i) SEQUENCE CHARACTERISTICS:
(A) LENGTH: 1249 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 503..749

(ix) FEATURE:
(A) NAME/KEY: exon
(B) LOCATION: 501..749

(xi) SEQUENCE DESCRIPTION: SEQ ID NO:19:

```
GACTACAGGC GTGTGCCACC ACGCTTGGCT AATTTTTTGT GTTTTTAGTA AAGATGGGGT     60

TTCAACGTGT TAGCAAGGTT GGTCTCGATC TGACCTCGTG ATCTGCTCGC CTCAGCCTCC    120

CAAAGTGTTG GGATTACAGG CGTGAGCCCC CGCACCTGGC CGAATTTTAT CGTGGAATGT    180

ATTCTTAATG TGAATAGTTT TTGATTCCGA ACCATGAATA ATAAGAAAAT AAATAAAATT    240
```

-continued

```
TAAATGAAAA TAAAAGCTAA TATATACAGC TTTTAATAAT ATAGTTAAAT GCCATCTTGT    300

AACTTTTGTG AACTCTTGTT ACACCTTTCT ATAGATTCGC AAGAGAATGG ATTAATGATC    360

TTGTTTAATT AATATGCCTT AACAAAAGTA ATCCATAGTC AAGATCTTAA GCATTTTTTT    420

CCTTATGATC TTTAACTGTT CTGGGTCACA AATTTGTCTG TCACTGGTTA AAACTAAGGT    480

GGGATTTTTT TTTTAAATAG AT TTA GGA CCA ATA AGT CTT AAT TGG TTT GAA     532
                     Asp Leu Gly Pro Ile Ser Leu Asn Trp Phe Glu
                      1               5                  10

GAA CTT TCT TCA GAA GCT CCA CCC TAT AAT TCT GAA CCT GCA GAA GAA      580
Glu Leu Ser Ser Glu Ala Pro Pro Tyr Asn Ser Glu Pro Ala Glu Glu
             15                  20                  25

TCT GAA CAT AAA AAC AAC AAT TAC GAA CCA AAC CTA TTT AAA ACT CCA      628
Ser Glu His Lys Asn Asn Asn Tyr Glu Pro Asn Leu Phe Lys Thr Pro
         30                  35                  40

CAA AGG AAA CCA TCT TAT AAT CAG CTG GCT TCA ACT CCA ATA ATA TTC      676
Gln Arg Lys Pro Ser Tyr Asn Gln Leu Ala Ser Thr Pro Ile Ile Phe
     45                  50                  55

AAA GAG CAA GGG CTG ACT CTG CCG CTG TAC CAA TCT CCT GTA AAA GAA      724
Lys Glu Gln Gly Leu Thr Leu Pro Leu Tyr Gln Ser Pro Val Lys Glu
 60                  65                  70                  75

TTA GAT AAA TTC AAA TTA GAC TTA G GTAAGTAATG CAATATGGTA              769
Leu Asp Lys Phe Lys Leu Asp Leu
                 80

GACTGGGGAG AACTACAAAC TAGGAATTTA GGCAAACCTG TGTTAAAATC TTAGCTCATT    829

CATTAATTGT GTCATGCTGG GCAAATCAGT CTCTCTGGCC TCTTTTTCCT CACTCGAAAA    889

ATGGAGACGA TGAAAATAAT GTCTCATAGG TTTGGATTAA ATTAAATAAT GTAGGTACTT    949

AGTAAATGTT CTCTTTCATC CCTCCTTTGA TAAATTTGCC AACTGAGATT TGCTGAATTA   1009

CGTCTTTCTT ATGCCAAAAA AACCTAGGAC TTGTTTTGAT GTTAATTAAA CTAAACTATA   1069

TTTCTGCAAG CTATCACAGA GGACAGAGAT TATTTTACCG ATATACTATA AGTATCATGA   1129

TTTGGAAGGA GTTTCCCTGG CGTAGGTGCC GCATGTTTCT AAGCAATTAT GTAATAAGAT   1189

TATATATTCA GTCATTCAAA TAATTATTAC CTACTTGACA TAAGTAATGA ACTTTCCCTT   1249
```

(2) INFORMATION FOR SEQ ID NO:20:

(i) SEQUENCE CHARACTERISTICS:
(A) LENGTH: 774 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 168..274

(ix) FEATURE:
(A) NAME/KEY: exon
(B) LOCATION: 166..274

(xi) SEQUENCE DESCRIPTION: SEQ ID NO:20:

```
TCCTTTTTAG GGGGTAATCA GCAAACTGAA AAACCTCTTC TTACAACTCC CTATACATTC     60

TCATTCCCAG TATAGAGGAG ACTTTTTGTT TTTAAACACT TCCAAAGAAT GCAAATTTAT    120

AATCCAGAGT ATATACATTC TCACTGAATT ATTGTACTGT TTCAG GA AGG AAT GTT     176
                                                  Gly Arg Asn Val
                                                   1

CCC AAT AGT AGA CAT AAA AGT CTT CGC ACA GTG AAA ACT AAA ATG GAT      224
Pro Asn Ser Arg His Lys Ser Leu Arg Thr Val Lys Thr Lys Met Asp
```

-continued

```
 5                   10                  15                  20

CAA GCA GAT GAT GTT TCC TGT CCA CTT CTA AAT TCT TGT CTT AGT GAA       272
Gln Ala Asp Asp Val Ser Cys Pro Leu Leu Asn Ser Cys Leu Ser Glu
                 25                  30                  35

AG GTATGATGAA GCTATTATAT TAAAATATTT AAATGAAACA TTTTCCTACA            324
Ser

TATATTTGTT CTATAAAGAT GAATCTGATT TTTATGCTAA TATTTTGGCT AAGAGCCTGG    384

TAGAAGATCT TACATTTTTA AATAATCTTT TAGGTTGAGT CCTTTAATAG AATAGTTTTT    444

ACATTAGAAA CATGTAAGTT GTTGTTCTTG TGATGTTGAA TTGGCTGGTT TTCTGTATAT    504

TCTGTGATTT TTTAAGTAAC AAAAATAACA GTGGTGAAAA GCAGTAAGTC AGTCCTTGAA    564

TTATCAATTT AAAATAAATT GTGTACTTTT CATCTTTGGA GAGAATATGA TTTACTTTAC    624

AAATTTTTTT TTTGTTTTTT TTTTTTTTGA GATGGAGTCT CTGTCACCCA GGCTGTAGTG    684

CAGTGGTGCG ATCTCAGCTC ACTGCAAGCT CCGCCTCCCG GGTTCACGCC ATTCTCCTGC    744

CTCAGCCTCC CAAGTAGCTG GGACTACAGG                                     774
```

(2) INFORMATION FOR SEQ ID NO:21:

(i) SEQUENCE CHARACTERISTICS:
- (A) LENGTH: 1050 base pairs
- (B) TYPE: nucleic acid
- (C) STRANDEDNESS: double
- (D) TOPOLOGY: linear (ii) MOLECULE TYPE: DNA (genomic)

(ix) FEATURE:
- (A) NAME/KEY: CDS
- (B) LOCATION: 502..550

(ix) FEATURE:
- (A) NAME/KEY: exon
- (B) LOCATION: 501..550

(xi) SEQUENCE DESCRIPTION: SEQ ID NO:21:

```
TGCGATCTCA GCTCACTGCA AGCTCCGCCT CCCGGGTTCA CGCCATTCTC CTGCCTCAGC     60

CTCCCAAGTA GCTGGGACTA CAGGCGCCCG CCACCATGCC CGGCTAATTT TTTGTATTTT    120

TAGTAGAGAC GGGGTTTCAC TGTGTTAGCT AGGATGGTCT CGATTTCCTG ACCTCGTGAT    180

CCGCCCGCCT CAGCCTCCCA GACTGCTGGG ATTACAGGCG TGAACCACTG TGCCCGGCCT    240

ACTTTACAAA ATTTTTGAGT TTAAAATACA CGGTTTCCAG CAGCTGAAAT TTGTGAGTAC    300

ATATGTGTTG GCATTTTAAA CATCACTTGA TGATTATTTA ATGCTTCATG AGAGATTTAC    360

TTTTTAAAAT GTAATATAAA ATATCTAAAA GTAGTATTCC AACAATTTAT ATGAATGAGA    420

ATCTTCTTTT AAAAATAAGA TAAACTAGTT TTTGCCAGTT TTTTAAAATA ACCTAAGGGA    480

TTTGCTTTGT TTTATTTTAG T CCT GTT GTT CTA CAA TGT ACA CAT GTA ACA      531
                        Pro Val Val Leu Gln Cys Thr His Val Thr
                          1               5                  10

CCA CAA AGA GAT AAG TCA G GTATGATTAA AAACAATGCT TTTTATTCTT           580
Pro Gln Arg Asp Lys Ser
                 15

AGAATACTAG AAATGTTAAT AAAAATAAAA CTTAACAATT TTCCCCTTTT TTTACCCCCA    640

GTGGTATGTG GGAGTTTGTT TCATACACCA AAGTTTGTGA AGGTAAATAT TCTACCTGGT    700

TTATTTTTAT GACTTAGTAA TTGAGAATTT GACAATAGCG TTATACCTTT GCCCTGAGAT    760

TTACAAATCT GTACCTAGCA TTCTGCCTCA TACAGGCAAT TCAGTAAACG TTAAGTGAAA    820

TAAAGAGTGA ATGAAAAAAT AATATCCTTA ATGATCAGGG CATTTCTATA AAAAATAAAC    880
```

-continued

```
TATTTTCTTT CCTCCCAGGG TCGTCAGACA CCAAAACATA TTTCTGAAAG TCTAGGAGCT    940

GAGGTGGATC CTGATATGTC TTGGTCAAGT TCTTTAGCTA CACCACCCAC CCTTAGTTCT   1000

ACTGTGCTCA TAGGTAATAA TAGCAAATGT GTATTTACAA GAAAGAGCAG              1050
```

(2) INFORMATION FOR SEQ ID NO:22:

(i) SEQUENCE CHARACTERISTICS:
(A) LENGTH: 1041 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 503..541

(ix) FEATURE:
(A) NAME/KEY: exon
(B) LOCATION: 501..541

(xi) SEQUENCE DESCRIPTION: SEQ ID NO:22:

```
GTGTTAGCTA GGATGGTCTC GATTTCCTGA CCTCGTGATC CGCCCGCCTC AGCCTCCCAG     60

ACTGCTGGGA TTACAGGCGT GAACCACTGT GCCCGGCCTA CTTTACAAAA TTTTTGAGTT    120

TAAAATACAC GGTTTCCAGC AGCTGAAATT TGTGAGTACA TATGTGTTGG CATTTTAAAC    180

ATCACTTGAT GATTATTTAA TGCTTCATGA GAGATTTACT TTTTAAAATG TAATATAAAA    240

TATCTAAAAG TAGTATTCCA ACAATTTATA TGAATGAGAA TCTTCTTTTA AAAATAAGAT    300

AAACTAGTTT TTGCCAGTTT TTTAAAATAA CCTAAGGGAT TTGCTTTGTT TTATTTTAGT    360

CCTGTTGTTC TACAATGTAC ACATGTAACA CCACAAAGAG ATAAGTCAGG TATGATTAAA    420

AACAATGCTT TTTATTCTTA GAATACTAGA AATGTTAATA AAAATAAAAC TTAACAATTT    480

TCCCCTTTTT TTACCCCCAG TG GTA TGT GGG AGT TTG TTT CAT ACA CCA AAG     532
                         Val Val Cys Gly Ser Leu Phe His Thr Pro Lys
                           1               5                  10

TTT GTG AAG GTAAATATTC TACCTGGTTT ATTTTTATGA CTTAGTAATT              581
Phe Val Lys

GAGAATTTGA CAATAGCGTT ATACCTTTGC CCTGAGATTT ACAAATCTGT ACCTAGCATT    641

CTGCCTCATA CAGGCAATTC AGTAAACGTT AAGTGAAATA AAGAGTGAAT GAAAAAATAA    701

TATCCTTAAT GATCAGGGCA TTTCTATAAA AAATAAACTA TTTTCTTTCC TCCCAGGGTC    761

GTCAGACACC AAAACATATT TCTGAAAGTC TAGGAGCTGA GGTGGATCCT GATATGTCTT    821

GGTCAAGTTC TTTAGCTACA CCACCCACCC TTAGTTCTAC TGTGCTCATA GGTAATAATA    881

GCAAATGTGT ATTTACAAGA AAGAGCAGAT GAGGTTGATA ATTGTCATCT CTAATACTTC    941

TGTTAAAAGG AAATATGAAA AGAAAATATT AGATAATGTC TTTGATAAGT GTGTTAGTAA   1001

CTGACAATAA TTTTATTCTA TTAAGTGTAG ATTGGAATAA                         1041
```

(2) INFORMATION FOR SEQ ID NO:23:

(i) SEQUENCE CHARACTERISTICS:
(A) LENGTH: 964 base pairs
(B) TYPE: nucleic acid
(C) STRANDEDNESS: double
(D) TOPOLOGY: linear (ii) MOLECULE TYPE: DNA (genomic)

(ix) FEATURE:

-continued (A) NAME/KEY: CDS
(B) LOCATION: 501..615

(ix) FEATURE:
(A) NAME/KEY: exon
(B) LOCATION: 501..615

(xi) SEQUENCE DESCRIPTION: SEQ ID NO:23:

```
CCAACAATTT ATATGAATGA GAATCTTCTT TTAAAAATAA GATAAACTAG TTTTTGCCAG     60

TTTTTTAAAA TAACCTAAGG GATTTGCTTT GTTTTATTTT AGTCCTGTTG TTCTACAATG    120

TACACATGTA ACACCACAAA GAGATAAGTC AGGTATGATT AAAAACAATG CTTTTTATTC    180

TTAGAATACT AGAAATGTTA ATAAAAATAA AACTTAACAA TTTTCCCCTT TTTTTACCCC    240

CAGTGGTATG TGGGAGTTTG TTTCATACAC CAAAGTTTGT GAAGGTAAAT ATTCTACCTG    300

GTTTATTTTT ATGACTTAGT AATTGAGAAT TTGACAATAG CGTTATACCT TTGCCCTGAG    360

ATTTACAAAT CTGTACCTAG CATTCTGCCT CATACAGGCA ATTCAGTAAA CGTTAAGTGA    420

AATAAAGAGT GAATGAAAAA ATAATATCCT TAATGATCAG GGCATTTCTA TAAAAAATAA    480

ACTATTTTCT TTCCTCCCAG GGT CGT CAG ACA CCA AAA CAT ATT TCT GAA        530
                      Gly Arg Gln Thr Pro Lys His Ile Ser Glu
                        1               5                  10

AGT CTA GGA GCT GAG GTG GAT CCT GAT ATG TCT TGG TCA AGT TCT TTA      578
Ser Leu Gly Ala Glu Val Asp Pro Asp Met Ser Trp Ser Ser Ser Leu
                15                  20                  25

GCT ACA CCA CCC ACC CTT AGT TCT ACT GTG CTC ATA G GTAATAATAG         625
Ala Thr Pro Pro Thr Leu Ser Ser Thr Val Leu Ile
            30                  35

CAAATGTGTA TTTACAAGAA AGAGCAGATG AGGTTGATAA TTGTCATCTC TAATACTTCT    685

GTTAAAAGGA AATATGAAAA GAAAATATTA GATAATGTCT TTGATAAGTG TGTTAGTAAC    745

TGACAATAAT TTTATTCTAT TAAGTGTAGA TTGGAATAAA TACAAATACA TTTAGTGGTA    805

GTCCAGTGGT GTCAAGCATT ATGTTTTAGT ACGATGTGAT TAACGTAGAA TAGCTTACAA    865

ATATTCCTTT ACTGGCCTAT ATAAGCGTTT AAGAGGCAGT ATTTGGTGTG ACTGAATTCT    925

TTTTACAAAT GATTGTGGTA ATTGGGGCAT TAAAGCAGC                           964
```

(2) INFORMATION FOR SEQ ID NO:24:

(i) SEQUENCE CHARACTERISTICS:
(A) LENGTH: 1050 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 503..550

(ix) FEATURE:
(A) NAME/KEY: exon
(B) LOCATION: 501..550

(xi) SEQUENCE DESCRIPTION: SEQ ID NO:24:

```
ACCAGTATTA CATTTTGTTT ATTCTAGCAA AATAGCATTC TGTTTTGATT CCTCTTTAGC     60

TGGGAGTAAG TTAACCCTAT TCTGTTGCTT AGATGAAATA ATATGGATAA AATCATTTTG    120

AAAATATGTA TTTAATATAT AGTATGCCTT TAGGCTGTAG TGTTGTCTAA ATGAATGCTA    180

AAGTCTCCAA GCTTTAGCTT TTAAGTCATA ACCTCACAGC ATCATCTGAC TTTCCAACTC    240

ATTGTGGACA GTATTACCAT AAAGTAATGA TCACCAAGCC ATATCTTACC ACCTTGTGAG    300
```

-continued

```
TAGTACTAAG GAAGTAAGTA TAGTTTATTC ACTGTGTTGA TTGACCTTTC TAATTACTAT    360

ACTTAAGTAC TTGAATCAAT TCATTTTGTT TCAAATGTGT CATGTAATCA AATAGTAGAT    420

GTGCTTTTTG ATGTCTGACA AAAAATAAGT TTTTGCATTC TAGTGATAAT ATACAATACA    480

CATAAATTTT TATCTTACAG TC AGA AAT GAA GAA GCA TCT GAA ACT GTA TTT     532
                     Val Arg Asn Glu Glu Ala Ser Glu Thr Val Phe
                       1               5                  10

CCT CAT GAT ACT ACT GCT GTAAGTAAAT ATGACATTGA TTAGACTGTT             580
Pro His Asp Thr Thr Ala
             15

GAAATTGCTA ACAATTTTGG AATGCCTTGT TAAATTATTT ATCTTACATT TTTAATTTCC    640

TAATCTGTAA TTTATCTAAG CCTTTGAGAA AGTCTCTAAA CCTGGTCCTA TATGTGATTT    700

TAACTTCCTG TGAAACTCTG CTGTCTCTCT GTTAAAGTTG CATATATACA ATATATACCG    760

TAGTCCCCTA TTCATGGGGT ATACATTCCA ATATCCCCCA GTGAATGCTT GAAACCTTAG    820

ATAGTACCGA ACCCTATATA TATATATTAA AAATGTGTAG TATTTATATA TATATATACC    880

TATAATCTTT TTTTCTATAA GCACATACCC TGTGATAAAG TTTAATTCAT AAATTAGGCA    940

CAGTAAGAGA TTAACAAGAA CTAATAATAA AATAGGACAA TTATAACAAA ATACCGTAAT   1000

AAAAGTTATG TGAATGTTGT CTCTCTGTCT CAAAATATCT TATTGTTCTG              1050
```

(2) INFORMATION FOR SEQ ID NO:25:

(i) SEQUENCE CHARACTERISTICS:
(A) LENGTH: 1112 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 501..612

(ix) FEATURE:
(A) NAME/KEY: exon
(B) LOCATION: 501..612

(xi) SEQUENCE DESCRIPTION: SEQ ID NO:25:

```
GCACTTTATG GCTTCTTTTT GGCATATTTG AATTGCCAGC ATCATTATAC TTGTGCTTTG     60

GGGCCATTGT TAAGTAAAAT AAGGGTGACT TGAACACAAG CACTGTGGTA CCACAATAGC    120

CGATCTGATA ACCAAGACAA CTACTAAGTG ACTAATAGGT GGGTACCATA TACAGCCTGG    180

ATACGCTGGA CAAAGGGATG ATTCATGTCC CAAGTGGGAT GGAGCAAGAT GGTGCAAGTT    240

TTTTTTTCTC CATTTCCATT TTCCTTTCCT AAGATTTCCA CATCCTAGTG GTGCAAGATT    300

TCATCACACT ACTCAGGATG ACACACAATT TAAAACTTAC TAATTGCTTA CTTCTGGAAT    360

TTTCCATTAA AAATTTTTGG ACCTAGGTTG ATTGCAGATA ACTGAAATCA CCAAAAGTGA    420

AACCATGGAT AAGGGGGGAC TACTACTATA TGTGCATTGA GAGTTTTTAT ACTAGTGATT    480

TTAAACTATA ATTTTTGCAG AAT GTG AAA AGC TAT TTT TCC AAT CAT GAT        530
                      Asn Val Lys Ser Tyr Phe Ser Asn His Asp
                        1               5                  10

GAA AGT CTG AAG AAA AAT GAT AGA TTT ATC GCT TCT GTG ACA GAC AGT      578
Glu Ser Leu Lys Lys Asn Asp Arg Phe Ile Ala Ser Val Thr Asp Ser
                15                  20                  25

GAA AAC ACA AAT CAA AGA GAA GCT GCA AGT CAT G GTAAGTCCTC             622
Glu Asn Thr Asn Gln Arg Glu Ala Ala Ser His
            30                  35
```

-continued

```
TGTTTAGTTG AACTACAGGT TTTTTTGTTG TTGTTGTTTT GATTTTTTTT TTTTGAGGTG    682

GAGTCTTGCT CTGTCACCCG TGATCTCAGT TTACCGCAAC CTCTGCCTCC CGTGCTCAAG    742

CGATCCTGCC TCAGCTTGCC AAGTAGCTGA GATTACAAGC ATGCACCACC ATGCCCAACT    802

ATTGTATTTT TAGTAGAGAT GGCATTTCAC CATGTTGGCC AGGCTGGTCT CAAATGGTCG    862

TGAGCCACCA TGCCCAGCCT GAACTACTCT TTTTAATTGG CACCATTGAA GGATTGCTCC    922

TCTTTTCTTA AAGAGAAAAT ATATTACCTT TCCTTTCTTG ACTACTGAAG TAGTATTTTA    982

TCTCAAAGTA TTGAGAGTAG AAACTAACTT GGTGTGCCTG TGATCCCAGC TACTCAGGAG   1042

GCTGAGGTGG GAGGATCGCT TAAGCCCAGG CGGTCAAGGT TGCAGTGAGC TGTGTGTGTG   1102

CCACTGCACT                                                          1112
```

(2) INFORMATION FOR SEQ ID NO:26:

(i) SEQUENCE CHARACTERISTICS:
(A) LENGTH: 2026 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 433..1546

(ix) FEATURE:
(A) NAME/KEY: exon
(B) LOCATION: 431..1546

(xi) SEQUENCE DESCRIPTION: SEQ ID NO:26:

```
TTTTTGTCTG TGTGGTATCA TGTACGTATG TATATGCATA TGTAAAATCA GATTTACCCT     60

TGTTATAGGG CCACAGAATT GATTTGGAAC ATCTGTTTTG ATAGGTCTTA GAATATTTAA    120

TTGTATATAT AGTAAGATTA GGTGAGTTTT AATTGTGTAG AACTGCTAAA GAAAGGTTTT    180

TAGGGATTGT TGTATGAATA AAAGGCTTTA GGTTCATTGG AATCAGGGGA ATCAGGCTTT    240

ACTAGAAGAA CAGGAGAAGG GGTGACTGAC CGAAAAATAA AATGCCAAGT ACTCAGAATA    300

ACCCTTTAAA TACTGATATG TAATATTTAG CACATTCTAC ATAAACTGTT TCTATGAGAA    360

AGGTTGTGAG AATAATATAA ATTATATGGC TTATAAAATA TTAATGTGCT TCTGTTTTAT    420

ACTTTAACAG GA TTT GGA AAA ACA TCA GGG AAT TCA TTT AAA GTA AAT       468
          Gly Phe Gly Lys Thr Ser Gly Asn Ser Phe Lys Val Asn
            1               5                  10

AGC TGC AAA GAC CAC ATT GGA AAG TCA ATG CCA AAT GTC CTA GAA GAT     516
Ser Cys Lys Asp His Ile Gly Lys Ser Met Pro Asn Val Leu Glu Asp
     15                  20                  25

GAA GTA TAT GAA ACA GTT GTA GAT ACC TCT GAA GAA GAT AGT TTT TCA     564
Glu Val Tyr Glu Thr Val Val Asp Thr Ser Glu Glu Asp Ser Phe Ser
 30                  35                  40                  45

TTA TGT TTT TCT AAA TGT AGA ACA AAA AAT CTA CAA AAA GTA AGA ACT     612
Leu Cys Phe Ser Lys Cys Arg Thr Lys Asn Leu Gln Lys Val Arg Thr
                 50                  55                  60

AGC AAG ACT AGG AAA AAA ATT TTC CAT GAA GCA AAC GCT GAT GAA TGT     660
Ser Lys Thr Arg Lys Lys Ile Phe His Glu Ala Asn Ala Asp Glu Cys
             65                  70                  75

GAA AAA TCT AAA AAC CAA GTG AAA GAA AAA TAC TCA TTT GTA TCT GAA     708
Glu Lys Ser Lys Asn Gln Val Lys Glu Lys Tyr Ser Phe Val Ser Glu
         80                  85                  90

GTG GAA CCA AAT GAT ACT GAT CCA TTA GAT TCA AAT GTA GCA CAT CAG     756
```

-continued

```
Val Glu Pro Asn Asp Thr Asp Pro Leu Asp Ser Asn Val Ala His Gln
     95                 100                 105

AAG CCC TTT GAG AGT GGA AGT GAC AAA ATC TCC AAG GAA GTT GTA CCG       804
Lys Pro Phe Glu Ser Gly Ser Asp Lys Ile Ser Lys Glu Val Val Pro
110                 115                 120                 125

TCT TTG GCC TGT GAA TGG TCT CAA CTA ACC CTT TCA GGT CTA AAT GGA       852
Ser Leu Ala Cys Glu Trp Ser Gln Leu Thr Leu Ser Gly Leu Asn Gly
                130                 135                 140

GCC CAG ATG GAG AAA ATA CCC CTA TTG CAT ATT TCT TCA TGT GAC CAA       900
Ala Gln Met Glu Lys Ile Pro Leu Leu His Ile Ser Ser Cys Asp Gln
            145                 150                 155

AAT ATT TCA GAA AAA GAC CTA TTA GAC ACA GAG AAC AAA AGA AAG AAA       948
Asn Ile Ser Glu Lys Asp Leu Leu Asp Thr Glu Asn Lys Arg Lys Lys
        160                 165                 170

GAT TTT CTT ACT TCA GAG AAT TCT TTG CCA CGT ATT TCT AGC CTA CCA       996
Asp Phe Leu Thr Ser Glu Asn Ser Leu Pro Arg Ile Ser Ser Leu Pro
    175                 180                 185

AAA TCA GAG AAG CCA TTA AAT GAG GAA ACA GTG GTA AAT AAG AGA GAT      1044
Lys Ser Glu Lys Pro Leu Asn Glu Glu Thr Val Val Asn Lys Arg Asp
190                 195                 200                 205

GAA GAG CAG CAT CTT GAA TCT CAT ACA GAC TGC ATT CTT GCA GTA AAG      1092
Glu Glu Gln His Leu Glu Ser His Thr Asp Cys Ile Leu Ala Val Lys
                210                 215                 220

CAG GCA ATA TCT GGA ACT TCT CCA GTG GCT TCT TCA TTT CAG GGT ATC      1140
Gln Ala Ile Ser Gly Thr Ser Pro Val Ala Ser Ser Phe Gln Gly Ile
            225                 230                 235

AAA AAG TCT ATA TTC AGA ATA AGA GAA TCA CCT AAA GAG ACT TTC AAT      1188
Lys Lys Ser Ile Phe Arg Ile Arg Glu Ser Pro Lys Glu Thr Phe Asn
        240                 245                 250

GCA AGT TTT TCA GGT CAT ATG ACT GAT CCA AAC TTT AAA AAA GAA ACT      1236
Ala Ser Phe Ser Gly His Met Thr Asp Pro Asn Phe Lys Lys Glu Thr
    255                 260                 265

GAA GCC TCT GAA AGT GGA CTG GAA ATA CAT ACT GTT TGC TCA CAG AAG      1284
Glu Ala Ser Glu Ser Gly Leu Glu Ile His Thr Val Cys Ser Gln Lys
270                 275                 280                 285

GAG GAC TCC TTA TGT CCA AAT TTA ATT GAT AAT GGA AGC TGG CCA GCC      1332
Glu Asp Ser Leu Cys Pro Asn Leu Ile Asp Asn Gly Ser Trp Pro Ala
                290                 295                 300

ACC ACC ACA CAG AAT TCT GTA GCT TTG AAG AAT GCA GGT TTA ATA TCC      1380
Thr Thr Thr Gln Asn Ser Val Ala Leu Lys Asn Ala Gly Leu Ile Ser
            305                 310                 315

ACT TTG AAA AAG AAA ACA AAT AAG TTT ATT TAT GCT ATA CAT GAT GAA      1428
Thr Leu Lys Lys Lys Thr Asn Lys Phe Ile Tyr Ala Ile His Asp Glu
        320                 325                 330

ACA TCT TAT AAA GGA AAA AAA ATA CCG AAA GAC CAA AAA TCA GAA CTA      1476
Thr Ser Tyr Lys Gly Lys Lys Ile Pro Lys Asp Gln Lys Ser Glu Leu
    335                 340                 345

ATT AAC TGT TCA GCC CAG TTT GAA GCA AAT GCT TTT GAA GCA CCA CTT      1524
Ile Asn Cys Ser Ala Gln Phe Glu Ala Asn Ala Phe Glu Ala Pro Leu
350                 355                 360                 365

ACA TTT GCA AAT GCT GAT TCA G GTACCTCTGT CTTTTTTTTT TTGTAAATAG      1576
Thr Phe Ala Asn Ala Asp Ser
                370

TACATATAGT TTTATAGATG ACGATTCCTT CTGTGTTTTT TTCTGCTTTT TAAAATCTTC   1636

ATATCTTATA TTTAATCTTA GGCATCATCT GTATACATGA TTGTTTAGGT CTTTAATTAC   1696

CAGTGTTTAG AATCAGGTCA CTCAAACATG GTAGATAAGT TTGCATAGTT TGTGTATATC   1756

CATCACTCTT GAGACAGTTT TATTTTAAGT TCCGGGGTAC ATGTGCAGGA TGTGCAGGTT   1816
```

-continued

```
TGTTACATAA GTAAACGTAT GCCATGTTGG TTTGCTGCAC CTGTCAACCC TTCACCTGAG   1876

TATTAAGCCC AGCATGCATT AGCTATTTTT CCTGGTGCTC TCCTTCCCCC CACACACCCC   1936

CACCTCCTGA CAGACCCTAG TGTGTGTTGT TCCCCTCCCT GTGTCCGTGT GTTCTCATTG   1996

TTCAGCTCCC ACTTATGAGT GAGAACATGT                                    2026


(2) INFORMATION FOR SEQ ID NO:27:

     (i) SEQUENCE CHARACTERISTICS:
          (A) LENGTH: 5892 base pairs
          (B) TYPE: nucleic acid
          (C) STRANDEDNESS: double
          (D) TOPOLOGY: linear

    (ii) MOLECULE TYPE: DNA (genomic)

    (ix) FEATURE:
          (A) NAME/KEY: CDS
          (B) LOCATION: 483..5412

    (ix) FEATURE:
          (A) NAME/KEY: exon
          (B) LOCATION: 481..5412

    (xi) SEQUENCE DESCRIPTION: SEQ ID NO:27:

CTGAAAAATA GAGCATATTT AGGATTCTTT CTGCTTTAAA TTTGACATTC AGTTATTTTC     60

ATGTAATTTG TGTTTTGAGC ACTACCTTTT AATTAATTTA TTTATTTTTA TTTTTTAGAG    120

ACTGTCTCAT TCTGTTACCT AGTCTGGAGT GCACTAGTGT GATCTCAGCT CACCGTAGCC    180

TCACCCTCCT GGGCTCAAGC AGTCCTTGCA CCTCACCCTC CTGAGTAACT GGCACCACAG    240

GCATACACCA CCACACCCAG CTAATTTTTA TTTTTCATAG AGTCATGGTC TCACTATGTT    300

GCCCAGGCTA GTCTCGAACT CCTGGGCTCA AGCAGTCTTC CTGCCTCAGC CTCCCAAAAG    360

TGCTGAGATT ACAGGCATGA GCCACTGTGC CCAAACACTA CCTTTTTAAC TTAGTGAAAA    420

ATATTTAGTG AATGTGATTG ATGGTACTTT AATTTTGTCA CTTTGTGTTT TTATGTTTAG    480

GT  TTA TTG CAT TCT TCT GTG AAA AGA AGC TGT TCA CAG AAT GAT TCT      527
Gly Leu Leu His Ser Ser Val Lys Arg Ser Cys Ser Gln Asn Asp Ser
 1               5                  10                  15

GAA GAA CCA ACT TTG TCC TTA ACT AGC TCT TTT GGG ACA ATT CTG AGG      575
Glu Glu Pro Thr Leu Ser Leu Thr Ser Ser Phe Gly Thr Ile Leu Arg
            20                  25                  30

AAA TGT TCT AGA AAT GAA ACA TGT TCT AAT AAT ACA GTA ATC TCT CAG      623
Lys Cys Ser Arg Asn Glu Thr Cys Ser Asn Asn Thr Val Ile Ser Gln
        35                  40                  45

GAT CTT GAT TAT AAA GAA GCA AAA TGT AAT AAG GAA AAA CTA CAG TTA      671
Asp Leu Asp Tyr Lys Glu Ala Lys Cys Asn Lys Glu Lys Leu Gln Leu
    50                  55                  60

TTT ATT ACC CCA GAA GCT GAT TCT CTG TCA TGC CTG CAG GAA GGA CAG      719
Phe Ile Thr Pro Glu Ala Asp Ser Leu Ser Cys Leu Gln Glu Gly Gln
 65                  70                  75                  80

TGT GRA AAT GAT CCA AAA AGC AAA AAA GTT TCA GAT ATA AAA GAA GAG      767
Cys Glu Asn Asp Pro Lys Ser Lys Lys Val Ser Asp Ile Lys Glu Glu
                 85                  90                  95

GTC TTG GCT GCA GCA TGT CAC CCA GTA CAA CAT TCA AAA GTG GAA TAC      815
Val Leu Ala Ala Ala Cys His Pro Val Gln His Ser Lys Val Glu Tyr
            100                 105                 110

AGT GAT ACT GAC TTT CAA TCC CAG AAA AAT CTT TTA TAT GAT CAT GAA      863
Ser Asp Thr Asp Phe Gln Ser Gln Lys Asn Leu Leu Tyr Asp His Glu
        115                 120                 125

AAT GCC AGC ACT CTT ATT TTA ACT CCT ACT TCC AAG GAT GTT CTG TCA      911
Asn Ala Ser Thr Leu Ile Leu Thr Pro Thr Ser Lys Asp Val Leu Ser
```

-continued

```
    130                 135                 140

AAC CTA GTC ATG ATT TCT AGA GGC AAA GAA TCA TAC AAA ATG TCA GAC      959
Asn Leu Val Met Ile Ser Arg Gly Lys Glu Ser Tyr Lys Met Ser Asp
145                 150                 155                 160

AAG CTC AAA GGT AAC AAT TAT GAA TCT GAT GTT GAA TTA ACC AAA AAT     1007
Lys Leu Lys Gly Asn Asn Tyr Glu Ser Asp Val Glu Leu Thr Lys Asn
                165                 170                 175

ATT CCC ATG GAA AAG AAT CAA GAT GTA TGT GCT TTA AAT GAA AAT TAT     1055
Ile Pro Met Glu Lys Asn Gln Asp Val Cys Ala Leu Asn Glu Asn Tyr
            180                 185                 190

AAA AAC GTT GAG CTG TTG CCA CCT GAA AAA TAC ATG AGA GTA GCA TCA     1103
Lys Asn Val Glu Leu Leu Pro Pro Glu Lys Tyr Met Arg Val Ala Ser
        195                 200                 205

CCT TCA AGA AAG GTA CAA TTC AAC CAA AAC ACA AAT CTA AGA GTA ATC     1151
Pro Ser Arg Lys Val Gln Phe Asn Gln Asn Thr Asn Leu Arg Val Ile
    210                 215                 220

CAA AAA AAT CAA GAA GAA ACT ACT TCA ATT TCA AAA ATA ACT GTC AAT     1199
Gln Lys Asn Gln Glu Glu Thr Thr Ser Ile Ser Lys Ile Thr Val Asn
225                 230                 235                 240

CCA GAC TCT GAA GAA CTT TTC TCA GAC AAT GAG AAT AAT TTT GTC TTC     1247
Pro Asp Ser Glu Glu Leu Phe Ser Asp Asn Glu Asn Asn Phe Val Phe
                245                 250                 255

CAA GTA GCT AAT GAA AGG AAT AAT CTT GCT TTA GGA AAT ACT AAG GAA     1295
Gln Val Ala Asn Glu Arg Asn Asn Leu Ala Leu Gly Asn Thr Lys Glu
            260                 265                 270

CTT CAT GAA ACA GAC TTG ACT TGT GTA AAC GAA CCC ATT TTC AAG AAC     1343
Leu His Glu Thr Asp Leu Thr Cys Val Asn Glu Pro Ile Phe Lys Asn
        275                 280                 285

TCT ACC ATG GTT TTA TAT GGA GAC ACA GGT GAT AAA CAA GCA ACC CAA     1391
Ser Thr Met Val Leu Tyr Gly Asp Thr Gly Asp Lys Gln Ala Thr Gln
    290                 295                 300

GTG TCA ATT AAA AAA GAT TTG GTT TAT GTT CTT GCA GAG GAG AAC AAA     1439
Val Ser Ile Lys Lys Asp Leu Val Tyr Val Leu Ala Glu Glu Asn Lys
305                 310                 315                 320

AAT AGT GTA AAG CAG CAT ATA AAA ATG ACT CTA GGT CAA GAT TTA AAA     1487
Asn Ser Val Lys Gln His Ile Lys Met Thr Leu Gly Gln Asp Leu Lys
                325                 330                 335

TCG GAC ATC TCC TTG AAT ATA GAT AAA ATA CCA GAA AAA AAT AAT GAT     1535
Ser Asp Ile Ser Leu Asn Ile Asp Lys Ile Pro Glu Lys Asn Asn Asp
            340                 345                 350

TAC ATG AAC AAA TGG GCA GGA CTC TTA GGT CCA ATT TCA AAT CAC AGT     1583
Tyr Met Asn Lys Trp Ala Gly Leu Leu Gly Pro Ile Ser Asn His Ser
        355                 360                 365

TTT GGA GGT AGC TTC AGA ACA GCT TCA AAT AAG GAA ATC AAG CTC TCT     1631
Phe Gly Gly Ser Phe Arg Thr Ala Ser Asn Lys Glu Ile Lys Leu Ser
    370                 375                 380

GAA CAT AAC ATT AAG AAG AGC AAA ATG TTC TTC AAA GAT ATT GAA GAA     1679
Glu His Asn Ile Lys Lys Ser Lys Met Phe Phe Lys Asp Ile Glu Glu
385                 390                 395                 400

CAA TAT CCT ACT AGT TTA GCT TGT GTT GAA ATT GTA AAT ACC TTG GCA     1727
Gln Tyr Pro Thr Ser Leu Ala Cys Val Glu Ile Val Asn Thr Leu Ala
                405                 410                 415

TTA GAT AAT CAA AAG AAA CTG AGC AAG CCT CAG TCA ATT AAT ACT GTA     1775
Leu Asp Asn Gln Lys Lys Leu Ser Lys Pro Gln Ser Ile Asn Thr Val
            420                 425                 430

TCT GCA CAT TTA CAG AGT AGT GTA GTT GTT TCT GAT TGT AAA AAT AGT     1823
Ser Ala His Leu Gln Ser Ser Val Val Val Ser Asp Cys Lys Asn Ser
        435                 440                 445

CAT ATA ACC CCT CAG ATG TTA TTT TCC AAG CAG GAT TTT AAT TCA AAC     1871
```

-continued

```
His Ile Thr Pro Gln Met Leu Phe Ser Lys Gln Asp Phe Asn Ser Asn
    450                 455                 460

CAT AAT TTA ACA CCT AGC CAA AAG GCA GAA ATT ACA GAA CTT TCT ACT     1919
His Asn Leu Thr Pro Ser Gln Lys Ala Glu Ile Thr Glu Leu Ser Thr
465                 470                 475                 480

ATA TTA GAA GAA TCA GGA AGT CAG TTT GAA TTT ACT CAG TTT AGA AAA     1967
Ile Leu Glu Glu Ser Gly Ser Gln Phe Glu Phe Thr Gln Phe Arg Lys
                485                 490                 495

CCA AGC TAC ATA TTG CAG AAG AGT ACA TTT GAA GTG CCT GAA AAC CAG     2015
Pro Ser Tyr Ile Leu Gln Lys Ser Thr Phe Glu Val Pro Glu Asn Gln
            500                 505                 510

ATG ACT ATC TTA AAG ACC ACT TCT GAG GAA TGC AGA GAT GCT GAT CTT     2063
Met Thr Ile Leu Lys Thr Thr Ser Glu Glu Cys Arg Asp Ala Asp Leu
        515                 520                 525

CAT GTC ATA ATG AAT GCC CCA TCG ATT GGT CAG GTA GAC AGC AGC AAG     2111
His Val Ile Met Asn Ala Pro Ser Ile Gly Gln Val Asp Ser Ser Lys
    530                 535                 540

CAA TTT GAA GGT ACA GTT GAA ATT AAA CGG AAG TTT GCT GGC CTG TTG     2159
Gln Phe Glu Gly Thr Val Glu Ile Lys Arg Lys Phe Ala Gly Leu Leu
545                 550                 555                 560

AAA AAT GAC TGT AAC AAA AGT GCT TCT GGT TAT TTA ACA GAT GAA AAT     2207
Lys Asn Asp Cys Asn Lys Ser Ala Ser Gly Tyr Leu Thr Asp Glu Asn
                565                 570                 575

GAA GTG GGG TTT AGG GGC TTT TAT TCT GCT CAT GGC ACA AAA CTG AAT     2255
Glu Val Gly Phe Arg Gly Phe Tyr Ser Ala His Gly Thr Lys Leu Asn
            580                 585                 590

GTT TCT ACT GAA GCT CTG CAA AAA GCT GTG AAA CTG TTT AGT GAT ATT     2303
Val Ser Thr Glu Ala Leu Gln Lys Ala Val Lys Leu Phe Ser Asp Ile
        595                 600                 605

GAG AAT ATT AGT GAG GAA ACT TCT GCA GAG GTA CAT CCA ATA AGT TTA     2351
Glu Asn Ile Ser Glu Glu Thr Ser Ala Glu Val His Pro Ile Ser Leu
    610                 615                 620

TCT TCA AGT AAA TGT CAT GAT TCT GTC GTT TCA ATG TTT AAG ATA GAA     2399
Ser Ser Ser Lys Cys His Asp Ser Val Val Ser Met Phe Lys Ile Glu
625                 630                 635                 640

AAT CAT AAT GAT AAA ACT GTA AGT GAA AAA AAT AAT AAA TGC CAA CTG     2447
Asn His Asn Asp Lys Thr Val Ser Glu Lys Asn Asn Lys Cys Gln Leu
                645                 650                 655

ATA TTA CAA AAT AAT ATT GAA ATG ACT ACT GGC ACT TTT GTT GAA GAA     2495
Ile Leu Gln Asn Asn Ile Glu Met Thr Thr Gly Thr Phe Val Glu Glu
            660                 665                 670

ATT ACT GAA AAT TAC AAG AGA AAT ACT GAA AAT GAA GAT AAC AAA TAT     2543
Ile Thr Glu Asn Tyr Lys Arg Asn Thr Glu Asn Glu Asp Asn Lys Tyr
        675                 680                 685

ACT GCT GCC AGT AGA AAT TCT CAT AAC TTA GAA TTT GAT GGC AGT GAT     2591
Thr Ala Ala Ser Arg Asn Ser His Asn Leu Glu Phe Asp Gly Ser Asp
    690                 695                 700

TCA AGT AAA AAT GAT ACT GTT TGT ATT CAT AAA GAT GAA ACG GAC TTG     2639
Ser Ser Lys Asn Asp Thr Val Cys Ile His Lys Asp Glu Thr Asp Leu
705                 710                 715                 720

CTA TTT ACT GAT CAG CAC AAC ATA TGT CTT AAA TTA TCT GGC CAG TTT     2687
Leu Phe Thr Asp Gln His Asn Ile Cys Leu Lys Leu Ser Gly Gln Phe
                725                 730                 735

ATG AAG GAG GGA AAC ACT CAG ATT AAA GAA GAT TTG TCA GAT TTA ACT     2735
Met Lys Glu Gly Asn Thr Gln Ile Lys Glu Asp Leu Ser Asp Leu Thr
            740                 745                 750

TTT TTG GAA GTT GCG AAA GCT CAA GAA GCA TGT CAT GGT AAT ACT TCA     2783
Phe Leu Glu Val Ala Lys Ala Gln Glu Ala Cys His Gly Asn Thr Ser
        755                 760                 765
```

-continued

```
AAT AAA GAA CAG TTA ACT GCT ACT AAA ACG GAG CAA AAT ATA AAA GAT     2831
Asn Lys Glu Gln Leu Thr Ala Thr Lys Thr Glu Gln Asn Ile Lys Asp
    770                 775                 780

TTT GAG ACT TCT GAT ACA TTT TTT CAG ACT GCA AGT GGG AAA AAT ATT     2879
Phe Glu Thr Ser Asp Thr Phe Phe Gln Thr Ala Ser Gly Lys Asn Ile
785                 790                 795                 800

AGT GTC GCC AAA GAG TCA TTT AAT AAA ATT GTA AAT TTC TTT GAT CAG     2927
Ser Val Ala Lys Glu Ser Phe Asn Lys Ile Val Asn Phe Phe Asp Gln
                805                 810                 815

AAA CCA GAA GAA TTG CAT AAC TTT TCC TTA AAT TCT GAA TTA CAT TCT     2975
Lys Pro Glu Glu Leu His Asn Phe Ser Leu Asn Ser Glu Leu His Ser
            820                 825                 830

GAC ATA AGA AAG AAC AAA ATG GAC ATT CTA AGT TAT GAG GAA ACA GAC     3023
Asp Ile Arg Lys Asn Lys Met Asp Ile Leu Ser Tyr Glu Glu Thr Asp
        835                 840                 845

ATA GTT AAA CAC AAA ATA CTG AAA GAA AGT GTC CCA GTT GGT ACT GGA     3071
Ile Val Lys His Lys Ile Leu Lys Glu Ser Val Pro Val Gly Thr Gly
    850                 855                 860

AAT CAA CTA GTG ACC TTC CAG GGA CAA CCC GAA CGT GAT GAA AAG ATC     3119
Asn Gln Leu Val Thr Phe Gln Gly Gln Pro Glu Arg Asp Glu Lys Ile
865                 870                 875                 880

AAA GAA CCT ACT CTG TTG GGT TTT CAT ACA GCT AGC GGG AAA AAA GTT     3167
Lys Glu Pro Thr Leu Leu Gly Phe His Thr Ala Ser Gly Lys Lys Val
                885                 890                 895

AAA ATT GCA AAG GAA TCT TTG GAC AAA GTG AAA AAC CTT TTT GAT GAA     3215
Lys Ile Ala Lys Glu Ser Leu Asp Lys Val Lys Asn Leu Phe Asp Glu
            900                 905                 910

AAA GAG CAA GGT ACT AGT GAA ATC ACC AGT TTT AGC CAT CAA TGG GCA     3263
Lys Glu Gln Gly Thr Ser Glu Ile Thr Ser Phe Ser His Gln Trp Ala
        915                 920                 925

AAG ACC CTA AAG TAC AGA GAG GCC TGT AAA GAC CTT GAA TTA GCA TGT     3311
Lys Thr Leu Lys Tyr Arg Glu Ala Cys Lys Asp Leu Glu Leu Ala Cys
    930                 935                 940

GAG ACC ATT GAG ATC ACA GCT GCC CCA AAG TGT AAA GAA ATG CAG AAT     3359
Glu Thr Ile Glu Ile Thr Ala Ala Pro Lys Cys Lys Glu Met Gln Asn
945                 950                 955                 960

TCT CTC AAT AAT GAT AAA AAC CTT GTT TCT ATT GAG ACT GTG GTG CCA     3407
Ser Leu Asn Asn Asp Lys Asn Leu Val Ser Ile Glu Thr Val Val Pro
                965                 970                 975

CCT AAG CTC TTA AGT GAT AAT TTA TGT AGA CAA ACT GAA AAT CTC AAA     3455
Pro Lys Leu Leu Ser Asp Asn Leu Cys Arg Gln Thr Glu Asn Leu Lys
            980                 985                 990

ACA TCA AAA AGT ATC TTT TTG AAA GTT AAA GTA CAT GAA AAT GTA GAA     3503
Thr Ser Lys Ser Ile Phe Leu Lys Val Lys Val His Glu Asn Val Glu
        995                 1000                1005

AAA GAA ACA GCA AAA AGT CCT GCA ACT TGT TAC ACA AAT CAG TCC CCT     3551
Lys Glu Thr Ala Lys Ser Pro Ala Thr Cys Tyr Thr Asn Gln Ser Pro
    1010                1015                1020

TAT TCA GTC ATT GAA AAT TCA GCC TTA GCT TTT TAC ACA AGT TGT AGT     3599
Tyr Ser Val Ile Glu Asn Ser Ala Leu Ala Phe Tyr Thr Ser Cys Ser
1025                1030                1035                1040

AGA AAA ACT TCT GTG AGT CAG ACT TCA TTA CTT GAA GCA AAA AAA TGG     3647
Arg Lys Thr Ser Val Ser Gln Thr Ser Leu Leu Glu Ala Lys Lys Trp
                1045                1050                1055

CTT AGA GAA GGA ATA TTT GAT GGT CAA CCA GAA AGA ATA AAT ACT GCA     3695
Leu Arg Glu Gly Ile Phe Asp Gly Gln Pro Glu Arg Ile Asn Thr Ala
            1060                1065                1070

GAT TAT GTA GGA AAT TAT TTG TAT GAA AAT AAT TCA AAC AGT ACT ATA     3743
Asp Tyr Val Gly Asn Tyr Leu Tyr Glu Asn Asn Ser Asn Ser Thr Ile
        1075                1080                1085
```

-continued

```
GCT GAA AAT GAC AAA AAT CAT CTC TCC GAA AAA CAA GAT ACT TAT TTA     3791
Ala Glu Asn Asp Lys Asn His Leu Ser Glu Lys Gln Asp Thr Tyr Leu
    1090                1095                1100

AGT AAC AGT AGC ATG TCT AAC AGC TAT TCC TAC CAT TCT GAT GAG GTA     3839
Ser Asn Ser Ser Met Ser Asn Ser Tyr Ser Tyr His Ser Asp Glu Val
1105                1110                1115                1120

TAT AAT GAT TCC AGG ATA CTC TCA AAA AAT AAC TTG GAT TCT GGT ATT     3887
Tyr Asn Asp Ser Arg Ile Leu Ser Lys Asn Asn Leu Asp Ser Gly Ile
                1125                1130                1135

GAG CCA GTA TTG AAG AAT GTT GAA GAT CAA AAA AAC ACT AGT TTT TCC     3935
Glu Pro Val Leu Lys Asn Val Glu Asp Gln Lys Asn Thr Ser Phe Ser
            1140                1145                1150

AAA GTA ATA TCC AAT GTA AAA GAT GCA AAT GCA TAC CCA CAA ACT GTA     3983
Lys Val Ile Ser Asn Val Lys Asp Ala Asn Ala Tyr Pro Gln Thr Val
        1155                1160                1165

AAT GAA GAT ATT TGC GTT GAG GAA CTT GTG ACT AGC TCT TCA CCC TGC     4031
Asn Glu Asp Ile Cys Val Glu Glu Leu Val Thr Ser Ser Ser Pro Cys
    1170                1175                1180

AAA AAT AAA AAT GCA GCC ATT AAA TTG TCC ATA TCT AAT AGT AAT AAT     4079
Lys Asn Lys Asn Ala Ala Ile Lys Leu Ser Ile Ser Asn Ser Asn Asn
1185                1190                1195                1200

TTT GAG GTA GGG CCA CCT GCA TTT AGG ATA GCC AGT GGT AAA ATC GTT     4127
Phe Glu Val Gly Pro Pro Ala Phe Arg Ile Ala Ser Gly Lys Ile Val
                1205                1210                1215

TGT GTT TCA CAT GAA ACA ATT AAA AAA GTG AAA GAC ATA TTT ACA GAC     4175
Cys Val Ser His Glu Thr Ile Lys Lys Val Lys Asp Ile Phe Thr Asp
            1220                1225                1230

AGT TTC AGT AAA GTA ATT AAG GAA AAC AAC GAG AAT AAA TCA AAA ATT     4223
Ser Phe Ser Lys Val Ile Lys Glu Asn Asn Glu Asn Lys Ser Lys Ile
        1235                1240                1245

TGC CAA ACG AAA ATT ATG GCA GGT TGT TAC GAG GCA TTG GAT GAT TCA     4271
Cys Gln Thr Lys Ile Met Ala Gly Cys Tyr Glu Ala Leu Asp Asp Ser
    1250                1255                1260

GAG GAT ATT CTT CAT AAC TCT CTA GAT AAT GAT GAA TGT AGC ACG CAT     4319
Glu Asp Ile Leu His Asn Ser Leu Asp Asn Asp Glu Cys Ser Thr His
1265                1270                1275                1280

TCA CAT AAG GTT TTT GCT GAC ATT CAG AGT GAA GAA ATT TTA CAA CAT     4367
Ser His Lys Val Phe Ala Asp Ile Gln Ser Glu Glu Ile Leu Gln His
                1285                1290                1295

AAC CAA AAT ATG TCT GGA TTG GAG AAA GTT TCT AAA ATA TCA CCT TGT     4415
Asn Gln Asn Met Ser Gly Leu Glu Lys Val Ser Lys Ile Ser Pro Cys
            1300                1305                1310

GAT GTT AGT TTG GAA ACT TCA GAT ATA TGT AAA TGT AGT ATA GGG AAG     4463
Asp Val Ser Leu Glu Thr Ser Asp Ile Cys Lys Cys Ser Ile Gly Lys
        1315                1320                1325

CTT CAT AAG TCA GTC TCA TCT GCA AAT ACT TGT GGG ATT TTT AGC ACA     4511
Leu His Lys Ser Val Ser Ser Ala Asn Thr Cys Gly Ile Phe Ser Thr
    1330                1335                1340

GCA AGT GGA AAA TCT GTC CAG GTA TCA GAT GCT TCA TTA CAA AAC GCA     4559
Ala Ser Gly Lys Ser Val Gln Val Ser Asp Ala Ser Leu Gln Asn Ala
1345                1350                1355                1360

AGA CAA GTG TTT TCT GAA ATA GAA GAT AGT ACC AAG CAA GTC TTT TCC     4607
Arg Gln Val Phe Ser Glu Ile Glu Asp Ser Thr Lys Gln Val Phe Ser
                1365                1370                1375

AAA GTA TTG TTT AAA AGT AAC GAA CAT TCA GAC CAG CTC ACA AGA GAA     4655
Lys Val Leu Phe Lys Ser Asn Glu His Ser Asp Gln Leu Thr Arg Glu
            1380                1385                1390

GAA AAT ACT GCT ATA CGT ACT CCA GAA CAT TTA ATA TCC CAA AAA GGC     4703
Glu Asn Thr Ala Ile Arg Thr Pro Glu His Leu Ile Ser Gln Lys Gly
```

-continued

```
        1395                1400                1405

TTT TCA TAT AAT GTG GTA AAT TCA TCT GCT TTC TCT GGA TTT AGT ACA     4751
Phe Ser Tyr Asn Val Val Asn Ser Ser Ala Phe Ser Gly Phe Ser Thr
    1410                1415                1420

GCA AGT GGA AAG CAA GTT TCC ATT TTA GAA AGT TCC TTA CAC AAA GTT     4799
Ala Ser Gly Lys Gln Val Ser Ile Leu Glu Ser Ser Leu His Lys Val
1425                1430                1435                1440

AAG GGA GTG TTA GAG GAA TTT GAT TTA ATC AGA ACT GAG CAT AGT CTT     4847
Lys Gly Val Leu Glu Glu Phe Asp Leu Ile Arg Thr Glu His Ser Leu
                1445                1450                1455

CAC TAT TCA CCT ACG TCT AGA CAA AAT GTA TCA AAA ATA CTT CCT CGT     4895
His Tyr Ser Pro Thr Ser Arg Gln Asn Val Ser Lys Ile Leu Pro Arg
            1460                1465                1470

GTT GAT AAG AGA AAC CCA GAG CAC TGT GTA AAC TCA GAA ATG GAA AAA     4943
Val Asp Lys Arg Asn Pro Glu His Cys Val Asn Ser Glu Met Glu Lys
        1475                1480                1485

ACC TGC AGT AAA GAA TTT AAA TTA TCA AAT AAC TTA AAT GTT GAA GGT     4991
Thr Cys Ser Lys Glu Phe Lys Leu Ser Asn Asn Leu Asn Val Glu Gly
    1490                1495                1500

GGT TCT TCA GAA AAT AAT CAC TCT ATT AAA GTT TCT CCA TAT CTC TCT     5039
Gly Ser Ser Glu Asn Asn His Ser Ile Lys Val Ser Pro Tyr Leu Ser
1505                1510                1515                1520

CAA TTT CAA CAA GAC AAA CAA CAG TTG GTA TTA GGA ACC AAA GTC TCA     5087
Gln Phe Gln Gln Asp Lys Gln Gln Leu Val Leu Gly Thr Lys Val Ser
                1525                1530                1535

CTT GTT GAG AAC ATT CAT GTT TTG GGA AAA GAA CAG GCT TCA CCT AAA     5135
Leu Val Glu Asn Ile His Val Leu Gly Lys Glu Gln Ala Ser Pro Lys
            1540                1545                1550

AAC GTA AAA ATG GAA ATT GGT AAA ACT GAA ACT TTT TCT GAT GTT CCT     5183
Asn Val Lys Met Glu Ile Gly Lys Thr Glu Thr Phe Ser Asp Val Pro
        1555                1560                1565

GTG AAA ACA AAT ATA GAA GTT TGT TCT ACT TAC TCC AAA GAT TCA GAA     5231
Val Lys Thr Asn Ile Glu Val Cys Ser Thr Tyr Ser Lys Asp Ser Glu
    1570                1575                1580

AAC TAC TTT GAA ACA GAA GCA GTA GAA ATT GCT AAA GCT TTT ATG GAA     5279
Asn Tyr Phe Glu Thr Glu Ala Val Glu Ile Ala Lys Ala Phe Met Glu
1585                1590                1595                1600

GAT GAT GAA CTG ACA GAT TCT AAA CTG CCA AGT CAT GCC ACA CAT TCT     5327
Asp Asp Glu Leu Thr Asp Ser Lys Leu Pro Ser His Ala Thr His Ser
                1605                1610                1615

CTT TTT ACA TGT CCC GAA AAT GAG GNA ATG GTN TTG TCA AAT TCA AGA     5375
Leu Phe Thr Cys Pro Glu Asn Glu Glu Met Val Leu Ser Asn Ser Arg
            1620                1625                1630

ATT GGA AAA AGA AGA GGA GAG CCC CTT ATC TTA GTG G GTAAGTGTTC        5422
Ile Gly Lys Arg Arg Gly Glu Pro Leu Ile Leu Val
        1635                1640

ATTTTTACCT TTCGTGTTGC CAATCACTAT TTTTAAAGTG TTTATTCAGT AGACTTGGTA   5482

TGCTAACAAT TAAGAGTGTT ATAAACTATG TCTTTTCAGC CATTTTTGTG TAGTCAGTTT   5542

GGGGGAGTAT GGTTTGATAT ACAGATACAC AGATTCAGTA TTCGTATACA GATTTGATAT   5602

CTTGGTATAC AGATTCGATA TCTCTGAATC TGTATACCAA GAAATCATGT TTTAAGGGTC   5662

TCAATATATT TTCAAAAAGA TTATTAGTAT AATAATTGAG AAATTACTGT TAAAAAGTTT   5722

TGAGTTTCTC TAGAAAATTT GAAACTCTTA ACAAAACCTG CATAATACTA ACTTAACTGT   5782

TTTCATATAC ATAGCAAGTT CAGACTCTGA CTTATATGAA CTTTAAAAGT TGGTTTCCGG   5842

GAGGCCGAGG CGGGCGGATC ACGAGGTCAG GAGATCGAGA CCATCCCGGC              5892
```

-continued (2) INFORMATION FOR SEQ ID NO:28:

```
     (i) SEQUENCE CHARACTERISTICS:
          (A) LENGTH: 1056 base pairs
          (B) TYPE: nucleic acid
          (C) STRANDEDNESS: double
          (D) TOPOLOGY: linear

    (ii) MOLECULE TYPE: DNA (genomic)

    (ix) FEATURE:
          (A) NAME/KEY: CDS
          (B) LOCATION: 483..576

    (ix) FEATURE:
          (A) NAME/KEY: exon
          (B) LOCATION: 481..576

    (xi) SEQUENCE DESCRIPTION: SEQ ID NO:28:

GTAATTTGAT AATTGTAAAA AGCCTCTTAA CTCTAATTCA AGGACCTACA TAATAAATTA      60

CTCCTTCAGT TAATGGCTGC CCCCGTGCTG AAAAAAAAAA AAAAAAGAGA GAAAAAGTTT     120

ATTTGAAGAA ATTTTGTTAG GCCTTATTGC CAGTAAACCT AGAGTTATAT TTAGTGTCAG     180

TTTTTCAAAA AGTAGCTTAT CTGTGGTATC TGGTAGCATC TGTTTATCCT ATTTAGGATT     240

TATCCTGTTT AGACCCTGTT AAATAGTGGT GTTTTAAAGT GGTCAAAACA GAACAAAAAT     300

GTAATTGACA TTGAAGACTG ACTTTACTCT TTCAAACATT AGGTCACTAT TTGTTGTAAG     360

TATTTTTGTT TAACATTTAA AGAGTCAATA CTTTAGCTTT AAAAAAATGG TCTATAGACT     420

TTTGAGAAAT AAAACTGATA TTATTTGCCT TAAAAACATA TATGAAATAT TTCTTTTTAG     480

GA  GAA CCC TCA ATC AAA AGA AAC TTA TTA AAT GAA TTT GAC AGG ATA       527
Gly Glu Pro Ser Ile Lys Arg Asn Leu Leu Asn Glu Phe Asp Arg Ile
 1               5                  10                  15

ATA GAA AAT CAA GAA AAA TCC TTA AAG GCT TCA AAA AGC ACT CCA GAT G     576
Ile Glu Asn Gln Glu Lys Ser Leu Lys Ala Ser Lys Ser Thr Pro Asp
            20                  25                  30

GTTAAAATTA GCTTTNTATT TNTATCTGTT CTCCCTCTAT AGGTNATGGG TATATAATAT     636

TCTGACCTCA GGTGGATCCA CCTGCCTCTC CAAAGTGCTG GGNATTACAG ACATGAGCCA     696

CTGTGCCTAA TCAAGGACCT CTTTATACTC TTAAAAATTA CTGAGGACCT AAAGNGGCAT     756

TTGTTTATGT GGGANTATAT CTATTGATAT TTACCATATT NGANATGTAA ATTGATTAAT     816

GGTTAAANTT AGTAANTATT ATGCGTTGGT CATTGGGAGG ATATGAGTTC ACTGAGTTAT     876

GCGGATCTTC CGAAAGTTGA ACAGTTTCTA TTATGCCAGT AATTAAAACA ATCCACCTTT     936

CCATTGGATG CCCATTACCC GATCCAGAAA AGNTTAAAGT AGTAGAAAGC TGTCAAGCTT     996

ACAGAGCCCA GATACAAGCT TCCCCAAAAA TTCTGATTTT CATCTAAAAG CTTGAATTTT    1056
```

(2) INFORMATION FOR SEQ ID NO:29:

```
     (i) SEQUENCE CHARACTERISTICS:
          (A) LENGTH: 1030 base pairs
          (B) TYPE: nucleic acid
          (C) STRANDEDNESS: double
          (D) TOPOLOGY: linear

    (ii) MOLECULE TYPE: DNA (genomic)

    (ix) FEATURE:
          (A) NAME/KEY: CDS
          (B) LOCATION: 483..550

    (ix) FEATURE:
          (A) NAME/KEY: exon
          (B) LOCATION: 481..550
```

-continued (xi) SEQUENCE DESCRIPTION: SEQ ID NO:29:

```
GAGATCGTCC TCATTCTTTT TTGTGGTTAC ATAGTAGTTG ATCATCTGGC TGTGTCAGTG     60

TTTCCTAGTT TATTTAACCA ATTTCCAACT AGTGGACTTA TTGAAGATTT AATTAGGTTC    120

CAGTTACATA CTGAAAATGA ACAATATCTA AAGCTTAGCT TTTAAACCTT CATAAGACTA    180

AATTTTAAAT TTGGTATTTG CATCAGAAAT TAGCTAACAC CTTTGAGTTA TGATGGTTAA    240

CATCAACTGA CTAAATTTAT GCTGATTTCT GTTGTATGCT TGTACTGTGA GTTATTTGGT    300

GCATAGTCAT TATCAATTTG TGAATCAATT TATTTTCATA GTTAACATTT ATTGAGCATC    360

CGTTACATTC ACTGAAAATT GTAAAGCCTA TAATTGTCTC AAATTTTTTG TGTATTTACA    420

GTAACATGGA TATTCTCTTA GATTTTAACT AATATGTAAT ATAAAATAAT TGTTTCCTAG    480

 GC ACA ATA AAA GAT CGA AGA TTG TTT ATG CAT CAT GTT TCT TTA          524
Gly Thr Ile Lys Asp Arg Arg Leu Phe Met His His Val Ser Leu
 1               5                  10                  15

GAG CCG ATT ACC TGT GTA CCC TTT CG GTAAGACATG TTTAAATTTT             570
Glu Pro Ile Thr Cys Val Pro Phe Arg
                20

TCTAAATTCT AATACAGTAT GAGAAAAGTC TCGTTTTTAT AAATGAACAT TTCTAAAAAT    630

AATGACACTA ACGTTAAGAA GTTAACACTT CCCGTTTTAT AAAATTTATA AAATACTTTG    690

GTAGTATTTT ATAGTGCTGT TCATATCATT ATTTTATTTT TTAATTTTAT GACAGCTTTG    750

TAAAGTAGAC AGATTTTATT CTAATTTTAT GGATGAAGTA CTAAGGTTGA GAGGAATTAA    810

GGAAATTGCT CCGAATCAGT TAACAAAAAG ATTGCAGATA TTAAAAAATAT CCTTTTATCT   870

CTCCTCTCTAAACCTTTAAA AAAGTACTAA GATAGTTTTT TTAATGTATA ATTCCCAAGG     930

ACAATGATGA GAAGAAACAA CAAAAGTTTG GAAGCCAAAA ACATAAAGGA TTTAGTAAGC    990

ATGAGAAAGC TAAAACCTGA CACTAGAGCA AACAGAGATG                         1030
```

(2) INFORMATION FOR SEQ ID NO:30:

(i) SEQUENCE CHARACTERISTICS:
(A) LENGTH: 1129 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 482..908

(ix) FEATURE:
(A) NAME/KEY: exon
(B) LOCATION: 481..908

(xi) SEQUENCE DESCRIPTION: SEQ ID NO:30:

```
TTCAAAGGTA GGCAAGATTT TTGGGCTAAA TAAAAAGGGC ACTTTAAAAA AGGTATAAAT     60

AGGTAGAAGA GAGAAAAGGG AGCGAGGTGG GATAATTGAA AGAGGGGATC TCCTGTGGAG    120

ACTGAGGTAT TAGGCGGAGT AGAGAGTTCA GGTGAAGATG TGAAGGTGAG AGAAGAGGAT    180

GGGTAGACAT TTCCCTGGTG AAGGAGGTAA GGAGTACTAT GATGGAATTA GAGGGGACAC    240

ACTGAGAGGG TCCACACTTG ACAGACTCTC TTCTATTATG TGTTATGTGA GGTAGATTGT    300

AAAGTCAAAG GCTAGCCTTG AAAAATGTGA TATTGTTTTG GAATGGCAAC CATGGTGAAT    360

ACAAAACAGT TACCAGAATA GTATCACCAT GTAGCAAATG AGGGTCTGCA ACAAAGGCAT    420

ATTCCTAAAT ATTTATATGT GTACTAGTCA ATAAACTTAT ATATTTTCTC CCCATTGCAG    480
```

-continued

```
C ACA ACT AAG GAA CGT CAA GAG ATA CAG AAT CCA AAT TTT ACC GCA        526

  Thr Thr Lys Glu Arg Gln Glu Ile Gln Asn Pro Asn Phe Thr Ala
    1               5                  10                  15

CCT GGT CAA GAA TTT CTG TCT AAA TCT CAT TTG TAT GAA CAT CTG ACT      574
Pro Gly Gln Glu Phe Leu Ser Lys Ser His Leu Tyr Glu His Leu Thr
                 20                  25                  30

TTG GAA AAA TCT TCA AGC AAT TTA GCA GTT TCA GGA CAT CCA TTT TAT      622
Leu Glu Lys Ser Ser Ser Asn Leu Ala Val Ser Gly His Pro Phe Tyr
             35                  40                  45

CAA GTT TCT GCT ACA AGA AAT GAA AAA ATG AGA CAC TTG ATT ACT ACA      670
Gln Val Ser Ala Thr Arg Asn Glu Lys Met Arg His Leu Ile Thr Thr
         50                  55                  60

GGC AGA CCA ACC AAA GTC TTT GTT CCA CCT TTT AAA ACT AAA TCA CAT      718
Gly Arg Pro Thr Lys Val Phe Val Pro Pro Phe Lys Thr Lys Ser His
     65                  70                  75

TTT CAC AGA GTT GAA CAG TGT GTT AGG AAT ATT AAC TTG GAG GAA AAC      766
Phe His Arg Val Glu Gln Cys Val Arg Asn Ile Asn Leu Glu Glu Asn
 80                  85                  90                  95

AGA CAA AAG CAA AAC ATT GAT GGA CAT GGC TCT GAT GAT AGT AAA AAT      814
Arg Gln Lys Gln Asn Ile Asp Gly His Gly Ser Asp Asp Ser Lys Asn
                100                 105                 110

AAG ATT AAT GAC AAT GAG ATT CAT CAG TTT AAC AAA AAC AAC TCC AAT      862
Lys Ile Asn Asp Asn Glu Ile His Gln Phe Asn Lys Asn Asn Ser Asn
            115                 120                 125

CAA GCA GCA GCT GTA ACT TTC ACA AAG TGT GAA GAA GAA CCT TTA G        908
Gln Ala Ala Ala Val Thr Phe Thr Lys Cys Glu Glu Glu Pro Leu
        130                 135                 140

GTATTGTATG ACAATTTGTG TGATGAATTT TTGCCTTTCA GTTAGATATT TCCGTTGTTA    968

AATAATGTCC TGATGGTTTT CCCCCTTTGG TGGTGGTAAT TTTAAAGCCC TTTTTAATGT   1028

TTTAGATTTT CTAAATCCAA AGATTAGGTT TAAATTATTC TAATGTTTCT TTCAAAGATA   1088

ACTTCTTGTG GACTTGTTAA AAAAAATTAG ACACACAATC T                       1129
```

(2) INFORMATION FOR SEQ ID NO:31:

(i) SEQUENCE CHARACTERISTICS:
(A) LENGTH: 722 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: exon
(B) LOCATION: 77..242

(ix) FEATURE:
(A) NAME/KEY: CDS
(B) LOCATION: 79..242

(xi) SEQUENCE DESCRIPTION: SEQ ID NO:31:

```
AACCCACTGT GCCTGGCCAG GGGTTGTGCT TTTTAAATTT CAATTTTATT TTTGCTAAGT     60

ATTTATTCTT TGATAG AT TTA ATT ACA AGT CTT CAG AAT GCC AGA GAT ATA     111
                 Asp Leu Ile Thr Ser Leu Gln Asn Ala Arg Asp Ile
                   1               5                  10

CAG GAT ATG CGA ATT AAG AAG AAA CAA AGG CAA CGC GTC TTT CCA CAG      159
Gln Asp Met Arg Ile Lys Lys Lys Gln Arg Gln Arg Val Phe Pro Gln
        15                  20                  25

CCA GGC AGT CTG TAT CTT GCA AAA ACA TCC ACT CTG CCT CGA ATC TCT      207
Pro Gly Ser Leu Tyr Leu Ala Lys Thr Ser Thr Leu Pro Arg Ile Ser
     30                  35                  40
```

-continued

```
CTG AAA GCA GCA GTA GGA GGC CAA GTT CCC TCT GC GTGTCCCCAT            252
Leu Lys Ala Ala Val Gly Gly Gln Val Pro Ser Ala
 45                 50                  55

AAACAGGTAT GTGTTTGNCT ACAATACTGA TGGCTTTTAT GACAGAGTGT AATTTTATTT    312

CATTAACTAG TATCCTACAA ATGGCTTTGT TTAAAGAATG AACACATTAG TGCAGGAATG    372

GATGAATGAA ATCATCCATA TTTTCCTAAT TAAGCCCTGC AGTGGCAGCC TCTGGCCCCT    432

TGCTAGGCCT GCCCTCATCC CTACTAAAGT GATCTGTGCC TTCCCAAATT ACTACTTCTT    492

TTCCCCCCTT CAAATCTTTC TTATTTTGTC ATTGTAAATG CTCTCAGCTA GGTGTTAAAG    552

TAGTCTTACT GATATTCAAA TGTGAATAAC TGATAGCCCT GAACCTTCTA TGAGCTATTT    612

ATATTTTCCA AAGAGGATTC TCCTTAAGCC AATATTATCT AGGTAGAATT TTAGGCAATG    672

GAGAGGTGAA AATAATATTG ATGACATTAA TAGCTAACTT TGAGCATTTT                722
```

(2) INFORMATION FOR SEQ ID NO:32:

(i) SEQUENCE CHARACTERISTICS:
(A) LENGTH: 1164 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: exon
(B) LOCATION: 481..684

(ix) FEATURE:
(A) NAME/KEY: CDS
(B) LOCATION: 482..684

(xi) SEQUENCE DESCRIPTION: SEQ ID NO:32:

```
GTCTGACTCC AGAGTCAAAC TCTGAACAAA CAAAAAGACA CTTTGGGTTA GATATCCTGG     60

GGTGAAAGCA AGCACTTTGA AAGTAAGCCA AGCCTGTGTA CAGATCTGAC CACCTGAGGT    120

CACATTCCCT AAAATACTTA AACTTCTCCC TTTTGTTTCC CATCTAAGTT TTTGAACTTA    180

AGAGATTTTG TAAAACATCA CATTTTTTTA TCCTCACAGT ACCTTCCTAT GGCAGATTTA    240

GCAGGAGGCG TATAAACGGG GTGGAAAAGG TACAGCAGAC TGTGGAATGT ATGGATCATT    300

TATATTACAT TAAAATTTTT AGTTTCTAGT AAATAACTTA AATGTTTTTG TAGTGAAGAT    360

TCTAGTAGTT AATGAAAATT TTTGGTAAAT TCAGTTTTGG TTTGTTATAA TTGTTTTTAT    420

TGTGTGATAC ATGTTTACTT TAAATTGTTT TTCTTTTTTG TGTGTGTTTA TTTTGTGTAG    480

G TGT TCT CAT AAA CAG CTG TAT ACG TAT GGC GTT TCT AAA CAT TGC        526
  Cys Ser His Lys Gln Leu Tyr Thr Tyr Gly Val Ser Lys His Cys
    1               5                  10                  15

ATA AAA ATT AAC AGC AAA AAT GCA GAG TCT TTT CAG TTT CAC ACT GAA      574
Ile Lys Ile Asn Ser Lys Asn Ala Glu Ser Phe Gln Phe His Thr Glu
                 20                  25                  30

GAT TAT TTT GGT AAG GAA AGT TTA TGG ACT GGA AAA GGA ATA CAG TTG      622
Asp Tyr Phe Gly Lys Glu Ser Leu Trp Thr Gly Lys Gly Ile Gln Leu
             35                  40                  45

GCT GAT GGT GGA TGG CTC ATA CCC TCC AAT GAT GGA AAG GCT GGA AAA      670
Ala Asp Gly Gly Trp Leu Ile Pro Ser Asn Asp Gly Lys Ala Gly Lys
         50                  55                  60

GAA GAA TTT TAT AG GTACTCTATG CAAAAAGATT GTGTGTTAAC TTTTATGTAT       724
Glu Glu Phe Tyr Arg
     65

TCCCTCATCC CTCTTTCTTC TCTTAACTGT CTCTCGAACT AAAAAGTTGG CTAGAAATCA    784
```

-continued

```
AATTTTTATG CATTTAATTG TTTTAAGTGC ATTATGGTTA AGCATTCTGT AGAAGTCTTT    844

TGAAAAGTGC TGTTTGTCCT GGGGTTTAAT GAACTGGATT TTCTTGATTT GGGACATTTT    904

TCTTAGGCAT TTATAAATAT AGCCCAATTT ATAAAGTTAA ATTTGGCCGG GTACAGTGGC    964

TCATGCCTGT AATCCCAGCA CTTTGGGAGG CCGAGGCGGG TAGATCACCT GAGGTCAGGA   1024

GTTCGAGACC AGCCTGGCCA ACGTGGCGAA ACCCCATCTC TACTAAAAGT ACAAGAACTA   1084

TCTGGGCGTG GTGGCAGGCA CCTGTAATCC CGGCTACTCT GGAGGCTGAG GCAGGAGAAT   1144

CGCTTGAACC TGGGAGGCAG                                               1164
```

(2) INFORMATION FOR SEQ ID NO:33:

```
     (i) SEQUENCE CHARACTERISTICS:
          (A) LENGTH: 1171 base pairs
          (B) TYPE: nucleic acid
          (C) STRANDEDNESS: double
          (D) TOPOLOGY: linear

    (ii) MOLECULE TYPE: DNA (genomic)

    (ix) FEATURE:
          (A) NAME/KEY: exon
          (B) LOCATION: 501..671

    (ix) FEATURE:
          (A) NAME/KEY: CDS
          (B) LOCATION: 502..671

    (xi) SEQUENCE DESCRIPTION: SEQ ID NO:33:
```

```
TTGTTTTGTT TTTATATTTT GAGATAGGGT CTCACTCTTG TCCAGGCTGG AGTGCAGTGG     60

CACTATCATG GCTCACTGCA GCCTCAACCT CCTGGGCTCA AGCAATCCTC CCACCACAGC    120

CTCCTAAGTA GCTGGGACCA CAGATGTGAG CTACCACTCT TGGCTGATTT TTTTTATTAT    180

TTTTTGTAGA GATGTGGGGG TCTCACTATG TTGCCTAGGC TGGTCTCAAA CTTCTGGCCT    240

CAAGCAATCC TCCTGCCTCA GCTTCCCAAA ATGCTGGGAG TATAGGCATG AGCCACCATG    300

CTCAGCAATG AAGTTTTTAT CAGTATGATA CTTTGATACA TGTCAAATAA TTTTCTGAAA    360

TTATATTGTA GATCATATGA ACTCATAAAA ACTTAATGAT CTTGAACAAT GTAGTTTTTG    420

TACAGAGAAT AGTTGTAGTT GTTGAATTCA GTATCATCCT ATGTGGTTTT TATGATAATA    480

TTCTACTTTT ATTTGTTCAG G GCT CTG TGT GAC ACT CCA GGT GTG GAT CCA      531
                        Ala Leu Cys Asp Thr Pro Gly Val Asp Pro
                          1               5                  10

AAG CTT ATT TCT AGA ATT TGG GTT TAT AAT CAC TAT AGA TGG ATC ATA      579
Lys Leu Ile Ser Arg Ile Trp Val Tyr Asn His Tyr Arg Trp Ile Ile
                 15                  20                  25

TGG AAA CTG GCA GCT ATG GAA TGT GCC TTT CCT AAG GAA TTT GCT AAT      627
Trp Lys Leu Ala Ala Met Glu Cys Ala Phe Pro Lys Glu Phe Ala Asn
             30                  35                  40

AGA TGC CTA AGC CCA GAA AGG GTG CTT CTT CAA CTA AAA TAC AG           671
Arg Cys Leu Ser Pro Glu Arg Val Leu Leu Gln Leu Lys Tyr Arg
         45                  50                  55

GCAAGTTTAA AGCATTACAT TACGTAATCA TATACGGCAG TATGGGTTAA GGTTTCTGTG    731

TAGTCTGTGA CTTCCATGTC AAAATGTTGC ACAAGCCAGT TGTCAGTGAC AGTTGCCATC    791

CCACACTGCT GTTCTCCTGT CATCCCTAGC CCCCATTTAA GAGAGATCAC ACATTCATGC    851

ATTGCTTGCT TCCCTCTTTC CCCACCCCCT CCTTAACCTC TTGATGTATG AGAAGAATAT    911

GAGTTACTAA TTTGATCCAC TATTTGGGGA TTGCTAATAA AGCATTTTTG CATTTTATTT    971

TTTGCTTTTT AAAAATAATT GATATTTTAA CAATATGAAA CAATATATTC CTAGCTACAA   1031
```

-continued

```
AATTTTTAAT TCTCAGTATT TCTTAGATAA ATTCAGTTTT TATTCTCAGT TATTCAGTGA   1091

CTTGTTTAAA CAGTGGAATT CTAGAGTCAC ACTTCCTAAA ATATGCATTT TTGTTTTCAC   1151

TTTTAGATAT GATACGGAAA                                               1171
```

(2) INFORMATION FOR SEQ ID NO:34:

(i) SEQUENCE CHARACTERISTICS:
(A) LENGTH: 1355 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: exon
(B) LOCATION: 501..855

(ix) FEATURE:
(A) NAME/KEY: CDS
(B) LOCATION: 502..855

(xi) SEQUENCE DESCRIPTION: SEQ ID NO:34:

```
CAACTAAAAT ACAGGCAAGT TTAAAGCATT ACATTACGTA ATCATATACG GCAGTATGGG     60

TTAAGGTTTC TGTGTAGTCT GTGACTTCCA TGTCAAAATG TTGCACAAGC CAGTTGTCAG    120

TGACAGTTGC CATCCCACAC TGCTGTTCTC CTGTCATCCC TAGCCCCCAT TTAAGAGAGA    180

TCACACATTC ATGCATTGCT TGCTTCCCTC TTTCCCCACC CCCTCCTTAA CCTCTTGATG    240

TATGAGAAGA ATATGAGTTA CTAATTTGAT CCACTATTTG GGGATTGCTA ATAAAGCATT    300

TTTGCATTTT ATTTTTTGCT TTTTAAAAAT AATTGATATT TTAACAATAT GAAACAATAT    360

ATTCCTAGCT ACAAAATTTT TAATTCTCAG TATTTCTTAG ATAAATTCAG TTTTTATTCT    420

CAGTTATTCA GTGACTTGTT TAAACAGTGG AATTCTAGAG TCACACTTCC TAAAATATGC    480

ATTTTTGTTT TCACTTTTAG A TAT GAT ACG GAA ATT GAT AGA AGC AGA AGA      531
                        Tyr Asp Thr Glu Ile Asp Arg Ser Arg Arg
                          1               5                  10

TCG GCT ATA AAA AAG ATA ATG GAA AGG GAT GAC ACA GCT GCA AAA ACA      579
Ser Ala Ile Lys Lys Ile Met Glu Arg Asp Asp Thr Ala Ala Lys Thr
                 15                  20                  25

CTT GTT CTC TGT GTT TCT GAC ATA ATT TCA TTG AGC GCA AAT ATA TCT      627
Leu Val Leu Cys Val Ser Asp Ile Ile Ser Leu Ser Ala Asn Ile Ser
             30                  35                  40

GAA ACT TCT AGC AAT AAA ACT AGT AGT GCA GAT ACC CAA AAA GTG GCC      675
Glu Thr Ser Ser Asn Lys Thr Ser Ser Ala Asp Thr Gln Lys Val Ala
         45                  50                  55

ATT ATT GAA CTT ACA GAT GGG TGG TAT GCT GTT AAG GCC CAG TTA GAT      723
Ile Ile Glu Leu Thr Asp Gly Trp Tyr Ala Val Lys Ala Gln Leu Asp
     60                  65                  70

CCT CCC CTC TTA GCT GTC TTA AAG AAT GGC AGA CTG ACA GTT GGT CAG      771
Pro Pro Leu Leu Ala Val Leu Lys Asn Gly Arg Leu Thr Val Gly Gln
 75                  80                  85                  90

AAG ATT ATT CTT CAT GGA GCA GAA CTG GTG GGC TCT CCT GAT GCC TGT      819
Lys Ile Ile Leu His Gly Ala Glu Leu Val Gly Ser Pro Asp Ala Cys
                 95                 100                 105

ACA CCT CTT GAA GCC CCA GAA TCT CTT ATG TTA AAG GTAAATTAAT           865
Thr Pro Leu Glu Ala Pro Glu Ser Leu Met Leu Lys
            110                 115

TTGCACTCTT GGTAAAAATC AGTCATTGAT TCAGTTAAAT TCTAGAAGTT TTACATTTAA    925

ATTTTAAATG CTTACTAAGG ATGCTCAATT TCTTAGATGT ACTGATAATT TTAGTATAAA    985
```

-continued

```
AAGCATATTC TTCAGACAGT TAAAGTTTTT GTGCAGTTTT TGGGAGGTCC AGAGATCTTT   1045

CTTGAGCTTA AATAATGCAT TTCCAATTAA AAAGCAAAAT AAATTTGCAC CATTTGATTT   1105

TGGTATCTGT AGCTTGCTGC CCTCTTGTTC TCATAGCTTT GCTTTGATCA GATCCCTATT   1165

CCACTCTGGA TTAGAGAATT ACATTTTAGT ACTTTTCAAA TATGTAATAG ATACACTTTT   1225

TATCTCTATG TAGATTTTAA ACTACATAAC AGGACTCTTT GTCATATTGA ATGGTCTGCA   1285

GTATTGCTAT CTGAAATTAC CGATAATATT GTACATTCAG ATTCACTTAA GAGGTAACCT   1345

TGCAGAGAAT                                                          1355
```

(2) INFORMATION FOR SEQ ID NO:35:

(i) SEQUENCE CHARACTERISTICS:
(A) LENGTH: 1155 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: exon
(B) LOCATION: 500..655

(ix) FEATURE:
(A) NAME/KEY: CDS
(B) LOCATION: 500..655

(xi) SEQUENCE DESCRIPTION: SEQ ID NO:35:

```
CTTAACACCA TGCCAGGTAC CTTAGTAAGT GTTCGATGAA TATTTGCTTT TTGTATTAGC     60

CATAATCATT CTCAGGCTGC TTTGTCATTT ACTTGTTCCA CAAATTCTTA GCTTCCAAAA    120

TTTTGGTGAT ACCTCATTTC CTATTCTCTC TAGTTGCCTT TGTCCATGTA GATTTTTTGA    180

GGAAGCTTGG GTAAATAAGT GTATTTTAAA CTATTATGTT TAAATCGAAG TTCCTTTTAT    240

CTGTTTTCTA ATAGAAACAT TTAAATAGCA TTAAGAACTT GTAGCAGTAT AAACAATATG    300

TTTGAGAAGT ACTATATTGT GAAAATATTT TCACTTTTAT ACAGTTTTTT ACTTATTTAC    360

TGTCTTACTA ATCTTCCTAA GACTTTTTAA AGTGAATATT TTTAAGGCAG TTCTAGAAGA    420

ATGAAAACTC TTATGATATC TGTAATAGAA TTGAATACAT ATTTAACTAC TAAATCAATA    480

TATTTATTAA TTTGTCCAG ATT TCT GCT AAC AGT ACT CGG CCT GCT CGC TGG    532
                     Ile Ser Ala Asn Ser Thr Arg Pro Ala Arg Trp
                      1               5                  10

TAT ACC AAA CTT GGA TTC TTT CCT GAC CCT AGA CCT TTT CCT CTG CCC      580
Tyr Thr Lys Leu Gly Phe Phe Pro Asp Pro Arg Pro Phe Pro Leu Pro
            15                  20                  25

TTA TCA TCG CTT TTC AGT GAT GGA GGA AAT GTT GGT TGT GTT GAT GTA      628
Leu Ser Ser Leu Phe Ser Asp Gly Gly Asn Val Gly Cys Val Asp Val
        30                  35                  40

ATT ATT CAA AGA GCA TAC CCT ATA CAG GTATGATGTA TTCTTGAAAC            675
Ile Ile Gln Arg Ala Tyr Pro Ile Gln
    45                  50

TTACCATATA TTTCTTTCTT TTGATACAAT TAATTTGTTT GTTTGTTTGA GATGGAGTTT    735

CGGTCTCTTG CCCAGGCTGG AGTGCAATGG CGTGATCTTG GTTCACTGCA GCCTCCCACC    795

TCCCGGGTTC AAGTGATTCT CCTGCCTCAG CCTCTCAAGT AGCTGAGCCA CCACACCTGG    855

CTAATTTTGT ATTTTTGGTA GAGAAGGGGT TTCATCATGT TGGTCAGGCT GATCTCGAAC    915

TCCTGACCTC AGGTGATCCA CTAATCTCAG CCTCCCAAAG TTCTGGGATT ACAGATGTGA    975

GCCACTGTGC CTGGCCTGAT ACAATTAACT TGAATGTTAT ATATGTGACT TTTTGGTGT    1035
```

-continued

```
GTGTAACACA TTATTACAGT GGATGGAGAA GACATCATCT GGATTATACA TATTTCGCAA   1095

TGAAAGAGAG GAAGAAAAGG AAGCAGCAAA ATATGTGGAG GCCCAACAAA AGAGACTAGA   1155
```

(2) INFORMATION FOR SEQ ID NO:36:

(i) SEQUENCE CHARACTERISTICS:
(A) LENGTH: 1145 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: exon
(B) LOCATION: 501..645

(ix) FEATURE:
(A) NAME/KEY: CDS
(B) LOCATION: 501..645

(xi) SEQUENCE DESCRIPTION: SEQ ID NO:36:

```
CTGACCCTAG ACCTTTTCCT CTGCCCTTAT CATCGCTTTT CAGTGATGGA GGAAATGTTG     60

GTTGTGTTGA TGTAATTATT CAAAGAGCAT ACCCTATACA GGTATGATGT ATTCTTGAAA    120

CTTACCATAT ATTTCTTTCT TTTGATACAA TTAATTTGTT TGTTTGTTTG AGATGGAGTT    180

TCGGTCTCTT GCCCAGGCTG GAGTGCAATG GCGTGATCTT GGTTCACTGC AGCCTCCCAC    240

CTCCCGGGTT CAAGTGATTC TCCTGCCTCA GCCTCTCAAG TAGCTGAGCC ACCACACCTG    300

GCTAATTTTG TATTTTTGGT AGAGAAGGGG TTTCATCATG TTGGTCAGGC TGATCTCGAA    360

CTCCTGACCT CAGGTGATCC ACTAATCTCA GCCTCCCAAA GTTCTGGGAT TACAGATGTG    420

AGCCACTGTG CCTGGCCTGA TACAATTAAC TTGAATGTTA TATATGTGAC TTTTTTGGTG    480

TGTGTAACAC ATTATTACAG TGG ATG GAG AAG ACA TCA TCT GGA TTA TAC        530
                      Trp Met Glu Lys Thr Ser Ser Gly Leu Tyr
                       1               5                  10

ATA TTT CGC AAT GAA AGA GAG GAA GAA AAG GAA GCA GCA AAA TAT GTG      578
Ile Phe Arg Asn Glu Arg Glu Glu Glu Lys Glu Ala Ala Lys Tyr Val
                15                  20                  25

GAG GCC CAA CAA AAG AGA CTA GAA GCC TTA TTC ACT AAA ATT CAG GAG      626
Glu Ala Gln Gln Lys Arg Leu Glu Ala Leu Phe Thr Lys Ile Gln Glu
            30                  35                  40

GAA TTT GAA GAA CAT GAA G GTAAAATTAG TTATATGGTA CACATTGTTA           675
Glu Phe Glu Glu His Glu
        45

TTTCTAATAT GAGAACAAAG TCTTAGAGAC TTTGAATTTA ACATTTTTAA TGAGTAAATT    735

GTTTTTATTT TGAGTAGTAA ATTGACTTTA TTTTTTAGTA TCTAGGGTAT TCTTTTTTGG    795

TGTTAGACAA AGAATAGCAA CAAGGGACAG AAATATCAGG TCTAAGCCAT TTGTAATATT    855

TTTCCTGAAT TCTTACCTAT ATGATGTGGC TTTTGCATTT TTGTCATGGT AGTTATTAGC    915

TTTCATGTGT TATTATGCCT GGAACTAGGA CCTATTGTGG TGTCAATTTT AATATTAAAA    975

ATCATGGTGT TTTGATGTTT ATATGACATA AATTTTATTT TTTCGTATCT CCCTTTTGTT   1035

GTTGCTGAAG ATTTTATGTT TTTCTGCATT TCCTCATGAT TTATATAGAT GTAACATGTT   1095

CTATAGGACA TGTAATTTAC ATGTCCTATA GAACTATAAG TTACATGTCC              1145
```

(2) INFORMATION FOR SEQ ID NO:37:

(i) SEQUENCE CHARACTERISTICS:
(A) LENGTH: 500 base pairs

-continued

```
          (B) TYPE: nucleic acid
          (C) STRANDEDNESS: double
          (D) TOPOLOGY: linear

    (ii) MOLECULE TYPE: DNA (genomic)

    (ix) FEATURE:
          (A) NAME/KEY: exon
          (B) LOCATION: 219..340

    (ix) FEATURE:
          (A) NAME/KEY: CDS
          (B) LOCATION: 221..340

    (xi) SEQUENCE DESCRIPTION: SEQ ID NO:37:

ATNCATTATA CGAAGTTATG GATCACACCA CTGCACTCCC AGATTGGGTG ACAGAGTGAG      60

ACCCTGTCTC AAAAAAAAAA AAAAGAAAAA ACTTTTAGCA GTTATATAGT TTCTTATCTT     120

TAAATCTCCC TTCTTTGGGT GTTTTATGCT TGGTTCTTTA GTTTTAGTTG CTTTTGAATT     180

TACAGTTTAG TGAATTAATA ATCCTTTTGT TTTCTTAG AA AAC ACA ACA AAA CCA      235
                                          Glu Asn Thr Thr Lys Pro
                                           1               5

TAT TTA CCA TCA CGT GCA CTA ACA AGA CAG CAA GTT CGT GCT TTG CAA      283
Tyr Leu Pro Ser Arg Ala Leu Thr Arg Gln Gln Val Arg Ala Leu Gln
             10                  15                  20

GAT GGT GCA GAG CTT TAT GAA GCA GTG AAG AAT GCA GCA GAC CCA GCT      331
Asp Gly Ala Glu Leu Tyr Glu Ala Val Lys Asn Ala Ala Asp Pro Ala
         25                  30                  35

TAC CTT GAG GTGAGAGAGT AAGAGGACAT ATAATGAGGC TTGATGATTA              380
Tyr Leu Glu
     40

TTCAAGGTGA GAAGCTGTTT TANACTCTCT GGCCATCACA GGAAGGAATA TGTTGAAATG     440

CTGCATTTCT CCAAAAGGGA TNTGTTCATT TCTGGGATTT TCCAGTGATG TTGCCCAGAC     500


(2) INFORMATION FOR SEQ ID NO:38:

     (i) SEQUENCE CHARACTERISTICS:
          (A) LENGTH: 1199 base pairs
          (B) TYPE: nucleic acid
          (C) STRANDEDNESS: double
          (D) TOPOLOGY: linear

    (ii) MOLECULE TYPE: DNA (genomic)

    (ix) FEATURE:
          (A) NAME/KEY: exon
          (B) LOCATION: 501..699

    (ix) FEATURE:
          (A) NAME/KEY: CDS
          (B) LOCATION: 501..699

    (xi) SEQUENCE DESCRIPTION: SEQ ID NO:38:

GTATCTACTA TTTCAAAGTT AATGGAATTA TACTCCTGGG GCTAAGAATG AGGGTTCTAG      60

GGCCAACCTC TACTACCTAT GTGGCTTGTG CAAATTAGTT GTCCCCTTTG TGCCTCAGTT     120

TTACCTACAA CACAGAAACA ATGATATTAC CTACCCCATG GACTGTTGTG AAGATTAAAT     180

GAATTAGTAC ATTTACTACA CATAGATCTA TTTCTCAAAA TAATGAGCAT TCAGATATTA     240

GCCATCTGTA ATGTAGTTGG TGATGATTAT GATTATTAGA GTACATTTAT AATTGGAGGA     300

TCATTTTTGC CGTAGGGAAA TAGAATTATT AATAGTTTGA GGCACCTGAG AATATTATGT     360

GAGAAACTGA TTACATTAAC CACACCCTTA AGATGAGCTC TAATTTTGTT GTATTTGTCC     420

TGTTTAAAGC CATCTAGTTA CAATAGATGG AACTTTTTTG TTCTGATTGC TTTTTATTCC     480
```

-continued

```
AATATCTTAA ATGGTCACAG GGT TAT TTC AGT GAA GAG CAG TTA AGA GCC        530
                      Gly Tyr Phe Ser Glu Glu Gln Leu Arg Ala
                        1               5                  10

TTG AAT AAT CAC AGG CAA ATG TTG AAT GAT AAG AAA CAA GCT CAG ATC      578
Leu Asn Asn His Arg Gln Met Leu Asn Asp Lys Lys Gln Ala Gln Ile
                 15                  20                  25

CAG TTG GAA ATT AGG AAG GCC ATG GAA TCT GCT GAA CAA AAG GAA CAA      626
Gln Leu Glu Ile Arg Lys Ala Met Glu Ser Ala Glu Gln Lys Glu Gln
             30                  35                  40

GGT TTA TCA AGG GAT GTC ACA ACC GTG TGG AAG TTG CGT ATT GTA AGC      674
Gly Leu Ser Arg Asp Val Thr Thr Val Trp Lys Leu Arg Ile Val Ser
         45                  50                  55

TAT TCA AAA AAA GAA AAA GAT TCA G GTAAGTATGT AAATGCTTTG              719
Tyr Ser Lys Lys Glu Lys Asp Ser
     60                  65

TTTTTATCAG TTTTATTAAC TTAAAAAATG ACCTTACTAA CAAAATGATT ATAAATCCAG    779

ATAAAGTATA AAGTTAGTTT ATATCAGAGA AGCAAAATCC ACTACTAATG CCCACAAAGA    839

GATAATATAA AAGAGGATCT GTATTTATTT TGAAACAAAC ATTTAAATGA TAATCACTTC    899

TTCCATTGCA TCTTTCTCAT CTTTCTCCAA ACAGTTATAC TGAGTATTTG GCGTCCATCA    959

TCAGATTTAT ATTCTCTGTT AACAGAAGGA AAGAGATACA GAATTTATCA TCTTGCAACT   1019

TCAAAATCTA AAAGTAAATC TGAAAGAGCT AACATACAGT TAGCAGCGAC AAAAAAAACT   1079

CAGTATCAAC AACTACCGGT ACAAACCTTT CATTGTAATT TTTCAGTTTT GATAAGTGCT   1139

TGTTAGTTTA TGGAATCTCC ATATGTTGAA TTTTTGTTTT GTTTTCTGTA GGTTTCAGAT   1199
```

(2) INFORMATION FOR SEQ ID NO:39:

(i) SEQUENCE CHARACTERISTICS:
(A) LENGTH: 1164 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: exon
(B) LOCATION: 501..664

(ix) FEATURE:
(A) NAME/KEY: CDS
(B) LOCATION: 503..664

(xi) SEQUENCE DESCRIPTION: SEQ ID NO:39:

```
CTAGTTACAA TAGATGGAAC TTTTTTGTTC TGATTGCTTT TTATTCCAAT ATCTTAAATG     60

GTCACAGGGT TATTTCAGTG AAGAGCAGTT AAGAGCCTTG AATAATCACA GGCAAATGTT    120

GAATGATAAG AAACAAGCTC AGATCCAGTT GGAAATTAGG AAGGCCATGG AATCTGCTGA    180

ACAAAAGGAA CAAGGTTTAT CAAGGGATGT CACAACCGTG TGGAAGTTGC GTATTGTAAG    240

CTATTCAAAA AAAGAAAAAG ATTCAGGTAA GTATGTAAAT GCTTTGTTTT TATCAGTTTT    300

ATTAACTTAA AAAATGACCT TACTAACAAA ATGATTATAA ATCCAGATAA AGTATAAAGT    360

TAGTTTATAT CAGAGAAGCA AAATCCACTA CTAATGCCCA CAAAGAGATA ATATAAAAGA    420

GGATCTGTAT TTATTTTGAA ACAAACATTT AAATGATAAT CACTTCTTCC ATTGCATCTT    480

TCTCATCTTT CTCCAAACAG TT ATA CTG AGT ATT TGG CGT CCA TCA TCA GAT     532
                     Val Ile Leu Ser Ile Trp Arg Pro Ser Ser Asp
                       1               5                  10

TTA TAT TCT CTG TTA ACA GAA GGA AAG AGA TAC AGA ATT TAT CAT CTT      580
Leu Tyr Ser Leu Leu Thr Glu Gly Lys Arg Tyr Arg Ile Tyr His Leu
```

-continued

```
            15                  20                  25

GCA ACT TCA AAA TCT AAA AGT AAA TCT GAA AGA GCT AAC ATA CAG TTA      628
Ala Thr Ser Lys Ser Lys Ser Lys Ser Glu Arg Ala Asn Ile Gln Leu
         30                  35                  40

GCA GCG ACA AAA AAA ACT CAG TAT CAA CAA CTA CCG GTACAAACCT           674
Ala Ala Thr Lys Lys Thr Gln Tyr Gln Gln Leu Pro
     45                  50                  55

TTCATTGTAA TTTTTCAGTT TTGATAAGTG CTTGTTAGTT TATGGAATCT CCATATGTTG    734

AATTTTTGTT TTGTTTTCTG TAGGTTTCAG ATGAAATTTT ATTTCAGATT TACCAGCCAC    794

GGGAGCCCCT TCACTTCAGC AAATTTTTAG ATCCAGACTT TCAGCCATCT TGTTCTGAGG    854

TGGACCTAAT AGGATTTGTC GTTTCTGTTG TGAAAAAAAC AGGTAATGCA CAATATAGTT    914

AATTTTTTTT ATTGATTCTT TTAAAAAACA TTGTCTTTTA AAATCTCTTA TGATTAGTTG    974

GAGCTACCAG TTGGCAAATT TGCTAGCTAA CTAGTGATCT GAAAGTAAGC CTCTTTGAAC   1034

CTCTGATTTT TCATGAAAAG CAATTCTCTC AATTCTATAT TATTTCAAGG GTAACAAGTT   1094

ACATCCTAGT CTGTGTACTT AATTTTATAG AAATTGTCCT TAATTTTATT TTCTGCAATT   1154

TATGTTTTCT                                                          1164
```

(2) INFORMATION FOR SEQ ID NO:40:

(i) SEQUENCE CHARACTERISTICS:
(A) LENGTH: 1139 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: exon
(B) LOCATION: 501..639

(ix) FEATURE:
(A) NAME/KEY: CDS
(B) LOCATION: 501..639

(xi) SEQUENCE DESCRIPTION: SEQ ID NO:40:

```
AAGATTCAGG TAAGTATGTA AATGCTTTGT TTTTATCAGT TTTATTAACT TAAAAAATGA     60

CCTTACTAAC AAAATGATTA TAAATCCAGA TAAAGTATAA AGTTAGTTTA TATCAGAGAA    120

GCAAAATCCA CTACTAATGC CCACAAAGAG ATAATATAAA AGAGGATCTG TATTTATTTT    180

GAAACAAACA TTTAAATGAT AATCACTTCT TCCATTGCAT CTTTCTCATC TTTCTCCAAA    240

CAGTTATACT GAGTATTTGG CGTCCATCAT CAGATTTATA TTCTCTGTTA ACAGAAGGAA    300

AGAGATACAG AATTTATCAT CTTGCAACTT CAAAATCTAA AAGTAAATCT GAAAGAGCTA    360

ACATACAGTT AGCAGCGACA AAAAAAACTC AGTATCAACA ACTACCGGTA CAAACCTTTC    420

ATTGTAATTT TTCAGTTTTG ATAAGTGCTT GTTAGTTTAT GGAATCTCCA TATGTTGAAT    480

TTTTGTTTTG TTTTCTGTAG GTT TCA GAT GAA ATT TTA TTT CAG ATT TAC        530
                      Val Ser Asp Glu Ile Leu Phe Gln Ile Tyr
                        1               5                  10

CAG CCA CGG GAG CCC CTT CAC TTC AGC AAA TTT TTA GAT CCA GAC TTT      578
Gln Pro Arg Glu Pro Leu His Phe Ser Lys Phe Leu Asp Pro Asp Phe
                15                  20                  25

CAG CCA TCT TGT TCT GAG GTG GAC CTA ATA GGA TTT GTC GTT TCT GTT      626
Gln Pro Ser Cys Ser Glu Val Asp Leu Ile Gly Phe Val Val Ser Val
            30                  35                  40

GTG AAA AAA ACA G GTAATGCACA ATATAGTTAA TTTTTTTTAT TGATTCTTTT        679
Val Lys Lys Thr
```

-continued

```
        45

AAAAAACATT GTCTTTTAAA ATCTCTTATG ATTAGTTGGA GCTACCAGTT GGCAAATTTG    739

CTAGCTAACT AGTGATCTGA AAGTAAGCCT CTTTGAACCT CTGATTTTTC ATGAAAAGCA    799

ATTCTCTCAA TTCTATATTA TTTCAAGGGT AACAAGTTAC ATCCTAGTCT GTGTACTTAA    859

TTTTATAGAA ATTGTCCTTA ATTTTATTTT CTGCAATTTA TGTTTTCTTA CTATTTCTGG    919

TGTATGTGTT TATCCCATTG TGATGTTATA TTGGTGTCCT CAATTTATTT CCTTAGCCAT    979

ACACTCTACT TTTCATTGTA CAGGGCTATT TATTATCTCA GAGTCAAGCT TTTTTTTTTT   1039

TTTTTTTTTC CCCGAGATGG AGTCTCACTC TGTTGCCCAG GCTGGAGTNC AGTGGCGNAA   1099

TNTCAGCCCA CNGCAAGTTC TGCCTCCCAG GTTNANACCA                         1139
```

(2) INFORMATION FOR SEQ ID NO:41:

(i) SEQUENCE CHARACTERISTICS:
(A) LENGTH: 1198 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: exon
(B) LOCATION: 501..745

(ix) FEATURE:
(A) NAME/KEY: CDS
(B) LOCATION: 503..745

(xi) SEQUENCE DESCRIPTION: SEQ ID NO:41:

```
TGTATATGAG CTAATAAAAG TTGCTTCCAA TATTTTATAA TTATAATGTT TTCAGTGAGT     60

AACCTTGTTC ATAGGTGTTT TCATGAACTT TATGTTCATG TGTATTTTAC TATTATTAGA    120

GGTCTATCTT CAGAGAGGAG TACAAGAAAT GGGATTACTG GGTGCAAAGG TAAATGGATA    180

TGTGTCTTTG CTAGGTATTG CCAAATTTAT CTCCAGAAAT CTTGCACAAA TCTGTACTCC    240

TGTTAGCAAT GTGTGCGTAT ACCTGCTTAC CACATGACCT CAGTAAAAGA ATGTGTTGTC    300

ATATTGGTAT TGAAATTTTA GCACTGTAAG CAACAGGTCA TTTTGGAAAA CCTGAGCTTT    360

CGCCAAATTC AGCTATTTTG ATTTGCTTTT ATTATTAGCA TATACCAAAA TAAATAGGCA    420

TATTAGAGTT TCCTTTCTTG CATCTTAAAA TTCATCTAAC ACATCTATAA TAACATTCTT    480

TTCTTTTTTT TCCATTCTAG GA CTT GCC CCT TTC GTC TAT TTG TCA GAC GAA      532
                         Gly Leu Ala Pro Phe Val Tyr Leu Ser Asp Glu
                          1               5                  10

TGT TAC AAT TTA CTG GCA ATA AAG TTT TGG ATA GAC CTT AAT GAG GAC      580
Cys Tyr Asn Leu Leu Ala Ile Lys Phe Trp Ile Asp Leu Asn Glu Asp
            15                  20                  25

ATT ATT AAG CCT CAT ATG TTA ATT GCT GCA AGC AAC CTC CAG TGG CGA      628
Ile Ile Lys Pro His Met Leu Ile Ala Ala Ser Asn Leu Gln Trp Arg
        30                  35                  40

CCA GAA TCC AAA TCA GGC CTT CTT ACT TTA TTT GCT GGA GAT TTT TCT      676
Pro Glu Ser Lys Ser Gly Leu Leu Thr Leu Phe Ala Gly Asp Phe Ser
    45                  50                  55

GTG TTT TCT GCT AGT CCA AAA GAG GGC CAC TTT CAA GAG ACA TTC AAC      724
Val Phe Ser Ala Ser Pro Lys Glu Gly His Phe Gln Glu Thr Phe Asn
 60                  65                  70                  75

AAA ATG AAA AAT ACT GTT GAG GTAAGGTTAC TTTTCAGCAT CACCACACAT         775
Lys Met Lys Asn Thr Val Glu
                80
```

-continued

```
TTTGGTATTT TTCTATTTTG ACAGTCCAGT ATCAAGGAAA TAGCTTTTAT ACAAATTGGA    835

TAGTTGAGGT AGTATGTGAG GTAAAGTTTA ATCATATATT AATTGCCCAT GAACCTCAGG    895

AGATGGGGGA ATGGGGAAAT GACAGCAGCT AGAAAGAGAA GAATGACTTG AAGGGAAATG    955

AGTTAGGAGA AATTGTGAGA AGGATGTTCA GAAATGCAGA CTTTGTAAGC AAACTGGAAA   1015

TTGGTTACAA GAATAATATG AGTTATCTGT GGTTTGCAGC AGTCAGCAGT GTGATTAGTT   1075

AATAATATAG AGACTACAGG TTTACATTTA AACTCCATAT CTAGTGTTTT ATACAGATTA   1135

TATTTCTTTG ACTTGATTTA ATCCCAGATA AGAGACACTG ATATTATTTT CCCTAGATCA   1195

TGT                                                                 1198
```

(2) INFORMATION FOR SEQ ID NO:42:

(i) SEQUENCE CHARACTERISTICS:
(A) LENGTH: 1147 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: exon
(B) LOCATION: 501..647

(ix) FEATURE:
(A) NAME/KEY: CDS
(B) LOCATION: 501..647

(xi) SEQUENCE DESCRIPTION: SEQ ID NO:42:

```
TATTTGACCA GTTGTGATTT CTCAAGCAAC AGTTTCATGT AGTTTAACCT ATAAATCATT     60

TCAATTAATT CTTGGAACAG ACGTGAGGTA GGTGAGGCAA TTCTTTCTTT TCTCTAACCA    120

AAGAAGTACC TTTATAGATG TGAGATGATT CCCAGCTATT AAGTAGTAAA TAGAGCTAGG    180

ACTTGAGCCC CAATCTTCCA GCTTCAATCC AGATCATATG ACAGCTTGCT GATTAAACTA    240

GATGACAGAG AAGATCTCTT TCCTTCAGAT ACACATACTT TTTCTCTGTT CCCCTCTCCC    300

TATCAGCTAG ATTCCCCTAA ATCACTGATA CTGGTTTTGT AATTTTGCAT CGGCATGTTT    360

GACAATTGGT ATCACATTTA GGGTTTTTCA TTCTTTTTTG GTCCCAAACT TTTCATTTCT    420

GCTTTTAAAG GAAATACTTT TGGAAACATA AATATGTGGG TTTGCAATTT ATAAAGCAGC    480

TTTTCCACTT ATTTTCTTAG AAT ATT GAC ATA CTT TGC AAT GAA GCA GAA        530
                      Asn Ile Asp Ile Leu Cys Asn Glu Ala Glu
                        1               5                  10

AAC AAG CTT ATG CAT ATA CTG CAT GCA AAT GAT CCC AAG TGG TCC ACC      578
Asn Lys Leu Met His Ile Leu His Ala Asn Asp Pro Lys Trp Ser Thr
                 15                  20                  25

CCA ACT AAA GAC TGT ACT TCA GGG CCG TAC ACT GCT CAA ATC ATT CCT      626
Pro Thr Lys Asp Cys Thr Ser Gly Pro Tyr Thr Ala Gln Ile Ile Pro
             30                  35                  40

GGT ACA GGA AAC AAG CTT CTG GTAAGTTAAT GTAAACTCAA GGAATATTAT         677
Gly Thr Gly Asn Lys Leu Leu
         45

AAGAAGTATA TATGGAGGCC ATCGTATATT CTGTTGTATA CCTAGTAAAC ATGGTAAAAT    737

GTAATTAAAC TTAATTAGAA AATGTGGTTG TTATGTGGCT CCTGTAAGTA TAGTTATTTA    797

GAAATTTTAT TTATTGAAGC AAGATATGAA ACTCTGGGTG CACACTTTCC AAACAGGTGC    857

TTTCATTTAC ATGTGATTGA AAAGTGTTTT TTGCCATTTA TTTCACTGTT CCATACAATT    917

AGGGTTGTTT CTAAGCTGTT TGTAAGCTGT TTCTAAGCTA TTTAAGTGGT TAAATCACAG    977
```

-continued

```
TAGATGCAAA TCAAGCTAAA GTCTTTAACA TTGGCTAATG GCTGATTCTT AAATAGCTAA   1037

TACTTGCTAA GGGTATCTAT ATTAACTCAT TTAATCCTCA TAACAACCCT ATGAGATAAA   1097

ACCTAAGTCC TCACTTAACA TTGTCAATAG GTTTTTGGAA ACTGATTTTA              1147
```

(2) INFORMATION FOR SEQ ID NO:43:

(i) SEQUENCE CHARACTERISTICS:
(A) LENGTH: 3233 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: exon
(B) LOCATION: 310..1757

(ix) FEATURE:
(A) NAME/KEY: CDS
(B) LOCATION: 310..915

(xi) SEQUENCE DESCRIPTION: SEQ ID NO:43:

```
TAATCTGTTA ATAATAAAAA ACAAAAGATT AAAGCATAAG TGACGTCCCC TACCTCCTTT     60

TTTATCTTTT ACTGTGATTA TTCTTCATCT TCCTTCCTTT TCATGTCATT TTATATGTTC    120

TTATGTAAAA TTACTTTCAT CTAGAATAGG AATAATGTGA ACTGAAATCA CCTAACCTAT    180

TAGGAGTTAG GGGAGGGAGA CTGTGTGTAA TATTTGCGTG CTTAAATATT TTCAATGAAA    240

AGTTACTTTG ATTTAGTTTT TTATGTTACT ACATAATTAT GATAGGCTAC GTTTTCATTT    300

TTTTATCAG ATG TCT TCT CCT AAT TGT GAG ATA TAT TAT CAA AGT CCT        348
          Met Ser Ser Pro Asn Cys Glu Ile Tyr Tyr Gln Ser Pro
            1               5                  10

TTA TCA CTT TGT ATG GCC AAA AGG AAG TCT GTT TCC ACA CCT GTC TCA      396
Leu Ser Leu Cys Met Ala Lys Arg Lys Ser Val Ser Thr Pro Val Ser
     15                  20                  25

GCC CAG ATG ACT TCA AAG TCT TGT AAA GGG GAG AAA GAG ATT GAT GAC      444
Ala Gln Met Thr Ser Lys Ser Cys Lys Gly Glu Lys Glu Ile Asp Asp
 30                  35                  40                  45

CAA AAG AAC TGC AAA AAG AGA AGA GCC TTG GAT TTC TTG AGT AGA CTG      492
Gln Lys Asn Cys Lys Lys Arg Arg Ala Leu Asp Phe Leu Ser Arg Leu
                 50                  55                  60

CCT TTA CCT CCA CCT GTT AGT CCC ATT TGT ACA TTT GTT TCT CCG GCT      540
Pro Leu Pro Pro Pro Val Ser Pro Ile Cys Thr Phe Val Ser Pro Ala
            65                  70                  75

GCA CAG AAG GCA TTT CAG CCA CCA AGG AGT TGT GGC ACC AAA TAC GAA      588
Ala Gln Lys Ala Phe Gln Pro Pro Arg Ser Cys Gly Thr Lys Tyr Glu
        80                  85                  90

ACA CCC ATA AAG AAA AAA GAA CTG AAT TCT CCT CAG ATG ACT CCA TTT      636
Thr Pro Ile Lys Lys Lys Glu Leu Asn Ser Pro Gln Met Thr Pro Phe
     95                 100                 105

AAA AAA TTC AAT GAA ATT TCT CTT TTG GAA AGT AAT TCA ATA GCT GAC      684
Lys Lys Phe Asn Glu Ile Ser Leu Leu Glu Ser Asn Ser Ile Ala Asp
110                 115                 120                 125

GAA GAA CTT GCA TTG ATA AAT ACC CAA GCT CTT TTG TCT GGT TCA ACA      732
Glu Glu Leu Ala Leu Ile Asn Thr Gln Ala Leu Leu Ser Gly Ser Thr
                130                 135                 140

GGA GAA AAA CAA TTT ATA TCT GTC AGT GAA TCC ACT AGG ACT GCT CCC      780
Gly Glu Lys Gln Phe Ile Ser Val Ser Glu Ser Thr Arg Thr Ala Pro
            145                 150                 155

ACC AGT TCA GAA GAT TAT CTC AGA CTG AAA CGA CGT TGT ACT ACA TCT      828
Thr Ser Ser Glu Asp Tyr Leu Arg Leu Lys Arg Arg Cys Thr Thr Ser
```

-continued

```
       160                165                170

CTG ATC AAA GAA CAG GAG AGT TCC CAG GCC AGT ACG GAA GAA TGT GAG       876
Leu Ile Lys Glu Gln Glu Ser Ser Gln Ala Ser Thr Glu Glu Cys Glu
    175                180                185

AAA AAT AAG CAG GAC ACA ATT ACA ACT AAA AAA TAT ATC TAAGCATTTG       925
Lys Asn Lys Gln Asp Thr Ile Thr Thr Lys Lys Tyr Ile
190                195                200

CAAAGGCGAC AATAAATTAT TGACGCTTAA CCTTTCCAGT TTATAAGACT GGAATATAAT    985

TTCAAACCAC ACATTAGTAC TTATGTTGCA CAATGAGCAA AGAAATTAGT TTCAAATTTA   1045

CCTCAGCGTT TGTGTATCGG GCAAAAATCG TTTTGCCCGA TTCCGTATTG GTATACTTTT   1105

GCTTCAGTTG CATATCTTAA AACTAAATGT AATTTATTAA CTAATCAAGA AAAACATCTT   1165

TGGCTGAGCT CGGTGGCTCA TGCCTGTAAT CCCAACACTT TGAGAAGCTG AGGTGGGAGG   1225

AGTGCTTGAG GCCAGGAGTT CAAGACCAGC CTGGGCAACA TAGGGAGACC CCCATCTTTA   1285

CAAAGAAAAA AAAAAGGGGA AAAGAAAATC TTTTAAATCT TTGGATTTGA TCACTACAAG   1345

TATTATTTTA CAAGTGAAAT AAACATACCA TTTTCTTTTA GATTGTGTCA TTAAATGGAA   1405

TGAGGTCTCT TAGTACAGTT ATTTTGATGC AGATAATTCC TTTTAGTTTA GCTACTATTT   1465

TAGGGGATTT TTTTTAGAGG TAACTCACTA TGAAATAGTT CTCCTTAATG CAAATATGTT   1525

GGTTCTGCTA TAGTTCCATC CTGTTCAAAA GTCAGGATGA ATATGAAGAG TGGTGTTTCC   1585

TTTTGAGCAA TTCTTCATCC TTAAGTCAGC ATGATTATAA GAAAAATAGA ACCCTCAGTG   1645

TAACTCTAAT TCCTTTTTAC TATTCCAGTG TGATCTCTGA AATTAAATTA CTTCAACTAA   1705

AAATTCAAAT ACTTTAAATC AGAAGATTTC ATAGTTAATT TATTTTTTTT TTCAACAAAA   1765

TGGTCATCCA AACTCAAACT TGAGAAAATA TCTTGCTTTC AAATTGGCAC TGATTCTGCC   1825

TGCTTTATTT TTAGCGCTAT CACAGGACCC AGAGCCTATG CCCTTTTAAA CTTACCACAA   1885

AAGCAGAAGA TTAATTCAAT TTAAGATGAT ACTCTCATTT GTTACGTCCT TTTTTTTTTT   1945

TTTTGGAGAT GGAGTCTTGC TTTGTCGCCC ATGCTGGAGT GCAGTGGCAT GATCCTGGCT   2005

CACTGCAGCC TCCACTTCCC GGGTTCAAGT AATTCTCCCA CCTCAAGCCT CCCTAGTAGC   2065

TGGGATTACA GGGACGCACC ACCATGCCCA GCTAATTTTT GCATTTTTAG TAGAGACTGG   2125

GTTTTACCAT GTTGGCCAAG CTGGTCTCAA ACTCCTGATG TCAGGTGATC CATCTGCCTC   2185

AGCCTCCCAA AGTGCTGGGA TTATAGGCGT GAGCCACTGT GCCCGGCCAA TATTTGTTAC   2245

TTTCTTAGGT TTAATAGAGA AAAGGGATAA AACATTTCTA ACTGGGAGTT AATAGCATGG   2305

AGAAGGTCTT AAATCAGATG TTTTAATGCC TTAAATGTCT GTATAATATC ATGTTTTCAA   2365

ATCTAATTAT AAATACGTTT AAAGCCAAGA ATAAATCTTT TAAAAAATTG ACTTGTTTCC   2425

TTCCATAACT CTGAGCCATG ATTTTTCTGT TCTGTAAAAA GCATTAACAA AATTGTCTAT   2485

TTTGCTACTC CCTGTAACTT AAGTATTCTG CAAGTCTTAT TAATGAGACT TGTTTTGTTT   2545

CTAAAACAGT TTGGTTTTCA CATCCTAATT TTGCAGTGAT CCACTCTAGA ACAAGGAAAT   2605

AAAACTTGGG TTTCAAACAG GAGAACAGAA AAAATTACAA GAATTTAACC TTTTCTTTTT   2665

TGAATCCTTG GTACAACTGC TATTGTCTGT TCTCATGTAG AACACCCATT ATGTTGATAG   2725

ATATGTAATG CGCACACTTT TTTATAAATT ATAAATAACA TCCAAGCTAC ATGAAACAAA   2785

ATATGAAGCT TGAGTATATG TGCATATTAT CCCCTCAAAA GTGACAATTT AATGACTACA   2845

AAGTCAACAT ACTGCATCAT AAGGGATAAT GGTAAAAATT TGTGTTATTT ATTCAGCAAT   2905

CATTTAATGA GACCCTATTG CCCATAAAGA GCATTTGCCA GTTCTATGAA TGATGCAAAC   2965

AGCGAACACA ATACAAGTCA ATATTGGGTG TTCAAAGAGT TACACAAATC AGAAGCCATG   3025
```

-continued

```
GGAGTTGAAA AACAGATCAC TTCTACAGGG GATAAAGTTG ATGGCATTTA ATCAATTTTT   3085

ATGGTTTACA AACCAAATAT TTCAGGGGTC AGCTAGGGAA AGAAGAGACA TTAAATAGGC   3145

CAGGAAACTA TTCTTTAGAG CTCTAGAAAA GTTATGTAAC CCAGAGCCAC TTCTCCATAG   3205

TGGTCACTCA CTTAACCCAA GTGAGCCA                                      3233
```

(2) INFORMATION FOR SEQ ID NO:44:

(i) SEQUENCE CHARACTERISTICS:
(A) LENGTH: 3418 amino acids
(B) TYPE: amino acid
(D) TOPOLOGY: linear (ii) MOLECULE TYPE: protein (xi) SEQUENCE DESCRIPTION: SEQ ID NO:44:

```
Met Pro Ile Gly Ser Lys Glu Arg Pro Thr Phe Phe Glu Ile Phe Lys
1               5                   10                  15

Thr Arg Cys Asn Lys Ala Asp Leu Gly Pro Ile Ser Leu Asn Trp Phe
            20                  25                  30

Glu Glu Leu Ser Ser Glu Ala Pro Pro Tyr Asn Ser Glu Pro Ala Glu
        35                  40                  45

Glu Ser Glu His Lys Asn Asn Asn Tyr Glu Pro Asn Leu Phe Lys Thr
    50                  55                  60

Pro Gln Arg Lys Pro Ser Tyr Asn Gln Leu Ala Ser Thr Pro Ile Ile
65                  70                  75                  80

Phe Lys Glu Gln Gly Leu Thr Leu Pro Leu Tyr Gln Ser Pro Val Lys
                85                  90                  95

Glu Leu Asp Lys Phe Lys Leu Asp Leu Gly Arg Asn Val Pro Asn Ser
            100                 105                 110

Arg His Lys Ser Leu Arg Thr Val Lys Thr Lys Met Asp Gln Ala Asp
        115                 120                 125

Asp Val Ser Cys Pro Leu Leu Asn Ser Cys Leu Ser Glu Ser Pro Val
    130                 135                 140

Val Leu Gln Cys Thr His Val Thr Pro Gln Arg Asp Lys Ser Val Val
145                 150                 155                 160

Cys Gly Ser Leu Phe His Thr Pro Lys Phe Val Lys Gly Arg Gln Thr
                165                 170                 175

Pro Lys His Ile Ser Glu Ser Leu Gly Ala Glu Val Asp Pro Asp Met
            180                 185                 190

Ser Trp Ser Ser Ser Leu Ala Thr Pro Pro Thr Leu Ser Ser Thr Val
        195                 200                 205

Leu Ile Val Arg Asn Glu Glu Ala Ser Glu Thr Val Phe Pro His Asp
    210                 215                 220

Thr Thr Ala Asn Val Lys Ser Tyr Phe Ser Asn His Asp Glu Ser Leu
225                 230                 235                 240

Lys Lys Asn Asp Arg Phe Ile Ala Ser Val Thr Asp Ser Glu Asn Thr
                245                 250                 255

Asn Gln Arg Glu Ala Ala Ser His Gly Phe Gly Lys Thr Ser Gly Asn
            260                 265                 270

Ser Phe Lys Val Asn Ser Cys Lys Asp His Ile Gly Lys Ser Met Pro
        275                 280                 285

Asn Val Leu Glu Asp Glu Val Tyr Glu Thr Val Val Asp Thr Ser Glu
    290                 295                 300

Glu Asp Ser Phe Ser Leu Cys Phe Ser Lys Cys Arg Thr Lys Asn Leu
```

-continued

```
305                 310                 315                 320

Gln Lys Val Arg Thr Ser Lys Thr Arg Lys Lys Ile Phe His Glu Ala
                325                 330                 335

Asn Ala Asp Glu Cys Glu Lys Ser Lys Asn Gln Val Lys Glu Lys Tyr
            340                 345                 350

Ser Phe Val Ser Glu Val Glu Pro Asn Asp Thr Asp Pro Leu Asp Ser
        355                 360                 365

Asn Val Ala His Gln Lys Pro Phe Glu Ser Gly Ser Asp Lys Ile Ser
    370                 375                 380

Lys Glu Val Val Pro Ser Leu Ala Cys Glu Trp Ser Gln Leu Thr Leu
385                 390                 395                 400

Ser Gly Leu Asn Gly Ala Gln Met Glu Lys Ile Pro Leu Leu His Ile
                405                 410                 415

Ser Ser Cys Asp Gln Asn Ile Ser Glu Lys Asp Leu Leu Asp Thr Glu
            420                 425                 430

Asn Lys Arg Lys Lys Asp Phe Leu Thr Ser Glu Asn Ser Leu Pro Arg
        435                 440                 445

Ile Ser Ser Leu Pro Lys Ser Glu Lys Pro Leu Asn Glu Glu Thr Val
    450                 455                 460

Val Asn Lys Arg Asp Glu Glu Gln His Leu Glu Ser His Thr Asp Cys
465                 470                 475                 480

Ile Leu Ala Val Lys Gln Ala Ile Ser Gly Thr Ser Pro Val Ala Ser
                485                 490                 495

Ser Phe Gln Gly Ile Lys Lys Ser Ile Phe Arg Ile Arg Glu Ser Pro
            500                 505                 510

Lys Glu Thr Phe Asn Ala Ser Phe Ser Gly His Met Thr Asp Pro Asn
        515                 520                 525

Phe Lys Lys Glu Thr Glu Ala Ser Glu Ser Gly Leu Glu Ile His Thr
    530                 535                 540

Val Cys Ser Gln Lys Glu Asp Ser Leu Cys Pro Asn Leu Ile Asp Asn
545                 550                 555                 560

Gly Ser Trp Pro Ala Thr Thr Thr Gln Asn Ser Val Ala Leu Lys Asn
                565                 570                 575

Ala Gly Leu Ile Ser Thr Leu Lys Lys Lys Thr Asn Lys Phe Ile Tyr
            580                 585                 590

Ala Ile His Asp Glu Thr Phe Tyr Lys Gly Lys Lys Ile Pro Lys Asp
        595                 600                 605

Gln Lys Ser Glu Leu Ile Asn Cys Ser Ala Gln Phe Glu Ala Asn Ala
    610                 615                 620

Phe Glu Ala Pro Leu Thr Phe Ala Asn Ala Asp Ser Gly Leu Leu His
625                 630                 635                 640

Ser Ser Val Lys Arg Ser Cys Ser Gln Asn Asp Ser Glu Glu Pro Thr
                645                 650                 655

Leu Ser Leu Thr Ser Ser Phe Gly Thr Ile Leu Arg Lys Cys Ser Arg
            660                 665                 670

Asn Glu Thr Cys Ser Asn Asn Thr Val Ile Ser Gln Asp Leu Asp Tyr
        675                 680                 685

Lys Glu Ala Lys Cys Asn Lys Glu Lys Leu Gln Leu Phe Ile Thr Pro
    690                 695                 700

Glu Ala Asp Ser Leu Ser Cys Leu Gln Glu Gly Gln Cys Glu Asn Asp
705                 710                 715                 720

Pro Lys Ser Lys Lys Val Ser Asp Ile Lys Glu Glu Val Leu Ala Ala
                725                 730                 735
```

-continued

```
Ala Cys His Pro Val Gln His Ser Lys Val Glu Tyr Ser Asp Thr Asp
            740                 745                 750

Phe Gln Ser Gln Lys Ser Leu Leu Tyr Asp His Glu Asn Ala Ser Thr
        755                 760                 765

Leu Ile Leu Thr Pro Thr Ser Lys Asp Val Leu Ser Asn Leu Val Met
    770                 775                 780

Ile Ser Arg Gly Lys Glu Ser Tyr Lys Met Ser Asp Lys Leu Lys Gly
785                 790                 795                 800

Asn Asn Tyr Glu Ser Asp Val Glu Leu Thr Lys Asn Ile Pro Met Glu
                805                 810                 815

Lys Asn Gln Asp Val Cys Ala Leu Asn Glu Asn Tyr Lys Asn Val Glu
            820                 825                 830

Leu Leu Pro Pro Glu Lys Tyr Met Arg Val Ala Ser Pro Ser Arg Lys
        835                 840                 845

Val Gln Phe Asn Gln Asn Thr Asn Leu Arg Val Ile Gln Lys Asn Gln
    850                 855                 860

Glu Glu Thr Thr Ser Ile Ser Lys Ile Thr Val Asn Pro Asp Ser Glu
865                 870                 875                 880

Glu Leu Phe Ser Asp Asn Glu Asn Asn Phe Val Phe Gln Val Ala Asn
                885                 890                 895

Glu Arg Asn Asn Leu Ala Leu Gly Asn Thr Lys Glu Leu His Glu Thr
            900                 905                 910

Asp Leu Thr Cys Val Asn Glu Pro Ile Phe Lys Asn Ser Thr Met Val
        915                 920                 925

Leu Tyr Gly Asp Thr Gly Asp Lys Gln Ala Thr Gln Val Ser Ile Lys
    930                 935                 940

Lys Asp Leu Val Tyr Val Leu Ala Glu Glu Asn Lys Asn Ser Val Lys
945                 950                 955                 960

Gln His Ile Lys Met Thr Leu Gly Gln Asp Leu Lys Ser Asp Ile Ser
                965                 970                 975

Leu Asn Ile Asp Lys Ile Pro Glu Lys Asn Asn Asp Tyr Met Asn Lys
            980                 985                 990

Trp Ala Gly Leu Leu Gly Pro Ile Ser Asn His Ser Phe Gly Gly Ser
        995                 1000                1005

Phe Arg Thr Ala Ser Asn Lys Glu Ile Lys Leu Ser Glu His Asn Ile
    1010                1015                1020

Lys Lys Ser Lys Met Phe Phe Lys Asp Ile Glu Glu Gln Tyr Pro Thr
1025                1030                1035                1040

Ser Leu Ala Cys Val Glu Ile Val Asn Thr Leu Ala Leu Asp Asn Gln
                1045                1050                1055

Lys Lys Leu Ser Lys Pro Gln Ser Ile Asn Thr Val Ser Ala His Leu
            1060                1065                1070

Gln Ser Ser Val Val Val Ser Asp Cys Lys Asn Ser His Ile Thr Pro
        1075                1080                1085

Gln Met Leu Phe Ser Lys Gln Asp Phe Asn Ser Asn His Asn Leu Thr
    1090                1095                1100

Pro Ser Gln Lys Ala Glu Ile Thr Glu Leu Ser Thr Ile Leu Glu Glu
1105                1110                1115                1120

Ser Gly Ser Gln Phe Glu Phe Thr Gln Phe Arg Lys Pro Ser Tyr Ile
                1125                1130                1135

Leu Gln Lys Ser Thr Phe Glu Val Pro Glu Asn Gln Met Thr Ile Leu
            1140                1145                1150
```

-continued

```
Lys Thr Thr Ser Glu Glu Cys Arg Asp Ala Asp Leu His Val Ile Met
        1155                1160                1165

Asn Ala Pro Ser Ile Gly Gln Val Asp Ser Ser Lys Gln Phe Glu Gly
    1170                1175                1180

Thr Val Glu Ile Lys Arg Lys Phe Ala Gly Leu Leu Lys Asn Asp Cys
1185                1190                1195                1200

Asn Lys Ser Ala Ser Gly Tyr Leu Thr Asp Glu Asn Glu Val Gly Phe
                1205                1210                1215

Arg Gly Phe Tyr Ser Ala His Gly Thr Lys Leu Asn Val Ser Thr Glu
            1220                1225                1230

Ala Leu Gln Lys Ala Val Lys Leu Phe Ser Asp Ile Glu Asn Ile Ser
        1235                1240                1245

Glu Glu Thr Ser Ala Glu Val His Pro Ile Ser Leu Ser Ser Ser Lys
    1250                1255                1260

Cys His Asp Ser Val Val Ser Met Phe Lys Ile Glu Asn His Asn Asp
1265                1270                1275                1280

Lys Thr Val Ser Glu Lys Asn Asn Lys Cys Gln Leu Ile Leu Gln Asn
                1285                1290                1295

Asn Ile Glu Met Thr Thr Gly Thr Phe Val Glu Glu Ile Thr Glu Asn
            1300                1305                1310

Tyr Lys Arg Asn Thr Glu Asn Glu Asp Asn Lys Tyr Thr Ala Ala Ser
        1315                1320                1325

Arg Asn Ser His Asn Leu Glu Phe Asp Gly Ser Asp Ser Ser Lys Asn
    1330                1335                1340

Asp Thr Val Cys Ile His Lys Asp Glu Thr Asp Leu Leu Phe Thr Asp
1345                1350                1355                1360

Gln His Asn Ile Cys Leu Lys Leu Ser Gly Gln Phe Met Lys Glu Gly
                1365                1370                1375

Asn Thr Gln Ile Lys Glu Asp Leu Ser Asp Leu Thr Phe Leu Glu Val
            1380                1385                1390

Ala Lys Ala Gln Glu Ala Cys His Gly Asn Thr Ser Asn Lys Glu Gln
        1395                1400                1405

Leu Thr Ala Thr Lys Thr Glu Gln Asn Ile Lys Asp Phe Glu Thr Ser
    1410                1415                1420

Asp Thr Phe Phe Gln Thr Ala Ser Gly Lys Asn Ile Ser Val Ala Lys
1425                1430                1435                1440

Glu Leu Phe Asn Lys Ile Val Asn Phe Phe Asp Gln Lys Pro Glu Glu
                1445                1450                1455

Leu His Asn Phe Ser Leu Asn Ser Glu Leu His Ser Asp Ile Arg Lys
            1460                1465                1470

Asn Lys Met Asp Ile Leu Ser Tyr Glu Glu Thr Asp Ile Val Lys His
        1475                1480                1485

Lys Ile Leu Lys Glu Ser Val Pro Val Gly Thr Gly Asn Gln Leu Val
    1490                1495                1500

Thr Phe Gln Gly Gln Pro Glu Arg Asp Glu Lys Ile Lys Glu Pro Thr
1505                1510                1515                1520

Leu Leu Gly Phe His Thr Ala Ser Gly Lys Lys Val Lys Ile Ala Lys
                1525                1530                1535

Glu Ser Leu Asp Lys Val Lys Asn Leu Phe Asp Glu Lys Glu Gln Gly
            1540                1545                1550

Thr Ser Glu Ile Thr Ser Phe Ser His Gln Trp Ala Lys Thr Leu Lys
        1555                1560                1565

Tyr Arg Glu Ala Cys Lys Asp Leu Glu Leu Ala Cys Glu Thr Ile Glu
```

-continued

```
    1570                1575                1580

Ile Thr Ala Ala Pro Lys Cys Lys Glu Met Gln Asn Ser Leu Asn Asn
1585                1590                1595                1600

Asp Lys Asn Leu Val Ser Ile Glu Thr Val Val Pro Pro Lys Leu Leu
                1605                1610                1615

Ser Asp Asn Leu Cys Arg Gln Thr Glu Asn Leu Lys Thr Ser Lys Ser
            1620                1625                1630

Ile Phe Leu Lys Val Lys Val His Glu Asn Val Glu Lys Glu Thr Ala
        1635                1640                1645

Lys Ser Pro Ala Thr Cys Tyr Thr Asn Gln Ser Pro Tyr Ser Val Ile
    1650                1655                1660

Glu Asn Ser Ala Leu Ala Phe Tyr Thr Ser Cys Ser Arg Lys Thr Ser
1665                1670                1675                1680

Val Ser Gln Thr Ser Leu Leu Glu Ala Lys Lys Trp Leu Arg Glu Gly
                1685                1690                1695

Ile Phe Asp Gly Gln Pro Glu Arg Ile Asn Thr Ala Asp Tyr Val Gly
            1700                1705                1710

Asn Tyr Leu Tyr Glu Asn Asn Ser Asn Ser Thr Ile Ala Glu Asn Asp
        1715                1720                1725

Lys Asn His Leu Ser Glu Lys Gln Asp Thr Tyr Leu Ser Asn Ser Ser
    1730                1735                1740

Met Ser Asn Ser Tyr Ser Tyr His Ser Asp Glu Val Tyr Asn Asp Ser
1745                1750                1755                1760

Arg Ile Leu Ser Lys Asn Lys Leu Asp Ser Gly Ile Glu Pro Val Leu
                1765                1770                1775

Lys Asn Val Glu Asp Gln Lys Asn Thr Ser Phe Ser Lys Val Ile Ser
            1780                1785                1790

Asn Val Lys Asp Ala Asn Ala Tyr Pro Gln Thr Val Asn Glu Asp Ile
        1795                1800                1805

Cys Val Glu Glu Leu Val Thr Ser Ser Ser Pro Cys Lys Asn Lys Asn
    1810                1815                1820

Ala Ala Ile Lys Leu Ser Ile Ser Asn Ser Asn Asn Phe Glu Val Gly
1825                1830                1835                1840

Pro Pro Ala Phe Arg Ile Ala Ser Gly Lys Ile Arg Leu Cys Ser His
                1845                1850                1855

Glu Thr Ile Lys Lys Val Lys Asp Ile Asp Ser Phe Ser Lys Val Ile
            1860                1865                1870

Phe Thr Lys Glu Asn Asn Glu Asn Lys Ser Lys Ile Cys Gln Thr Lys
        1875                1880                1885

Ile Met Ala Gly Cys Tyr Glu Ala Leu Asp Asp Ser Glu Asp Ile Leu
    1890                1895                1900

His Asn Ser Leu Asp Asn Asp Glu Cys Ser Met His Ser His Lys Val
1905                1910                1915                1920

Phe Ala Asp Ile Gln Ser Glu Glu Ile Leu Gln His Asn Gln Asn Met
                1925                1930                1935

Ser Gly Leu Glu Lys Val Ser Lys Ile Ser Pro Cys Asp Val Ser Leu
            1940                1945                1950

Glu Thr Ser Asp Ile Cys Lys Cys Ser Ile Gly Lys Leu His Lys Ser
        1955                1960                1965

Val Ser Ser Ala Asn Thr Cys Gly Ile Phe Ser Thr Ala Ser Gly Lys
    1970                1975                1980

Ser Val Gln Val Ser Asp Ala Ser Leu Gln Asn Ala Arg Gln Val Phe
1985                1990                1995                2000
```

-continued

```
Ser Glu Ile Glu Asp Ser Thr Lys Gln Val Phe Ser Lys Val Leu Phe
                2005                2010                2015

Lys Ser Asn Glu His Ser Asp Gln Leu Thr Arg Glu Glu Asn Thr Ala
            2020                2025                2030

Ile Arg Thr Pro Glu His Leu Ile Ser Gln Lys Gly Phe Ser Tyr Asn
        2035                2040                2045

Val Val Asn Ser Ser Ala Phe Ser Gly Phe Ser Thr Ala Ser Gly Lys
    2050                2055                2060

Gln Val Ser Ile Leu Glu Ser Ser Leu His Lys Val Lys Gly Val Leu
2065                2070                2075                2080

Glu Glu Phe Asp Leu Ile Arg Thr Glu His Ser Leu His Tyr Ser Pro
                2085                2090                2095

Thr Ser Arg Gln Asn Val Ser Lys Ile Leu Pro Arg Val Asp Lys Arg
            2100                2105                2110

Asn Pro Glu His Cys Val Asn Ser Glu Met Glu Lys Thr Cys Ser Lys
        2115                2120                2125

Glu Phe Lys Leu Ser Asn Asn Leu Asn Val Glu Gly Gly Ser Ser Glu
    2130                2135                2140

Asn Asn His Ser Ile Lys Val Ser Pro Tyr Leu Ser Gln Phe Gln Gln
2145                2150                2155                2160

Asp Lys Gln Gln Leu Val Leu Gly Thr Lys Val Ser Leu Val Glu Asn
                2165                2170                2175

Ile His Val Leu Gly Lys Glu Gln Ala Ser Pro Lys Asn Val Lys Met
            2180                2185                2190

Glu Ile Gly Lys Thr Glu Thr Phe Ser Asp Val Pro Val Lys Thr Asn
        2195                2200                2205

Ile Glu Val Cys Ser Thr Tyr Ser Lys Asp Ser Glu Asn Tyr Phe Glu
    2210                2215                2220

Thr Glu Ala Val Glu Ile Ala Lys Ala Phe Met Glu Asp Asp Glu Leu
2225                2230                2235                2240

Thr Asp Ser Lys Leu Pro Ser His Ala Thr His Ser Leu Phe Thr Cys
                2245                2250                2255

Pro Glu Asn Glu Glu Met Val Leu Ser Asn Ser Arg Ile Gly Lys Arg
            2260                2265                2270

Arg Gly Glu Pro Leu Ile Leu Val Gly Glu Pro Ser Ile Lys Arg Asn
        2275                2280                2285

Leu Leu Asn Glu Phe Asp Arg Ile Ile Glu Asn Gln Glu Lys Ser Leu
    2290                2295                2300

Lys Ala Ser Lys Ser Thr Pro Asp Gly Thr Ile Lys Asp Arg Arg Leu
2305                2310                2315                2320

Phe Met His His Val Ser Leu Glu Pro Ile Thr Cys Val Pro Phe Arg
                2325                2330                2335

Thr Thr Lys Glu Arg Gln Glu Ile Gln Asn Pro Asn Phe Thr Ala Pro
            2340                2345                2350

Gly Gln Glu Phe Leu Ser Lys Ser His Leu Tyr Glu His Leu Thr Leu
        2355                2360                2365

Glu Lys Ser Ser Ser Asn Leu Ala Val Ser Gly His Pro Phe Tyr Gln
    2370                2375                2380

Val Ser Ala Thr Arg Asn Glu Lys Met Arg His Leu Ile Thr Thr Gly
2385                2390                2395                2400

Arg Pro Thr Lys Val Phe Val Pro Pro Phe Lys Thr Lys Ser His Phe
                2405                2410                2415
```

-continued

```
His Arg Val Glu Gln Cys Val Arg Asn Ile Asn Leu Glu Glu Asn Arg
            2420                2425                2430

Gln Lys Gln Asn Ile Asp Gly His Gly Ser Asp Asp Ser Lys Asn Lys
        2435                2440                2445

Ile Asn Asp Asn Glu Ile His Gln Phe Asn Lys Asn Asn Ser Asn Gln
    2450                2455                2460

Ala Ala Ala Val Thr Phe Thr Lys Cys Glu Glu Glu Pro Leu Asp Leu
2465                2470                2475                2480

Ile Thr Ser Leu Gln Asn Ala Arg Asp Ile Gln Asp Met Arg Ile Lys
                2485                2490                2495

Lys Lys Gln Arg Gln Arg Val Phe Pro Gln Pro Gly Ser Leu Tyr Leu
            2500                2505                2510

Ala Lys Thr Ser Thr Leu Pro Arg Ile Ser Leu Lys Ala Ala Val Gly
        2515                2520                2525

Gly Gln Val Pro Ser Ala Cys Ser His Lys Gln Leu Tyr Thr Tyr Gly
    2530                2535                2540

Val Ser Lys His Cys Ile Lys Ile Asn Ser Lys Asn Ala Glu Ser Phe
2545                2550                2555                2560

Gln Phe His Thr Glu Asp Tyr Phe Gly Lys Glu Ser Leu Trp Thr Gly
                2565                2570                2575

Lys Gly Ile Gln Leu Ala Asp Gly Gly Trp Leu Ile Pro Ser Asn Asp
            2580                2585                2590

Gly Lys Ala Gly Lys Glu Glu Phe Tyr Arg Ala Leu Cys Asp Thr Pro
        2595                2600                2605

Gly Val Asp Pro Lys Leu Ile Ser Arg Ile Trp Val Tyr Asn His Tyr
    2610                2615                2620

Arg Trp Ile Ile Trp Lys Leu Ala Ala Met Glu Cys Ala Phe Pro Lys
2625                2630                2635                2640

Glu Phe Ala Asn Arg Cys Leu Ser Pro Glu Arg Val Leu Leu Gln Leu
                2645                2650                2655

Lys Tyr Arg Tyr Asp Thr Glu Ile Asp Arg Ser Arg Arg Ser Ala Ile
            2660                2665                2670

Lys Lys Ile Met Glu Arg Asp Asp Thr Ala Ala Lys Thr Leu Val Leu
        2675                2680                2685

Cys Val Ser Asp Ile Ile Ser Leu Ser Ala Asn Ile Ser Glu Thr Ser
    2690                2695                2700

Ser Asn Lys Thr Ser Ser Ala Asp Thr Gln Lys Val Ala Ile Ile Glu
2705                2710                2715                2720

Leu Thr Asp Gly Trp Tyr Ala Val Lys Ala Gln Leu Asp Pro Pro Leu
                2725                2730                2735

Leu Ala Val Leu Lys Asn Gly Arg Leu Thr Val Gly Gln Lys Ile Ile
            2740                2745                2750

Leu His Gly Ala Glu Leu Val Gly Ser Pro Asp Ala Cys Thr Pro Leu
        2755                2760                2765

Glu Ala Pro Glu Ser Leu Met Leu Lys Ile Ser Ala Asn Ser Thr Arg
    2770                2775                2780

Pro Ala Arg Trp Tyr Thr Lys Leu Gly Phe Phe Pro Asp Pro Arg Pro
2785                2790                2795                2800

Phe Pro Leu Pro Leu Ser Ser Leu Phe Ser Asp Gly Gly Asn Val Gly
                2805                2810                2815

Cys Val Asp Val Ile Ile Gln Arg Ala Tyr Pro Ile Gln Trp Met Glu
            2820                2825                2830

Lys Thr Ser Ser Gly Leu Tyr Ile Phe Arg Asn Glu Arg Glu Glu Glu
```

-continued

```
        2835                2840                2845

Lys Glu Ala Ala Lys Tyr Val Glu Ala Gln Gln Lys Arg Leu Glu Ala
    2850                2855                2860

Leu Phe Thr Lys Ile Gln Glu Glu Phe Glu Glu His Glu Glu Asn Thr
2865                2870                2875                2880

Thr Lys Pro Tyr Leu Pro Ser Arg Ala Leu Thr Arg Gln Gln Val Arg
                2885                2890                2895

Ala Leu Gln Asp Gly Ala Glu Leu Tyr Glu Ala Val Lys Asn Ala Ala
            2900                2905                2910

Asp Pro Ala Tyr Leu Glu Gly Tyr Phe Ser Glu Glu Gln Leu Arg Ala
        2915                2920                2925

Leu Asn Asn His Arg Gln Met Leu Asn Asp Lys Lys Gln Ala Gln Ile
    2930                2935                2940

Gln Leu Glu Ile Arg Lys Ala Met Glu Ser Ala Glu Gln Lys Glu Gln
2945                2950                2955                2960

Gly Leu Ser Arg Asp Val Thr Thr Val Trp Lys Leu Arg Ile Val Ser
                2965                2970                2975

Tyr Ser Lys Lys Glu Lys Asp Ser Val Ile Leu Ser Ile Trp Arg Pro
            2980                2985                2990

Ser Ser Asp Leu Tyr Ser Leu Leu Thr Glu Gly Lys Arg Tyr Arg Ile
        2995                3000                3005

Tyr His Leu Ala Thr Ser Lys Ser Lys Ser Lys Ser Glu Arg Ala Asn
    3010                3015                3020

Ile Gln Leu Ala Ala Thr Lys Lys Thr Gln Tyr Gln Gln Leu Pro Val
3025                3030                3035                3040

Ser Asp Glu Ile Leu Phe Gln Ile Tyr Gln Pro Arg Glu Pro Leu His
                3045                3050                3055

Phe Ser Lys Phe Leu Asp Pro Asp Phe Gln Pro Ser Cys Ser Glu Val
            3060                3065                3070

Asp Leu Ile Gly Phe Val Val Ser Val Val Lys Lys Thr Gly Leu Ala
        3075                3080                3085

Pro Phe Val Tyr Leu Ser Asp Glu Cys Tyr Asn Leu Leu Ala Ile Lys
    3090                3095                3100

Phe Trp Ile Asp Leu Asn Glu Asp Ile Ile Lys Pro His Met Leu Ile
3105                3110                3115                3120

Ala Ala Ser Asn Leu Gln Trp Arg Pro Glu Ser Lys Ser Gly Leu Leu
                3125                3130                3135

Thr Leu Phe Ala Gly Asp Phe Ser Val Phe Ser Ala Ser Pro Lys Glu
            3140                3145                3150

Gly His Phe Gln Glu Thr Phe Asn Lys Met Lys Asn Thr Val Glu Asn
        3155                3160                3165

Ile Asp Ile Leu Cys Asn Glu Ala Glu Asn Lys Leu Met His Ile Leu
    3170                3175                3180

His Ala Asn Asp Pro Lys Trp Ser Thr Pro Thr Lys Asp Cys Thr Ser
3185                3190                3195                3200

Gly Pro Tyr Thr Ala Gln Ile Ile Pro Gly Thr Gly Asn Lys Leu Leu
                3205                3210                3215

Met Ser Ser Pro Asn Cys Glu Ile Tyr Tyr Gln Ser Pro Leu Ser Leu
            3220                3225                3230

Cys Met Ala Lys Arg Lys Ser Val Ser Thr Pro Val Ser Ala Gln Met
        3235                3240                3245

Thr Ser Lys Ser Cys Lys Gly Glu Lys Glu Ile Asp Asp Gln Lys Asn
    3250                3255                3260
```

-continued

```
Cys Lys Lys Arg Arg Ala Leu Asp Phe Leu Ser Arg Leu Pro Leu Pro
3265                3270                3275                3280

Pro Pro Val Ser Pro Ile Cys Thr Phe Val Ser Pro Ala Ala Gln Lys
                3285                3290                3295

Ala Phe Gln Pro Pro Arg Ser Cys Gly Thr Lys Tyr Glu Thr Pro Ile
            3300                3305                3310

Lys Lys Lys Glu Leu Asn Ser Pro Gln Met Thr Pro Phe Lys Lys Phe
        3315                3320                3325

Asn Glu Ile Ser Leu Leu Glu Ser Asn Ser Ile Ala Asp Glu Glu Leu
    3330                3335                3340

Ala Leu Ile Asn Thr Gln Ala Leu Leu Ser Gly Ser Thr Gly Glu Lys
3345                3350                3355                3360

Gln Phe Ile Ser Val Ser Glu Ser Thr Arg Thr Ala Pro Thr Ser Ser
                3365                3370                3375

Glu Asp Tyr Leu Arg Leu Lys Arg Arg Cys Thr Thr Ser Leu Ile Lys
            3380                3385                3390

Glu Gln Glu Ser Ser Gln Ala Ser Thr Glu Glu Cys Glu Lys Asn Lys
        3395                3400                3405

Gln Asp Thr Ile Thr Thr Lys Lys Tyr Ile
    3410                3415
```

(2) INFORMATION FOR SEQ ID NO:45:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:45:

CTCAGTCACA TAATAAGGAA T 21

(2) INFORMATION FOR SEQ ID NO:46:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:46:

ACACTGTGAC GTACTGGGTT TT 22

(2) INFORMATION FOR SEQ ID NO:47:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:47:

TCTGGGTCAC AAATTTGTCT GTCA 24

(2) INFORMATION FOR SEQ ID NO:48:

(i) SEQUENCE CHARACTERISTICS:
(A) LENGTH: 26 base pairs
(B) TYPE: nucleic acid
(C) STRANDEDNESS: single
(D) TOPOLOGY: linear -continued (xi) SEQUENCE DESCRIPTION: SEQ ID NO:48:

TTCCTAGTTT GTAGTTCTCC CCAGTC 26

(2) INFORMATION FOR SEQ ID NO:49:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:49:

AGAATGCAAA TTTATAATCC AGAGTA 26

(2) INFORMATION FOR SEQ ID NO:50:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:50:

AATCAGATTC ATCTTTATAG AACAAA 26

(2) INFORMATION FOR SEQ ID NO:51:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:51:

AACAATTTAT ATGAATGAGA ATC 23

(2) INFORMATION FOR SEQ ID NO:52:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:52:

AATTGTTAAG TTTTATTTTT ATTA 24

(2) INFORMATION FOR SEQ ID NO:53:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:53:

CCACAAAGAG ATAAGTCAGG TA 22

(2) INFORMATION FOR SEQ ID NO:54:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:54:

-continued

TGTAAATCTC AGGGCAAAGG TA 22

(2) INFORMATION FOR SEQ ID NO:55:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:55:

TAAGTGAAAT AAAGAGTGAA 20

(2) INFORMATION FOR SEQ ID NO:56:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:56:

AACAGAAGTA TTAGAGATGA C 21

(2) INFORMATION FOR SEQ ID NO:57:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:57:

AATAGTAGAT GTGCTTTTTG A 21

(2) INFORMATION FOR SEQ ID NO:58:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:58:

ACATATAGGA CCAGGTTTAG AGAC 24

(2) INFORMATION FOR SEQ ID NO:59:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:59:

GTTCAACTAA ACAGAGGACT 20

(2) INFORMATION FOR SEQ ID NO:60:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:60:

-continued

CTAGTGATTT TAAACTATAA TTTTTG 26

(2) INFORMATION FOR SEQ ID NO:61:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:61:

TATAAAATAT TAATGTGCTT CTGTT 25

(2) INFORMATION FOR SEQ ID NO:62:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:62:

AAAGGGCTTC TGATTTGCTA C 21

(2) INFORMATION FOR SEQ ID NO:63:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:63:

ATCTGAAGTG GAACCAAATG ATAC 24

(2) INFORMATION FOR SEQ ID NO:64:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:64:

ACGTGGCAAA GAATTCTCTG AAGTAA 26

(2) INFORMATION FOR SEQ ID NO:65:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:65:

TTTCAGAAAA AGACCTATTA GACA 24

(2) INFORMATION FOR SEQ ID NO:66:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:66:

CTTTTTGATA CCCTGAAATG AAGAAG 26

(2) INFORMATION FOR SEQ ID NO:67:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:67:

TAAAGCAGGC AATATCTGGA ACTTCT 26

(2) INFORMATION FOR SEQ ID NO:68:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:68:

GTGGATATTA AACCTGCATT CTTCAA 26

(2) INFORMATION FOR SEQ ID NO:69:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:69:

TATGTCCAAA TTTAATTGAT AAT 23

(2) INFORMATION FOR SEQ ID NO:70:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:70:

AAACACAGAA GGAATCGTCA TC 22

(2) INFORMATION FOR SEQ ID NO:71:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:71:

GATGGTACTT TAATTTTGTC ACTTTG 26

(2) INFORMATION FOR SEQ ID NO:72:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:72:

TTCCTTATTA CATTTTGCTT CTTTAT 26

-continued (2) INFORMATION FOR SEQ ID NO:73:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:73:

CTAGCTCTTT TGGGACAATT CTGAGG 26

(2) INFORMATION FOR SEQ ID NO:74:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:74:

TTTCATGATC ATATAAAAGA NT 22

(2) INFORMATION FOR SEQ ID NO:75:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:75:

CAAAAGTGGA ATACAGTGAT AC 22

(2) INFORMATION FOR SEQ ID NO:76:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:76:

ATAATTTTCA TTTAAAGCAC ATACAT 26

(2) INFORMATION FOR SEQ ID NO:77:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:77:

TCTAGAGGCA AAGAATCATA 20

(2) INFORMATION FOR SEQ ID NO:78:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:78:

TCATTGTCTG AGAAAAGTTC 20

-continued (2) INFORMATION FOR SEQ ID NO:79:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:79:

TTCAAAAATA ACTGTCAATC C 21

(2) INFORMATION FOR SEQ ID NO:80:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:80:

GTTGCTTGTT TATCACCTGT 20

(2) INFORMATION FOR SEQ ID NO:81:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:81:

AACCCATTTT CAAGAACTCT ACCA 24

(2) INFORMATION FOR SEQ ID NO:82:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:82:

CTGAAGCTAC CTCCAAAACT GTG 23

(2) INFORMATION FOR SEQ ID NO:83:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:83:

ACAAATGGGC AGGACTCTTA GG 22

(2) INFORMATION FOR SEQ ID NO:84:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:84:

CCTGCTTGGA AAATAACATC TG 22

(2) INFORMATION FOR SEQ ID NO:85:

-continued (i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:85:

AGTTGTTTCT GATTGTAAAA ATAGTC 26

(2) INFORMATION FOR SEQ ID NO:86:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:86:

GCTGCTGTCT ACCTGACCAA 20

(2) INFORMATION FOR SEQ ID NO:87:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:87:

GATGCTGATC TTCATGTCAT AA 22

(2) INFORMATION FOR SEQ ID NO:88:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:88:

TACCTCTGCA GAAGTTTCCT CACTA 25

(2) INFORMATION FOR SEQ ID NO:89:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:89:

GGGTTTAGGG GCTTTTATTC 20

(2) INFORMATION FOR SEQ ID NO:90:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:90:

TATCAGTTGG CATTTATTAT TTTT 24

(2) INFORMATION FOR SEQ ID NO:91:

-continued (i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:91:

CTTCAAGTAA ATGTCATGAT TCTGTC 26

(2) INFORMATION FOR SEQ ID NO:92:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:92:

CTGGCAGCAG TATATTTGTT ATCT 24

(2) INFORMATION FOR SEQ ID NO:93:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:93:

ATTACTGAAA ATTACAAGAG AAATA 25

(2) INFORMATION FOR SEQ ID NO:94:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:94:

AAAAAGTTAA ATCTGACTCA AATCT 25

(2) INFORMATION FOR SEQ ID NO:95:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:95:

TTTATGAAGG AGGGAAACAC TCA 23

(2) INFORMATION FOR SEQ ID NO:96:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:96:

TTCAGAATTT AAGGAAAAGT TATGC 25

(2) INFORMATION FOR SEQ ID NO:97:

(i) SEQUENCE CHARACTERISTICS:

-continued (A) LENGTH: 24 base pairs
(B) TYPE: nucleic acid
(C) STRANDEDNESS: single
(D) TOPOLOGY: linear (xi) SEQUENCE DESCRIPTION: SEQ ID NO:97:

AAAAATATTA GTGTCGCCAA AGAG 24

(2) INFORMATION FOR SEQ ID NO:98:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:98:

TGTATGAAAA CCCAACAGAG TAGG 24

(2) INFORMATION FOR SEQ ID NO:99:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:99:

GTTAAACACA AAATACTGAA AG 22

(2) INFORMATION FOR SEQ ID NO:100:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:100:

CATTGATGGC TAAAACTGGT G 21

(2) INFORMATION FOR SEQ ID NO:101:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:101:

TCATACAGCT AGCGGGAAAA A 21

(2) INFORMATION FOR SEQ ID NO:102:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:102:

TGGCACCACA GTCTCAATAG 20

(2) INFORMATION FOR SEQ ID NO:103:

(i) SEQUENCE CHARACTERISTICS:
(A) LENGTH: 22 base pairs

-continued (B) TYPE: nucleic acid
(C) STRANDEDNESS: single
(D) TOPOLOGY: linear (xi) SEQUENCE DESCRIPTION: SEQ ID NO:103:

CTGCCCCAAA GTGTAAAGAA AT 22

(2) INFORMATION FOR SEQ ID NO:104:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:104:

AATGACTGAA TAAGGGGACT GAT 23

(2) INFORMATION FOR SEQ ID NO:105:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:105:

GTCCTGCAAC TTGTTACAC 19

(2) INFORMATION FOR SEQ ID NO:106:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:106:

GATTTTTGTC ATTTTCAGC 19

(2) INFORMATION FOR SEQ ID NO:107:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:107:

AACCAGAAAG AATAAATACT 20

(2) INFORMATION FOR SEQ ID NO:108:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:108:

TCCTCAACGC AAATATCTTC AT 22

(2) INFORMATION FOR SEQ ID NO:109:

(i) SEQUENCE CHARACTERISTICS:
(A) LENGTH: 23 base pairs
(B) TYPE: nucleic acid

-continued (C) STRANDEDNESS: single
(D) TOPOLOGY: linear (xi) SEQUENCE DESCRIPTION: SEQ ID NO:109:

TTTCCAAAGT AATATCCAAT GTA 23

(2) INFORMATION FOR SEQ ID NO:110:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:110:

ATTTTTGATT TATTCTCGTT GTT 23

(2) INFORMATION FOR SEQ ID NO:111:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:111:

AAGACATATT TACAGACAGT 20

(2) INFORMATION FOR SEQ ID NO:112:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:112:

TGAAGCTTCC CTATACTACA T 21

(2) INFORMATION FOR SEQ ID NO:113:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:113:

CACCTTGTGA TGTTAGTTTG 20

(2) INFORMATION FOR SEQ ID NO:114:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:114:

TTGGGATATT AAATGTTCTG GAGTA 25

(2) INFORMATION FOR SEQ ID NO:115:

(i) SEQUENCE CHARACTERISTICS:
(A) LENGTH: 22 base pairs
(B) TYPE: nucleic acid
(C) STRANDEDNESS: single -continued (D) TOPOLOGY: linear (xi) SEQUENCE DESCRIPTION: SEQ ID NO:115:

AAAGTAACGA ACATTCAGAC CA 22

(2) INFORMATION FOR SEQ ID NO:116:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:116:

CTGGGTTTCT CTTATCAACN CGA 23

(2) INFORMATION FOR SEQ ID NO:117:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:117:

AGTCTTCACT ATTCACCTAC G 21

(2) INFORMATION FOR SEQ ID NO:118:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:118:

GTGAGACTTT GGTTCCTAAT 20

(2) INFORMATION FOR SEQ ID NO:119:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:119:

TTCAACAAGA CAAACAACAG T 21

(2) INFORMATION FOR SEQ ID NO:120:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:120:

TGTCAGTTCA TCATCTTCCA TAAA 24

(2) INFORMATION FOR SEQ ID NO:121:

(i) SEQUENCE CHARACTERISTICS:
(A) LENGTH: 25 base pairs
(B) TYPE: nucleic acid
(C) STRANDEDNESS: single
(D) TOPOLOGY: linear -continued (xi) SEQUENCE DESCRIPTION: SEQ ID NO:121:

TTACTCCAAA GATTCAGAAA ACTAC 25

(2) INFORMATION FOR SEQ ID NO:122:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:122:

AGCATACCAA GTCTACTGAA TAAAC 25

(2) INFORMATION FOR SEQ ID NO:123:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:123:

AGGTCACTAT TTGTTGTAAG 20

(2) INFORMATION FOR SEQ ID NO:124:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:124:

AGTGGCTCAT GTCTGTAAT 19

(2) INFORMATION FOR SEQ ID NO:125:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:125:

TAAAGCCTAT AATTGTCTCA 20

(2) INFORMATION FOR SEQ ID NO:126:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:126:

CTTCTTAACG TTAGTGTCAT T 21

(2) INFORMATION FOR SEQ ID NO:127:

(i) SEQUENCE CHARACTERISTICS:
(A) LENGTH: 20 base pairs
(B) TYPE: nucleic acid
(C) STRANDEDNESS: single
(D) TOPOLOGY: linear -continued (xi) SEQUENCE DESCRIPTION: SEQ ID NO:127:

ATGTAGCAAA TGAGGGTCTG 20

(2) INFORMATION FOR SEQ ID NO:128:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:128:

GTCTGCCTGT AGTAATCAAG TGT 23

(2) INFORMATION FOR SEQ ID NO:129:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:129:

CTTCAAGCAA TTTAGCAGTT TCAG 24

(2) INFORMATION FOR SEQ ID NO:130:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:130:

TGCTGCTTGA TTGGAGTTGT T 21

(2) INFORMATION FOR SEQ ID NO:131:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:131:

TATTAACTTG GAGGAAAACA GACA 24

(2) INFORMATION FOR SEQ ID NO:132:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:132:

CAAAGGGGGA AAACCATCAG 20

(2) INFORMATION FOR SEQ ID NO:133:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:133:

-continued

GGCCAGGGGT TGTGCTTTTT 20

(2) INFORMATION FOR SEQ ID NO:134:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:134:

AGGATACTAG TTAATGAAAT A 21

(2) INFORMATION FOR SEQ ID NO:135:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:135:

TTTGGTAAAT TCAGTTTTGG TTT 23

(2) INFORMATION FOR SEQ ID NO:136:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:136:

AACACACAAT CTTTTTGCAT AGA 23

(2) INFORMATION FOR SEQ ID NO:137:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:137:

CAGAGAATAG TTGTAGTTGT TGAA 24

(2) INFORMATION FOR SEQ ID NO:138:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:138:

AGAAACCTTA ACCCATACTG C 21

(2) INFORMATION FOR SEQ ID NO:139:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:139:

-continued

ATTCAGTTTT TATTCTCAGT TATTC 25

(2) INFORMATION FOR SEQ ID NO:140:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:140:

ACCACCCATC TGTAAGTTCA 20

(2) INFORMATION FOR SEQ ID NO:141:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:141:

ATCTGAAACT TCTAGCAATA A 21

(2) INFORMATION FOR SEQ ID NO:142:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:142:

TTTAACTGAA TCAATGACTG 20

(2) INFORMATION FOR SEQ ID NO:143:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:143:

AAGTGAATAT TTTTAAGGCA GTT 23

(2) INFORMATION FOR SEQ ID NO:144:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:144:

TATATGGTAA GTTTCAAGAA T 21

(2) INFORMATION FOR SEQ ID NO:145:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:145:

CACTGTGCCT GGCCTGATAC 20

-continued (2) INFORMATION FOR SEQ ID NO:146:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:146:

ATGTTAAATT CAAAGTCTCT A 21

(2) INFORMATION FOR SEQ ID NO:147:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:147:

GGGTGTTTTA TGCTTGGTTC T 21

(2) INFORMATION FOR SEQ ID NO:148:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:148:

CATTTCAACA TATTCCTTCC TG 22

(2) INFORMATION FOR SEQ ID NO:149:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:149:

TTTTGTTCTG ATTGCTTTTT ATTC 24

(2) INFORMATION FOR SEQ ID NO:150:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:150:

AATCATTTTG TTAGTAAGGT CAT 23

(2) INFORMATION FOR SEQ ID NO:151:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:151:

ACTTCTTCCA TTGCATCTTT CTCA 24

-continued (2) INFORMATION FOR SEQ ID NO:152:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:152:

AAAACAAAAC AAAAATTCAA CATA 24

(2) INFORMATION FOR SEQ ID NO:153:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:153:

CAGTTTTGAT AAGTGCTTGT T 21

(2) INFORMATION FOR SEQ ID NO:154:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:154:

AGCTCCAACT AATCATAAGA 20

(2) INFORMATION FOR SEQ ID NO:155:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:155:

TAAAATTCAT CTAACACATC TAT 23

(2) INFORMATION FOR SEQ ID NO:156:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:156:

ACCTCAACAG TATTTTTCAT T 21

(2) INFORMATION FOR SEQ ID NO:157:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:157:

AATCCCAAAT CAGGCCTTCT TACTT 25

-continued (2) INFORMATION FOR SEQ ID NO:158:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:158:

ATTTCCCCAT TCCCCCATCT 20

(2) INFORMATION FOR SEQ ID NO:159:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:159:

AAGGAAATAC TTTTGGAAAC ATAA 24

(2) INFORMATION FOR SEQ ID NO:160:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:160:

TTTACTAGGT ATACAACAGA A 21

(2) INFORMATION FOR SEQ ID NO:161:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:161:

TAGGAGTTAG GGGAGGGAGA CTGTGT 26

(2) INFORMATION FOR SEQ ID NO:162:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:162:

TTTCTCCCCT TTACAAGACT TTGAAG 26

(2) INFORMATION FOR SEQ ID NO:163:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:163:

TTGTATGGCC AAAAGGAAGT CTG 23

(2) INFORMATION FOR SEQ ID NO:164:

-continued (i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:164:

TTTTTAAATG GAGTCATCTG AGGAGA 26

(2) INFORMATION FOR SEQ ID NO:165:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:165:

AAGGCATTTC AGCCACCAAG GAGT 24

(2) INFORMATION FOR SEQ ID NO:166:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:166:

CAACGTCGTT TCAGTCTGAG ATAATC 26

(2) INFORMATION FOR SEQ ID NO:167:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:167:

AGGAGAAAAA CAATTTATAT CTGTCA 26

(2) INFORMATION FOR SEQ ID NO:168:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:168:

GTGGTTTGAA ATTATATTCC AGTCTT 26

(2) INFORMATION FOR SEQ ID NO:169:

(i) SEQUENCE CHARACTERISTICS:
(A) LENGTH: 8 amino acids
(B) TYPE: amino acid
(D) TOPOLOGY: linear (xi) SEQUENCE DESCRIPTION: SEQ ID NO:169:

Ala Leu Cys Asp Val Lys Ala Thr
1 5

(2) INFORMATION FOR SEQ ID NO:170:

-continued (i) SEQUENCE CHARACTERISTICS:
(A) LENGTH: 2184 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:170:

GTTGCTTCTG TTTACTGCTC AAGCACCTTC TGGAAGCAGC AAGGCCCCCA TGGGAGCAAC 60

TCTCACTGAA TCCATTTGAA GGTTTTGTAG GTCTTACAAC AAACCCTATT CAGCCTTGTA 120

TTAGGCATGT TACAGAACCA ACGAATTCGG AGATGAAGTC AGGTCTTCCA GTTCAGCCTG 180

CGAGGAAGAC AGGTGATCCG AATCCTAAGA ATGCAAAAGA TGGGCTGGGT GTGGTGGCTC 240

ATGCCTGTAA TCCCAGCGCT TTGGGAGGCC GAGGCAGGCA GATCACCTGA GGTCGGGAGG 300

TTGAGACCAG ACTGACCAAC AACGGAGAAA CCCCGTCTCT ACTTAAAAAT GCAAAGTTAG 360

CCGTGCGTGG TGGCCCATGC CTGTATTCCC AGCTACTCGG GAGGCTGAGG CAGGAGAACC 420

ACTTGATCCC TGGAGGCGGA AGTTGCGGTG AGCGGAGATT GCGCCATTGC ACACCAGCCC 480

GGGCCACAAG AGCGAAACTC CGTCTCAAAA AAAAAAGCAA AAGATACTAC CAAGCCCTGC 540

GGAGCAAGGT ACCTCACACT TCATGAGCGA GTTAAGATGG GTTTCACAAT TTTTCAAGCA 600

AGGAAACGGG CTCGGAGGTC TTGAACACCT GCTACCCAAT AGCAGAACAG CTACTGGAAC 660

TAAAATCCTC TGATTTCAAA TAACAGCCCC GCCCACTACC ACTAAGTGAA GTCATCCACA 720

ACCACACACC GACCACTCTA AGCTTTTGTA AGATCGGCTC GCTTTGGGGA ACAGGTCTTG 780

AGAGAACATC CCTTTTAAGG TCAGAACAAA GGTATTTCAT AGGTCCCAGG TCGTGTCCCG 840

AGGGCGCCCA CCCAAACATG AGCTGGAGCA AAAAGAAAGG GATGGGGGAC TTGGAGTAGG 900

CATAGGGGCG GCCCCTCCAA GCAGGGTGGC CTGGGACTCT TAAGGGTCAG CGAGAAGAGA 960

ACACACACTC CAAATCCCGC TTTATTCGGT CAGATACTGA CGGTTGGGAT GCCTGACAAG 1020

GAATTTCCTT TCGCCACACT GAGAAATACC CGCAGCGGCC CACCCAGGCC TGACTTCCGG 1080

GTGGTGCGTG TGCTGCGTGT CGCGTCACGG CGTCACGTGG CCAGCGCGGG CTTGTGGCGC 1140

GAGCGTCTGA AACTAGCGGC AGAGCGGAGC CGCTGTGGCA CTCTGCGCCT CTCTGCGCCT 1200

CGGGTGTCTT TTCGGCGGTG GGTCGCCGCC GGGAGAAGCG TGAGGGGACA GATTTGTGAC 1260

CGGCGCGGTT TTTGTCAGCT TACTCCGGCC AAAAAAGAAC TGCGCCTCTG GAGCGGGTTA 1320

GTGGTGGTGG TAGTGGGTTG GGACGAGCGC GTCTTCCGCA GTCCCAGTCC AGCGTGGCGG 1380

GGGAGCGCCT CACGCCCCGG GTCGCTGCCG CGGCTTCTTG CCCTTTTGTC TCTGCCAACC 1440

CCCACCCATG CCTGAGAGAA AGGTCCTTGC CCGAAGGCAA ATTTTCGCCA AGCAAATTCG 1500

AGCCCCGCCC CTTCCCTGGG TCTCCATTTC CCGCCTCCGG CCCGGCCTTT GGGCTCCGCC 1560

TTCAGCTCAA GACTTAACTT CCCTCCCAGC TGTCCCAGAT GACGCCATCT GAAATTTCTT 1620

GGAAACACGA TCACTTTAAC GGAATATTGC TGTTTTGGGG AAGTGTTTTA CAGCTGCTGG 1680

GCACGCTGTA TTTGCCTTAC TTAAGCCCCT GGTAATTGCT GTATTCCGAA GACATGCTGA 1740

TGGGAATTAC CAGGCGGCGT TGGTCTCTAA ACTGAGCCCT CTGTCCCAAC TAGCCACGCG 1800

TCACTGGTTA GCGTGATTGA AACTAAATCG TATGAAAATC CTCTTCTCTA GTCGCACTAG 1860

CCACGTTTCG AGTGCTTAAT GTGGCTAGTG GCACCGGTTT GGACAGCACA GCTGTAAAAT 1920

GTTCCCATCC TCACAGTAAG CTGTTACCGT TCCAGGAGAT GGGACTGAAT TAGAATTCAA 1980

ACAAATTTTC CAGCGCTTCT GAGTTTTACC TCAGTCACAT AATAAGGAAT GCATCCCTGT 2040

GTAAGTGCAT TTTGGTCTTC TGTTTTGCAG ACTTATTTAC CAAGCATTGG AGGAATATCG 2100

-continued

TAGGTAAAAA TGCCTATTGG ATCCAAAGAG AGGCCAACAT TTTTTGAAAT TTTTAAGACA 2160

CGCTGCAACA AAGCAGGTAT TGAC 2184

(2) INFORMATION FOR SEQ ID NO:171:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:171:

CAAAGACCAC ATTGGAAAGT C 21

(2) INFORMATION FOR SEQ ID NO:172:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:172:

GCAAATGTAA GTGGTGCTTC 20

(2) INFORMATION FOR SEQ ID NO:173:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:173:

GAAACAGTTG TAGATACCTC TGAAGA 26

(2) INFORMATION FOR SEQ ID NO:174:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:174:

GATGGTACTT TAATTTTGTC AC 22

(2) INFORMATION FOR SEQ ID NO:175:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:175:

AAATGACTCT TTGGCGACAC 20

(2) INFORMATION FOR SEQ ID NO:176:

(i) SEQUENCE CHARACTERISTICS:
(A) LENGTH: 24 base pairs
(B) TYPE: nucleic acid
(C) STRANDEDNESS: single
(D) TOPOLOGY: linear -continued (xi) SEQUENCE DESCRIPTION: SEQ ID NO:176:

GATTCTGAAG AACCAACTTT GTCC 24

(2) INFORMATION FOR SEQ ID NO:177:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:177:

AGATTTTGAG ACTTCTGATA C 21

(2) INFORMATION FOR SEQ ID NO:178:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:178:

AGCATACCAA GTCTACTGAA TAAAC 25

(2) INFORMATION FOR SEQ ID NO:179:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:179:

GACATTCTAA GTTATGAGGA 20

(2) INFORMATION FOR SEQ ID NO:180:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:180:

ACATAATTAT GATAGGCTAC G 21

(2) INFORMATION FOR SEQ ID NO:181:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:181:

AAGCGTCAAT AATTTATTGT C 21

(2) INFORMATION FOR SEQ ID NO:182:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:182:

-continued

```
TCTTCTCCTA ATTGTGAGAT A                                               21

(2) INFORMATION FOR SEQ ID NO:183:

    (i) SEQUENCE CHARACTERISTICS:
        (A) LENGTH: 1683 amino acids
        (B) TYPE: amino acid
        (D) TOPOLOGY: linear

   (xi) SEQUENCE DESCRIPTION: SEQ ID NO:183:

Xaa Xaa Xaa Gly Ser Xaa Xaa Lys Asn Cys Ser Xaa Asn Asp Pro Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Asn Asn Thr Ile Ile Ser Gln
        35                  40                  45

Asp Leu Asp Tyr Lys Glu Ala Lys Cys Asn Lys Glu Lys Leu Gln Leu
    50                  55                  60

Phe Ile Thr Pro Glu Ala Asp Ser Leu Ser Cys Leu Gln Glu Gly Gln
65                  70                  75                  80

Cys Glu Asn Asp Pro Lys Ser Pro Lys Val Ser Asp Ile Lys Glu Glu
                85                  90                  95

Val Leu Ala Ala Ala Cys His Pro Xaa Val Gln His Ser Xaa Val Glu
            100                 105                 110

Tyr Ser Asp Ile Ser Phe Gln Ser Gln Lys Ser Pro Leu Tyr Asp His
        115                 120                 125

Glu Asn Thr Ser Thr Leu Ile Leu Thr Pro Ser Ser Lys Asp Val Leu
    130                 135                 140

Ser Asn Leu Val Met Ile Ser Arg Gly Lys Glu Ser Tyr Lys Met Ser
145                 150                 155                 160

Glu Lys Leu Lys Cys Glu Asn Tyr Glu Ser Asp Phe Glu Leu Thr Lys
                165                 170                 175

Asn Ile Pro Met Glu Lys Asn Gln Asp Ile Cys Ala Leu Ser Glu Asn
            180                 185                 190

Ser Lys Asn Val Glu Leu Leu Pro Pro Glu Lys Tyr Ile Thr Val Ala
        195                 200                 205

Ser Pro Ser Val Lys Val Gln Phe Asn Gln Thr Asn Leu Arg Val Ile
    210                 215                 220

Gln Lys Asp Gln Glu Glu Thr Thr Leu Ile Ser Lys Ile Thr Val Asn
225                 230                 235                 240

Pro Asp Ser Glu Glu Leu Phe Pro Asp Asn Glu Asn Asn Phe Val Phe
                245                 250                 255

Gln Val Thr Asn Glu Arg Asn Asn Pro Ala Leu Gly Asn Thr Lys Glu
            260                 265                 270

Leu His Glu Thr Asp Leu Thr Cys Val Asn Gly Pro Ile Leu Lys Asn
        275                 280                 285

Ser Thr Met Val Val Asp Gly Asp Ile Gly Asp Lys Gln Ala Ala Gln
    290                 295                 300

Val Ser Ile Lys Lys Asp Leu Asp Ser Ser Ala Ile Val His Asp Leu
305                 310                 315                 320

Ala Glu Glu Asn Arg Asn Ser Lys Gln His Leu Lys Met Thr Leu Asp
                325                 330                 335

Gln Asp Leu Lys Ser Asp Ile Ser Leu Asn Ile Xaa Xaa Lys Ser Asp
            340                 345                 350
```

-continued

Gly Asn Ser Asp Tyr Met Asp Lys Trp Ala Gly Leu Leu Asp Pro Ile
355 360 365

Ser Asn His Ser Phe Gly Gly Ser Phe Arg Thr Ala Ser Asn Lys Glu
370 375 380

Ile Lys Leu Ser Glu His Asn Ile Lys Lys Ser Lys Met Phe Phe Lys
385 390 395 400

Asp Ile Glu Glu Gln Tyr Pro Thr Ser Leu Ala Cys Val Glu Ile Val
405 410 415

Asn Thr Leu Ala Leu Ala Asn Gln Lys Lys Leu Ser Lys Xaa Xaa Xaa
420 425 430

Xaa Asp Pro Gln Ile Asn Thr Val Ser Ala His Leu Gln Ser Ser Val
435 440 445

Val Val Ser Asp Cys Glu Asp Ser His Thr Ala Pro Gln Met Leu Ser
450 455 460

Ser Lys Gln Asp Phe Asn Ser Asn His Asn Leu Thr Pro Ser Gln Lys
465 470 475 480

Ala Glu Ile Thr Glu Leu Ser Thr Ile Leu Glu Glu Ser Gly Ser Gln
485 490 495

Phe Glu Phe Thr Gln Phe Arg Lys Pro Ser His Ile Ala Gln Lys Asn
500 505 510

Thr Phe Glu Val Pro Glu Asn Gln Met Thr Ile Leu Asn Thr Thr Ser
515 520 525

Glu Glu Trp Lys Asp Ala Asp Leu His Leu Ile Val Asn Ala Pro Ser
530 535 540

Ile Gln Val Asp Ser Ser Lys Gln Phe Glu Gly Ser Ala Gly Ile Lys
545 550 555 560

Gln Lys Phe Ala Cys Leu Leu Lys Ser Ser Cys Asn Lys Ser Ala Ser
565 570 575

Gly Tyr Leu Thr Asp Glu Asn Glu Val Glu Phe Arg Gly Phe Tyr Ser
580 585 590

Ala Leu Gly Thr Lys Leu Asn Val Ser Ser Glu Ala Leu Gln Lys Ala
595 600 605

Val Lys Leu Phe Ser Asp Ile Glu Asn Ile Ser Glu Glu Thr Ser Ala
610 615 620

Glu Val Asp Pro Ile Ser Leu Ser Ser Ser Lys Tyr His Asp Ser Val
625 630 635 640

Ala Ser Met Phe Lys Ile Glu Asn Gln Asn Xaa Asp Lys Ser Ser Glu
645 650 655

Lys Asn Asn Lys Cys Gln Leu Ile Leu Gln Asn Asn Ile Glu Met Thr
660 665 670

Thr Gly Ile Phe Val Glu Glu Asn Thr Glu Asn Tyr Lys Arg Asn Thr
675 680 685

Glu Asn Glu Asp Asn Lys Tyr Thr Gly Ala Ser Arg Asn Ser Xaa Asn
690 695 700

Leu Glu Xaa Ser Asp Gly Ser Asp Ser Ser Lys Asn Asp Thr Val Tyr
705 710 715 720

Ile His Lys Asp Glu Thr Asp Leu Pro Phe Ile Asp Gln His Xaa Asn
725 730 735

Ile Cys Leu Lys Leu Ser Gly Gln Phe Met Lys Glu Gly Asn Thr Gln
740 745 750

Ile Lys Glu Gly Leu Ser Asp Leu Thr Cys Leu Val Met Lys Ala Glu
755 760 765

Glu Thr Cys His Gly Asn Thr Ser Asn Lys Glu Gln Leu Thr Ala Thr

-continued

```
    770                 775                 780

Lys Thr Glu Gln Asn Ile Lys Asp Phe Asp Thr Phe Asp Ile Ser Phe
785                 790                 795                 800

Gln Thr Ala Ser Gly Lys Asn Ile Arg Val Ser Lys Glu Ser Leu Asn
                805                 810                 815

Lys Ala Val Asn Phe Phe Asp Gln Lys Xaa Thr Thr Glu Glu Leu Asn
            820                 825                 830

Asn Phe Ser Asp Ser Leu Asn Ser Glu Leu Leu Ser Gly Ile Asn Lys
        835                 840                 845

Asn Lys Met Asp Ile Ser Ser His Glu Xaa Xaa Glu Thr Asp Ile Val
    850                 855                 860

Lys Asn Lys Ile Leu Lys Glu Ser Pro Val Gly Thr Gly Asn Gln Leu
865                 870                 875                 880

Val Thr Leu Gln Gln Arg Pro Glu Cys Glu Ile Glu Lys Ile Lys Glu
                885                 890                 895

Pro Thr Leu Leu Gly Phe His Thr Ala Ser Gly Lys Lys Val Lys Ile
            900                 905                 910

Ala Lys Glu Ser Leu Asp Lys Val Lys Asn Leu Phe Asp Glu Thr Glu
        915                 920                 925

Gln Gly Val Ser Glu Ile Thr Ser Phe Ser His Gln Gly Ala Lys Thr
    930                 935                 940

Leu Lys Asp Arg Glu Ala Cys Lys Asp Gly Leu Glu Leu Ala Cys Glu
945                 950                 955                 960

Thr Val Glu Ile Thr Ala Ala Pro Lys Cys Glu Glu Met Gln Asn Ser
                965                 970                 975

Leu Glu Asn Asp Lys Val Ser Lys Glu Ile Thr Val Leu Pro Pro Gln
            980                 985                 990

Leu Leu Ser Asp Asn Leu Tyr Arg Gln Thr Glu Asn Leu Lys Thr Ser
        995                 1000                1005

Asn Ser Ile Ser Leu Lys Val Lys Val His Glu Asn Val Glu Lys Glu
    1010                1015                1020

Thr Ala Lys Ser Pro Thr Thr Cys Tyr Thr Asn Gln Ser Ser Tyr Ser
1025                1030                1035                1040

Val Ile Glu Asn Ser Ala Leu Ala Phe Tyr Thr Gly His Ser Arg Lys
                1045                1050                1055

Thr Ser Val Ser Glu Ala Ser Leu Leu Glu Ala Lys Lys Trp Leu Arg
            1060                1065                1070

Glu Gly Ile Phe Asp Asp Gln Pro Glu Arg Ile Asn Thr Ala Lys Val
        1075                1080                1085

Glu Cys Lys Glu His Thr Glu Asp Tyr Val Gly Asn Ala Leu Tyr Glu
    1090                1095                1100

Asn Ser Ser Asn Ser Ile Ile Thr Glu Asn Asp Lys Asn His Leu Ser
1105                1110                1115                1120

Glu Lys Gln Asp Ser Thr Tyr Leu Ser Asn Ser Ser Met Ser Asn Ser
                1125                1130                1135

Tyr Ser Tyr His Ser Asp Phe Cys His Ser Asp Glu Val Tyr Asn Asp
            1140                1145                1150

Ser Gly Tyr Leu Ser Lys Asn Lys Ile Asp Xaa Ser Gly Ile Glu Pro
        1155                1160                1165

Val Leu Lys Asn Val Glu Asp Gln Lys Asn Ile Ser Phe Ser Glu Val
    1170                1175                1180

Ile Ser Ala Val Lys Glu Ala Asn Thr Tyr Pro Gln Thr Val Asn Asp
1185                1190                1195                1200
```

-continued

```
Ile Cys Val Glu Lys Leu Val Thr Asn Ser Ser Pro Cys Lys Asn Lys
                1205                1210                1215

Asn Ala Ala Ile Lys Leu Ser Ile Ser Asp Ser Asn Asn Phe Glu Val
            1220                1225                1230

Xaa Xaa Xaa Xaa Xaa Xaa Xaa Xaa Xaa Xaa Gly Pro Pro Ala Phe Ser
        1235                1240                1245

Thr Ala Ser Gly Lys Ile Val Phe Val Ser His Glu Thr Ile Lys Lys
    1250                1255                1260

Val Lys Glu Ile Phe Thr Asp Asn Phe Ser Lys Val Ile Lys Gln Asn
1265                1270                1275                1280

Thr Glu Ser Lys Ser Asp Thr Cys Gln Thr Lys Ile Val Ala Gly Cys
                1285                1290                1295

His Lys Ala Leu Asp Asp Ser Glu Asp Xaa Ile Phe Asn Ser Leu Asp
            1300                1305                1310

Ser Asp Glu Cys Ser Thr Asn Ser His Lys Val Phe Ala Asp Ile Gln
        1315                1320                1325

Ser Glu Gln Ile Leu Gln His Asn Gln Ser Met Ser Gly Leu Glu Lys
    1330                1335                1340

Val Ser Glu Ile Pro Pro Cys Asp Val Ser Leu Glu Thr Ser Asp Ile
1345                1350                1355                1360

Cys Lys Cys Ser Ile Gly Lys Leu Pro Lys Ser Val Ser Ser Ser Asn
                1365                1370                1375

Thr Cys Gly Ile Phe Ser Thr Ala Ser Gly Lys Ser Val Gln Val Ser
            1380                1385                1390

Asp Ala Ser Leu Gln Lys Ala Arg Gln Val Phe Ser Glu Ile Glu Asp
        1395                1400                1405

Ser Ala Lys Gln Leu Phe Ser Lys Val Leu Lys Ser Asn Glu Xaa His
    1410                1415                1420

Ser Asp Gln Leu Thr Arg Glu Glu Asn Thr Val Val His Thr Pro Glu
1425                1430                1435                1440

Asn Leu Leu Ser Ser Gln Lys Xaa Phe Ser Xaa Asn Val Val Asn Ser
                1445                1450                1455

Ser Ala Phe Ser Gly Phe Ser Thr Ala Ser Gly Lys Gln Val Ser Val
            1460                1465                1470

Ser Glu Ser Ala Leu His Lys Val Lys Gly Met Leu Glu Glu Phe Asp
        1475                1480                1485

Leu Ile Arg Thr Glu His Ser Leu Gln His Ser Pro Thr Ser Arg Gln
    1490                1495                1500

Asp Val Ser Lys Ile Leu Pro Gln Ser Cys Val Asp Lys Arg Thr Pro
1505                1510                1515                1520

Glu His Ser Val Asn Ser Leu Glu Lys Thr Tyr Ser Asp Glu Phe Ser
                1525                1530                1535

Leu Pro Asn Asn Tyr Asn Val Glu Ser Gly Ser Ser Glu Asn Asn His
            1540                1545                1550

Ser Ile Lys Val Ser Pro Gln Leu Ser Gln Phe Lys Gln Asp Lys Gln
        1555                1560                1565

Xaa Gln Leu Val Leu Gly Thr Lys Val Ser Leu Val Glu Asn Ile His
    1570                1575                1580

Val Leu Gly Lys Glu Gln Thr Ser Pro Glu Asn Val Lys Met Glu Ile
1585                1590                1595                1600

Gly Lys Thr Glu Thr Phe Ser Asp Val Pro Val Lys Thr Asn Xaa Xaa
                1605                1610                1615
```

-continued

```
Xaa Xaa Xaa Xaa Tyr Ser Lys Xaa Xaa Xaa Xaa Xaa Xaa Xaa Xaa Xaa
            1620                1625                1630

Xaa Xaa Xaa Xaa Xaa Xaa Xaa Xaa Xaa Xaa Xaa Xaa Xaa Xaa Xaa Xaa
        1635                1640                1645

Xaa Xaa Xaa Xaa Xaa Xaa Xaa Xaa Xaa Xaa Xaa Xaa Xaa Xaa Xaa Xaa
    1650                1655                1660

Xaa Xaa Xaa Xaa Xaa Xaa Xaa Xaa Xaa Xaa Xaa Xaa Xaa Xaa Xaa Xaa
1665                1670                1675                1680

Xaa Xaa Xaa
```

(2) INFORMATION FOR SEQ ID NO:184:

(i) SEQUENCE CHARACTERISTICS:
(A) LENGTH: 1579 amino acids
(B) TYPE: amino acid
(D) TOPOLOGY: linear (xi) SEQUENCE DESCRIPTION: SEQ ID NO:184:

```
Gly Thr Ile Leu Arg Lys Cys Ser Arg Asn Glu Thr Cys Ser Asn Asn
1               5                   10                  15

Thr Val Ile Ser Gln Asp Leu Asp Tyr Lys Glu Ala Lys Cys Asn Lys
            20                  25                  30

Glu Lys Leu Gln Leu Phe Ile Thr Pro Glu Ala Asp Ser Leu Ser Cys
        35                  40                  45

Leu Gln Glu Gly Gln Cys Xaa Asn Asp Pro Lys Ser Lys Lys Val Ser
    50                  55                  60

Asp Ile Lys Glu Glu Val Leu Ala Ala Ala Cys His Pro Val Gln His
65                  70                  75                  80

Ser Val Glu Tyr Ser Asp Thr Asp Phe Gln Ser Gln Lys Asn Leu Leu
                85                  90                  95

Tyr Asp His Glu Asn Ala Ser Thr Leu Ile Leu Thr Pro Thr Ser Lys
            100                 105                 110

Asp Val Leu Ser Asn Leu Val Met Ile Ser Arg Gly Lys Glu Ser Tyr
        115                 120                 125

Lys Met Ser Asp Lys Leu Lys Gly Asn Asn Tyr Glu Ser Asp Val Glu
    130                 135                 140

Leu Thr Lys Asn Ile Pro Met Glu Lys Asn Gln Asp Val Cys Ala Leu
145                 150                 155                 160

Asn Glu Asn Tyr Lys Asn Val Glu Leu Leu Pro Pro Glu Lys Tyr Met
                165                 170                 175

Arg Val Ala Ser Pro Ser Arg Lys Val Gln Phe Asn Gln Thr Asn Leu
            180                 185                 190

Arg Val Ile Gln Lys Asn Gln Glu Glu Thr Thr Ser Ile Ser Lys Ile
        195                 200                 205

Thr Val Asn Pro Asp Ser Glu Glu Leu Phe Ser Asp Asn Glu Asn Asn
    210                 215                 220

Phe Val Phe Gln Val Ala Asn Glu Arg Asn Asn Leu Ala Leu Gly Asn
225                 230                 235                 240

Thr Lys Glu Leu His Glu Thr Asp Leu Thr Cys Val Asn Glu Pro Ile
                245                 250                 255

Phe Lys Asn Ser Thr Met Val Leu Tyr Gly Asp Thr Gly Asp Lys Gln
            260                 265                 270

Ala Thr Gln Val Ser Ile Lys Lys Asp Leu Val Tyr Val Leu Ala Glu
        275                 280                 285

Glu Asn Lys Asn Ser Lys Gln His Ile Lys Met Thr Leu Gly Gln Asp
```

-continued

```
    290                 295                 300

Leu Lys Ser Asp Ile Ser Leu Asn Ile Asp Lys Ile Pro Glu Lys Asn
305                 310                 315                 320

Asn Asp Tyr Met Asn Lys Trp Ala Gly Leu Leu Gly Pro Ile Ser Asn
                325                 330                 335

His Ser Phe Gly Gly Ser Phe Arg Thr Ala Ser Asn Lys Glu Ile Lys
            340                 345                 350

Leu Ser Glu His Asn Ile Lys Lys Ser Lys Met Phe Phe Lys Asp Ile
        355                 360                 365

Glu Glu Gln Tyr Pro Thr Ser Leu Ala Cys Val Glu Ile Val Asn Thr
    370                 375                 380

Leu Ala Leu Asp Asn Gln Lys Lys Leu Ser Lys Pro Gln Ile Asn Thr
385                 390                 395                 400

Val Ser Ala His Leu Gln Ser Ser Val Val Val Ser Asp Cys Lys Asn
                405                 410                 415

Ser His Ile Thr Pro Gln Met Leu Phe Ser Lys Gln Asp Phe Asn Ser
            420                 425                 430

Asn His Asn Leu Thr Pro Ser Gln Lys Ala Glu Ile Thr Glu Leu Ser
        435                 440                 445

Thr Ile Leu Glu Glu Ser Gly Ser Gln Phe Glu Phe Thr Gln Phe Arg
    450                 455                 460

Lys Pro Ser Tyr Ile Leu Gln Lys Ser Thr Phe Glu Val Pro Glu Asn
465                 470                 475                 480

Gln Met Thr Ile Leu Lys Thr Thr Ser Glu Glu Cys Arg Asp Ala Asp
                485                 490                 495

Leu His Val Ile Met Asn Ala Pro Ser Ile Gln Val Asp Ser Ser Lys
            500                 505                 510

Gln Phe Glu Gly Thr Val Glu Ile Lys Arg Lys Phe Ala Gly Leu Leu
        515                 520                 525

Lys Asn Asp Cys Asn Lys Ser Ala Ser Gly Tyr Leu Thr Asp Glu Asn
    530                 535                 540

Glu Val Gly Phe Arg Gly Phe Tyr Ser Ala His Gly Thr Lys Leu Asn
545                 550                 555                 560

Val Ser Thr Glu Ala Leu Gln Lys Ala Val Lys Leu Phe Ser Asp Ile
                565                 570                 575

Glu Asn Ile Ser Glu Glu Thr Ser Ala Glu Val His Pro Ile Ser Leu
            580                 585                 590

Ser Ser Ser Lys Cys His Asp Ser Val Val Ser Met Phe Lys Ile Glu
        595                 600                 605

Asn His Asn Asp Lys Thr Ser Glu Lys Asn Asn Lys Cys Gln Leu Ile
    610                 615                 620

Leu Gln Asn Asn Ile Glu Met Thr Thr Gly Thr Phe Val Glu Glu Ile
625                 630                 635                 640

Thr Glu Asn Tyr Lys Arg Asn Thr Glu Asn Glu Asp Asn Lys Tyr Thr
                645                 650                 655

Ala Ala Ser Arg Asn Ser His Asn Leu Glu Phe Asp Gly Ser Asp Ser
            660                 665                 670

Ser Lys Asn Asp Thr Val Cys Ile His Lys Asp Glu Thr Asp Leu Leu
        675                 680                 685

Phe Thr Asp Gln His Asn Ile Cys Leu Lys Leu Ser Gly Gln Phe Met
    690                 695                 700

Lys Glu Gly Asn Thr Gln Ile Lys Glu Asp Leu Ser Asp Leu Thr Phe
705                 710                 715                 720
```

-continued

```
Leu Val Ala Lys Ala Gln Glu Ala Cys His Gly Asn Thr Ser Asn Lys
                725                 730                 735

Glu Gln Leu Thr Ala Thr Lys Thr Glu Gln Asn Ile Lys Asp Phe Glu
            740                 745                 750

Thr Ser Asp Thr Phe Phe Gln Thr Ala Ser Gly Lys Asn Ile Ser Val
        755                 760                 765

Ala Lys Glu Ser Phe Asn Lys Ile Val Asn Phe Phe Asp Gln Lys Pro
    770                 775                 780

Glu Glu Leu His Asn Phe Ser Leu Asn Ser Glu Leu His Ser Asp Ile
785                 790                 795                 800

Arg Lys Asn Lys Met Asp Ile Leu Ser Tyr Glu Glu Thr Asp Ile Val
                805                 810                 815

Lys His Lys Ile Leu Lys Glu Ser Pro Val Gly Thr Gly Asn Gln Leu
            820                 825                 830

Val Thr Phe Gln Gly Gln Pro Glu Arg Asp Glu Lys Ile Lys Glu Pro
        835                 840                 845

Thr Leu Leu Gly Phe His Thr Ala Ser Gly Lys Lys Val Lys Ile Ala
    850                 855                 860

Lys Glu Ser Leu Asp Lys Val Lys Asn Leu Phe Asp Glu Lys Glu Gln
865                 870                 875                 880

Gly Thr Ser Glu Ile Thr Ser Phe Ser His Gln Trp Ala Lys Thr Leu
                885                 890                 895

Lys Tyr Arg Glu Ala Cys Lys Asp Leu Glu Leu Ala Cys Glu Thr Ile
            900                 905                 910

Glu Ile Thr Ala Ala Pro Lys Cys Lys Glu Met Gln Asn Ser Leu Asn
        915                 920                 925

Asn Asp Lys Leu Val Ser Ile Glu Thr Val Val Pro Pro Lys Leu Leu
    930                 935                 940

Ser Asp Asn Leu Cys Arg Gln Thr Glu Asn Leu Lys Thr Ser Lys Ser
945                 950                 955                 960

Ile Phe Leu Lys Val Lys Val His Glu Asn Val Glu Lys Glu Thr Ala
                965                 970                 975

Lys Ser Pro Ala Thr Cys Tyr Thr Asn Gln Ser Pro Tyr Ser Val Ile
            980                 985                 990

Glu Asn Ser Ala Leu Ala Phe Tyr Thr Ser Cys Ser Arg Lys Thr Ser
        995                 1000                1005

Val Ser Gln Thr Ser Leu Leu Glu Ala Lys Lys Trp Leu Arg Glu Gly
    1010                1015                1020

Ile Phe Asp Gly Gln Pro Glu Arg Ile Asn Thr Ala Asp Tyr Val Gly
1025                1030                1035                1040

Asn Tyr Leu Tyr Glu Asn Asn Ser Asn Ser Thr Ile Ala Glu Asn Asp
                1045                1050                1055

Lys Asn His Leu Ser Glu Lys Gln Asp Thr Tyr Leu Ser Asn Ser Ser
            1060                1065                1070

Met Ser Asn Ser Tyr Ser Tyr His Ser Asp Glu Val Tyr Asn Asp Ser
        1075                1080                1085

Arg Ile Leu Ser Lys Asn Asn Leu Asp Ser Gly Ile Glu Pro Val Leu
    1090                1095                1100

Lys Asn Val Glu Asp Gln Lys Asn Thr Ser Phe Ser Lys Val Ile Ser
1105                1110                1115                1120

Asn Val Lys Asp Ala Asn Ala Tyr Pro Gln Thr Val Asn Asp Ile Cys
                1125                1130                1135
```

-continued

```
Val Glu Glu Leu Val Thr Ser Ser Ser Pro Cys Lys Asn Lys Asn Ala
            1140                1145                1150

Ala Ile Lys Leu Ser Ile Ser Asn Ser Asn Asn Phe Glu Val Gly Pro
        1155                1160                1165

Pro Ala Phe Arg Ile Ala Ser Gly Lys Ile Val Cys Val Ser His Glu
    1170                1175                1180

Thr Ile Lys Lys Val Lys Asp Ile Phe Thr Asp Ser Phe Ser Lys Val
1185                1190                1195                1200

Ile Lys Glu Asn Asn Glu Asn Lys Ser Lys Ile Cys Gln Thr Lys Ile
                1205                1210                1215

Met Ala Gly Cys Tyr Glu Ala Leu Asp Asp Ser Glu Asp Ile Leu Asn
            1220                1225                1230

Ser Leu Asp Asn Asp Glu Cys Ser Thr His Ser His Lys Val Phe Ala
        1235                1240                1245

Asp Ile Gln Ser Glu Glu Ile Leu Gln His Asn Gln Asn Met Ser Gly
    1250                1255                1260

Leu Glu Lys Val Ser Lys Ile Ser Pro Cys Asp Val Ser Leu Glu Thr
1265                1270                1275                1280

Ser Asp Ile Cys Lys Cys Ser Ile Gly Lys Leu His Lys Ser Val Ser
                1285                1290                1295

Ser Ala Asn Thr Cys Gly Ile Phe Ser Thr Ala Ser Gly Lys Ser Val
            1300                1305                1310

Gln Val Ser Asp Ala Ser Leu Gln Asn Ala Arg Gln Val Phe Ser Glu
        1315                1320                1325

Ile Glu Asp Ser Thr Lys Gln Val Phe Ser Lys Val Phe Lys Ser Asn
    1330                1335                1340

Glu His Ser Asp Gln Leu Thr Arg Glu Glu Asn Thr Ala Ile Arg Thr
1345                1350                1355                1360

Pro Glu His Leu Ile Ser Gln Lys Gly Phe Ser Tyr Asn Val Val Asn
                1365                1370                1375

Ser Ser Ala Phe Ser Gly Phe Ser Thr Ala Ser Gly Lys Gln Val Ser
            1380                1385                1390

Ile Leu Glu Ser Ser Leu His Lys Val Lys Gly Val Leu Glu Glu Phe
        1395                1400                1405

Asp Leu Ile Arg Thr Glu His Ser Leu His Tyr Ser Pro Thr Ser Arg
    1410                1415                1420

Gln Asn Val Ser Lys Ile Leu Pro Arg Val Asp Lys Arg Asn Pro Glu
1425                1430                1435                1440

His Cys Val Asn Ser Met Glu Lys Thr Cys Ser Lys Glu Phe Lys Leu
                1445                1450                1455

Ser Asn Asn Leu Asn Val Glu Gly Gly Ser Ser Glu Asn Asn His Ser
            1460                1465                1470

Ile Lys Val Ser Pro Tyr Leu Ser Gln Phe Gln Gln Asp Lys Gln Gln
        1475                1480                1485

Leu Val Leu Gly Thr Lys Val Ser Leu Val Glu Asn Ile His Val Leu
    1490                1495                1500

Gly Lys Glu Gln Ala Ser Pro Lys Asn Val Lys Met Glu Ile Gly Lys
1505                1510                1515                1520

Thr Glu Thr Phe Ser Asp Val Pro Val Lys Thr Asn Ile Glu Val Cys
                1525                1530                1535

Ser Thr Tyr Ser Lys Asp Ser Glu Asn Tyr Phe Glu Thr Glu Ala Val
            1540                1545                1550

Glu Ala Lys Ala Phe Met Glu Asp Asp Glu Leu Thr Asp Ser Xaa Leu
```

-continued

```
        1555                1560                1565

Pro Xaa His Ala Thr His Ser Leu Phe Thr Cys
    1570                1575
```

(2) INFORMATION FOR SEQ ID NO:185:

(i) SEQUENCE CHARACTERISTICS:
(A) LENGTH: 1535 amino acids
(B) TYPE: amino acid
(D) TOPOLOGY: linear (xi) SEQUENCE DESCRIPTION: SEQ ID NO:185:

```
Cys Ser Ser Asn Asn Thr Ile Ile Ser Gln Asp Leu Asp Tyr Lys Glu
1               5                   10                  15

Ala Lys Cys Asn Lys Glu Lys Leu Gln Leu Phe Ile Thr Pro Glu Ala
            20                  25                  30

Asp Ser Leu Ser Phe Leu Gln Glu Gly Gln Tyr Glu Asn Asp Pro Lys
        35                  40                  45

Ser Arg Lys Val Ser Asp Ile Lys Glu Glu Val Leu Ala Ala Ala His
    50                  55                  60

His Pro Val Gln His Ser Ala Glu Tyr Ser Asp Thr Asp Phe Gln Ser
65                  70                  75                  80

Gln Lys Ser Pro Leu Tyr Asp His Glu Asn Ala Ser Thr Leu Ile Leu
                85                  90                  95

Thr Pro Thr Ser Lys Asp Val Leu Ser Asn Leu Leu Met Ile Ser Arg
            100                 105                 110

Gly Lys Lys Ser Tyr Lys Met Ser Asp Glu Leu Lys Gly Asn Asn Tyr
        115                 120                 125

Glu Ser Asp Phe Glu Leu Thr Lys Asn Ile Pro Met Glu Lys Asn Gln
    130                 135                 140

Asp Val Cys Ala Leu Ser Glu Asn Ser Lys His Val Glu Leu Leu Pro
145                 150                 155                 160

Pro Glu Lys Tyr Ile Arg Gly Ala Ser Pro Ser Arg Lys Val Gln Phe
                165                 170                 175

Asn Gln Thr Asn Leu Arg Val Ile Gln Lys Asp Gln Glu Glu Thr Thr
            180                 185                 190

Leu Ile Pro Lys Ile Thr Val His Pro Asp Ser Glu Glu Leu Phe Ser
        195                 200                 205

Asp Asn Glu Asn Asn Phe Val Phe Gln Val Ala Asn Glu Arg Asn Asn
    210                 215                 220

Phe Ala Leu Gly Asn Thr Lys Glu Leu His Glu Thr Asp Leu Thr Cys
225                 230                 235                 240

Val Asn Glu Pro Ile Phe Lys Asn Ser Thr Met Val Leu Tyr Ala Asp
                245                 250                 255

Ile Gly Asp Lys Gln Ala Thr Gln Val Ser Ile Lys Lys Asp Leu Asp
            260                 265                 270

Ser Ser Asn Ile Val Tyr Asp Leu Ala Glu Glu Asn Lys Asn Ser Lys
        275                 280                 285

Gln His Leu Lys Met Thr Leu Gly Gln Asp Leu Gln Pro Asp Ile Leu
    290                 295                 300

Asn Ile Asp Lys Ile Pro Asp Lys Ile Asp Asp Cys Met Asp Lys Trp
305                 310                 315                 320

Ala Gly Pro Leu Asp Pro Ile Ser Asn His Ser Phe Gly Gly Ser Phe
                325                 330                 335

Arg Thr Ala Ser Asn Lys Glu Ile Lys Val Ser Glu His Asn Ile Lys
```

-continued

```
            340                 345                 350

Lys Ser Lys Met Phe Phe Lys Asp Ile Glu Glu Gln Tyr Pro Thr Ser
        355                 360                 365

Leu Ala Cys Val Glu Ile Val Asn Thr Leu Ala Leu Asp Asn Gln Lys
    370                 375                 380

Lys Leu Ser Lys Pro Gln Ile Asn Thr Val Ser Ala His Leu Gln Ser
385                 390                 395                 400

Ser Val Val Val Ser Asp Cys Lys Asn Ser His Ile Thr Pro Gln Met
                405                 410                 415

Ser Phe Ser Lys Gln Asp Phe Asn Ser Asn His Asn Leu Thr Pro Ser
            420                 425                 430

Gln Lys Ala Glu Ile Thr Glu Leu Ser Thr Ile Leu Glu Glu Ser Gly
        435                 440                 445

Ser Gln Phe Glu Phe Thr Gln Phe Arg Lys Pro Ser Tyr Ile Leu Gln
    450                 455                 460

Lys Asn Thr Phe Glu Val Pro Glu Asn Gln Val Thr Ile Leu Asn Thr
465                 470                 475                 480

Thr Thr Glu Glu Asn Arg Asp Ala Gly Leu Val Ile Met Asn Ala Pro
                485                 490                 495

Ser Ile Gln Val Asn Ser Ser Lys Gln Phe Glu Gly Thr Val Gly Ile
            500                 505                 510

Lys Gln Lys Phe Ala Gly Leu Leu Lys Ser Asp Cys Asn Lys Ser Ala
        515                 520                 525

Ser Gly Tyr Leu Thr Asp Glu Asn Glu Val Glu Phe Arg Gly Phe Tyr
    530                 535                 540

Ser Ala His Gly Val Lys Leu Asn Val Ser Thr Glu Ala Leu Gln Lys
545                 550                 555                 560

Ala Val Lys Leu Phe Ser Asp Ile Glu Asn Ile Ser Glu Lys Thr Ser
                565                 570                 575

Ala Glu Val Asp Pro Ile Ser Leu Ser Ser Ser Lys Phe His Asp Ser
            580                 585                 590

Val Val Ser Met Phe Lys Ile Glu Asn His Asn Asp Lys Thr Ser Glu
        595                 600                 605

Lys Asn Lys Cys Gln Leu Met Leu Gln Asn Asn Ile Glu Met Thr Thr
    610                 615                 620

Gly Thr Phe Val Glu Glu Ile Thr Glu Asn Tyr Lys Ile Asn Thr Glu
625                 630                 635                 640

Asn Glu Asp Asn Lys Tyr Thr Ala Ala Ser Arg Asn Ser Arg Asn Leu
                645                 650                 655

Glu Phe Val Gly Ser Asp Ser Ser Lys Asn Asp Thr Val Cys Ile His
            660                 665                 670

Lys Asp Glu Lys Asp Leu Pro Phe Thr Asp Gln Arg Asn Ile Cys Leu
        675                 680                 685

Lys Leu Ser Gly Gln Leu Met Lys Glu Gly Asn Thr Gln Ile Lys Glu
    690                 695                 700

Gly Leu Ser Asp Leu Thr Phe Leu Val Val Lys Ala Gln Glu Thr Cys
705                 710                 715                 720

His Gly Asn Thr Ser Asn Lys Glu Gln Leu Thr Ala Thr Lys Thr Glu
                725                 730                 735

Gln Asn Ile Lys Asp Phe Glu Thr Phe Asp Ile Ser Phe Gln Thr Ala
            740                 745                 750

Ser Gly Lys Asn Ile Ser Val Thr Lys Glu Ser Phe Asn Lys Ile Val
        755                 760                 765
```

-continued

```
Asn Phe Phe Asp Pro Lys Pro Glu Glu Leu His Asn Phe Ser Leu Asn
    770                 775                 780

Ser Lys Leu His Ser Asp Ile Arg Lys Asn Lys Met Asp Ile Leu Ser
785                 790                 795                 800

His Glu Glu Thr Asp Thr Val Lys Asn Lys Ile Leu Lys Glu Ser Pro
                805                 810                 815

Val Gly Thr Gly Asn Gln Leu Val Thr Phe Gln Glu Arg Pro Gln Gly
            820                 825                 830

Asp Glu Glu Ile Lys Glu Pro Thr Leu Leu Gly Phe His Thr Ala Ser
        835                 840                 845

Gly Lys Lys Val Lys Ile Thr Lys Glu Ser Leu Asp Lys Val Lys Asn
    850                 855                 860

Leu Phe Asp Glu Lys Glu Gln Gly Thr Ser Glu Ile Thr Ser Phe Ser
865                 870                 875                 880

His Gln Trp Ala Lys Thr Leu Lys Tyr Arg Glu Ala Cys Gln Asp Leu
                885                 890                 895

Glu Leu Ala Cys Glu Thr Val Glu Ile Thr Thr Ala Pro Lys Cys Lys
            900                 905                 910

Glu Met Gln Asn Ser Leu Asn Asn Asp Lys Leu Val Cys Ile Glu Thr
        915                 920                 925

Val Val Pro Pro Lys Leu Leu Ser Asp Asn Leu Cys Thr Gln Thr Glu
    930                 935                 940

Asn Leu Lys Thr Ser Lys Ser Ile Phe Leu Lys Val Lys Val His Glu
945                 950                 955                 960

Asn Val Glu Lys Glu Thr Ala Lys Ser Pro Thr Thr Cys Tyr Thr Asn
                965                 970                 975

Gln Ser Pro Tyr Ser Val Ile Glu Asn Ser Ala Leu Ala Phe Tyr Thr
            980                 985                 990

Ser Cys Ser Arg Lys Cys Ser Val Ser Gln Thr Ser Leu Leu Glu Ala
        995                 1000                1005

Lys Gln Trp Leu Arg Glu Gly Ile Phe Asp Asp Gln Pro Glu Arg Ile
    1010                1015                1020

Asn Thr Ala Asp Tyr Val Gly Asn Ser Leu Tyr Glu Asn Asn Ser Lys
1025                1030                1035                1040

Asn Thr Ile Ala Glu Ser Asp Lys Asn His Pro Ser Glu Lys Gln Asp
                1045                1050                1055

Thr Thr Leu Asn Asn Ser Ser Met Ser Asn Ser Tyr Ser Tyr Leu Ser
            1060                1065                1070

Asp Glu Val Tyr Ser Asp Ser Gly Tyr Leu Ser Lys Asn Lys Leu Asp
        1075                1080                1085

Ser Gly Ile Glu Pro Val Leu Lys Lys Val Glu Asp Gln Lys Asn Ile
    1090                1095                1100

Ser Phe Ser Lys Val Ile Ser Ser Val Lys Asp Ala Asn Thr Tyr Ser
1105                1110                1115                1120

Gln Thr Val Asn Gly Ile Cys Val Glu Glu Leu Val Thr Ser Ser Ser
                1125                1130                1135

Pro Cys Lys Asn Lys Asn Ala Ala Ile Lys Leu Ser Ile Ser Asn Cys
            1140                1145                1150

Asp Asn Phe Glu Val Gly Pro Pro Ala Phe Ser Thr Ala Ser Gly Lys
        1155                1160                1165

Ile Ile Cys Val Ser His Glu Thr Ile Lys Lys Val Lys Glu Ile Phe
    1170                1175                1180
```

-continued

```
Thr Asp Ser Phe Gly Lys Val Ile Lys Glu Asn Asn Glu Asn Lys Ser
1185                1190                1195                1200

Asn Ile Cys Gln Thr Lys Ile Val Ala Gly Cys Tyr Glu Ala Leu Asp
                1205                1210                1215

Asp Ser Glu Asp Ile Phe Asn Ser Leu Asp Ser Asp Glu Cys Ser Met
            1220                1225                1230

His Ser His Lys Val Phe Ala Asp Ile Gln Ser Asp Glu Ile Leu Gln
        1235                1240                1245

His Asn Gln Asn Met Ser Gly Leu Glu Gln Val Ser Lys Met Ser Pro
    1250                1255                1260

Cys Asp Val Ser Leu Glu Thr Ser Asp Ile Cys Lys Cys Ser Ile Gly
1265                1270                1275                1280

Lys Leu Pro Lys Ser Ile Pro Ser Thr Asn Thr Cys Gly Ile Phe Ser
                1285                1290                1295

Thr Ala Ser Gly Lys Ser Val Gln Val Ser Asp Ala Ser Leu Gln Lys
            1300                1305                1310

Ala Arg Gln Val Phe Ser Glu Ile Glu Asp Asn Thr Lys Gln Val Phe
        1315                1320                1325

Ser Lys Val Phe Lys Ser Asn Glu His Ser Asp Gln Leu Thr Arg Glu
    1330                1335                1340

Glu Asn Thr Thr Val His Thr Pro Lys His Leu Ile Ser Ser Gln Lys
1345                1350                1355                1360

Asp Phe Ser Tyr Asn Val Val Asn Ser Ser Ala Phe Ser Gly Phe Ser
                1365                1370                1375

Thr Ala Ser Gly Lys Gln Val Ser Ile Ser Glu Ser Ser Leu His Lys
            1380                1385                1390

Val Lys Gly Met Leu Glu Glu Phe Asp Ile Ile Arg Thr Glu His Ser
        1395                1400                1405

Leu His Tyr Ser Pro Thr Ser Arg Gln Asn Val Ser Lys Thr Leu Pro
    1410                1415                1420

Cys Val Asp Lys Arg Thr Pro Glu His Cys Val Asn Ser Met Glu Lys
1425                1430                1435                1440

Ala Cys Ser Lys Glu Phe Asn Leu Ser Asn Asn Phe Asn Val Glu Gly
                1445                1450                1455

Gly Ser Ser Glu Asn Asn His Ser Ile Lys Val Ser Pro Ser Leu Ser
            1460                1465                1470

Gln Phe Lys Gln Asp Lys Gln Gln Leu Val Leu Gly Thr Lys Val Ser
        1475                1480                1485

Leu Val Glu Asn Ile His Val Leu Gly Lys Glu Gln Thr Ser Pro Glu
    1490                1495                1500

Asn Val Lys Met Glu Ile Gly Lys Thr Glu Ala Phe Ser Asp Val Pro
1505                1510                1515                1520

Val Lys Thr Asn Ile Glu Val Cys Ser Thr Tyr Ser Lys Asp Ser
                1525                1530                1535
```

(2) INFORMATION FOR SEQ ID NO:186:

(i) SEQUENCE CHARACTERISTICS:
(A) LENGTH: 1494 amino acids
(B) TYPE: amino acid
(D) TOPOLOGY: linear (xi) SEQUENCE DESCRIPTION: SEQ ID NO:186:

```
Ser Ser Ile Lys Lys Asn Cys Leu Gln Asn Asp Ser Glu Lys Pro Ala
1               5                   10                  15
```

-continued

```
Leu Ser Leu Thr Ser Ser Phe Gly Thr Ile Leu Arg Lys Val Ser Ser
            20                  25                  30

Asn Gly Ala Ser Ser Pro Asn Asn Lys Ile Ile Ser Gln Asp Pro Asp
        35                  40                  45

Tyr Lys Glu Ala Lys Ile Asn Lys Lys Lys Leu Glu Ser Phe Ile Thr
    50                  55                  60

Thr Glu Thr Asp Cys Leu Ser Ser Leu Gln Glu Lys His Trp Glu Asp
65                  70                  75                  80

Asp Ala Lys Lys Gln Arg Val Ser Asp Ile Lys Glu Lys Val Leu Pro
                85                  90                  95

Thr Val Ser His Pro Pro Val Pro His Ser Val Glu Gly Ser Asp Ile
            100                 105                 110

His Phe Gln Ser Pro Lys Ser Phe Ser Phe Asp Cys Asp Asn Thr Ser
        115                 120                 125

Leu Leu Thr Pro Ser Ser Arg Asp Ser Pro Ser Ser Leu Val Val Met
    130                 135                 140

Ser Arg Gly Lys Glu Ser Tyr Lys Ile Ser Glu Lys Leu Lys Cys Lys
145                 150                 155                 160

Asn His Glu Thr Gly Phe Glu Leu Thr Lys Asn Ile Pro Met Glu Lys
                165                 170                 175

Asn Gln Asp Ile His Val Leu Asn Ala Asp Ser Lys Asn Ala Lys Leu
            180                 185                 190

Leu Ser Thr Glu Lys His Ile Thr Val Ala Ser Ser Ser Val Lys Val
        195                 200                 205

Gln Phe Asn Gln Ala Asn Leu Thr Thr Ile Gln Lys Asp Gln Lys Glu
    210                 215                 220

Thr Thr Leu Ile Ser Lys Ile Thr Val Asn Pro Asn Ser Glu Glu Leu
225                 230                 235                 240

Phe Pro Asp Asp Glu Asn Asn Phe Val Leu Lys Ile Thr Asn Glu Ser
                245                 250                 255

Asn Thr Pro Val Leu Gly Asn Thr Lys Glu Leu His Asp Ser Asn Leu
            260                 265                 270

Cys Cys Val Arg Asp Ser Val Pro Lys Asn Ser Thr Met Val Val Cys
        275                 280                 285

Thr Asp Leu Asp Asp Lys Gln Thr Ala Lys Val Ser Ile Met Lys Asp
    290                 295                 300

Cys Tyr Ser Ser Ser Ile Asp Asp Leu Thr Glu Arg Asn Arg Ser Thr
305                 310                 315                 320

Lys Gln Gln Leu Lys Met Thr Leu Asp Gln Asp Ser Lys Ser Asp Ile
                325                 330                 335

Thr Ser Asp Ile Val Arg Lys Ser Asn Gly Asn Ser Asp Tyr Met Asp
            340                 345                 350

Asn Trp Ala Arg Leu Ser Asp Pro Ile Ser Asn His Ser Phe Glu Asn
        355                 360                 365

Gly Phe Lys Thr Ala Ser Asn Lys Glu Ile Lys Leu Ser Glu Asn Asn
    370                 375                 380

Ile Arg Lys Ser Lys Met Leu Phe Lys Asp Ile Glu Glu His Tyr Pro
385                 390                 395                 400

Thr Asn Leu Ala Cys Leu Glu Ile Val Asn Thr Ser Ser Leu Glu Ser
                405                 410                 415

Gln Lys Lys Pro Ser Lys Ser His Ala Leu Asp Pro Gln Ile Asn Ile
            420                 425                 430

Ile Ser Gly Phe Val Gln Asn Ser Thr Tyr Val Ser Asp Ser Glu Ser
```

-continued

```
        435                 440                 445

Gly His Thr Ala Pro Pro Thr Leu Ser Leu Lys Gln Asp Phe Asp Ser
    450                 455                 460

Asn Arg Asn Leu Thr Pro Ser Gln Lys Ala Glu Ile Thr Glu Leu Ser
465                 470                 475                 480

Thr Ile Leu Glu Glu Ser Gly Ser Gln Phe Glu Phe Thr Gln Phe Arg
                485                 490                 495

Lys Pro Ser His Ile Ile Gln Lys Asn Pro Phe Glu Met Pro Glu Asn
            500                 505                 510

Gln Leu Thr Ile Leu Asn Ser Thr Ser Lys Glu Trp Lys Asp Asp Asp
        515                 520                 525

Leu His Leu Thr Thr Asn Ala Pro Ser Ile Gln Val Asp Ser Lys Lys
    530                 535                 540

Ser Glu Gly Ile Ile Gly Gly Lys Gln Lys Phe Ala Cys Leu Ser Arg
545                 550                 555                 560

Thr Ser Cys Asn Arg Ser Ala Ser Gly Tyr Ser Thr Asp Lys Asn Glu
                565                 570                 575

Val Glu Phe Arg Gly Phe Tyr Ser Ala Arg Gly Thr Lys Leu Asn Val
            580                 585                 590

Gly Ser Glu Ala Leu Gln Lys Ala Lys Lys Leu Phe Ser Asp Leu Glu
        595                 600                 605

Asn Ile Asn Glu Glu Thr Ser Val Glu Val Asp Arg Ser Phe Ser Ser
    610                 615                 620

Ser Lys Tyr Asn Asp Ser Val Ser Met Ile Gln Ile Glu Asp Cys Asn
625                 630                 635                 640

Asp Lys Asn Asn Glu Pro Asn Asn Lys Cys Arg Leu Ile Leu Gln Asn
                645                 650                 655

Asn Ile Glu Met Thr Thr Asp Ile Phe Val Glu Glu Tyr Thr Glu Ser
            660                 665                 670

Tyr Arg Arg Asn Thr Glu Asn Glu Gly Asn Gln Cys Thr Asp Ala Gly
        675                 680                 685

Arg Asn Thr Cys Asn Ser Glu Ser Asp Gly Ser Asp Ser Ser Lys Asn
    690                 695                 700

Asp Thr Val Tyr Ile His Glu Glu Glu Asn Gly Leu Pro Cys Ile Asp
705                 710                 715                 720

Gln His Asn Ile Asp Leu Lys Leu Phe Ser Gln Phe Met Lys Glu Gly
                725                 730                 735

Asn Thr Gln Ile Lys Glu Gly Leu Ser Asp Leu Thr Cys Leu Val Met
            740                 745                 750

Lys Ala Glu Glu Thr Ser His Val Thr Met Ser Asn Lys Gln Gln Leu
        755                 760                 765

Thr Ala Asn Thr Gly Gln Asn Ile Lys Asp Phe Asp Thr Phe Tyr Leu
    770                 775                 780

Ser Phe Gln Thr Ala Ser Arg Lys Asn Ile Arg Val Ser Arg Glu Ser
785                 790                 795                 800

Leu Asn Lys Ala Arg Ser Leu Leu Asn Gln Lys Trp Thr Glu Glu Glu
                805                 810                 815

Leu Asn Asn Phe Ser Asp Ser Leu Asn Ser Glu Leu Leu Pro Gly Ile
            820                 825                 830

Asp Ile Lys Lys Thr Asp Ile Ser Asn His Glu Val Ile Glu Asn Thr
        835                 840                 845

Glu Arg Lys Asp Lys Ile Thr Lys Glu Ser Leu Ile Gly Thr Glu Asn
    850                 855                 860
```

-continued

```
Ile Leu Leu Ile Leu Gln Gln Arg Pro Glu Ser Lys Ile Lys Lys Ile
865                 870                 875                 880

Lys Glu Ser Ala Val Leu Gly Phe His Thr Ala Ser Gly Lys Lys Ile
                885                 890                 895

Glu Ile Thr Lys Glu Ser Leu Asp Lys Val Lys Asn Leu Phe Glu Glu
            900                 905                 910

Lys Glu Gln Asp Asn Ser Glu Ile Thr Asn Phe Ser His Arg Gly Ala
        915                 920                 925

Lys Met Ser Lys Asp Arg Glu Glu Cys Lys Asp Gly Arg Glu Leu Ala
    930                 935                 940

Cys Gly Thr Thr Glu Ile Thr Thr Thr Pro Glu Tyr Glu Glu Thr His
945                 950                 955                 960

Ser Ser Leu Glu Lys Lys Lys Val Ser Asn Glu Ile Ala Ala Leu Arg
                965                 970                 975

Pro Arg Leu Leu Ser Asp Asn Leu Tyr Lys Gln Thr Glu Asn Leu Lys
            980                 985                 990

Ile Ser Asp His Ala Ser Gln Lys Val Asp Val His Glu Asn Thr Glu
        995                 1000                1005

Lys Glu Thr Ala Lys Lys Pro Thr Met Tyr Thr Asn Gln Ser Thr Tyr
    1010                1015                1020

Ser Ala Ile Glu Asn Ser Pro Leu Thr Phe Thr Gln Asp Thr Glu Glu
1025                1030                1035                1040

Lys Phe Ser Val Ser Glu Ala Ser Leu Phe Glu Ala Lys Lys Trp Leu
                1045                1050                1055

Arg Glu Gly Glu Trp Asp Asp Gln Ser Glu Arg Ile Asn Ala Ala Lys
            1060                1065                1070

Val Asn Cys Lys Glu Tyr Pro Asp Asp Tyr Val Glu Asn Pro Ser Cys
        1075                1080                1085

Gly Asn Ser Ser Asn Ser Ala Ile Thr Glu Asn Asp Lys Asn His Leu
    1090                1095                1100

Ser Glu Lys Gln Gly Ser Thr Tyr Leu Ser Asn Ser Thr Met Ser Asn
1105                1110                1115                1120

Ser Tyr Ser Tyr His Pro Gly Phe Cys His Ser Ser Glu Val Tyr Asn
                1125                1130                1135

Lys Ser Glu Tyr Leu Ser Arg Ser Lys Ile Asp Asn Ser Gly Ile Glu
            1140                1145                1150

Pro Val Ile Lys Asn Ile Arg Glu Arg Lys Asn Ile Gly Phe Ser Glu
        1155                1160                1165

Ile Met Ser Pro Gly Arg Glu Ala Asp Thr Asp Pro Gln Ser Val Asn
    1170                1175                1180

Asp Ile Cys Val Glu Lys Leu Ala Thr Asn Ser Ser Cys Lys Asn Lys
1185                1190                1195                1200

Asn Thr Ala Ile Lys Val Ala Ile Ser Asp Ser Asn Asn Phe Asn Thr
                1205                1210                1215

Ile Gln Lys Leu Asn Ser Asp Ser Asn Asn Ser Val Pro Ala Tyr Ser
            1220                1225                1230

Thr Val Asn Ser Lys Arg Val Phe Val Ala His Gln Thr Lys Val Thr
        1235                1240                1245

Glu Gly Phe Thr Asp Asn Cys Ser Met Val Thr Lys Gln Asn Thr Lys
    1250                1255                1260

Ser Lys Ser Asp Thr Cys His Ala Glu Ile Val Ala Asp Tyr Pro Lys
1265                1270                1275                1280
```

-continued

```
Ala Leu Asp Asp Ser Glu Ala Ile Phe Asn Ser Leu Gly Ala Ile Glu
                1285                1290                1295

Cys Ser Pro Ser His Lys Val Phe Ala Asp Ile Gln Ser Glu Gln Thr
            1300                1305                1310

Ser Gln Leu Asn Gln Ser Met Ser Gly Leu Glu Lys Val Ser Glu Thr
        1315                1320                1325

Pro Pro Cys Gln Ile Asn Ser Lys Thr Ser Asp Arg Cys Glu Leu Pro
    1330                1335                1340

Arg Gly Lys Leu Pro Lys Ser Val Ser Tyr Thr Asn Ala Cys Gly Ile
1345                1350                1355                1360

Phe Ser Thr Ala Ser Gly Lys Ser Val Gln Val Ser Asp Ala Ala Ile
                1365                1370                1375

Gln Lys Ala Arg Glu Val Phe Ser Lys Leu Glu Asp Ser Ala Lys Gln
            1380                1385                1390

Leu Phe Pro Glu Val Leu Lys Asp Asn Glu Glu His Ser Glu Lys Phe
        1395                1400                1405

Thr Asn Glu Glu Asn Thr Val Ile Tyr Thr Ser Gln Asn Leu Leu Ser
    1410                1415                1420

Ser Ala Phe Ser Gly Phe Arg Thr Ala Ser Gly Lys Gln Val Pro Val
1425                1430                1435                1440

Ser Glu Ser Ala Leu Cys Lys Val Lys Gly Met Leu Glu Glu Phe Asn
                1445                1450                1455

Leu Ile Arg Thr Glu Ser Cys Leu Gln His Ser Ser Thr Ser Arg Gln
            1460                1465                1470

Asp Val Ser Lys Met Pro Pro Pro Ser Cys Ile Gly Lys Arg Thr Pro
        1475                1480                1485

Glu His Ser Arg Asn Ser
    1490
```

(2) INFORMATION FOR SEQ ID NO:187:

(i) SEQUENCE CHARACTERISTICS:
(A) LENGTH: 926 amino acids
(B) TYPE: amino acid
(D) TOPOLOGY: linear (xi) SEQUENCE DESCRIPTION: SEQ ID NO:187:

```
Gly Pro Gly Cys Phe Ser Ser Ser Lys Cys Asn Asp Ser Asp Val Ser
1               5                   10                  15

Ile Phe Lys Val Glu Asn Tyr Ser Ser Asp Lys Ser Ser Glu Lys Tyr
            20                  25                  30

Asn Lys Cys Gln Leu Ile Leu Lys Asn Asn Ile Glu Arg Thr Ala Asp
        35                  40                  45

Ile Phe Val Glu Glu Asn Thr Asp Gly Tyr Lys Arg Asn Thr Glu Asn
    50                  55                  60

Lys Asp Asn Lys Cys Thr Gly Leu Ala Ser Asn Leu Gly Gly Ser Trp
65                  70                  75                  80

Met Asp Ser Ala Ser Ser Lys Thr Asp Thr Val Tyr Met His Glu Asp
                85                  90                  95

Glu Thr Gly Leu Pro Phe Ile Asp His Asn Ile His Leu Lys Leu Pro
            100                 105                 110

Asn His Phe Met Lys Lys Gly Asn Thr Gln Ile Lys Glu Gly Leu Ser
        115                 120                 125

Asp Leu Thr Cys Leu Val Met Arg Ala Glu Glu Thr Phe His Ile Asn
    130                 135                 140
```

-continued

```
Thr Ser Asn Lys Gln Ser Thr Val Asn Lys Arg Ser Gln Lys Ile Lys
145                 150                 155                 160

Asp Phe Asp Val Phe Asp Leu Ser Phe Gln Ser Ala Ser Gly Lys Asn
                165                 170                 175

Ile Arg Val Ser Lys Glu Ser Leu Asn Lys Ala Val Asn Phe Phe Asp
            180                 185                 190

Glu Lys Cys Thr Glu Glu Glu Leu Asn Asn Phe Ser Asp Ser Ser Asn
        195                 200                 205

Ser Glu Ile Leu Pro Gly Ile Asn Ile Asn Lys Ile Asn Ile Ser Ser
    210                 215                 220

His Lys Glu Thr Asp Ser Asp Lys Asn Lys Leu Leu Lys Glu Ser Pro
225                 230                 235                 240

Val Gly Ile Glu Asn Gln Leu Leu Thr Leu Gln Gln Arg Ser Glu Cys
                245                 250                 255

Glu Ile Lys Lys Ile Glu Glu Pro Thr Met Leu Gly Phe His Thr Ala
            260                 265                 270

Ser Gly Lys Lys Val Lys Ile Ala Lys Glu Ser Leu Asp Lys Val Lys
        275                 280                 285

Asn Leu Phe Asp Glu Thr Lys Gln Asp Ser Ser Glu Thr Thr Asn Ser
    290                 295                 300

Ser His Gln Gly Val Lys Thr Gln Lys Asp Arg Glu Val Cys Lys Glu
305                 310                 315                 320

Glu Leu Glu Leu Thr Phe Glu Thr Val Glu Ile Thr Ala Ser Lys His
                325                 330                 335

Glu Glu Ile Arg Asn Phe Leu Glu Glu Lys Lys Val Ser Lys Glu Ile
            340                 345                 350

Thr Met Pro Pro Arg Leu Leu Arg His His Leu His Arg Gln Thr Glu
        355                 360                 365

Asn Leu Ser Met Ser Asn Ser Ile Pro Leu Lys Gly Lys Val His Glu
    370                 375                 380

Asn Met Glu Glu Glu Thr Ser Cys His Thr Asp Gln Ser Thr Cys Ser
385                 390                 395                 400

Ala Ile Glu Asn Ser Ala Leu Thr Phe Tyr Thr Gly His Gly Arg Lys
                405                 410                 415

Ile Ser Val Asn Gln Ala Ser Val Phe Glu Ala Lys Lys Trp Leu Arg
            420                 425                 430

Glu Gly Glu Leu Asp Asp Gln Pro Glu Asn Val Asp Ser Ala Lys Val
        435                 440                 445

Ile Cys Lys Glu Tyr Ala Arg Asp Tyr Val Gly Asn Pro Leu Cys Gly
    450                 455                 460

Ser Ser Ser Asn Ser Ile Ile Thr Glu Asn Asp Lys Asn Leu Pro Glu
465                 470                 475                 480

Lys Gln Asn Ser Thr Tyr Leu Ser Asn Ser Val Ser Asn Asn Tyr Ser
                485                 490                 495

Tyr His Ser Asp Phe Cys His Ser Asn Glu Val Leu Ser Lys Ser Glu
            500                 505                 510

Ser Leu Ser Glu Asn Lys Ile Gly Asn Ser Asp Thr Glu Pro Ala Val
        515                 520                 525

Lys Asn Val Lys Asp Arg Lys Asp Thr Cys Phe Ser Glu Glu Ile Ser
    530                 535                 540

Thr Val Arg Glu Ala Asn Thr His Pro Gln Ala Val Asp Asp Ser Trp
545                 550                 555                 560

Val Arg Lys Leu Val Ile Asn Ser Thr Pro Cys Lys Asn Lys Asn Thr
```

-continued

```
                565                 570                 575

Pro Gly Glu Val Ser Xaa Ser Asn Ser Asn Asn Phe Glu Ile Glu Pro
            580                 585                 590

Pro Ala Phe Ser Thr Ser Gly Asn Ile Ala Phe Val Ser His Glu Thr
        595                 600                 605

Asp Val Arg Glu Arg Phe Ala Asp Asn Asn Arg Lys Ala Ile Lys Gln
    610                 615                 620

Asn Thr Glu Ser Met Ser Gly Ser Cys Gln Met Lys Ile Met Thr Gly
625                 630                 635                 640

Ala His Lys Ala Leu Gly Asp Ser Glu Asp Val Ile Phe Asn Ser Pro
                645                 650                 655

Asp Ser Glu Glu His Ile Thr Arg Ser Gln Glu Val Phe Pro Glu Ile
            660                 665                 670

Gln Ser Glu Gln Ile Leu Gln His Asp Pro Ser Val Ser Gly Leu Glu
        675                 680                 685

Lys Val Ser Glu Met Pro Pro Cys His Ile Asn Leu Lys Thr Phe Asp
    690                 695                 700

Ile His Lys Phe Asp Met Lys Arg His Pro Met Ser Val Ser Ser Met
705                 710                 715                 720

Asn Asp Cys Gly Val Phe Ser Thr Ala Ser Gly Lys Ser Val Gln Val
                725                 730                 735

Ser Asp Thr Ala Leu Gln Lys Ala Arg Gln Val Phe Ser Lys Thr Glu
            740                 745                 750

Asp Val Ala Lys Pro Phe Phe Ser Arg Val Lys Ser Asp Glu Glu His
        755                 760                 765

Ser Asp Lys Tyr Thr Arg Glu Glu Asn Ala Met Met His Pro Pro Pro
    770                 775                 780

Asn Phe Leu Ser Ser Ala Phe Ser Gly Phe Ser Thr Ala Ser Gly Lys
785                 790                 795                 800

Gln Val Pro Val Ser Glu Ser Ala Leu Cys Lys Val Lys Gly Met Phe
                805                 810                 815

Glu Glu Phe Asp Leu Met Gly Thr Glu Cys Arg Leu Gln His Ser Pro
            820                 825                 830

Thr Ser Arg Gln Asp Val Ser Lys Ile Leu Pro Leu Ser Glu Ile Asp
        835                 840                 845

Glu Arg Thr Pro Glu His Ser Val Ser Ser Thr Glu Lys Ala Tyr Asn
    850                 855                 860

Glu Gln Phe Lys Leu Pro Asp Ser Cys Asn Thr Glu Ser Ser Ser Ser
865                 870                 875                 880

Glu Asn Asn His Ser Val Lys Val Ser Pro Asp Leu Ser Arg Phe Lys
                885                 890                 895

Gln Asp Lys Gln Leu Val Ser Gly Ala Lys Val Ser Leu Val Glu Asn
            900                 905                 910

Ile His Pro Ser Gly Lys Arg Thr Gln Thr Glu Asn Leu Lys
        915                 920                 925
```

(2) INFORMATION FOR SEQ ID NO:188:

(i) SEQUENCE CHARACTERISTICS:
(A) LENGTH: 1471 amino acids
(B) TYPE: amino acid
(D) TOPOLOGY: linear (xi) SEQUENCE DESCRIPTION: SEQ ID NO:188:

```
Lys Asn Cys Ser His Ile Gln Pro Trp Glu Thr Asp Cys Leu Ser Cys
```

-continued

```
1               5                   10                  15

Leu Pro Glu Arg Gln Cys Glu Tyr Asp Pro Lys Gly Pro Lys Val Ser
            20                  25                  30

Asp Gly Lys Glu Glu Val Leu Val Ser Ala Cys His Pro Ala Gly Gln
        35                  40                  45

His Thr Ala Ala Gln Pro Ser Ser Ile Ser Phe Glu Leu Gln Glu Asp
    50                  55                  60

Pro Val Asn Gly His Asn Ser Thr Ser Pro Lys Glu Thr Pro Ser Leu
65                  70                  75                  80

Lys Val Leu Leu Ser Lys Pro Val Val Leu Ser Arg Gly Lys Val Ser
                85                  90                  95

Cys Lys Met Pro Glu Lys Leu Gln Cys Glu Ser Tyr Lys Asp Asn Thr
            100                 105                 110

Glu Leu Ser Lys Ser Ile Pro Leu Gly Gly Asn Lys Ile His Ile Leu
        115                 120                 125

Ser Glu Asn Ser Lys Pro Pro Glu Leu Leu Pro Pro Gly Lys Tyr Val
    130                 135                 140

Thr Glu Ala Ser Pro Thr Val Lys Ser Gln Phe Asn Gln Thr Asn Leu
145                 150                 155                 160

Ala Val Lys Lys Asn Asp Gln Glu Glu Thr Pro Phe Ile Ser Glu Val
                165                 170                 175

Thr Val Asn Val Ser Ser Gly Glu Leu Phe Pro Asp Asn Glu Asn Asn
            180                 185                 190

Phe Ala Phe Gln Val Thr His Glu Asn Asn Lys Thr Ala Leu Gly Ser
        195                 200                 205

Thr Val Glu Leu Gln Glu Glu Asp Leu Arg His Ala Lys Gly Pro Asn
    210                 215                 220

Leu Asn Asn Ser Pro Thr Ala Val Asp Gly Asp Ile Gly Asp Glu Gln
225                 230                 235                 240

Ala Ala His Ala Leu Ile Met Glu Asp Ser Asp Ser Ser Ala Leu Val
                245                 250                 255

His Glu Cys Ala Lys Lys Ser Arg Asn Thr Glu Gln His Leu Lys Gly
            260                 265                 270

Thr Thr Asp Lys Asp Phe Asn Ser Ser Leu Asp Val Lys Ser Asp Gly
        275                 280                 285

Asn Asn Asp Tyr Thr Asp Lys Trp Pro Gly Phe Leu Asp Pro Val Phe
    290                 295                 300

Lys His Lys Phe Gly Gly Ser Phe Arg Thr Ala Ser Asn Lys Glu Ile
305                 310                 315                 320

Lys Leu Ser Glu His Asn Val Lys Lys Ser Lys Met Phe Phe Lys Asp
                325                 330                 335

Ile Glu Glu Glu Tyr Pro Thr Ser Leu Thr Cys Ile Asp Ile Val Asn
            340                 345                 350

Ala Ser Pro Leu Ala Asn Gln Glu Ile Leu Ser Gly Pro Tyr Thr Phe
        355                 360                 365

Asp Leu Gln Val Thr Thr Met Ser Ala His Pro Gln Ser Gln Ala Ser
    370                 375                 380

Val Ser Cys Glu Asp Thr His Thr Ser Leu Gln Val Leu Pro Ser Lys
385                 390                 395                 400

Gln Asp Phe His Ser Asn His Asn Leu Thr Pro Ser Gln Lys Ala Glu
                405                 410                 415

Ile Thr Glu Leu Ser Thr Ile Leu Glu Glu Ser Gly Ser Gln Phe Glu
            420                 425                 430
```

-continued

```
Phe Thr Gln Phe Lys Lys Pro Ser His Val Ala Gln Asn Asn Ile Pro
        435                 440                 445

Glu Val Pro Gly Lys Gln Thr Val Ala Ile Asn Thr Thr Ser Glu Gly
    450                 455                 460

Trp Lys Arg Ile Gly Leu His Leu Thr Val Asp Pro Ala Ser Val Gln
465                 470                 475                 480

Thr Asp Asp Ser Lys Lys Phe Glu Gly Ser Ala Gly Phe Arg Gln Ser
                485                 490                 495

Phe Pro Cys Leu Leu Lys Ser Ser Cys Asn Lys Asn Thr Ser Ser Phe
            500                 505                 510

Leu Ala Asn Val Asn Glu Met Glu Phe Arg Gly Phe Arg Ser Ala Leu
        515                 520                 525

Gly Thr Lys Leu Ser Val Ser Ser Glu Ala Leu Gln Lys Ala Val Lys
    530                 535                 540

Leu Phe Ser Asp Ile Glu Ser Gly Ser Glu Glu Thr Ser Thr Lys Val
545                 550                 555                 560

Asp Pro Arg Ala Leu Ser Ser Gly Ala Arg His Asp Ser Gly Ala Ser
                565                 570                 575

Val Phe Lys Ile Arg Lys Gln Asn Ser Gly Lys Ser Asp Glu Lys Thr
            580                 585                 590

Ser Lys Cys Gln Val Thr Leu Gln Asn Asn Thr Glu Val Thr Thr Gly
        595                 600                 605

Ile Phe Val Asp Arg Asn Pro Glu Asn Tyr Ala Arg Asn Thr Lys Cys
    610                 615                 620

Glu Asp Asn Asn Ser Thr Gly Phe Gln Arg Ser Pro Tyr Lys Leu Lys
625                 630                 635                 640

Asn Ser Glu Asp Ser Glu Ser Ser Thr Ser Gly Thr Val Ser Val His
                645                 650                 655

Gln Asp Asp Gly Asp Leu Pro Cys Ala Ala Asp His Cys Ser Lys Tyr
            660                 665                 670

Pro Glu Ser Cys Ser Gln Tyr Val Arg Glu Glu Asn Thr Gln Ile Lys
        675                 680                 685

Glu Cys Val Ser Asp Leu Thr Cys Leu Val Met Lys Ala Glu Glu Thr
    690                 695                 700

Cys Tyr Ile Gln Pro Ser Asp Lys Glu Gln Leu Pro Ser Gly Lys Met
705                 710                 715                 720

Glu Gln Asn Arg Lys Asp Phe Asn Ile Ser Phe Gln Thr Ala Ser Gly
                725                 730                 735

Lys Asn Val Arg Val Ser Glu Glu Ser Leu Ser Lys Ser Met Asn Ile
            740                 745                 750

Leu Asn Gln Val Thr Asp Glu Ser Ile Ile Ser Ser Asp Ser Leu Asn
        755                 760                 765

Ser Lys Phe His Cys Gly Thr Asn Asn Asn Lys Met Gly Ile Ser His
    770                 775                 780

His Lys Glu Thr Thr Ser Thr Lys Lys Val Phe Glu Glu Arg Pro Val
785                 790                 795                 800

Gly Thr Val Ser Gln Leu Pro Thr Leu Gln Gln His Pro Arg Cys Glu
                805                 810                 815

Ile Glu Ser Ile Lys Glu Pro Ala Leu Leu Gly Phe His Thr Ala Ser
            820                 825                 830

Gly Lys Lys Val Lys Ile Met Gln Lys Ser Leu Asp Lys Val Lys Asn
        835                 840                 845
```

-continued

```
Leu Phe Asp Glu Thr Gln Tyr Val Ser His Gln Gly Ser Lys Pro Leu
    850                 855                 860

Lys Asp Arg Glu Asn Cys Lys Glu Gly Leu Ala Leu Asp Val Arg Gln
865                 870                 875                 880

Leu Lys Tyr Leu Pro Pro Ser Val Glu Glu Met Gln Lys Ser Phe Leu
                885                 890                 895

Ser Lys Glu Ser Glu Val Leu Ser Lys Gln Ser Asp Arg Leu Tyr Arg
            900                 905                 910

Ser Thr Glu Asn Leu Arg Thr Ser Asn Gly Thr Ser Ser Lys Ala Asn
        915                 920                 925

Val His Gly Asn Ile Glu Ser Glu Ile Glu Lys Ser Pro Thr Thr Cys
    930                 935                 940

Cys Ile Ser His Leu Ser Tyr Ser Val Thr Glu Asp Ser Ala Leu Thr
945                 950                 955                 960

Cys Asp Thr Gly His Gly Arg Lys Thr Cys Val Ser Glu Ser Ser Leu
                965                 970                 975

Ser Lys Asp Arg Lys Trp Leu Arg Asp Gly Thr Gly Asp Lys Leu Gln
            980                 985                 990

Lys Arg Asp Ala Ala Glu Ile Glu Cys Lys Glu His Thr Glu Gly Tyr
        995                 1000                1005

Ala Gly Asp Ala Ser Cys Glu His Ser Leu Asp Ser Ile Arg Asn Glu
    1010                1015                1020

Val Asp Ile Asn Cys Val Ser Glu Asn Gln Thr Ser Ala Phe Phe Ser
1025                1030                1035                1040

Asp Pro Ser Met Cys His Ser Cys Pro Ser His Phe Gly Cys His Cys
                1045                1050                1055

Asp Asn Lys His Asn Asp Ser Gly Tyr Phe Ser Lys Asn Lys Ile Tyr
            1060                1065                1070

Ser Asp Thr Gln Pro Asp Thr Lys Asn Glu Asp Thr Ala Asn Phe Ser
        1075                1080                1085

Ser Val Tyr Ala Thr Lys Glu Val Asn Ile Tyr Pro Pro Thr Val Asn
    1090                1095                1100

Asp Ile Cys Val Gln Lys Leu Glu Thr Asn Ser Ser Pro His Thr Asn
1105                1110                1115                1120

Lys Asn Val Ala Ile Asp Leu Ala Ile Ala Asp Ser Arg Asn Cys Lys
                1125                1130                1135

Val Cys Pro Ser Lys Phe Ile Thr Asp His Ser Gln Glu Thr Val Lys
            1140                1145                1150

Thr Val Lys Ala Ile Phe Thr His Asn Ser Asp Lys Thr Ile Lys Gln
        1155                1160                1165

Asn Thr Lys Ser Lys Pro Asp Thr Cys Arg Thr Ser Cys Gln Lys Ala
    1170                1175                1180

Leu Asp Asn Ser Glu Asp Phe Ile Cys Ala Leu Arg Asp Asp Tyr Met
1185                1190                1195                1200

Asn Ser His Lys Ile Leu Phe Ile Thr His Asp Glu Gln Ile Leu Gln
                1205                1210                1215

His Asn Leu Ser Val Ser Gly Leu Glu Lys Ala Gln Ile Pro Pro Val
            1220                1225                1230

His Leu Glu Thr Trp Asp Lys Cys Lys Ser Thr Arg Glu Leu Ala Gln
        1235                1240                1245

Ala Ala Cys Ser Ser His Met Pro Gly Ile Phe Ser Thr Ala Ser Gly
    1250                1255                1260

Lys Ala Val Gln Val Ser Asp Ala Ser Leu Glu Lys Ala Arg Gln Val
```

-continued

```
1265                1270                1275                1280

Phe Ser Glu Met Asp Gly Gly Ala Lys Gln Leu Leu Ser Thr Leu Leu
                1285                1290                1295

Glu Ser His Glu Gln Ser Asp His Ser Gly Arg Arg Glu Asn Ser Val
            1300                1305                1310

Thr His Asn Pro Glu Asp Val Leu Ser Leu Pro Lys Thr Phe Ala Ser
        1315                1320                1325

Asn Ala Asn Ser Ser Val Phe Ser Gly Phe Ser Thr Ala Gly Gly Lys
    1330                1335                1340

Arg Val Thr Val Ser Glu Ser Ala Leu His Lys Val Lys Gly Met Leu
1345                1350                1355                1360

Glu Glu Phe Asp Leu Ile Gly Thr Glu His Thr Leu Gln Cys Pro Pro
                1365                1370                1375

Thr Ser Glu Gly Val Ser Lys Ile Leu Pro Gln Tyr Cys Val Glu Lys
            1380                1385                1390

Arg Thr Pro Glu Tyr Pro Ile Asn Ser Leu Gln Lys Thr Tyr Asp Asp
        1395                1400                1405

Lys Phe Ser Leu Pro Asn Asn Tyr Lys Glu Ser Ala Ser Leu Gly Asn
    1410                1415                1420

Thr His Ser Leu Glu Ala Ser Pro Gln Leu Ser Gln Phe Lys Gln Asp
1425                1430                1435                1440

Thr Arg Leu Val Leu Gly Thr Lys Val Ser Leu Leu Glu Lys Glu Gln
                1445                1450                1455

Thr Phe Pro Gln Asn Ile Lys Thr Glu Ser Gly Val Met Glu Thr
            1460                1465                1470
```

(2) INFORMATION FOR SEQ ID NO:189:

(i) SEQUENCE CHARACTERISTICS:
(A) LENGTH: 1589 amino acids
(B) TYPE: amino acid
(D) TOPOLOGY: linear (xi) SEQUENCE DESCRIPTION: SEQ ID NO:189:

```
Ile Pro Asp Ser Ser Asp Lys Lys Arg Cys Leu Pro Asn Asp Pro Glu
1               5                   10                  15

Glu Pro Ser Leu Thr Asn Ser Phe Gly Thr Ala Thr Ser Lys Glu Ile
            20                  25                  30

Ser Tyr Ile His Ala Leu Ile Ser Gln Asp Leu Asn Asp Lys Glu Ala
        35                  40                  45

Ile Val Ile Glu Glu Lys Pro Gln Pro Tyr Thr Ala Arg Glu Ala Asp
    50                  55                  60

Phe Leu Leu Cys Leu Pro Glu Arg Thr Cys Glu Asn Asp Gln Lys Ser
65                  70                  75                  80

Pro Lys Val Ser Asn Gly Lys Glu Lys Val Leu Val Ser Ala Cys Leu
                85                  90                  95

Pro Ser Ala Val Gln Leu Ser Ser Ile Ser Phe Glu Ser Gln Glu Asn
            100                 105                 110

Pro Leu Gly Asp His Asn Gly Thr Ser Thr Leu Lys Leu Thr Pro Ser
        115                 120                 125

Ser Lys Leu Pro Leu Ser Lys Ala Asp Met Val Ser Arg Glu Lys Met
    130                 135                 140

Cys Lys Met Pro Glu Lys Leu Gln Cys Glu Ser Cys Lys Val Asn Ile
145                 150                 155                 160

Glu Leu Ser Lys Asn Ile Leu Glu Val Asn Glu Ile Cys Ile Leu Ser
```

-continued

```
                165                 170                 175

Glu Asn Ser Lys Thr Pro Gly Leu Leu Pro Pro Gly Glu Asn Ile Ile
            180                 185                 190

Glu Val Ala Ser Ser Met Lys Ser Gln Phe Asn Gln Ala Lys Ile Val
        195                 200                 205

Ile Gln Lys Asp Gln Lys Gly Ser Pro Phe Ile Ser Glu Val Ala Val
    210                 215                 220

Asn Met Asn Ser Glu Glu Leu Phe Pro Asp Ser Gly Asn Asn Phe Ala
225                 230                 235                 240

Phe Gln Val Thr Asn Lys Cys Asn Lys Pro Asp Leu Gly Ser Ser Val
                245                 250                 255

Glu Leu Gln Glu Glu Asp Leu Ser His Thr Gln Gly Pro Ser Leu Lys
            260                 265                 270

Asn Ser Pro Met Ala Val Asp Glu Asp Val Asp Asp Ala His Ala Ala
        275                 280                 285

Gln Val Leu Ile Thr Lys Asp Ser Asp Ser Leu Ala Val Val His Asp
    290                 295                 300

Tyr Thr Glu Lys Ser Arg Asn Asn Glu Gln His Gln Lys Gly Thr Glu
305                 310                 315                 320

Asp Lys Asp Phe Lys Ser Asn Ser Ser Leu Asn Met Lys Ser Asp Gly
                325                 330                 335

Asn Ser Asp Cys Ser Asp Lys Trp Ser Glu Phe Leu Asp Pro Val Leu
            340                 345                 350

Asn His Asn Phe Gly Gly Ser Phe Arg Thr Ala Ser Asn Lys Glu Ile
        355                 360                 365

Lys Leu Ser Glu His Asn Val Lys Lys Ser Lys Met Phe Phe Lys Asp
    370                 375                 380

Ile Glu Glu Gln Tyr Pro Thr Arg Leu Ala Cys Ile Asp Ile Val Asn
385                 390                 395                 400

Thr Leu Pro Leu Ala Asn Gln Lys Lys Ile Ser Glu Pro His Ile Phe
                405                 410                 415

Asp Leu Lys Val Thr Thr Val Ser Thr Gln Ser His Asn Gln Ser Ser
            420                 425                 430

Val Ser His Glu Asp Thr Asp Thr Ala Pro Gln Met Leu Ser Ser Lys
        435                 440                 445

Gln Asp Phe His Ser Asn Asn Leu Thr Thr Ser Gln Lys Ala Glu Ile
    450                 455                 460

Thr Glu Leu Ser Thr Ile Leu Glu Glu Ser Gly Ser Gln Phe Glu Phe
465                 470                 475                 480

Thr Gln Phe Arg Lys Pro Ser His Ile Ala Gln Asn Thr Ser Glu Val
                485                 490                 495

Pro Gly Asn Gln Met Val Val Leu Ser Thr Ala Ser Lys Glu Trp Lys
            500                 505                 510

Asp Thr Asp Leu His Leu Pro Val Asp Pro Ser Val Gln Thr Asp His
        515                 520                 525

Ser Lys Gln Phe Glu Gly Ser Ala Gly Val Lys Gln Ser Phe Pro His
    530                 535                 540

Leu Leu Glu Asp Thr Cys Asn Lys Asn Thr Ser Cys Phe Leu Pro Asn
545                 550                 555                 560

Ile Asn Glu Met Glu Phe Gly Gly Phe Cys Ser Ala Leu Gly Thr Lys
                565                 570                 575

Leu Ser Val Ser Asn Glu Ala Leu Arg Lys Ala Met Lys Leu Phe Ser
            580                 585                 590
```

-continued

```
Asp Ile Glu Asn Ser Glu Glu Pro Ser Ala Lys Val Gly Pro Arg Gly
        595                 600                 605

Phe Ser Ser Ser Ala His His Asp Ser Val Ala Ser Val Phe Lys Ile
    610                 615                 620

Lys Lys Gln Asn Thr Glu Lys Ser Asp Glu Lys Ser Ser Lys Cys Gln
625                 630                 635                 640

Val Thr Leu Gln Asn Asn Ile Glu Met Thr Thr Cys Ile Phe Val Gly
                645                 650                 655

Arg Asn Pro Glu Lys Tyr Ile Lys Asn Thr Lys His Glu Asp Ser Tyr
            660                 665                 670

Thr Ser Ser Gln Arg Asn Asn Leu Glu Asn Ser Asp Gly Ser Met Ser
        675                 680                 685

Ser Thr Ser Gly Pro Val Tyr Ile His Lys Gly Asp Ser Asp Leu Pro
    690                 695                 700

Ala Asp Gln Gly Ser Lys Cys Pro Glu Ser Cys Thr Gln Tyr Ala Arg
705                 710                 715                 720

Glu Glu Asn Thr Gln Ile Lys Glu Asn Ile Ser Asp Leu Thr Cys Leu
                725                 730                 735

Ile Met Lys Ala Glu Glu Thr Cys Met Lys Ser Ser Asp Lys Lys Gln
            740                 745                 750

Leu Pro Ser Asp Lys Met Glu Gln Asn Ile Lys Glu Phe Asn Ile Ser
        755                 760                 765

Phe Gln Thr Ala Ser Gly Lys Asn Thr Arg Val Ser Lys Glu Ser Leu
    770                 775                 780

Asn Lys Ser Val Asn Ile Phe Asn Arg Glu Thr Asp Glu Leu Thr Val
785                 790                 795                 800

Ile Ser Asp Ser Leu Asn Ser Lys Ile Leu His Gly Ile Asn Lys Asp
                805                 810                 815

Lys Met His Thr Ser Cys His Lys Lys Ala Ile Ser Ile Lys Lys Val
            820                 825                 830

Phe Glu Asp His Pro Ile Val Thr Val Ser Gln Leu Pro Ala Gln Gln
        835                 840                 845

His Pro Glu Tyr Glu Ile Glu Ser Thr Lys Glu Pro Thr Leu Leu Ser
    850                 855                 860

Phe His Thr Ala Ser Gly Lys Lys Val Lys Ile Met Gln Glu Ser Leu
865                 870                 875                 880

Asp Lys Val Lys Asn Leu Phe Asp Glu Thr Gln Tyr Val Arg Lys Thr
                885                 890                 895

Ala Ser Phe Ser Gln Gly Ser Lys Pro Leu Lys Asp Ser Lys Lys Glu
            900                 905                 910

Leu Thr Leu Ala Tyr Glu Lys Ile Glu Val Thr Ala Ser Lys Cys Glu
        915                 920                 925

Glu Met Gln Asn Phe Val Ser Lys Glu Thr Glu Met Leu Pro Gln Gln
    930                 935                 940

Asn Tyr His Met Tyr Arg Gln Thr Glu Asn Leu Lys Thr Ser Asn Gly
945                 950                 955                 960

Thr Ser Ser Lys Val Gln Glu Asn Ile Glu Asn Asn Val Glu Lys Asn
                965                 970                 975

Pro Arg Ile Cys Cys Ile Cys Gln Ser Ser Tyr Pro Val Thr Glu Asp
            980                 985                 990

Ser Ala Leu Ala Tyr Tyr Thr Glu Asp Ser Arg Lys Thr Cys Val Arg
        995                 1000                1005
```

-continued

```
Glu Ser Ser Leu Ser Lys Gly Arg Lys Trp Leu Arg Glu Gln Gly Asp
    1010                1015                1020

Lys Leu Gly Thr Arg Asn Thr Ile Lys Ile Glu Cys Lys Glu His Thr
1025                1030                1035                1040

Glu Asp Phe Ala Gly Asn Ala Ser Tyr Glu His Ser Leu Val Ile Ile
                1045                1050                1055

Arg Thr Glu Ile Asp Thr Asn His Val Ser Glu Asn Gln Val Ser Thr
            1060                1065                1070

Leu Leu Ser Asp Pro Asn Val Cys His Ser Tyr Leu Ser Gln Ser Ser
        1075                1080                1085

Phe Cys His Cys Asp Asp Met His Asn Asp Ser Gly Tyr Phe Leu Lys
    1090                1095                1100

Asn Lys Ile Asp Ser Asp Val Pro Pro Asp Met Lys Asn Ala Glu Gly
1105                1110                1115                1120

Asn Thr Ile Ser Pro Arg Val Ser Ala Thr Lys Glu Arg Asn Leu His
                1125                1130                1135

Pro Gln Thr Ile Asn Tyr Cys Val Gln Lys Leu Glu Thr Asn Thr Ser
            1140                1145                1150

Pro His Ala Asn Lys Asp Val Ala Ile Asp Pro Ser Leu Leu Asp Ser
        1155                1160                1165

Arg Asn Cys Lys Val Gly Ser Leu Val Phe Ile Thr Ala His Ser Gln
    1170                1175                1180

Glu Thr Glu Arg Thr Lys Glu Ile Val Thr Asp Asn Cys Tyr Lys Ile
1185                1190                1195                1200

Val Glu Gln Asn Arg Gln Ser Lys Pro Asp Thr Cys Gln Thr Ser Cys
                1205                1210                1215

His Lys Val Leu Asp Asp Ser Lys Asp Phe Ile Cys Ser Ser Ser Gly
            1220                1225                1230

Asp Val Cys Ile Asn Ser Arg Lys Asp Ser Phe Cys Pro His Asn Glu
        1235                1240                1245

Gln Ile Leu Gln His Asn Gln Ser Met Ser Gly Leu Lys Lys Ala Ala
    1250                1255                1260

Thr Pro Pro Val Gly Leu Glu Thr Trp Asp Thr Ser Lys Ser Ile Arg
1265                1270                1275                1280

Glu Pro Pro Gln Ala Ala His Pro Ser Arg Thr Tyr Gly Ile Phe Ser
                1285                1290                1295

Thr Ala Ser Gly Lys Ala Ile Gln Val Ser Asp Ala Ser Leu Glu Lys
            1300                1305                1310

Ala Arg Gln Val Phe Ser Glu Met Asp Gly Asp Ala Lys Gln Leu Ser
        1315                1320                1325

Ser Met Val Leu Glu Gly Asn Glu Lys Pro His His Ser Val Lys Arg
    1330                1335                1340

Glu Asn Ser Val Val His Ser Thr Gln Gly Val Leu Ser Leu Pro Lys
1345                1350                1355                1360

Pro Leu Pro Gly Asn Val Asn Ser Ser Val Phe Ser Gly Phe Ser Thr
                1365                1370                1375

Ala Gly Gly Lys Leu Val Thr Val Ser Glu Ser Ala Leu His Lys Val
            1380                1385                1390

Lys Gly Met Leu Glu Glu Phe Asp Leu Ile Arg Thr Glu His Thr Leu
        1395                1400                1405

Gln His Ser Pro Ile Pro Glu Asp Val Ser Lys Ile Leu Pro Gln Pro
    1410                1415                1420

Cys Ala Glu Ile Arg Thr Pro Glu Tyr Pro Val Asn Ser Leu Gln Lys
```

-continued

```
1425                1430                1435                1440

Thr Tyr Asn Asp Lys Ser Ser Leu Pro Ser Asn Tyr Lys Glu Ser Gly
                1445                1450                1455

Ser Ser Gly Asn Thr Gln Ser Ile Glu Val Ser Leu Gln Leu Ser Gln
            1460                1465                1470

Met Glu Arg Asn Gln Asp Thr Gln Leu Val Leu Gly Thr Lys Val Ser
        1475                1480                1485

His Ser Lys Ala Asn Leu Leu Gly Lys Glu Gln Thr Leu Pro Gln Asn
    1490                1495                1500

Ile Lys Val Lys Thr Asp Glu Met Lys Thr Phe Ser Asp Val Pro Val
1505                1510                1515                1520

Lys Thr Asn Val Gly Glu Tyr Tyr Ser Lys Glu Ser Glu Asn Tyr Phe
                1525                1530                1535

Glu Thr Glu Ala Val Glu Ala Lys Ala Phe Met Glu Asp Asp Glu Leu
            1540                1545                1550

Thr Asp Ser Glu Gln Thr His Ala Lys Cys Ser Leu Phe Thr Cys Pro
        1555                1560                1565

Gln Asn Glu Thr Leu Phe Asn Ser Arg Thr Arg Lys Arg Arg Arg Met
    1570                1575                1580

Thr Val Asp Ala Val
1585
```

(2) INFORMATION FOR SEQ ID NO:190:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:190:

CCCTTTCGGT AA 12

(2) INFORMATION FOR SEQ ID NO:191:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:191:

CATAACTCTC TA 12

(2) INFORMATION FOR SEQ ID NO:192:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:192:

AAAACTGAAA CT 12

(2) INFORMATION FOR SEQ ID NO:193:

(i) SEQUENCE CHARACTERISTICS:
(A) LENGTH: 12 base pairs
(B) TYPE: nucleic acid
(C) STRANDEDNESS: single
(D) TOPOLOGY: linear -continued (xi) SEQUENCE DESCRIPTION: SEQ ID NO:193:

GATAAACAAG CA 12

(2) INFORMATION FOR SEQ ID NO:194:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:194:

CATTGGAGGA ATATCGTAGG 20

(2) INFORMATION FOR SEQ ID NO:195:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:195:

GACAGAGAAT CAGCTTCTGG 20

(2) INFORMATION FOR SEQ ID NO:196:

(i) SEQUENCE CHARACTERISTICS:
(A) LENGTH: 48 base pairs
(B) TYPE: nucleic acid
(C) STRANDEDNESS: double
(D) TOPOLOGY: linear (xi) SEQUENCE DESCRIPTION: SEQ ID NO:196:

GTACCGCCGC CATGGAACAG AAGATTTCCG AAGAAGATCT GCCTATTG 48

(2) INFORMATION FOR SEQ ID NO:197:

(i) SEQUENCE CHARACTERISTICS:
(A) LENGTH: 48 base pairs
(B) TYPE: nucleic acid
(C) STRANDEDNESS: double
(D) TOPOLOGY: linear (xi) SEQUENCE DESCRIPTION: SEQ ID NO:197:

GATCCAATAG GCAGATCTTC TTCGGAAATC TTCTGTTCCA TGGCGGCG 48

(2) INFORMATION FOR SEQ ID NO:198:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:198:

AAAAGTAACG AACATTCAGA CCA 23

(2) INFORMATION FOR SEQ ID NO:199:

(i) SEQUENCE CHARACTERISTICS:
(A) LENGTH: 20 base pairs
(B) TYPE: nucleic acid
(C) STRANDEDNESS: single
(D) TOPOLOGY: linear -continued (xi) SEQUENCE DESCRIPTION: SEQ ID NO:199:

ATTGTCGCCT TTGCAAATGC 20

(2) INFORMATION FOR SEQ ID NO:200:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:200:

GTACTCCAGA ACATTTAATA TCC 23

(2) INFORMATION FOR SEQ ID NO:201:

(i) SEQUENCE CHARACTERISTICS:
(A) LENGTH: 50 base pairs
(B) TYPE: nucleic acid
(C) STRANDEDNESS: double
(D) TOPOLOGY: linear (xi) SEQUENCE DESCRIPTION: SEQ ID NO:201:

CGGGTACCAG ATCTGCCGCC ACCATGGATT ACAAGGACGA CGATGACAAG 50

(2) INFORMATION FOR SEQ ID NO:202:

(i) SEQUENCE CHARACTERISTICS:
(A) LENGTH: 58 base pairs
(B) TYPE: nucleic acid
(C) STRANDEDNESS: double
(D) TOPOLOGY: linear (xi) SEQUENCE DESCRIPTION: SEQ ID NO:202:

GATCCTTGTC ATCGTCGTCC TTGTAATCCA TGGTGGCGGC AGATCTGGTA CCCGAGCT 58

(2) INFORMATION FOR SEQ ID NO:203:

(i) SEQUENCE CHARACTERISTICS:
(A) LENGTH: 37 base pairs
(B) TYPE: nucleic acid
(C) STRANDEDNESS: single
(D) TOPOLOGY: linear (xi) SEQUENCE DESCRIPTION: SEQ ID NO:203:

GGATCCTAAT ACGACTCACT ATAGGGAGAC CACCATG 37

(2) INFORMATION FOR SEQ ID NO:204:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:204:

AAAGCTGTGA AACTGTT 17

(2) INFORMATION FOR SEQ ID NO:205:

(i) SEQUENCE CHARACTERISTICS:
(A) LENGTH: 17 base pairs
(B) TYPE: nucleic acid
(C) STRANDEDNESS: single
(D) TOPOLOGY: linear (ix) FEATURE:

-continued (A) NAME/KEY: misc_feature
(B) LOCATION: 6
(D) OTHER INFORMATION: /note= "N is i"

(ix) FEATURE:
(A) NAME/KEY: misc_feature
(B) LOCATION: 7
(D) OTHER INFORMATION: /note= "N is i"

(ix) FEATURE:
(A) NAME/KEY: misc_feature
(B) LOCATION: 8
(D) OTHER INFORMATION: /note= "N is i"

(ix) FEATURE:
(A) NAME/KEY: misc_feature
(B) LOCATION: 9
(D) OTHER INFORMATION: /note= "N is i"

(ix) FEATURE:
(A) NAME/KEY: misc_feature
(B) LOCATION: 15
(D) OTHER INFORMATION: /note= "N is i"

(xi) SEQUENCE DESCRIPTION: SEQ ID NO:205:

AARGCNNNNA ARCTNTT 17

(2) INFORMATION FOR SEQ ID NO:206:

(i) SEQUENCE CHARACTERISTICS:
(A) LENGTH: 17 base pairs
(B) TYPE: nucleic acid
(C) STRANDEDNESS: single
(D) TOPOLOGY: linear (ix) FEATURE:
(A) NAME/KEY: misc_feature
(B) LOCATION: 6
(D) OTHER INFORMATION: /note= "N is i"

(ix) FEATURE:
(A) NAME/KEY: misc_feature
(B) LOCATION: 7
(D) OTHER INFORMATION: /note= "N is i"

(ix) FEATURE:
(A) NAME/KEY: misc_feature
(B) LOCATION: 8
(D) OTHER INFORMATION: /note= "N is i"

(ix) FEATURE:
(A) NAME/KEY: misc_feature
(B) LOCATION: 9
(D) OTHER INFORMATION: /note= "N is i"

(xi) SEQUENCE DESCRIPTION: SEQ ID NO:206:

AARGCNNNNA ARTTRTT 17

(2) INFORMATION FOR SEQ ID NO:207:

(i) SEQUENCE CHARACTERISTICS:
(A) LENGTH: 17 base pairs
(B) TYPE: nucleic acid
(C) STRANDEDNESS: single
(D) TOPOLOGY: linear (ix) FEATURE:
(A) NAME/KEY: misc_feature
(B) LOCATION: 6
(D) OTHER INFORMATION: /note= "N is i"

(ix) FEATURE:
(A) NAME/KEY: misc_feature
(B) LOCATION: 9
(D) OTHER INFORMATION: /note= "N is i"

-continued (ix) FEATURE:
(A) NAME/KEY: misc_feature
(B) LOCATION: 15
(D) OTHER INFORMATION: /note= "N is i"

(xi) SEQUENCE DESCRIPTION: SEQ ID NO:207:

AARGCNGTNA ARCTNTT 17

(2) INFORMATION FOR SEQ ID NO:208:

(i) SEQUENCE CHARACTERISTICS:
(A) LENGTH: 17 base pairs
(B) TYPE: nucleic acid
(C) STRANDEDNESS: single
(D) TOPOLOGY: linear (ix) FEATURE:
(A) NAME/KEY: misc_feature
(B) LOCATION: 6
(D) OTHER INFORMATION: /note= "N is i"

(ix) FEATURE:
(A) NAME/KEY: misc_feature
(B) LOCATION: 9
(D) OTHER INFORMATION: /note= "N is i"

(xi) SEQUENCE DESCRIPTION: SEQ ID NO:208:

AARGCNGTNA ARTTRTT 17

(2) INFORMATION FOR SEQ ID NO:209:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:209:

TTCCCACTTG CAGTCTGAAA 20

(2) INFORMATION FOR SEQ ID NO:210:

(i) SEQUENCE CHARACTERISTICS:
(A) LENGTH: 19 base pairs
(B) TYPE: nucleic acid
(C) STRANDEDNESS: single
(D) TOPOLOGY: linear (ix) FEATURE:
(A) NAME/KEY: misc_feature
(B) LOCATION: 2
(D) OTHER INFORMATION: /note= "N is i"

(ix) FEATURE:
(A) NAME/KEY: misc_feature
(B) LOCATION: 8
(D) OTHER INFORMATION: /note= "N is i"

(ix) FEATURE:
(A) NAME/KEY: misc_feature
(B) LOCATION: 11
(D) OTHER INFORMATION: /note= "N is i"

(xi) SEQUENCE DESCRIPTION: SEQ ID NO:210:

TNCCRCTNGC NGTYTGRAA 19

(2) INFORMATION FOR SEQ ID NO:211:

(i) SEQUENCE CHARACTERISTICS:
(A) LENGTH: 20 base pairs

-continued (B) TYPE: nucleic acid
(C) STRANDEDNESS: single
(D) TOPOLOGY: linear (ix) FEATURE:
(A) NAME/KEY: misc_feature
(B) LOCATION: 3
(D) OTHER INFORMATION: /note= "N is i"

(ix) FEATURE:
(A) NAME/KEY: misc_feature
(B) LOCATION: 6
(D) OTHER INFORMATION: /note= "N is i"

(ix) FEATURE:
(A) NAME/KEY: misc_feature
(B) LOCATION: 9
(D) OTHER INFORMATION: /note= "N is i"

(ix) FEATURE:
(A) NAME/KEY: misc_feature
(B) LOCATION: 12
(D) OTHER INFORMATION: /note= "N is i"

(xi) SEQUENCE DESCRIPTION: SEQ ID NO:211:

TTNCCNGANG CNGTYTGRAA 20

(2) INFORMATION FOR SEQ ID NO:212:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:212:

AGCAAGCAAT TTCAAGG 17

(2) INFORMATION FOR SEQ ID NO:213:

(i) SEQUENCE CHARACTERISTICS:
(A) LENGTH: 17 base pairs
(B) TYPE: nucleic acid
(C) STRANDEDNESS: single
(D) TOPOLOGY: linear (ix) FEATURE:
(A) NAME/KEY: misc_feature
(B) LOCATION: 3
(D) OTHER INFORMATION: /note= "N is i"

(xi) SEQUENCE DESCRIPTION: SEQ ID NO:213:

TCNAARCART TYGARGG 17

(2) INFORMATION FOR SEQ ID NO:214:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:214:

AGYAARCART TYGARGG 17

(2) INFORMATION FOR SEQ ID NO:215:

(i) SEQUENCE CHARACTERISTICS:
(A) LENGTH: 26 amino acids
(B) TYPE: amino acid
(D) TOPOLOGY: linear -continued (xi) SEQUENCE DESCRIPTION: SEQ ID NO:215:

Ser Phe Arg Thr Ala Ser Asn Lys Glu Ile Lys Leu Ser Glu His Asn
1 5 10 15

Ile Lys Lys Ser Lys Met Phe Phe Lys Asp
20 25

(2) INFORMATION FOR SEQ ID NO:216:

(i) SEQUENCE CHARACTERISTICS:
(A) LENGTH: 26 amino acids
(B) TYPE: amino acid
(D) TOPOLOGY: linear (xi) SEQUENCE DESCRIPTION: SEQ ID NO:216:

Gly Phe Tyr Ser Ala Leu Gly Thr Lys Leu Asn Val Ser Ser Glu Ala
1 5 10 15

Leu Gln Lys Ala Val Lys Leu Phe Ser Asp
20 25

(2) INFORMATION FOR SEQ ID NO:217:

(i) SEQUENCE CHARACTERISTICS:
(A) LENGTH: 26 amino acids
(B) TYPE: amino acid
(D) TOPOLOGY: linear (xi) SEQUENCE DESCRIPTION: SEQ ID NO:217:

Ser Phe Gln Thr Ala Ser Gly Lys Asn Ile Arg Val Ser Lys Glu Ser
1 5 10 15

Leu Asn Lys Ala Val Asn Phe Phe Asp Gln
20 25

(2) INFORMATION FOR SEQ ID NO:218:

(i) SEQUENCE CHARACTERISTICS:
(A) LENGTH: 26 amino acids
(B) TYPE: amino acid
(D) TOPOLOGY: linear (xi) SEQUENCE DESCRIPTION: SEQ ID NO:218:

Gly Phe His Thr Ala Ser Gly Lys Lys Val Lys Ile Ala Lys Glu Ser
1 5 10 15

Leu Asp Lys Val Lys Asn Leu Phe Asp Glu
20 25

(2) INFORMATION FOR SEQ ID NO:219:

(i) SEQUENCE CHARACTERISTICS:
(A) LENGTH: 26 amino acids
(B) TYPE: amino acid
(D) TOPOLOGY: linear (xi) SEQUENCE DESCRIPTION: SEQ ID NO:219:

Ala Phe Tyr Thr Gly His Ser Arg Lys Thr Ser Val Ser Glu Ala Ser
1 5 10 15

Leu Leu Glu Ala Lys Lys Trp Leu Arg Glu
20 25

(2) INFORMATION FOR SEQ ID NO:220:

(i) SEQUENCE CHARACTERISTICS:
(A) LENGTH: 15 amino acids
(B) TYPE: amino acid

-continued

```
        (D) TOPOLOGY: linear

    (xi) SEQUENCE DESCRIPTION: SEQ ID NO:220:

Ala Phe Ser Thr Ala Ser Gly Lys Ile Val Phe Val Ser His Glu
1               5                   10                  15


(2) INFORMATION FOR SEQ ID NO:221:

     (i) SEQUENCE CHARACTERISTICS:
          (A) LENGTH: 26 amino acids
          (B) TYPE: amino acid
          (D) TOPOLOGY: linear

    (xi) SEQUENCE DESCRIPTION: SEQ ID NO:221:

Ile Phe Ser Thr Ala Ser Gly Lys Ser Val Gln Val Ser Asp Ala Ser
1               5                   10                  15

Leu Gln Lys Ala Arg Gln Val Phe Ser Glu
            20                  25


(2) INFORMATION FOR SEQ ID NO:222:

     (i) SEQUENCE CHARACTERISTICS:
          (A) LENGTH: 26 amino acids
          (B) TYPE: amino acid
          (D) TOPOLOGY: linear

    (xi) SEQUENCE DESCRIPTION: SEQ ID NO:222:

Gly Phe Ser Thr Ala Ser Gly Lys Gln Val Ser Val Ser Glu Ser Ala
1               5                   10                  15

Leu His Lys Val Lys Gly Met Leu Glu Glu
            20                  25
```